(12) United States Patent
Hasegawa et al.

(10) Patent No.: US 9,150,657 B2
(45) Date of Patent: Oct. 6, 2015

(54) ANTI-EPHA2 ANTIBODY

(71) Applicant: Daiichi Sankyo Company, Limited, Chuo-ku, Tokyo (JP)

(72) Inventors: Jun Hasegawa, Tokyo (JP); Toshiaki Ohtsuka, Saitama (JP); Atsushi Urano, Tokyo (JP); Junko Yamaguchi, Tokyo (JP); Toshinori Agatsuma, Saitama (JP); Kaori Nakahara, Tokyo (JP); Takeshi Takizawa, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/899,996

(22) Filed: May 22, 2013

(65) Prior Publication Data

US 2014/0212439 A1    Jul. 31, 2014

Related U.S. Application Data

(60) Division of application No. 12/713,041, filed on Feb. 25, 2010, now Pat. No. 8,449,882, which is a continuation-in-part of application No. PCT/JP2008/065486, filed on Aug. 29, 2008.

(30) Foreign Application Priority Data

Aug. 30, 2007 (JP) ................................. 2007-224007

(51) Int. Cl.
*C07K 16/00* (2006.01)
*C07K 16/30* (2006.01)
*C07K 16/28* (2006.01)
*A61K 39/00* (2006.01)

(52) U.S. Cl.
CPC ............. *C07K 16/30* (2013.01); *C07K 16/2866* (2013.01); *A61K 2039/505* (2013.01); *C07K 2317/24* (2013.01); *C07K 2317/56* (2013.01); *C07K 2317/732* (2013.01); *C07K 2317/734* (2013.01)

(58) Field of Classification Search
None
See application file for complete search history.

(56) References Cited

U.S. PATENT DOCUMENTS

| 6,931,956 | B2 | 8/2005 | Thery |
| 7,101,976 | B1 | 9/2006 | Kilpatrick |
| 7,326,552 | B1 | 2/2008 | Cronin |
| 7,402,298 | B1 * | 7/2008 | Kinch et al. ................ 424/9.34 |
| 2005/0048617 | A1 | 3/2005 | Wu |
| 2005/0152899 | A1 | 7/2005 | Kinch |
| 2006/0034856 | A1 | 2/2006 | Kosmatopoulos |
| 2007/0292383 | A1 | 12/2007 | Schepky |
| 2008/0003210 | A1 | 1/2008 | Bruckheimer |
| 2008/0199426 | A1 | 8/2008 | Sukhatme |

FOREIGN PATENT DOCUMENTS

| EP | 1 852 441 | A2 | 11/2007 |
| WO | 01/12172 | A1 | 2/2001 |
| WO | 01/12840 | A2 | 2/2001 |
| WO | 01/74382 | A1 | 10/2001 |
| WO | 02/00728 | A2 | 1/2002 |
| WO | 02/099313 | A1 | 12/2002 |
| WO | 02/102972 | A2 | 12/2002 |
| WO | 03/004057 | A1 | 1/2003 |
| WO | 03/091383 | A2 | 11/2003 |
| WO | 03/094859 | A2 | 11/2003 |
| WO | 03/099313 | A1 | 12/2003 |
| WO | 2004/014292 | A2 | 2/2004 |
| WO | 2004/028551 | A1 | 4/2004 |
| WO | 2004/069264 | A1 | 8/2004 |
| WO | 2004/091375 | A2 | 10/2004 |
| WO | 2004/091510 | A2 | 10/2004 |
| WO | 2004/092343 | A2 | 10/2004 |
| WO | 2004/101764 | A2 | 11/2004 |
| WO | 2004/106380 | A2 | 12/2004 |
| WO | 2005/007097 | A2 | 1/2005 |
| WO | 2005/012350 | A2 | 2/2005 |
| WO | 2005/016381 | A2 | 2/2005 |
| WO | 2005/035575 | A2 | 4/2005 |
| WO | 2005/037233 | A2 | 4/2005 |
| WO | 2005/042743 | A2 | 5/2005 |
| WO | 2005/048971 | A1 | 6/2005 |
| WO | 2005/051307 | A2 | 6/2005 |
| WO | 2005/055948 | A2 | 6/2005 |
| WO | 2005/056766 | A2 | 6/2005 |
| WO | 2005/067460 | A2 | 7/2005 |
| WO | 2005/113596 | A2 | 12/2005 |

(Continued)

OTHER PUBLICATIONS

Brantley, D.M., et al., "Soluble Eph A Receptors Inhibit Tumor Angiogenesis and Progression In Vivo," Oncogene 21(46):7011-7026, Oct. 2002.
Brantley-Sieders, D.M., et al., "EphA2 Receptor Tyrosine Kinase Regulates Endothelial Cell Migration and Vascular Assembly Through Phosphoinositide 3-Kinase-Mediated Rac1 GTPase Activation," Journal of Cell Science 117(10):2037-2049, Apr. 2004.
Carles-Kinch, K., et al., "Antibody Targeting of the EphA2 Tyrosine Kinase Inhibits Malignant Cell Behavior," Cancer Research 62(10):2840-2847, May 2002.
Casset, F, et al., "A Peptide Mimetic of an Anti-CD4 Monoclonal Antibody by Rational Design," Biochemical and Biophysical Research Communications 307(1):198-205, Jul. 2003.

(Continued)

*Primary Examiner* — Laura B Goddard
*Assistant Examiner* — Meera Natarajan
(74) *Attorney, Agent, or Firm* — Christensen O'Connor Johnson Kindness PLLC

(57) ABSTRACT

The present invention provides an antibody which recognizes an epitope recognized by an antibody produced by a hybridoma SH348-1 (FERM BP-10836) or a hybridoma SH357-1 (FERM BP-10837), an antibody produced by the hybridoma SH348-1 or the hybridoma SH357-1, an antibody obtained by humanizing the antibody produced by the hybridoma SH348-1 or the hybridoma SH357-1, a pharmaceutical agent comprising the antibody as an active ingredient, etc.

15 Claims, 16 Drawing Sheets

(56) References Cited

FOREIGN PATENT DOCUMENTS

| WO | 2006/023403 A2 | 3/2006 |
| WO | 2006/047637 A1 | 5/2006 |
| WO | 2006/047638 A2 | 5/2006 |
| WO | 2006/047639 A2 | 5/2006 |
| WO | 2006/052409 A2 | 5/2006 |
| WO | 2006/084226 A2 | 8/2006 |
| WO | 2006/099481 A2 | 9/2006 |
| WO | 2007/018671 A2 | 2/2007 |
| WO | 2007/030642 A2 | 3/2007 |
| WO | 2007/035451 A2 | 3/2007 |
| WO | 2007/073499 A2 | 6/2007 |
| WO | 2007/075706 A2 | 7/2007 |
| WO | 2007/089871 A2 | 8/2007 |
| WO | 2007/146968 A2 | 12/2007 |
| WO | 2008/010101 A2 | 1/2008 |
| WO | 2008/066498 A1 | 6/2008 |
| WO | 2008/070042 A2 | 6/2008 |
| WO | 2008/126002 A2 | 10/2008 |
| WO | 2008/157490 A1 | 12/2008 |
| WO | 2009/008901 A2 | 1/2009 |
| WO | 2009/030285 A1 | 3/2009 |
| WO | 2009/052830 A1 | 4/2009 |

OTHER PUBLICATIONS

Chen, Y., et al., "Selection and Analysis of an Optimized Anti-VEGF Antibody: Crystal Structure of an Affinity-Matured Fab in Complex With Antigen," Journal of Molecular Biology 293(4):865-881, Nov. 1999.

Clynes, R.A., et al., "Inhibitory Fc Receptors Modulate In Vivo Cytoxicity Against Tumor Targets," Nature Medicine 6(4):443-446, Apr. 2000.

Coffman, K.T., et al., "Differential EphA2 Epitope Display on Normal Versus Malignant Cells," Cancer Research 63(22):7907-7912, Nov. 2003.

Coiffier, B., "Rituximab Therapy in Malignant Lymphoma," Oncogene 26(25):3603-3613, May 2007.

Cragg, M.S., and M.J. Glennie, "Antibody Specificity Controls In Vivo Effector Mechanisms of Anti-CD20 Reagents," Blood 103(7):2738-2743, Apr. 2004.

Dall'Acqua, W.F., et al., "Antibody Humanization by Framework Shuffling," Methods 36(1):43-60, May 2005.

Dall'Acqua, W.F., et al., "Modulation of the Effector Functions of a Human IgG1 Through Engineering of Its Hinge Region," Journal of Immunology 177(2):1129-38, Jul. 2006.

Damschroder, M.M., et al., "Framework Shuffling of Antibodies to Reduce Immunogenicity and Manipulate Functional and Biophysical Properties," Molecular Immunology 44(11):3049-60, Mar. 2007.

De Pascalis, R., et al., "Grafting of 'Abbreviated' Complementarity-Determining Regions Containing Specificity-Determining Residues Essential for Ligand Contact to Engineer a Less Immunogenic Humanized Monoclonal Antibody," Journal of Immunology 169(6):3076-3084, Sep. 2002.

Duxbury, M.S., et al., "EphA2: A Determinant of Malignant Cellular Behavior and a Potential Therapeutic Target in Pancreatic Adenocarcinoma," Oncogene 23(7):1448-1456, Feb. 2004.

Duxbury, M.S., et al., "Ligation of EphA2 by Ephrin A1-Fc Inhibits Pancreatic Adenocarcinoma Cellular Invasiveness," Biochemical and Biophysical Research Communications 320(4):1096-1102, Aug. 2004.

Flanagan, J.G., and P. Vanderhaeghen, "The Ephrins and Eph Receptors in Neural Development," Annual Review of Neuroscience 21:309-345, Mar. 1998.

Hammond, S.A., et al., "Selective Targeting and Potent Control of Tumor Growth Using an EphA2/CD3-Bispecific Single-Chain Antibody Construct," Cancer Research 67(8):3927-3935, Apr. 2007.

Hudis, C.A., "Trastuzumab—Mechanism of Action and Use in Clinical Practice," New England Journal of Medicine 357(1):39-51, Jul. 2007.

Jackson, D., et al., "A Human Antibody-Drug Conjugate Targeting EphA2 Inhibits Tumor Growth In Vivo," Cancer Research 68(22):9367-9374, Nov. 2008.

Kiewlich, D., et al., "Anti-EphA2 Antibodies Decrease EphA2 Protein Levels in Murine CT26 Colorectal and Human MDA-231 Breast Tumors but Do Not Inhibit Tumor Growth," Neoplasia 8(1):18-30, Jan. 2006.

Kinch, M.S., et al., "Predictive Value of the EphA2 Receptor Tyrosine Kinase in Lung Cancer Recurrence and Survival," Clinical Cancer Research 9(2):613-618, Feb. 2003.

Lamminmäki, U., and J.A. Kankare, "Crystal Structure of a Recombinant Anti-Estradiol Fab Fragment in Complex With 17β-Estradiol," Journal of Biological Chemistry 276(39):36687-36694, Sep. 2001.

Landen, C.N., Jr., et al., "Efficacy and Antivascular Effects of EphA2 Reduction With an Agonistic Antibody in Ovarian Cancer," Journal of the National Cancer Institute 98(21):1558-1570, Nov. 2006.

MacCallum, R.M., et al., "Antibody-Antigen Interactions: Contact Analysis and Binding Site Topography," Journal of Molecular Biology 262(5):732-745, Oct. 1996.

Miyazaki, T., et al., "EphA2 Overexpression Correlates With Poor Prognosis in Esophageal Squamous Cell Carcinoma," International Journal of Cancer 103(5):657-663, Feb. 2003.

Nakamura, R., et al., "EPHA2/EFNA1 Expression in Human Gastric Cancer," Cancer Science 98(1):42-47, Jan. 2005.

Ogawa, K., et al., "The Ephrin-A1 Ligand and Its Receptor, EphA2, Are Expressed During Tumor Neovascularization," Oncogene 19(52):6043-6052, Dec. 2000.

Padlan, E.A., et al., "Structure of an Antibody—Antigen Complex: Crystal Structure of the HyHEL-10 Fab—Lysozyme Complex," Proceedings of the National Academy of Sciences of the United States of America (PNAS) 86(15):5938-5942, Aug. 1989.

Pfeiffer, P., et al., "Current Role of Antibody Therapy in Patients With Metastatic Colorectal Cancer," Oncogene 26(25):3661-3678, May 2007.

Rudikoff, S., et al., "Single Amino Acid Substitution Altering Antigen-Binding Specificity," Proceedings of the National Academy of Sciences of the United States of America (PNAS) 79(6):1979-1983, Mar. 1982.

Saito, T., et al., "Expression of EphA2 and E-Cadherin in Colorectal Cancer: Correlation With Cancer Metastasis," Oncology Reports 11(3):605-611, Mar. 2004.

Vajdos, F.F., et al., "Comprehensive Functional Maps of the Antigen-Binding Site of an Anti-ErbB2 Antibody Obtained With Shotgun Scanning Mutagenesis," Journal of Molecular Biology 320(2):415-428, Jul. 2002.

Walker-Daniels, J., et al., "c-Cbl-Dependent EphA2 Protein Degradation Is Induced by Ligand Binding," Molecular Cancer Research 1(1):79-87, Nov. 2002.

Walker-Daniels, J., et al., "Overexpression of the EphA2 Tyrosine Kinase in Prostate Cancer," Prostate 41(4):275-280, Dec. 1999.

Wu, H., et al., "Humanization of a Murine Monoclonal Antibody by Simultaneous Optimization of Framework and CDR Residues," Journal of Molecular Biology 294(1):151-162, Nov. 1999.

Wykosky, J., et al., "EphA2 as a Novel Molecular Marker and Target in Glioblastoma Multiforme," Molecular Cancer Research 3(10):541-551, Oct. 2005.

Zelinski, D.P., et al., "EphA2 Overexpression Causes Tumorigenesis of Mammary Epithelial Cells," Cancer Research 61(5):2301-2306, Mar. 2001.

Zeng, G., et al., "High-Level Expression of EphA2 Receptor Tyrosine Kinase in Prostatic Intraepithelial Neoplasia," American Journal of Pathology 163(6):2271-2276, Dec. 2003.

Canadian Office Action mailed Jun. 1, 2011, issued in corresponding Canadian Application No. 2,698,146, filed Feb. 26, 2010.

Extended European Search Report mailed Nov. 14, 2012, issued in corresponding European Application No. EP 08 82 8482.3, filed Aug. 29, 2008.

Office Action mailed Nov. 6, 2013, issued in related Israeli Patent Application No. 204211, filed Feb. 28, 2010, 3 pages.

\* cited by examiner

SH348-1 anti-S-Tag

SH357-1 anti-S-Tag

```
                              SEQUENCE LISTING

<160> NUMBER OF SEQ ID NOS: 163

<210> SEQ ID NO 1
<211> LENGTH: 2931
<212> TYPE: DNA
<213> ORGANISM: Homo sapiens
<220> FEATURE:
<221> NAME/KEY: CDS
<222> LOCATION: (1)..(2931)

<400> SEQUENCE: 1 atg gag ctc cag gca gcc cgc gcc tgc ttc gcc ctg ctg tgg ggc tgt     48
Met Glu Leu Gln Ala Ala Arg Ala Cys Phe Ala Leu Leu Trp Gly Cys
1               5                   10                  15 gcg ctg gcc gcg gcc gcg gcg gcg cag ggc aag gaa gtg gta ctg ctg     96
Ala Leu Ala Ala Ala Ala Ala Ala Gln Gly Lys Glu Val Val Leu Leu
                20                  25                  30 gac ttt gct gca gct gga ggg gag ctc ggc tgg ctc aca cac ccg tat    144
Asp Phe Ala Ala Ala Gly Gly Glu Leu Gly Trp Leu Thr His Pro Tyr
            35                  40                  45 ggc aaa ggg tgg gac ctg atg cag aac atc atg aat gac atg ccg atc    192
Gly Lys Gly Trp Asp Leu Met Gln Asn Ile Met Asn Asp Met Pro Ile
        50                  55                  60 tac atg tac tcc gtg tgc aac gtg atg tct ggc gac cag gac aac tgg    240
Tyr Met Tyr Ser Val Cys Asn Val Met Ser Gly Asp Gln Asp Asn Trp
65                  70                  75                  80 ctc cgc acc aac tgg gtg tac cga gga gag gct gag cgt atc ttc att    288
Leu Arg Thr Asn Trp Val Tyr Arg Gly Glu Ala Glu Arg Ile Phe Ile
                85                  90                  95 gag ctc aag ttt act gta cgt gac tgc aac agc ttc cct ggt ggc gcc    336
Glu Leu Lys Phe Thr Val Arg Asp Cys Asn Ser Phe Pro Gly Gly Ala
            100                 105                 110 agc tcc tgc aag gag act ttc aac ctc tac tat gcc gag tcg gac ctg    384
Ser Ser Cys Lys Glu Thr Phe Asn Leu Tyr Tyr Ala Glu Ser Asp Leu
        115                 120                 125 gac tac ggc acc aac ttc cag aag cgc ctg ttc acc aag att gac acc    432
Asp Tyr Gly Thr Asn Phe Gln Lys Arg Leu Phe Thr Lys Ile Asp Thr
    130                 135                 140 att gcg ccc gat gag atc acc gtc agc agc gac ttc gag gca cgc cac    480
Ile Ala Pro Asp Glu Ile Thr Val Ser Ser Asp Phe Glu Ala Arg His
145                 150                 155                 160 gtg aag ctg aac gtg gag gag cgc tcc gtg ggg ccg ctc acc cgc aaa    528
Val Lys Leu Asn Val Glu Glu Arg Ser Val Gly Pro Leu Thr Arg Lys
                165                 170                 175 ggc ttc tac ctg gcc ttc cag gat atc ggt gcc tgt gtg gcg ctg ctc    576
Gly Phe Tyr Leu Ala Phe Gln Asp Ile Gly Ala Cys Val Ala Leu Leu
            180                 185                 190 tcc gtc cgt gtc tac tac aag aag tgc ccc gag ctg ctg cag ggc ctg    624
Ser Val Arg Val Tyr Tyr Lys Lys Cys Pro Glu Leu Leu Gln Gly Leu
        195                 200                 205 gcc cac ttc cct gag acc atc gcc ggc tct gat gca cct tcc ctg gcc    672
Ala His Phe Pro Glu Thr Ile Ala Gly Ser Asp Ala Pro Ser Leu Ala
    210                 215                 220 act gtg gcc ggc acc tgt gtg gac cat gcc gtg gtg cca ccg ggg ggt    720
Thr Val Ala Gly Thr Cys Val Asp His Ala Val Val Pro Pro Gly Gly
225                 230                 235                 240 gaa gag ccc cgt atg cac tgt gca gtg gat ggc gag tgg ctg gtg ccc    768
Glu Glu Pro Arg Met His Cys Ala Val Asp Gly Glu Trp Leu Val Pro
                245                 250                 255
```

```
att ggg cag tgc ctg tgc cag gca ggc tac gag aag gtg gag gat gcc     816
Ile Gly Gln Cys Leu Cys Gln Ala Gly Tyr Glu Lys Val Glu Asp Ala
        260                 265                 270 tgc cag gcc tgc tcg cct gga ttt ttt aag ttt gag gca tct gag agc     864
Cys Gln Ala Cys Ser Pro Gly Phe Phe Lys Phe Glu Ala Ser Glu Ser
    275                 280                 285 ccc tgc ttg gag tgc cct gag cac acg ctg cca tcc cct gag ggt gcc     912
Pro Cys Leu Glu Cys Pro Glu His Thr Leu Pro Ser Pro Glu Gly Ala
290                 295                 300 acc tcc tgc gag tgt gag gaa ggc ttc ttc cgg gca cct cag gac cca     960
Thr Ser Cys Glu Cys Glu Glu Gly Phe Phe Arg Ala Pro Gln Asp Pro
305                 310                 315                 320 gcg tcg atg cct tgc aca cga ccc ccc tcc gcc cca cac tac ctc aca    1008
Ala Ser Met Pro Cys Thr Arg Pro Pro Ser Ala Pro His Tyr Leu Thr
                325                 330                 335 gcc gtg ggc atg ggt gcc aag gtg gag ctg cgc tgg acg ccc cct cag    1056
Ala Val Gly Met Gly Ala Lys Val Glu Leu Arg Trp Thr Pro Pro Gln
            340                 345                 350 gac agc ggg ggc cgc gag gac att gtc tac agc gtc acc tgc gaa cag    1104
Asp Ser Gly Gly Arg Glu Asp Ile Val Tyr Ser Val Thr Cys Glu Gln
        355                 360                 365 tgc tgg ccc gag tct ggg gaa tgc ggg ccg tgt gag gcc agt gtg cgc    1152
Cys Trp Pro Glu Ser Gly Glu Cys Gly Pro Cys Glu Ala Ser Val Arg
    370                 375                 380 tac tcg gag cct cct cac gga ctg acc cgc acc agt gtg aca gtg agc    1200
Tyr Ser Glu Pro Pro His Gly Leu Thr Arg Thr Ser Val Thr Val Ser
385                 390                 395                 400 gac ctg gag ccc cac atg aac tac acc ttc acc gtg gag gcc cgc aat    1248
Asp Leu Glu Pro His Met Asn Tyr Thr Phe Thr Val Glu Ala Arg Asn
                405                 410                 415 ggc gtc tca ggc ctg gta acc agc cgc agc ttc cgt act gcc agt gtc    1296
Gly Val Ser Gly Leu Val Thr Ser Arg Ser Phe Arg Thr Ala Ser Val
            420                 425                 430 agc atc aac cag aca gag ccc ccc aag gtg agg ctg gag ggc cgc agc    1344
Ser Ile Asn Gln Thr Glu Pro Pro Lys Val Arg Leu Glu Gly Arg Ser
        435                 440                 445 acc acc tcg ctt agc gtc tcc tgg agc atc ccc ccg cag cag agc        1392
Thr Thr Ser Leu Ser Val Ser Trp Ser Ile Pro Pro Pro Gln Gln Ser
    450                 455                 460 cga gtg tgg aag tac gag gtc act tac cgc aag aag gga gac tcc aac    1440
Arg Val Trp Lys Tyr Glu Val Thr Tyr Arg Lys Lys Gly Asp Ser Asn
465                 470                 475                 480 agc tac aat gtg cgc cgc acc gag ggt ttc tcc gtg acc ctg gac gac    1488
Ser Tyr Asn Val Arg Arg Thr Glu Gly Phe Ser Val Thr Leu Asp Asp
                485                 490                 495 ctg gcc cca gac acc acc tac ctg gtc cag gtg cag gca ctg acg cag    1536
Leu Ala Pro Asp Thr Thr Tyr Leu Val Gln Val Gln Ala Leu Thr Gln
            500                 505                 510 gag ggc cag ggg gcc ggc agc aag gtg cac gaa ttc cag acg ctg tcc    1584
Glu Gly Gln Gly Ala Gly Ser Lys Val His Glu Phe Gln Thr Leu Ser
        515                 520                 525 ccg gag gga tct ggc aac ttg gcg gtg att ggc ggc gtg gct gtc ggt    1632
Pro Glu Gly Ser Gly Asn Leu Ala Val Ile Gly Gly Val Ala Val Gly
    530                 535                 540 gtg gtc ctg ctt ctg gtg ctg gca gga gtt ggc ttc ttt atc cac cgc    1680
Val Val Leu Leu Leu Val Leu Ala Gly Val Gly Phe Phe Ile His Arg
545                 550                 555                 560 agg agg aag aac cag cgt gcc cgc cag tcc ccg gag gac gtt tac ttc    1728
Arg Arg Lys Asn Gln Arg Ala Arg Gln Ser Pro Glu Asp Val Tyr Phe
```

```
                         565                 570                  575
tcc aag tca gaa caa ctg aag ccc ctg aag aca tac gtg gac ccc cac    1776
Ser Lys Ser Glu Gln Leu Lys Pro Leu Lys Thr Tyr Val Asp Pro His
            580                 585                 590 aca tat gag gac ccc aac cag gct gtg ttg aag ttc act acc gag atc    1824
Thr Tyr Glu Asp Pro Asn Gln Ala Val Leu Lys Phe Thr Thr Glu Ile
            595                 600                 605 cat cca tcc tgt gtc act cgg cag aag gtg atc gga gca gga gag ttt    1872
His Pro Ser Cys Val Thr Arg Gln Lys Val Ile Gly Ala Gly Glu Phe
610                 615                 620 ggg gag gtg tac aag ggc atg ctg aag aca tcc tcg ggg aag aag gag    1920
Gly Glu Val Tyr Lys Gly Met Leu Lys Thr Ser Ser Gly Lys Lys Glu
625                 630                 635                 640 gtg ccg gtg gcc atc aag acg ctg aaa gcc ggc tac aca gag aag cag    1968
Val Pro Val Ala Ile Lys Thr Leu Lys Ala Gly Tyr Thr Glu Lys Gln
                645                 650                 655 cga gtg gac ttc ctc ggc gag gcc ggc atc atg ggc cag ttc agc cac    2016
Arg Val Asp Phe Leu Gly Glu Ala Gly Ile Met Gly Gln Phe Ser His
            660                 665                 670 cac aac atc atc cgc cta gag ggc gtc atc tcc aaa tac aag ccc atg    2064
His Asn Ile Ile Arg Leu Glu Gly Val Ile Ser Lys Tyr Lys Pro Met
        675                 680                 685 atg atc atc act gag tac atg gag aat ggg gcc ctg gac aag ttc ctt    2112
Met Ile Ile Thr Glu Tyr Met Glu Asn Gly Ala Leu Asp Lys Phe Leu
690                 695                 700 cgg gag aag gat ggc gag ttc agc gtg ctg cag ctg gtg ggc atg ctg    2160
Arg Glu Lys Asp Gly Glu Phe Ser Val Leu Gln Leu Val Gly Met Leu
705                 710                 715                 720 cgg ggc atc gca gct ggc atg aag tac ctg gcc aac atg aac tat gtg    2208
Arg Gly Ile Ala Ala Gly Met Lys Tyr Leu Ala Asn Met Asn Tyr Val
                725                 730                 735 cac cgt gac ctg gct gcc cgc aac atc ctc gtc aac agc aac ctg gtc    2256
His Arg Asp Leu Ala Ala Arg Asn Ile Leu Val Asn Ser Asn Leu Val
            740                 745                 750 tgc aag gtg tct gac ttt ggc ctg tcc cgc gtg ctg gag gac gac ccc    2304
Cys Lys Val Ser Asp Phe Gly Leu Ser Arg Val Leu Glu Asp Asp Pro
        755                 760                 765 gag gcc acc tac acc acc agt ggc ggc aag atc ccc atc cgc tgg acc    2352
Glu Ala Thr Tyr Thr Thr Ser Gly Gly Lys Ile Pro Ile Arg Trp Thr
770                 775                 780 gcc ccg gag gcc att tcc tac cgg aag ttc acc tct gcc agc gac gtg    2400
Ala Pro Glu Ala Ile Ser Tyr Arg Lys Phe Thr Ser Ala Ser Asp Val
785                 790                 795                 800 tgg agc ttt ggc att gtc atg tgg gag gtg atg acc tat ggc gag cgg    2448
Trp Ser Phe Gly Ile Val Met Trp Glu Val Met Thr Tyr Gly Glu Arg
                805                 810                 815 ccc tac tgg gag ttg tcc aac cac gag gtg atg aaa gcc atc aat gat    2496
Pro Tyr Trp Glu Leu Ser Asn His Glu Val Met Lys Ala Ile Asn Asp
            820                 825                 830 ggc ttc cgg ctc ccc aca ccc atg gac tgc ccc tcc gcc atc tac cag    2544
Gly Phe Arg Leu Pro Thr Pro Met Asp Cys Pro Ser Ala Ile Tyr Gln
        835                 840                 845 ctc atg atg cag tgc tgg cag cag gag cgt gcc cgc cgc ccc aag ttc    2592
Leu Met Met Gln Cys Trp Gln Gln Glu Arg Ala Arg Arg Pro Lys Phe
850                 855                 860 gct gac atc gtc agc atc ctg gac aag ctc att cgt gcc cct gac tcc    2640
Ala Asp Ile Val Ser Ile Leu Asp Lys Leu Ile Arg Ala Pro Asp Ser
865                 870                 875                 880 ctc aag acc ctg gct gac ttt gac ccc cgc gtg tct atc cgg ctc ccc    2688
Leu Lys Thr Leu Ala Asp Phe Asp Pro Arg Val Ser Ile Arg Leu Pro
```

```
                Leu Lys Thr Leu Ala Asp Phe Asp Pro Arg Val Ser Ile Arg Leu Pro
                                885                 890                 895 agc acg agc ggc tcg gag ggg gtg ccc ttc cgc acg gtg tcc gag tgg             2736
Ser Thr Ser Gly Ser Glu Gly Val Pro Phe Arg Thr Val Ser Glu Trp
            900                 905                 910 ctg gag tcc atc aag atg cag cag tat acg gag cac ttc atg gcg gcc             2784
Leu Glu Ser Ile Lys Met Gln Gln Tyr Thr Glu His Phe Met Ala Ala
            915                 920                 925 ggc tac act gcc atc gag aag gtg gtg cag atg acc aac gac gac atc             2832
Gly Tyr Thr Ala Ile Glu Lys Val Val Gln Met Thr Asn Asp Asp Ile
        930                 935                 940 aag agg att ggg gtg cgg ctg ccc ggc cac cag aag cgc atc gcc tac             2880
Lys Arg Ile Gly Val Arg Leu Pro Gly His Gln Lys Arg Ile Ala Tyr
945                 950                 955                 960 agc ctg ctg gga ctc aag gac cag gtg aac act gtg ggg atc ccc atc             2928
Ser Leu Leu Gly Leu Lys Asp Gln Val Asn Thr Val Gly Ile Pro Ile
                965                 970                 975 tga                                                                          2931

<210> SEQ ID NO 2
<211> LENGTH: 976
<212> TYPE: PRT
<213> ORGANISM: Homo sapiens

<400> SEQUENCE: 2

Met Glu Leu Gln Ala Ala Arg Ala Cys Phe Ala Leu Leu Trp Gly Cys
1               5                   10                  15

Ala Leu Ala Ala Ala Ala Ala Gln Gly Lys Glu Val Val Leu Leu
            20                  25                  30

Asp Phe Ala Ala Ala Gly Gly Glu Leu Gly Trp Leu Thr His Pro Tyr
        35                  40                  45

Gly Lys Gly Trp Asp Leu Met Gln Asn Ile Met Asn Asp Met Pro Ile
    50                  55                  60

Tyr Met Tyr Ser Val Cys Asn Val Met Ser Gly Asp Gln Asp Asn Trp
65                  70                  75                  80

Leu Arg Thr Asn Trp Val Tyr Arg Gly Glu Ala Glu Arg Ile Phe Ile
                85                  90                  95

Glu Leu Lys Phe Thr Val Arg Asp Cys Asn Ser Phe Pro Gly Gly Ala
            100                 105                 110

Ser Ser Cys Lys Glu Thr Phe Asn Leu Tyr Tyr Ala Glu Ser Asp Leu
        115                 120                 125

Asp Tyr Gly Thr Asn Phe Gln Lys Arg Leu Phe Thr Lys Ile Asp Thr
    130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                165                 170                 175

Gly Phe Tyr Leu Ala Phe Gln Asp Ile Gly Ala Cys Val Ala Leu Leu
            180                 185                 190

Ser Val Arg Val Tyr Tyr Lys Lys Cys Pro Glu Leu Leu Gln Gly Leu
        195                 200                 205

Ala His Phe Pro Glu Thr Ile Ala Gly Ser Asp Ala Pro Ser Leu Ala
    210                 215                 220

Thr Val Ala Gly Thr Cys Val Asp His Ala Val Val Pro Pro Gly Gly
225                 230                 235                 240

Glu Glu Pro Arg Met His Cys Ala Val Asp Gly Glu Trp Leu Val Pro
```

245                 250                 255
Ile Gly Gln Cys Leu Cys Gln Ala Gly Tyr Glu Lys Val Glu Asp Ala
            260                 265                 270

Cys Gln Ala Cys Ser Pro Gly Phe Phe Lys Phe Glu Ala Ser Glu Ser
        275                 280                 285

Pro Cys Leu Glu Cys Pro Glu His Thr Leu Pro Ser Pro Glu Gly Ala
    290                 295                 300

Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
            325                 330                 335

Ala Val Gly Met Gly Ala Lys Val Glu Leu Arg Trp Thr Pro Pro Gln
            340                 345                 350

Asp Ser Gly Gly Arg Glu Asp Ile Val Tyr Ser Val Thr Cys Glu Gln
            355                 360                 365

Cys Trp Pro Glu Ser Gly Glu Cys Gly Pro Cys Glu Ala Ser Val Arg
        370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                405                 410                 415

Gly Val Ser Gly Leu Val Thr Ser Arg Ser Phe Arg Thr Ala Ser Val
            420                 425                 430

Ser Ile Asn Gln Thr Glu Pro Pro Lys Val Arg Leu Glu Gly Arg Ser
        435                 440                 445

Thr Thr Ser Leu Ser Val Ser Trp Ser Ile Pro Pro Pro Gln Gln Ser
    450                 455                 460

Arg Val Trp Lys Tyr Glu Val Thr Tyr Arg Lys Lys Gly Asp Ser Asn
465                 470                 475                 480

Ser Tyr Asn Val Arg Arg Thr Glu Gly Phe Ser Val Thr Leu Asp Asp
            485                 490                 495

Leu Ala Pro Asp Thr Thr Tyr Leu Val Gln Val Gln Ala Leu Thr Gln
            500                 505                 510

Glu Gly Gln Gly Ala Gly Ser Lys Val His Glu Phe Gln Thr Leu Ser
        515                 520                 525

Pro Glu Gly Ser Gly Asn Leu Ala Val Ile Gly Gly Val Ala Val Gly
    530                 535                 540

Val Val Leu Leu Leu Val Leu Ala Gly Val Gly Phe Phe Ile His Arg
545                 550                 555                 560

Arg Arg Lys Asn Gln Arg Ala Arg Gln Ser Pro Glu Asp Val Tyr Phe
                565                 570                 575

Ser Lys Ser Glu Gln Leu Lys Pro Leu Lys Thr Tyr Val Asp Pro His
            580                 585                 590

Thr Tyr Glu Asp Pro Asn Gln Ala Val Leu Lys Phe Thr Thr Glu Ile
        595                 600                 605

His Pro Ser Cys Val Thr Arg Gln Lys Val Ile Gly Ala Gly Glu Phe
    610                 615                 620

Gly Glu Val Tyr Lys Gly Met Leu Lys Thr Ser Ser Gly Lys Lys Glu
625                 630                 635                 640

Val Pro Val Ala Ile Lys Thr Leu Lys Ala Gly Tyr Thr Glu Lys Gln
                645                 650                 655

Arg Val Asp Phe Leu Gly Glu Ala Gly Ile Met Gly Gln Phe Ser His
            660                 665                 670

```
His Asn Ile Ile Arg Leu Glu Gly Val Ile Ser Lys Tyr Lys Pro Met
            675                 680                 685
Met Ile Ile Thr Glu Tyr Met Glu Asn Gly Ala Leu Asp Lys Phe Leu
        690                 695                 700
Arg Glu Lys Asp Gly Glu Phe Ser Val Leu Gln Leu Val Gly Met Leu
705                 710                 715                 720
Arg Gly Ile Ala Ala Gly Met Lys Tyr Leu Ala Asn Met Asn Tyr Val
                725                 730                 735
His Arg Asp Leu Ala Ala Arg Asn Ile Leu Val Asn Ser Asn Leu Val
            740                 745                 750
Cys Lys Val Ser Asp Phe Gly Leu Ser Arg Val Leu Glu Asp Asp Pro
        755                 760                 765
Glu Ala Thr Tyr Thr Thr Ser Gly Gly Lys Ile Pro Ile Arg Trp Thr
770                 775                 780
Ala Pro Glu Ala Ile Ser Tyr Arg Lys Phe Thr Ser Ala Ser Asp Val
785                 790                 795                 800
Trp Ser Phe Gly Ile Val Met Trp Glu Val Met Thr Tyr Gly Glu Arg
                805                 810                 815
Pro Tyr Trp Glu Leu Ser Asn His Glu Val Met Lys Ala Ile Asn Asp
            820                 825                 830
Gly Phe Arg Leu Pro Thr Pro Met Asp Cys Pro Ser Ala Ile Tyr Gln
        835                 840                 845
Leu Met Met Gln Cys Trp Gln Gln Glu Arg Ala Arg Arg Pro Lys Phe
850                 855                 860
Ala Asp Ile Val Ser Ile Leu Asp Lys Leu Ile Arg Ala Pro Asp Ser
865                 870                 875                 880
Leu Lys Thr Leu Ala Asp Phe Asp Pro Arg Val Ser Ile Arg Leu Pro
                885                 890                 895
Ser Thr Ser Gly Ser Glu Gly Val Pro Phe Arg Thr Val Ser Glu Trp
            900                 905                 910
Leu Glu Ser Ile Lys Met Gln Gln Tyr Thr Glu His Phe Met Ala Ala
        915                 920                 925
Gly Tyr Thr Ala Ile Glu Lys Val Val Gln Met Thr Asn Asp Asp Ile
930                 935                 940
Lys Arg Ile Gly Val Arg Leu Pro Gly His Gln Lys Arg Ile Ala Tyr
945                 950                 955                 960
Ser Leu Leu Gly Leu Lys Asp Gln Val Asn Thr Val Gly Ile Pro Ile
                965                 970                 975

<210> SEQ ID NO 3
<211> LENGTH: 55
<212> TYPE: DNA
<213> ORGANISM: Artificial Sequence
<220> FEATURE:
<223> OTHER INFORMATION: PCR primer 1

<400> SEQUENCE: 3
ggggacaagt ttgtacaaaa aagcaggctt cggggatcgg accgagagcg agaag      55

<210> SEQ ID NO 4
<211> LENGTH: 66
<212> TYPE: DNA
<213> ORGANISM: Artificial Sequence
<220> FEATURE:
<223> OTHER INFORMATION: PCR primer 2

<400> SEQUENCE: 4
```

-continued

```
ggggaccact tgtacaaga aagctgggtc ctagatgggg atccccacag tgttcacctg    60
gtcctt                                                              66
```

<210> SEQ ID NO 5
<211> LENGTH: 29
<212> TYPE: DNA
<213> ORGANISM: Artificial Sequence
<220> FEATURE:
<223> OTHER INFORMATION: Primer 3

<400> SEQUENCE: 5

```
ctgtggggat ccccatcgac ccagctttc                                     29
```

<210> SEQ ID NO 6
<211> LENGTH: 30
<212> TYPE: DNA
<213> ORGANISM: Artificial Sequence
<220> FEATURE:
<223> OTHER INFORMATION: Primer 4

<400> SEQUENCE: 6

```
gatggggatc cccacagtgt tcacctggtc                                    30
```

<210> SEQ ID NO 7
<211> LENGTH: 2961
<212> TYPE: DNA
<213> ORGANISM: Artificial Sequence
<220> FEATURE:
<223> OTHER INFORMATION: EPHA2 mutated sequence
<220> FEATURE:
<221> NAME/KEY: CDS
<222> LOCATION: (33)..(2960)

<400> SEQUENCE: 7

```
tcggggatcg gaccgagagc gagaagcgcg gc atg gag ctc cag gca gcc cgc    53
                                  Met Glu Leu Gln Ala Ala Arg
                                    1               5 gcc tgc ttc gcc ctg ctg tgg ggc tgt gcg ctg gcc gcg gcc gcg gcg   101
Ala Cys Phe Ala Leu Leu Trp Gly Cys Ala Leu Ala Ala Ala Ala Ala
         10                  15                  20 gcg cag ggc aag gaa gtg gta ctg ctg gac ttt gct gca gct gga ggg   149
Ala Gln Gly Lys Glu Val Val Leu Leu Asp Phe Ala Ala Ala Gly Gly
     25                  30                  35 gag ctc ggc tgg ctc aca cac ccg tat ggc aaa ggg tgg gac ctg atg   197
Glu Leu Gly Trp Leu Thr His Pro Tyr Gly Lys Gly Trp Asp Leu Met
40                  45                  50                  55 cag aac atc atg aat gac atg ccg atc tac atg tac tcc gtg tgc aac   245
Gln Asn Ile Met Asn Asp Met Pro Ile Tyr Met Tyr Ser Val Cys Asn
                 60                  65                  70 gtg atg tct ggc gac cag gac aac tgg ctc cgc acc aac tgg gtg tac   293
Val Met Ser Gly Asp Gln Asp Asn Trp Leu Arg Thr Asn Trp Val Tyr
             75                  80                  85 cga gga gag gct gag cgt atc ttc att gag ctc aag ttt act gta cgt   341
Arg Gly Glu Ala Glu Arg Ile Phe Ile Glu Leu Lys Phe Thr Val Arg
         90                  95                 100 gac tgc aac agc ttc cct ggt ggc gcc agc tcc tgc aag gag act ttc   389
Asp Cys Asn Ser Phe Pro Gly Gly Ala Ser Ser Cys Lys Glu Thr Phe
    105                 110                 115 aac ctc tac tat gcc gag tcg gac ctg gac tac ggc acc aac ttc cag   437
Asn Leu Tyr Tyr Ala Glu Ser Asp Leu Asp Tyr Gly Thr Asn Phe Gln
120                 125                 130                 135 aag cgc ctg ttc acc aag att gac acc att gcg ccc gat gag atc acc   485
```

```
         Lys Arg Leu Phe Thr Lys Ile Asp Thr Ile Ala Pro Asp Glu Ile Thr
                         140                 145                 150 gtc agc agc gac ttc gag gca cgc cac gtg aag ctg aac gtg gag gag         533
Val Ser Ser Asp Phe Glu Ala Arg His Val Lys Leu Asn Val Glu Glu
            155                 160                 165 cgc tcc gtg ggg ccg ctc acc cgc aaa ggc ttc tac ctg gcc ttc cag         581
Arg Ser Val Gly Pro Leu Thr Arg Lys Gly Phe Tyr Leu Ala Phe Gln
170                 175                 180 gat atc ggt gcc tgt gtg gca cta ctc tcc gtc cgt gtc tac tac aag         629
Asp Ile Gly Ala Cys Val Ala Leu Leu Ser Val Arg Val Tyr Tyr Lys
            185                 190                 195 aag tgc ccc gag ctg ctg cag ggc ctg gcc cac ttc cct gag acc atc         677
Lys Cys Pro Glu Leu Leu Gln Gly Leu Ala His Phe Pro Glu Thr Ile
200                 205                 210                 215 gcc ggc tct gat gca cct tcc ctg gcc act gtg gcc ggc acc tgt gtg         725
Ala Gly Ser Asp Ala Pro Ser Leu Ala Thr Val Ala Gly Thr Cys Val
            220                 225                 230 gac cat gcc gtg gtg cca ccg ggg ggt gaa gag ccc cgt atg cac tgt         773
Asp His Ala Val Val Pro Pro Gly Gly Glu Glu Pro Arg Met His Cys
            235                 240                 245 gca gtg gat ggc gag tgg ctg gtg ccc att ggg cag tgc ctg tgc cag         821
Ala Val Asp Gly Glu Trp Leu Val Pro Ile Gly Gln Cys Leu Cys Gln
            250                 255                 260 gca ggc tac gag aag gtg gag gat gcc tgc cag gcc tgc tcg cct gga         869
Ala Gly Tyr Glu Lys Val Glu Asp Ala Cys Gln Ala Cys Ser Pro Gly
265                 270                 275 ttt ttt aag ttt gag gca tct gag agc ccc tgc ttg gag tgc cct gag         917
Phe Phe Lys Phe Glu Ala Ser Glu Ser Pro Cys Leu Glu Cys Pro Glu
280                 285                 290                 295 cac acg ctg cca tcc cct gag ggt gcc acc tcc tgc gag tgt gag gaa         965
His Thr Leu Pro Ser Pro Glu Gly Ala Thr Ser Cys Glu Cys Glu Glu
                300                 305                 310 ggc ttc ttc cgg gca cct cag gac cca gcg tcg atg cct tgc aca cga        1013
Gly Phe Phe Arg Ala Pro Gln Asp Pro Ala Ser Met Pro Cys Thr Arg
            315                 320                 325 ccc cct tcc gcc cca cac tac ctc aca gcc gtg ggc atg ggt gcc aag        1061
Pro Pro Ser Ala Pro His Tyr Leu Thr Ala Val Gly Met Gly Ala Lys
            330                 335                 340 gtg gag ctg cgc tgg acg ccc cct cag gac agc ggg ggc cgc gag gac        1109
Val Glu Leu Arg Trp Thr Pro Pro Gln Asp Ser Gly Gly Arg Glu Asp
345                 350                 355 att gtc tac agc gtc acc tgc gaa cag tgc tgg ccc gag tct ggg gaa        1157
Ile Val Tyr Ser Val Thr Cys Glu Gln Cys Trp Pro Glu Ser Gly Glu
360                 365                 370                 375 tgc ggg ccg tgt gag gcc agt gtg cgc tac tcg gag cct cct cac gga        1205
Cys Gly Pro Cys Glu Ala Ser Val Arg Tyr Ser Glu Pro Pro His Gly
                380                 385                 390 ctg acc cgc acc agt gtg aca gtg agc gac ctg gag ccc cac atg aac        1253
Leu Thr Arg Thr Ser Val Thr Val Ser Asp Leu Glu Pro His Met Asn
            395                 400                 405 tac acc ttc acc gtg gag gcc cgc aat ggc gtc tca ggc ctg gta acc        1301
Tyr Thr Phe Thr Val Glu Ala Arg Asn Gly Val Ser Gly Leu Val Thr
                410                 415                 420 agc cgc agc ttc cgt act gcc agt gtc agc atc aac cag aca gag ccc        1349
Ser Arg Ser Phe Arg Thr Ala Ser Val Ser Ile Asn Gln Thr Glu Pro
425                 430                 435 ccc aag gtg agg ctg gag ggc cgc agc acc acc tcg ctt agc gtc tcc        1397
Pro Lys Val Arg Leu Glu Gly Arg Ser Thr Thr Ser Leu Ser Val Ser
440                 445                 450                 455
```

```
                                          -continued tgg agc atc ccc ccg ccg cag cag agc cga gtg tgg aag tac gag gtc    1445
Trp Ser Ile Pro Pro Pro Gln Gln Ser Arg Val Trp Lys Tyr Glu Val
                460                 465                 470 act tac cgc aag aag gga gac tcc aac agc tac aat gtg cgc cgc acc    1493
Thr Tyr Arg Lys Lys Gly Asp Ser Asn Ser Tyr Asn Val Arg Arg Thr
            475                 480                 485 gag ggt ttc tcc gtg acc ctg gac gac ctg gcc cca gac acc acc tac    1541
Glu Gly Phe Ser Val Thr Leu Asp Asp Leu Ala Pro Asp Thr Thr Tyr
        490                 495                 500 ctg gtc cag gtg cag gca ctg acg cag gag ggc cag ggg gcc ggc agc    1589
Leu Val Gln Val Gln Ala Leu Thr Gln Glu Gly Gln Gly Ala Gly Ser
    505                 510                 515 aag gtg cac gaa ttc cag acg ctg tcc ccg gag gga tct ggc aac ttg    1637
Lys Val His Glu Phe Gln Thr Leu Ser Pro Glu Gly Ser Gly Asn Leu
520                 525                 530                 535 gcg gtg att ggc ggc gtg gct gtc ggt gtc ctg ctt ctg gtg ctg          1685
Ala Val Ile Gly Gly Val Ala Val Gly Val Leu Leu Leu Val Leu
                540                 545                 550 gca gga gtt ggc ttc ttt atc cac cgc agg agg aag aac cag cgt gcc    1733
Ala Gly Val Gly Phe Phe Ile His Arg Arg Arg Lys Asn Gln Arg Ala
            555                 560                 565 cgc cag tcc ccg gag gac gtt tac ttc tcc aag tca gaa caa ctg aag    1781
Arg Gln Ser Pro Glu Asp Val Tyr Phe Ser Lys Ser Glu Gln Leu Lys
        570                 575                 580 ccc ctg aag aca tac gtg gac ccc cac aca tat gag gac ccc aac cag    1829
Pro Leu Lys Thr Tyr Val Asp Pro His Thr Tyr Glu Asp Pro Asn Gln
    585                 590                 595 gct gtg ttg aag ttc act acc gag atc cat cca tcc tgt gtc act cgg    1877
Ala Val Leu Lys Phe Thr Thr Glu Ile His Pro Ser Cys Val Thr Arg
600                 605                 610                 615 cag aag gtg atc gga gca gga gag ttt ggg gag gtg tac aag ggc atg    1925
Gln Lys Val Ile Gly Ala Gly Glu Phe Gly Glu Val Tyr Lys Gly Met
                620                 625                 630 ctg aag aca tcc tcg ggg aag aag gag gtg ccg gtg gcc atc aag acg    1973
Leu Lys Thr Ser Ser Gly Lys Lys Glu Val Pro Val Ala Ile Lys Thr
            635                 640                 645 ctg aaa gcc ggc tac aca gag aag cag cga gtg gac ttc ctc ggc gag    2021
Leu Lys Ala Gly Tyr Thr Glu Lys Gln Arg Val Asp Phe Leu Gly Glu
        650                 655                 660 gcc ggc atc atg ggc cag ttc agc cac cac aac atc atc cgc cta gag    2069
Ala Gly Ile Met Gly Gln Phe Ser His His Asn Ile Ile Arg Leu Glu
    665                 670                 675 ggc gtc atc tcc aaa tac aag ccc atg atg atc atc act gag tac atg    2117
Gly Val Ile Ser Lys Tyr Lys Pro Met Met Ile Ile Thr Glu Tyr Met
680                 685                 690                 695 gag aat ggg gcc ctg gac aag ttc ctt cgg gag aag gat ggc gag ttc    2165
Glu Asn Gly Ala Leu Asp Lys Phe Leu Arg Glu Lys Asp Gly Glu Phe
                700                 705                 710 agc gtg ctg cag ctg gtg ggc atg ctg cgg ggc atc gca gct ggc atg    2213
Ser Val Leu Gln Leu Val Gly Met Leu Arg Gly Ile Ala Ala Gly Met
            715                 720                 725 aag tac ctg gcc aac atg aac tat gtg cac cgt gac ctg gct gcc cgc    2261
Lys Tyr Leu Ala Asn Met Asn Tyr Val His Arg Asp Leu Ala Ala Arg
        730                 735                 740 aac atc ctc gtc aac agc aac ctg gtc tgc aag gtg tct gac ttt ggc    2309
Asn Ile Leu Val Asn Ser Asn Leu Val Cys Lys Val Ser Asp Phe Gly
    745                 750                 755 ctg tcc cgc gtg ctg gag gac gac ccc gag gcc acc tac acc acc agt    2357
Leu Ser Arg Val Leu Glu Asp Asp Pro Glu Ala Thr Tyr Thr Thr Ser
760                 765                 770                 775
```

| | | | | | | | | | | | | | | | | |
|---|---|---|---|---|---|---|---|---|---|---|---|---|---|---|---|---|
| ggc | ggc | aag | atc | ccc | atc | cgc | tgg | acc | gcc | ccg | gag | gcc | att | tcc | tac | 2405 |
| Gly | Gly | Lys | Ile | Pro | Ile | Arg | Trp | Thr | Ala | Pro | Glu | Ala | Ile | Ser | Tyr | |
| | | | 780 | | | | | 785 | | | | | 790 | | | |
| cgg | aag | ttc | acc | tct | gcc | agc | gac | gtg | tgg | agc | ttt | ggc | att | gtc | atg | 2453 |
| Arg | Lys | Phe | Thr | Ser | Ala | Ser | Asp | Val | Trp | Ser | Phe | Gly | Ile | Val | Met | |
| | | | 795 | | | | | 800 | | | | | 805 | | | |
| tgg | gag | gtg | atg | acc | tat | ggc | gag | cgg | ccc | tac | tgg | gag | ttg | tcc | aac | 2501 |
| Trp | Glu | Val | Met | Thr | Tyr | Gly | Glu | Arg | Pro | Tyr | Trp | Glu | Leu | Ser | Asn | |
| | | 810 | | | | | 815 | | | | | 820 | | | | |
| cac | gag | gtg | atg | aaa | gcc | atc | aat | gat | ggc | ttc | cgg | ctc | ccc | aca | ccc | 2549 |
| His | Glu | Val | Met | Lys | Ala | Ile | Asn | Asp | Gly | Phe | Arg | Leu | Pro | Thr | Pro | |
| | | 825 | | | | | 830 | | | | | 835 | | | | |
| atg | gac | tgc | ccc | tcc | gcc | atc | tac | cag | ctc | atg | atg | cag | tgc | tgg | cag | 2597 |
| Met | Asp | Cys | Pro | Ser | Ala | Ile | Tyr | Gln | Leu | Met | Met | Gln | Cys | Trp | Gln | |
| 840 | | | | 845 | | | | | 850 | | | | | 855 | | |
| cag | gag | cgt | gcc | cgc | cgc | ccc | aag | ttc | gct | gac | atc | gtc | agc | atc | ctg | 2645 |
| Gln | Glu | Arg | Ala | Arg | Arg | Pro | Lys | Phe | Ala | Asp | Ile | Val | Ser | Ile | Leu | |
| | | | 860 | | | | | 865 | | | | | 870 | | | |
| gac | aag | ctc | att | cgt | gcc | cct | gac | tcc | ctc | aag | acc | ctg | gct | gac | ttt | 2693 |
| Asp | Lys | Leu | Ile | Arg | Ala | Pro | Asp | Ser | Leu | Lys | Thr | Leu | Ala | Asp | Phe | |
| | | | 875 | | | | | 880 | | | | | 885 | | | |
| gac | ccc | cgc | gtg | tct | atc | cgg | ctc | ccc | agc | acg | agc | ggc | tcg | gag | ggg | 2741 |
| Asp | Pro | Arg | Val | Ser | Ile | Arg | Leu | Pro | Ser | Thr | Ser | Gly | Ser | Glu | Gly | |
| | | 890 | | | | | 895 | | | | | 900 | | | | |
| gtg | ccc | ttc | cgc | acg | gtg | tcc | gag | tgg | ctg | gag | tcc | atc | aag | atg | cag | 2789 |
| Val | Pro | Phe | Arg | Thr | Val | Ser | Glu | Trp | Leu | Glu | Ser | Ile | Lys | Met | Gln | |
| | | 905 | | | | | 910 | | | | | 915 | | | | |
| cag | tat | acg | gag | cac | ttc | atg | gcg | gcc | ggc | tac | act | gcc | atc | gag | aag | 2837 |
| Gln | Tyr | Thr | Glu | His | Phe | Met | Ala | Ala | Gly | Tyr | Thr | Ala | Ile | Glu | Lys | |
| 920 | | | | 925 | | | | | 930 | | | | | 935 | | |
| gtg | gtg | cag | atg | acc | aac | gac | gac | atc | aag | agg | att | ggg | gtg | cgg | ctg | 2885 |
| Val | Val | Gln | Met | Thr | Asn | Asp | Asp | Ile | Lys | Arg | Ile | Gly | Val | Arg | Leu | |
| | | | 940 | | | | | 945 | | | | | 950 | | | |
| ccc | ggc | cac | cag | aag | cgc | atc | gcc | tac | agc | ctg | ctg | gga | ctc | aag | gac | 2933 |
| Pro | Gly | His | Gln | Lys | Arg | Ile | Ala | Tyr | Ser | Leu | Leu | Gly | Leu | Lys | Asp | |
| | | | 955 | | | | | 960 | | | | | 965 | | | |
| cag | gtg | aac | act | gtg | ggg | atc | ccc | atc | g | | | | | | | 2961 |
| Gln | Val | Asn | Thr | Val | Gly | Ile | Pro | Ile | | | | | | | | |
| | | | 970 | | | | | 975 | | | | | | | | |

<210> SEQ ID NO 8
<211> LENGTH: 976
<212> TYPE: PRT
<213> ORGANISM: Artificial Sequence
<220> FEATURE:
<223> OTHER INFORMATION: Synthetic Construct

<400> SEQUENCE: 8

Met Glu Leu Gln Ala Ala Arg Ala Cys Phe Ala Leu Leu Trp Gly Cys
1               5                   10                  15

Ala Leu Ala Ala Ala Ala Ala Gln Gly Lys Glu Val Val Leu Leu
            20                  25                  30

Asp Phe Ala Ala Ala Gly Gly Glu Leu Gly Trp Leu Thr His Pro Tyr
        35                  40                  45

Gly Lys Gly Trp Asp Leu Met Gln Asn Ile Met Asn Asp Met Pro Ile
    50                  55                  60

Tyr Met Tyr Ser Val Cys Asn Val Met Ser Gly Asp Gln Asp Asn Trp
65                  70                  75                  80

Leu Arg Thr Asn Trp Val Tyr Arg Gly Glu Ala Glu Arg Ile Phe Ile

-continued

```
                    85                  90                  95
Glu Leu Lys Phe Thr Val Arg Asp Cys Asn Ser Phe Pro Gly Gly Ala
                100                 105                 110

Ser Ser Cys Lys Glu Thr Phe Asn Leu Tyr Tyr Ala Glu Ser Asp Leu
            115                 120                 125

Asp Tyr Gly Thr Asn Phe Gln Lys Arg Leu Phe Thr Lys Ile Asp Thr
        130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                165                 170                 175

Gly Phe Tyr Leu Ala Phe Gln Asp Ile Gly Ala Cys Val Ala Leu Leu
            180                 185                 190

Ser Val Arg Val Tyr Tyr Lys Lys Cys Pro Glu Leu Leu Gln Gly Leu
        195                 200                 205

Ala His Phe Pro Glu Thr Ile Ala Gly Ser Asp Ala Pro Ser Leu Ala
    210                 215                 220

Thr Val Ala Gly Thr Cys Val Asp His Ala Val Val Pro Pro Gly Gly
225                 230                 235                 240

Glu Glu Pro Arg Met His Cys Ala Val Asp Gly Glu Trp Leu Val Pro
                245                 250                 255

Ile Gly Gln Cys Leu Cys Gln Ala Gly Tyr Glu Lys Val Glu Asp Ala
            260                 265                 270

Cys Gln Ala Cys Ser Pro Gly Phe Phe Lys Phe Glu Ala Ser Glu Ser
        275                 280                 285

Pro Cys Leu Glu Cys Pro Glu His Thr Leu Pro Ser Pro Glu Gly Ala
    290                 295                 300

Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
                325                 330                 335

Ala Val Gly Met Gly Ala Lys Val Glu Leu Arg Trp Thr Pro Pro Gln
            340                 345                 350

Asp Ser Gly Gly Arg Glu Asp Ile Val Tyr Ser Val Thr Cys Glu Gln
        355                 360                 365

Cys Trp Pro Glu Ser Gly Glu Cys Gly Pro Cys Glu Ala Ser Val Arg
    370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                405                 410                 415

Gly Val Ser Gly Leu Val Thr Ser Arg Ser Phe Arg Thr Ala Ser Val
            420                 425                 430

Ser Ile Asn Gln Thr Glu Pro Pro Lys Val Arg Leu Glu Gly Arg Ser
        435                 440                 445

Thr Thr Ser Leu Ser Val Ser Trp Ser Ile Pro Pro Pro Gln Gln Ser
    450                 455                 460

Arg Val Trp Lys Tyr Glu Val Thr Tyr Arg Lys Lys Gly Asp Ser Asn
465                 470                 475                 480

Ser Tyr Asn Val Arg Arg Thr Glu Gly Phe Ser Val Thr Leu Asp Asp
                485                 490                 495

Leu Ala Pro Asp Thr Thr Tyr Leu Val Gln Val Gln Ala Leu Thr Gln
            500                 505                 510
```

```
Glu Gly Gln Gly Ala Gly Ser Lys Val His Glu Phe Gln Thr Leu Ser
            515                 520                 525

Pro Glu Gly Ser Gly Asn Leu Ala Val Ile Gly Val Ala Val Gly
        530                 535                 540

Val Val Leu Leu Leu Val Leu Ala Gly Val Gly Phe Phe Ile His Arg
545                 550                 555                 560

Arg Arg Lys Asn Gln Arg Ala Arg Gln Ser Pro Glu Asp Val Tyr Phe
                565                 570                 575

Ser Lys Ser Glu Gln Leu Lys Pro Leu Lys Thr Tyr Val Asp Pro His
            580                 585                 590

Thr Tyr Glu Asp Pro Asn Gln Ala Val Leu Lys Phe Thr Thr Glu Ile
        595                 600                 605

His Pro Ser Cys Val Thr Arg Gln Lys Val Ile Gly Ala Gly Glu Phe
    610                 615                 620

Gly Glu Val Tyr Lys Gly Met Leu Lys Thr Ser Ser Gly Lys Lys Glu
625                 630                 635                 640

Val Pro Val Ala Ile Lys Thr Leu Lys Ala Gly Tyr Thr Glu Lys Gln
                645                 650                 655

Arg Val Asp Phe Leu Gly Glu Ala Gly Ile Met Gly Gln Phe Ser His
            660                 665                 670

His Asn Ile Ile Arg Leu Glu Gly Val Ile Ser Lys Tyr Lys Pro Met
        675                 680                 685

Met Ile Ile Thr Glu Tyr Met Glu Asn Gly Ala Leu Asp Lys Phe Leu
    690                 695                 700

Arg Glu Lys Asp Gly Glu Phe Ser Val Leu Gln Leu Val Gly Met Leu
705                 710                 715                 720

Arg Gly Ile Ala Ala Gly Met Lys Tyr Leu Ala Asn Met Asn Tyr Val
                725                 730                 735

His Arg Asp Leu Ala Ala Arg Asn Ile Leu Val Asn Ser Asn Leu Val
            740                 745                 750

Cys Lys Val Ser Asp Phe Gly Leu Ser Arg Val Leu Glu Asp Asp Pro
        755                 760                 765

Glu Ala Thr Tyr Thr Thr Ser Gly Gly Lys Ile Pro Ile Arg Trp Thr
    770                 775                 780

Ala Pro Glu Ala Ile Ser Tyr Arg Lys Phe Thr Ser Ala Ser Asp Val
785                 790                 795                 800

Trp Ser Phe Gly Ile Val Met Trp Glu Val Met Thr Tyr Gly Glu Arg
                805                 810                 815

Pro Tyr Trp Glu Leu Ser Asn His Glu Val Met Lys Ala Ile Asn Asp
            820                 825                 830

Gly Phe Arg Leu Pro Thr Pro Met Asp Cys Pro Ser Ala Ile Tyr Gln
        835                 840                 845

Leu Met Met Gln Cys Trp Gln Gln Glu Arg Ala Arg Arg Pro Lys Phe
    850                 855                 860

Ala Asp Ile Val Ser Ile Leu Asp Lys Leu Ile Arg Ala Pro Asp Ser
865                 870                 875                 880

Leu Lys Thr Leu Ala Asp Phe Asp Pro Arg Val Ser Ile Arg Leu Pro
                885                 890                 895

Ser Thr Ser Gly Ser Glu Gly Val Pro Phe Arg Thr Val Ser Glu Trp
            900                 905                 910

Leu Glu Ser Ile Lys Met Gln Gln Tyr Thr Glu His Phe Met Ala Ala
        915                 920                 925
```

Gly Tyr Thr Ala Ile Glu Lys Val Val Gln Met Thr Asn Asp Asp Ile
            930                 935                 940

Lys Arg Ile Gly Val Arg Leu Pro Gly His Gln Lys Arg Ile Ala Tyr
945                 950                 955                 960

Ser Leu Leu Gly Leu Lys Asp Gln Val Asn Thr Val Gly Ile Pro Ile
                965                 970                 975

<210> SEQ ID NO 9
<211> LENGTH: 30
<212> TYPE: DNA
<213> ORGANISM: Artificial Sequence
<220> FEATURE:
<223> OTHER INFORMATION: PCR primer 5

<400> SEQUENCE: 9
aaaaagctta tggagctcca ggcagcccgc                                    30

<210> SEQ ID NO 10
<211> LENGTH: 30
<212> TYPE: DNA
<213> ORGANISM: Artificial Sequence
<220> FEATURE:
<223> OTHER INFORMATION: PCR primer 6

<400> SEQUENCE: 10
aaagggccct cagttgccag atccctccgg                                    30

<210> SEQ ID NO 11
<211> LENGTH: 43
<212> TYPE: DNA
<213> ORGANISM: Artificial Sequence
<220> FEATURE:
<223> OTHER INFORMATION: PCR primer 7

<400> SEQUENCE: 11
gcaggcttca tcgaaggtcg tgggcgggca cctcaggacc cag                     43

<210> SEQ ID NO 12
<211> LENGTH: 40
<212> TYPE: DNA
<213> ORGANISM: Artificial Sequence
<220> FEATURE:
<223> OTHER INFORMATION: PCR primer 8

<400> SEQUENCE: 12
gtacaagaaa gctgggtgct agccgccaat caccgccaag                         40

<210> SEQ ID NO 13
<211> LENGTH: 40
<212> TYPE: DNA
<213> ORGANISM: Artificial Sequence
<220> FEATURE:
<223> OTHER INFORMATION: PCR primer 9

<400> SEQUENCE: 13
gtacaagaaa gctgggtgct aggcagtacg gaagctgcgg                         40

<210> SEQ ID NO 14
<211> LENGTH: 43
<212> TYPE: DNA
<213> ORGANISM: Artificial Sequence
<220> FEATURE:
<223> OTHER INFORMATION: PCR primer 10

<400> SEQUENCE: 14
gcaggcttca tcgaaggtcg tgggagcttc cgtactgcca gtg    43

<210> SEQ ID NO 15
<211> LENGTH: 46
<212> TYPE: DNA
<213> ORGANISM: Artificial Sequence
<220> FEATURE:
<223> OTHER INFORMATION: PCR primer 11

<400> SEQUENCE: 15
ggggacaagt ttgtacaaaa aagcaggctt catcgaaggt cgtggg    46

<210> SEQ ID NO 16
<211> LENGTH: 29
<212> TYPE: DNA
<213> ORGANISM: Artificial Sequence
<220> FEATURE:
<223> OTHER INFORMATION: PCR primer 12

<400> SEQUENCE: 16
ggggaccact ttgtacaaga aagctgggt    29

<210> SEQ ID NO 17
<211> LENGTH: 49
<212> TYPE: DNA
<213> ORGANISM: Artificial Sequence
<220> FEATURE:
<223> OTHER INFORMATION: PCR primer 13

<400> SEQUENCE: 17
ggggacaagt ttgtacaaaa aagcaggctt cgccccggga agcgcagcc    49

<210> SEQ ID NO 18
<211> LENGTH: 63
<212> TYPE: DNA
<213> ORGANISM: Artificial Sequence
<220> FEATURE:
<223> OTHER INFORMATION: PCR primer 14

<400> SEQUENCE: 18
ggggaccact ttgtacaaga aagctgggtc ctaaacctcc acagactgaa tctggttcat    60
ctg    63

<210> SEQ ID NO 19
<211> LENGTH: 2961
<212> TYPE: DNA
<213> ORGANISM: Homo sapiens
<220> FEATURE:
<221> NAME/KEY: CDS
<222> LOCATION: (1)..(2961)

<400> SEQUENCE: 19 atg gct ctg cgg agg ctg ggg gcc gcg ctg ctg ctg ccg ctg ctc    48
Met Ala Leu Arg Arg Leu Gly Ala Ala Leu Leu Leu Pro Leu Leu
1               5                   10                  15 gcc gcc gtg gaa gaa acg cta atg gac tcc act aca gcg act gct gag    96
Ala Ala Val Glu Glu Thr Leu Met Asp Ser Thr Thr Ala Thr Ala Glu
                20                  25                  30 ctg ggc tgg atg gtg cat cct cca tca ggg tgg gaa gag gtg agt ggc    144
Leu Gly Trp Met Val His Pro Pro Ser Gly Trp Glu Glu Val Ser Gly
            35                  40                  45 tac gat gag aac atg aac acg atc cgc acg tac cag gtg tgc aac gtg    192
Tyr Asp Glu Asn Met Asn Thr Ile Arg Thr Tyr Gln Val Cys Asn Val
        50                  55                  60

-continued

| | | |
|---|---|---|
| ttt gag tca agc cag aac aac tgg cta cgg acc aag ttt atc cgg cgc<br>Phe Glu Ser Ser Gln Asn Asn Trp Leu Arg Thr Lys Phe Ile Arg Arg<br>65                              70                        75                        80 | | 240 |
| cgt ggc gcc cac cgc atc cac gtg gag atg aag ttt tcg gtg cgt gac<br>Arg Gly Ala His Arg Ile His Val Glu Met Lys Phe Ser Val Arg Asp<br>                       85                        90                        95 | | 288 |
| tgc agc agc atc ccc agc gtg cct ggc tcc tgc aag gag acc ttc aac<br>Cys Ser Ser Ile Pro Ser Val Pro Gly Ser Cys Lys Glu Thr Phe Asn<br>                      100                     105                     110 | | 336 |
| ctc tat tac tat gag gct gac ttt gac tcg gcc acc aag acc ttc ccc<br>Leu Tyr Tyr Tyr Glu Ala Asp Phe Asp Ser Ala Thr Lys Thr Phe Pro<br>         115                     120                     125 | | 384 |
| aac tgg atg gag aat cca tgg gtg aag gtg gat acc att gca gcc gac<br>Asn Trp Met Glu Asn Pro Trp Val Lys Val Asp Thr Ile Ala Ala Asp<br>     130                     135                     140 | | 432 |
| gag agc ttc tcc cag gtg gac ctg ggt ggc cgc gtc atg aaa atc aac<br>Glu Ser Phe Ser Gln Val Asp Leu Gly Gly Arg Val Met Lys Ile Asn<br>145                            150                     155                     160 | | 480 |
| acc gag gtg cgg agc ttc gga cct gtg tcc cgc agc ggc ttc tac ctg<br>Thr Glu Val Arg Ser Phe Gly Pro Val Ser Arg Ser Gly Phe Tyr Leu<br>                      165                     170                     175 | | 528 |
| gcc ttc cag gac tat ggc ggc tgc atg tcc ctc atc gcc gtg cgt gtc<br>Ala Phe Gln Asp Tyr Gly Gly Cys Met Ser Leu Ile Ala Val Arg Val<br>              180                     185                     190 | | 576 |
| ttc tac cgc aag tgc ccc cgc atc atc cag aat ggc gcc atc ttc cag<br>Phe Tyr Arg Lys Cys Pro Arg Ile Ile Gln Asn Gly Ala Ile Phe Gln<br>         195                     200                     205 | | 624 |
| gaa acc ctg tcg ggg gct gag agc aca tcg ctg gtg gct gcc cgg ggc<br>Glu Thr Leu Ser Gly Ala Glu Ser Thr Ser Leu Val Ala Ala Arg Gly<br>     210                     215                     220 | | 672 |
| agc tgc atc gcc aat gcg gaa gag gtg gat gta ccc atc aag ctc tac<br>Ser Cys Ile Ala Asn Ala Glu Glu Val Asp Val Pro Ile Lys Leu Tyr<br>225                            230                     235                     240 | | 720 |
| tgt aac ggg gac ggc gag tgg ctg gtg ccc atc ggg cgc tgc atg tgc<br>Cys Asn Gly Asp Gly Glu Trp Leu Val Pro Ile Gly Arg Cys Met Cys<br>                      245                     250                     255 | | 768 |
| aaa gca ggc ttc gag gcc gtt gag aat ggc acc gtc tgc cga ggt tgt<br>Lys Ala Gly Phe Glu Ala Val Glu Asn Gly Thr Val Cys Arg Gly Cys<br>         260                     265                     270 | | 816 |
| cca tct ggg act ttc aag gcc aac caa ggg gat gag gcc tgt acc cac<br>Pro Ser Gly Thr Phe Lys Ala Asn Gln Gly Asp Glu Ala Cys Thr His<br>              275                     280                     285 | | 864 |
| tgt ccc atc aac agc cgg acc act tct gaa ggg gcc acc aac tgt gtc<br>Cys Pro Ile Asn Ser Arg Thr Thr Ser Glu Gly Ala Thr Asn Cys Val<br>         290                     295                     300 | | 912 |
| tgc cgc aat ggc tac tac aga gca gac ctg gac ccc ctg gac atg ccc<br>Cys Arg Asn Gly Tyr Tyr Arg Ala Asp Leu Asp Pro Leu Asp Met Pro<br>305                            310                     315                     320 | | 960 |
| tgc aca acc atc ccc tcc gcg ccc cag gct gtg att tcc agt gtc aat<br>Cys Thr Thr Ile Pro Ser Ala Pro Gln Ala Val Ile Ser Ser Val Asn<br>                         325                     330                     335 | | 1008 |
| gag acc tcc ctc atg ctg gag tgg acc cct ccc cgc gac tcc gga ggc<br>Glu Thr Ser Leu Met Leu Glu Trp Thr Pro Pro Arg Asp Ser Gly Gly<br>              340                     345                     350 | | 1056 |
| cga gag gac ctc gtc tac aac atc atc tgc aag agc tgt ggc tcg ggc<br>Arg Glu Asp Leu Val Tyr Asn Ile Ile Cys Lys Ser Cys Gly Ser Gly<br>         355                     360                     365 | | 1104 |
| cgg ggt gcc tgc acc cgc tgc ggg gac aat gta cag tac gca cca cgc<br>Arg Gly Ala Cys Thr Arg Cys Gly Asp Asn Val Gln Tyr Ala Pro Arg<br>     370                     375                     380 | | 1152 |

```
cag cta ggc ctg acc gag cca cgc att tac atc agt gac ctg ctg gcc    1200
Gln Leu Gly Leu Thr Glu Pro Arg Ile Tyr Ile Ser Asp Leu Leu Ala
385                 390                 395                 400 cac acc cag tac acc ttc gag atc cag gct gtg aac ggc gtt act gac    1248
His Thr Gln Tyr Thr Phe Glu Ile Gln Ala Val Asn Gly Val Thr Asp
            405                 410                 415 cag agc ccc ttc tcg cct cag ttc gcc tct gtg aac atc acc acc aac    1296
Gln Ser Pro Phe Ser Pro Gln Phe Ala Ser Val Asn Ile Thr Thr Asn
        420                 425                 430 cag gca gct cca tcg gca gtg tcc atc atg cat cag gtg agc cgc acc    1344
Gln Ala Ala Pro Ser Ala Val Ser Ile Met His Gln Val Ser Arg Thr
    435                 440                 445 gtg gac agc att acc ctg tcg tgg tcc cag ccg gac cag ccc aat ggc    1392
Val Asp Ser Ile Thr Leu Ser Trp Ser Gln Pro Asp Gln Pro Asn Gly
450                 455                 460 gtg atc ctg gac tat gag ctg cag tac tat gag aag gag ctc agt gag    1440
Val Ile Leu Asp Tyr Glu Leu Gln Tyr Tyr Glu Lys Glu Leu Ser Glu
465                 470                 475                 480 tac aac gcc aca gcc ata aaa agc ccc acc aac acg gtc acc gtg cag    1488
Tyr Asn Ala Thr Ala Ile Lys Ser Pro Thr Asn Thr Val Thr Val Gln
            485                 490                 495 ggc ctc aaa gcc ggc gcc atc tat gtc ttc cag gtg cgg gca cgc acc    1536
Gly Leu Lys Ala Gly Ala Ile Tyr Val Phe Gln Val Arg Ala Arg Thr
        500                 505                 510 gtg gca ggc tac ggg cgc tac agc ggc aag atg tac ttc cag acc atg    1584
Val Ala Gly Tyr Gly Arg Tyr Ser Gly Lys Met Tyr Phe Gln Thr Met
    515                 520                 525 aca gaa gcc gag tac cag aca agc atc cag gag aag ttg cca ctc atc    1632
Thr Glu Ala Glu Tyr Gln Thr Ser Ile Gln Glu Lys Leu Pro Leu Ile
530                 535                 540 atc ggc tcc tcg gcc gct ggc ctg gtc ttc ctc att gct gtg gtt gtc    1680
Ile Gly Ser Ser Ala Ala Gly Leu Val Phe Leu Ile Ala Val Val Val
545                 550                 555                 560 atc gcc atc gtg tgt aac aga cgg ggg ttt gag cgt gct gac tcg gag    1728
Ile Ala Ile Val Cys Asn Arg Arg Gly Phe Glu Arg Ala Asp Ser Glu
            565                 570                 575 tac acg gac aag ctg caa cac tac acc agt ggc cac atg acc cca ggc    1776
Tyr Thr Asp Lys Leu Gln His Tyr Thr Ser Gly His Met Thr Pro Gly
        580                 585                 590 atg aag atc tac atc gat cct ttc acc tac gag gac ccc aac gag gca    1824
Met Lys Ile Tyr Ile Asp Pro Phe Thr Tyr Glu Asp Pro Asn Glu Ala
    595                 600                 605 gtg cgg gag ttt gcc aag gaa att gac atc tcc tgt gtc aaa att gag    1872
Val Arg Glu Phe Ala Lys Glu Ile Asp Ile Ser Cys Val Lys Ile Glu
610                 615                 620 cag gtg atc gga gca ggg gag ttt ggc gag gtc tgc agt ggc cac ctg    1920
Gln Val Ile Gly Ala Gly Glu Phe Gly Glu Val Cys Ser Gly His Leu
625                 630                 635                 640 aag ctg cca ggc aag aga gag atc ttt gtg gcc atc aag acg ctc aag    1968
Lys Leu Pro Gly Lys Arg Glu Ile Phe Val Ala Ile Lys Thr Leu Lys
            645                 650                 655 tcg ggc tac acg gag aag cag cgc cgg gac ttc ctg agc gaa gcc tcc    2016
Ser Gly Tyr Thr Glu Lys Gln Arg Arg Asp Phe Leu Ser Glu Ala Ser
        660                 665                 670 atc atg ggc cag ttc gac cat ccc aac gtc atc cac ctg gag ggt gtc    2064
Ile Met Gly Gln Phe Asp His Pro Asn Val Ile His Leu Glu Gly Val
    675                 680                 685 gtg acc aag agc aca cct gtg atg atc atc acc gag ttc atg gag aat    2112
Val Thr Lys Ser Thr Pro Val Met Ile Ile Thr Glu Phe Met Glu Asn
```

```
                690             695             700
ggc tcc ctg gac tcc ttt ctc cgg caa aac gat ggg cag ttc aca gtc      2160
Gly Ser Leu Asp Ser Phe Leu Arg Gln Asn Asp Gly Gln Phe Thr Val
705             710             715             720 atc cag ctg gtg ggc atg ctt cgg ggc atc gca gct ggc atg aag tac      2208
Ile Gln Leu Val Gly Met Leu Arg Gly Ile Ala Ala Gly Met Lys Tyr
            725             730             735 ctg gca gac atg aac tat gtt cac cgt gac ctg gct gcc cgc aac atc      2256
Leu Ala Asp Met Asn Tyr Val His Arg Asp Leu Ala Ala Arg Asn Ile
        740             745             750 ctc gtc aac agc aac ctg gtc tgc aag gtg tcg gac ttt ggg ctc tca      2304
Leu Val Asn Ser Asn Leu Val Cys Lys Val Ser Asp Phe Gly Leu Ser
    755             760             765 cgc ttt cta gag gac gat acc tca gac ccc acc tac acc agt gcc ctg      2352
Arg Phe Leu Glu Asp Asp Thr Ser Asp Pro Thr Tyr Thr Ser Ala Leu
770             775             780 ggc gga aag atc ccc atc cgc tgg aca gcc ccg gaa gcc atc cag tac      2400
Gly Gly Lys Ile Pro Ile Arg Trp Thr Ala Pro Glu Ala Ile Gln Tyr
785             790             795             800 cgg aag ttc acc tcg gcc agt gat gtg tgg agc tac ggc att gtc atg      2448
Arg Lys Phe Thr Ser Ala Ser Asp Val Trp Ser Tyr Gly Ile Val Met
            805             810             815 tgg gag gtg atg tcc tat ggg gag cgg ccc tac tgg gac atg acc aac      2496
Trp Glu Val Met Ser Tyr Gly Glu Arg Pro Tyr Trp Asp Met Thr Asn
        820             825             830 cag gat gta atc aat gcc att gag cag gac tat cgg ctg cca ccg ccc      2544
Gln Asp Val Ile Asn Ala Ile Glu Gln Asp Tyr Arg Leu Pro Pro Pro
    835             840             845 atg gac tgc ccg agc gcc ctg cac caa ctc atg ctg gac tgt tgg cag      2592
Met Asp Cys Pro Ser Ala Leu His Gln Leu Met Leu Asp Cys Trp Gln
850             855             860 aag gac cgc aac cac cgg ccc aag ttc ggc caa att gtc aac acg cta      2640
Lys Asp Arg Asn His Arg Pro Lys Phe Gly Gln Ile Val Asn Thr Leu
865             870             875             880 gac aag atg atc cgc aat ccc aac agc ctc aaa gcc atg gcg ccc ctc      2688
Asp Lys Met Ile Arg Asn Pro Asn Ser Leu Lys Ala Met Ala Pro Leu
            885             890             895 tcc tct ggc atc aac ctg ccg ctg ctg gac cgc acg atc ccc gac tac      2736
Ser Ser Gly Ile Asn Leu Pro Leu Leu Asp Arg Thr Ile Pro Asp Tyr
        900             905             910 acc agc ttt aac acg gtg gac gag tgg ctg gag gcc atc aag atg ggg      2784
Thr Ser Phe Asn Thr Val Asp Glu Trp Leu Glu Ala Ile Lys Met Gly
    915             920             925 cag tac aag gag agc ttc gcc aat gcc ggc ttc acc tcc ttt gac gtc      2832
Gln Tyr Lys Glu Ser Phe Ala Asn Ala Gly Phe Thr Ser Phe Asp Val
930             935             940 gtg tct cag atg atg atg gag gac att ctc cgg gtt ggg gtc act ttg      2880
Val Ser Gln Met Met Met Glu Asp Ile Leu Arg Val Gly Val Thr Leu
945             950             955             960 gct ggc cac cag aaa aaa atc ctg aac agt atc cag gtg atg cgg gcg      2928
Ala Gly His Gln Lys Lys Ile Leu Asn Ser Ile Gln Val Met Arg Ala
            965             970             975 cag atg aac cag att cag tct gtg gag gtt tag                          2961
Gln Met Asn Gln Ile Gln Ser Val Glu Val
        980             985

<210> SEQ ID NO 20
<211> LENGTH: 986
<212> TYPE: PRT
<213> ORGANISM: Homo sapiens
```

<400> SEQUENCE: 20

```
Met Ala Leu Arg Arg Leu Gly Ala Ala Leu Leu Leu Pro Leu Leu
1               5                   10                  15

Ala Ala Val Glu Glu Thr Leu Met Asp Ser Thr Ala Thr Ala Glu
            20                  25                  30

Leu Gly Trp Met Val His Pro Pro Ser Gly Trp Glu Val Ser Gly
                35                  40                  45

Tyr Asp Glu Asn Met Asn Thr Ile Arg Thr Tyr Gln Val Cys Asn Val
    50                  55                  60

Phe Glu Ser Ser Gln Asn Asn Trp Leu Arg Thr Lys Phe Ile Arg Arg
65                  70                  75                  80

Arg Gly Ala His Arg Ile His Val Glu Met Lys Phe Ser Val Arg Asp
                85                  90                  95

Cys Ser Ser Ile Pro Ser Val Pro Gly Ser Cys Lys Glu Thr Phe Asn
                100                 105                 110

Leu Tyr Tyr Tyr Glu Ala Asp Phe Asp Ser Ala Thr Lys Thr Phe Pro
            115                 120                 125

Asn Trp Met Glu Asn Pro Trp Val Lys Val Asp Thr Ile Ala Ala Asp
130                 135                 140

Glu Ser Phe Ser Gln Val Asp Leu Gly Gly Arg Val Met Lys Ile Asn
145                 150                 155                 160

Thr Glu Val Arg Ser Phe Gly Pro Val Ser Arg Ser Gly Phe Tyr Leu
                165                 170                 175

Ala Phe Gln Asp Tyr Gly Gly Cys Met Ser Leu Ile Ala Val Arg Val
            180                 185                 190

Phe Tyr Arg Lys Cys Pro Arg Ile Ile Gln Asn Gly Ala Ile Phe Gln
        195                 200                 205

Glu Thr Leu Ser Gly Ala Glu Ser Thr Ser Leu Val Ala Ala Arg Gly
210                 215                 220

Ser Cys Ile Ala Asn Ala Glu Glu Val Asp Val Pro Ile Lys Leu Tyr
225                 230                 235                 240

Cys Asn Gly Asp Gly Glu Trp Leu Val Pro Ile Gly Arg Cys Met Cys
                245                 250                 255

Lys Ala Gly Phe Glu Ala Val Glu Asn Gly Thr Val Cys Arg Gly Cys
            260                 265                 270

Pro Ser Gly Thr Phe Lys Ala Asn Gln Gly Asp Glu Ala Cys Thr His
        275                 280                 285

Cys Pro Ile Asn Ser Arg Thr Thr Ser Glu Gly Ala Thr Asn Cys Val
    290                 295                 300

Cys Arg Asn Gly Tyr Tyr Arg Ala Asp Leu Asp Pro Leu Asp Met Pro
305                 310                 315                 320

Cys Thr Thr Ile Pro Ser Ala Pro Gln Ala Val Ile Ser Ser Val Asn
                325                 330                 335

Glu Thr Ser Leu Met Leu Glu Trp Thr Pro Pro Arg Asp Ser Gly Gly
            340                 345                 350

Arg Glu Asp Leu Val Tyr Asn Ile Ile Cys Lys Ser Cys Gly Ser Gly
        355                 360                 365

Arg Gly Ala Cys Thr Arg Cys Gly Asp Asn Val Gln Tyr Ala Pro Arg
    370                 375                 380

Gln Leu Gly Leu Thr Glu Pro Arg Ile Tyr Ile Ser Asp Leu Leu Ala
385                 390                 395                 400

His Thr Gln Tyr Thr Phe Glu Ile Gln Ala Val Asn Gly Val Thr Asp
```

```
            405                 410                 415
Gln Ser Pro Phe Ser Pro Gln Phe Ala Ser Val Asn Ile Thr Thr Asn
                420                 425                 430
Gln Ala Ala Pro Ser Ala Val Ser Ile Met His Gln Val Ser Arg Thr
            435                 440                 445
Val Asp Ser Ile Thr Leu Ser Trp Ser Gln Pro Asp Gln Pro Asn Gly
        450                 455                 460
Val Ile Leu Asp Tyr Glu Leu Gln Tyr Glu Lys Glu Leu Ser Glu
465                 470                 475                 480
Tyr Asn Ala Thr Ala Ile Lys Ser Pro Thr Asn Thr Val Thr Val Gln
                485                 490                 495
Gly Leu Lys Ala Gly Ala Ile Tyr Val Phe Gln Val Arg Ala Arg Thr
            500                 505                 510
Val Ala Gly Tyr Gly Arg Tyr Ser Gly Lys Met Tyr Phe Gln Thr Met
        515                 520                 525
Thr Glu Ala Glu Tyr Gln Thr Ser Ile Gln Glu Lys Leu Pro Leu Ile
    530                 535                 540
Ile Gly Ser Ser Ala Ala Gly Leu Val Phe Leu Ile Ala Val Val Val
545                 550                 555                 560
Ile Ala Ile Val Cys Asn Arg Arg Gly Phe Glu Arg Ala Asp Ser Glu
                565                 570                 575
Tyr Thr Asp Lys Leu Gln His Tyr Thr Ser Gly His Met Thr Pro Gly
            580                 585                 590
Met Lys Ile Tyr Ile Asp Pro Phe Thr Tyr Glu Asp Pro Asn Glu Ala
        595                 600                 605
Val Arg Glu Phe Ala Lys Glu Ile Asp Ile Ser Cys Val Lys Ile Glu
    610                 615                 620
Gln Val Ile Gly Ala Gly Glu Phe Gly Glu Val Cys Ser Gly His Leu
625                 630                 635                 640
Lys Leu Pro Gly Lys Arg Glu Ile Phe Val Ala Ile Lys Thr Leu Lys
                645                 650                 655
Ser Gly Tyr Thr Glu Lys Gln Arg Arg Asp Phe Leu Ser Glu Ala Ser
            660                 665                 670
Ile Met Gly Gln Phe Asp His Pro Asn Val Ile His Leu Glu Gly Val
        675                 680                 685
Val Thr Lys Ser Thr Pro Val Met Ile Ile Thr Glu Phe Met Glu Asn
    690                 695                 700
Gly Ser Leu Asp Ser Phe Leu Arg Gln Asn Asp Gly Gln Phe Thr Val
705                 710                 715                 720
Ile Gln Leu Val Gly Met Leu Arg Gly Ile Ala Ala Gly Met Lys Tyr
                725                 730                 735
Leu Ala Asp Met Asn Tyr Val His Arg Asp Leu Ala Ala Arg Asn Ile
            740                 745                 750
Leu Val Asn Ser Asn Leu Val Cys Lys Val Ser Asp Phe Gly Leu Ser
        755                 760                 765
Arg Phe Leu Glu Asp Asp Thr Ser Asp Pro Thr Tyr Thr Ser Ala Leu
    770                 775                 780
Gly Gly Lys Ile Pro Ile Arg Trp Thr Ala Pro Glu Ala Ile Gln Tyr
785                 790                 795                 800
Arg Lys Phe Thr Ser Ala Ser Asp Val Trp Ser Tyr Gly Ile Val Met
                805                 810                 815
Trp Glu Val Met Ser Tyr Gly Glu Arg Pro Tyr Trp Asp Met Thr Asn
            820                 825                 830
```

```
Gln Asp Val Ile Asn Ala Ile Glu Gln Asp Tyr Arg Leu Pro Pro Pro
            835                 840                 845

Met Asp Cys Pro Ser Ala Leu His Gln Leu Met Leu Asp Cys Trp Gln
    850                 855                 860

Lys Asp Arg Asn His Arg Pro Lys Phe Gly Gln Ile Val Asn Thr Leu
865                 870                 875                 880

Asp Lys Met Ile Arg Asn Pro Asn Ser Leu Lys Ala Met Ala Pro Leu
                885                 890                 895

Ser Ser Gly Ile Asn Leu Pro Leu Leu Asp Arg Thr Ile Pro Asp Tyr
            900                 905                 910

Thr Ser Phe Asn Thr Val Asp Glu Trp Leu Glu Ala Ile Lys Met Gly
            915                 920                 925

Gln Tyr Lys Glu Ser Phe Ala Asn Ala Gly Phe Thr Ser Phe Asp Val
            930                 935                 940

Val Ser Gln Met Met Met Glu Asp Ile Leu Arg Val Gly Val Thr Leu
945                 950                 955                 960

Ala Gly His Gln Lys Lys Ile Leu Asn Ser Ile Gln Val Met Arg Ala
                965                 970                 975

Gln Met Asn Gln Ile Gln Ser Val Glu Val
                980                 985
```

<210> SEQ ID NO 21
<211> LENGTH: 30
<212> TYPE: DNA
<213> ORGANISM: Artificial Sequence
<220> FEATURE:
<223> OTHER INFORMATION: PCR primer 15

<400> SEQUENCE: 21
aaaaagctta tggctctgcg gaggctgggg                                    30

<210> SEQ ID NO 22
<211> LENGTH: 30
<212> TYPE: DNA
<213> ORGANISM: Artificial Sequence
<220> FEATURE:
<223> OTHER INFORMATION: PCR primer 16

<400> SEQUENCE: 22
aaagatatct catggcaact tctcctggat                                    30

<210> SEQ ID NO 23
<211> LENGTH: 22
<212> TYPE: DNA
<213> ORGANISM: Artificial Sequence
<220> FEATURE:
<223> OTHER INFORMATION: PCR primer 17

<400> SEQUENCE: 23
caccatggag ctggcggcct tg                                            22

<210> SEQ ID NO 24
<211> LENGTH: 21
<212> TYPE: DNA
<213> ORGANISM: Artificial Sequence
<220> FEATURE:
<223> OTHER INFORMATION: PCR primer 18

<400> SEQUENCE: 24
tcccactggc acgtccagac c                                             21

<210> SEQ ID NO 25
<211> LENGTH: 3804
<212> TYPE: DNA
<213> ORGANISM: Homo sapiens

<400> SEQUENCE: 25

```
ccgcggccgc cccttcacc atggagctgg cggccttgtg ccgctggggg ctcctcctcg      60
ccctcttgcc ccccggagcc gcgagcaccc aagtgtgcac cggcacagac atgaagctgc    120
ggctccctgc cagtcccgag acccacctgg acatgctccg ccacctctac cagggctgcc    180
aggtggtgca gggaaacctg gaactcacct acctgcccac caatgccagc ctgtccttcc    240
tgcaggatat ccaggaggtg cagggctacg tgctcatcgc tcacaaccaa gtgaggcagg    300
tcccactgca gaggctgcgg attgtgcgag cacccagct ctttgaggac aactatgccc     360
tggccgtgct agacaatgga gacccgctga acaataccac ccctgtcaca ggggcctccc    420
caggaggcct gcgggagctg cagcttcgaa gcctcacaga gatcttgaaa ggaggggtct    480
tgatccagcg gaaccccag ctctgctacc aggacacgat tttgtggaag acatcttcc     540
acaagaacaa ccagctggct ctcacactga tagacaccaa ccgctctcgg gcctgccacc    600
cctgttctcc gatgtgtaag ggctcccgct gctggggaga gagttctgag gattgtcaga    660
gcctgacgcg cactgtctgt gccggtggct gtgcccgctg caaggggcca ctgcccactg    720
actgctgcca tgagcagtgt gctgccggct gcacgggccc caagcactct gactgcctgg    780
cctgcctcca cttcaaccac agtggcatct gtgagctgca ctgcccagcc tggtcacct    840
acaaacagag cacgtttgag tccatgccca atccgagg ccggtataca ttcggcgcca      900
gctgtgtgac tgcctgtccc tacaactacc tttctacgga cgtgggatcc tgcaccctcg    960
tctgccccct gcacaaccaa gaggtgacag cagaggatgg aacacagcgg tgtgagaagt   1020
gcagcaagcc ctgtgcccga gtgtgctatg gtctgggcat ggagcacttg cgagaggtga   1080
gggcagttac cagtgccaat atccaggagt ttgctggctg caagaagatc tttgggagcc   1140
tggcatttct gccggagagc tttgatgggg acccagcctc caacactgcc ccgctccagc   1200
cagagcagct ccaagtgttt gagactctgg aagagatcac aggttaccta tacatctcag   1260
catggccgga cagcctgcct gacctcagcg tcttccagaa cctgcaagta atccggggac   1320
gaattctgca caatgcgcc tactcgctga ccctgcaagg gctgggcatc agctggctgg   1380
ggctgcgctc actgagggaa ctgggcagtg actggcccct catccaccat aacacccacc   1440
tctgcttcgt gcacacggtg cctgggacc agctcttcg gaacccgcac caagctctgc   1500
tccacactgc caaccggcca gaggacgagt gtgtgggcga gggcctggcc tgccaccagc   1560
tgtgcgcccg agggcactgc tggggtccag ggcccaccca gtgtgtcaac tgcagccagt   1620
tccttcgggg ccaggagtgc gtggaggaat gccgagtact gcagggctc cccagggagt   1680
atgtgaatgc caggcactgt ttgccgtgcc accctgagtg tcagcccag aatggctcag   1740
tgacctgttt tggaccggag gctgaccagt gtgtggcctg tgcccactat aaggaccctc   1800
ccttctgcgt ggcccgctgc cccagcggtg tgaaacctga cctctcctac atgcccatct   1860
ggaagtttcc agatgaggag ggcgcatgcc agccttgccc catcaactgc acccactcct   1920
gtgtggacct ggatgacaag ggctgcccg ccgagcagag agccagccct ctgacgtcca   1980
tcatctctgc ggtggttggc attctgctgg tcgtggtctt ggggtggtc tttgggatcc   2040
tcatcaagcg acggcagcag aagatccgga agtacacgat gcgagactg ctgcaggaaa   2100
cggagctggt ggagccgctg acacctagcg gagcgatgcc caaccaggcg cagatgcgga   2160
```

```
tcctgaaaga cggagctg aggaaggtga aggtgcttgg atctggcgct tttggcacag   2220
tctacaaggg catctggatc cctgatgggg agaatgtgaa aattccagtg gccatcaaag   2280
tgttgaggga aaacacatcc cccaaagcca acaaagaaat cttagacgaa gcatacgtga   2340
tggctggtgt gggctcccca tatgtctccc gccttctggg catctgcctg acatccacgg   2400
tgcagctggt gacacagctt atgccctatg gctgcctctt agaccatgtc cgggaaaacc   2460
gcggacgcct gggctcccag gacctgctga actggtgtat gcagattgcc aaggggatga   2520
gctacctgga ggatgtgcgg ctcgtacaca gggacttggc cgctcggaac gtgctggtca   2580
agagtcccaa ccatgtcaaa attacagact tcgggctggc tcggctgctg acattgacg   2640 agacagagta ccatgcagat gggggcaagg tgcccatcaa gtggatggcg ctggagtcca   2700
ttctccgccg gcggttcacc caccagagtg atgtgtggag ttatggtgtg actgtgtggg   2760
agctgatgac ttttggggcc aaaccttacg atgggatccc agcccgggag atccctgacc   2820
tgctggaaaa gggggagcgg ctgccccagc cccccatctg caccattgat gtctacatga   2880
tcatggtcaa atgttggatg attgactctg aatgtcggcc aagattccgg gagttggtgt   2940
ctgaattctc ccgcatggcc agggacccc agcgctttgt ggtcatccag aatgaggact   3000
tgggcccagc cagtcccttg gacagcacct tctaccgctc actgctggag gacgatgaca   3060
tgggggacct ggtggatgct gaggagtatc tggtacccca gcagggcttc ttctgtccag   3120
accctgcccc gggcgctggg ggcatggtcc accacaggca ccgcagctca tctaccagga   3180
gtggcggtgg ggacctgaca ctagggctgg agccctctga agaggaggcc cccaggtctc   3240
cactggcacc ctccgaaggg gctggctccg atgtatttga tggtgacctg ggaatggggg   3300
cagccaaggg gctgcaaagc ctccccacac atgaccccag ccctctacag cggtacagtg   3360 aggacccca gtaccctg ccctctgaga ctgatggcta cgttgccccc ctgacctgca   3420
gcccccagcc tgaatatgtg aaccagccag atgttcggcc ccagcccct tcgcccgag   3480 agggccctct gcctgctgcc cgacctgctg gtgccactct ggaaagggcc aagactctct   3540
ccccagggaa gaatgggtc gtcaaagacg tttttgcctt tgggggtgcc gtggagaacc   3600
ccgagtactt gacaccccag ggaggagctg ccctcagcc caccctcct cctgccttca   3660 gcccagcctt cgacaacctc tattactggg accaggaccc accagagcgg ggggctccac   3720
ccagcacctt caagggaca cctacggcag agaacccaga gtacctgggt ctggacgtgc   3780
cagtgggaaa gggtgggcgc gccg                                        3804
```

<210> SEQ ID NO 26
<211> LENGTH: 8
<212> TYPE: PRT
<213> ORGANISM: Mus musculus

<400> SEQUENCE: 26

Ile Gln Leu Val Gln Ser Gly Pro
1               5

<210> SEQ ID NO 27
<211> LENGTH: 11
<212> TYPE: PRT
<213> ORGANISM: Mus musculus

<400> SEQUENCE: 27

Asp Val Leu Met Thr Gln Ser Pro Leu Ser Leu
1               5                   10

<210> SEQ ID NO 28
<211> LENGTH: 9
<212> TYPE: PRT
<213> ORGANISM: Mus musculus

<400> SEQUENCE: 28

Gln Ile Gln Leu Val Gln Ser Gly Pro
1               5

<210> SEQ ID NO 29
<211> LENGTH: 19
<212> TYPE: PRT
<213> ORGANISM: Mus musculus

<400> SEQUENCE: 29

Asp Val Leu Met Thr Gln Thr Pro Leu Ser Leu Pro Val Ser Leu Gly
1               5                   10                  15

Asp Gln Ala

<210> SEQ ID NO 30
<211> LENGTH: 27
<212> TYPE: DNA
<213> ORGANISM: Artificial Sequence
<220> FEATURE:
<223> OTHER INFORMATION: PCR primer DB3F1

<400> SEQUENCE: 30
cagatccagt tggtgcagtc tggacct                                27

<210> SEQ ID NO 31
<211> LENGTH: 32
<212> TYPE: DNA
<213> ORGANISM: Artificial Sequence
<220> FEATURE:
<223> OTHER INFORMATION: PCR primer MIG2AEVR1

<400> SEQUENCE: 31
aagatatctc atttacccgg agtccgggag aa                          32

<210> SEQ ID NO 32
<211> LENGTH: 26
<212> TYPE: DNA
<213> ORGANISM: Artificial Sequence
<220> FEATURE:
<223> OTHER INFORMATION: PCR primer MK19EIF1

<400> SEQUENCE: 32
aagaattcat gaagttgcct gttagg                                 26

<210> SEQ ID NO 33
<211> LENGTH: 32
<212> TYPE: DNA
<213> ORGANISM: Artificial Sequence
<220> FEATURE:
<223> OTHER INFORMATION: PCR primer KEVR1

<400> SEQUENCE: 33
aagatatctt aacactcatt cctgttgaag ct                          32

<210> SEQ ID NO 34
<211> LENGTH: 1350
<212> TYPE: DNA
<213> ORGANISM: Mus musculus
<220> FEATURE:
<221> NAME/KEY: CDS

<222> LOCATION: (1)..(1350)

<400> SEQUENCE: 34

| | | |
|---|---|---|
| cag atc cag ttg gtg cag tct gga cct gag ctg aag aag cct gga gag<br>Gln Ile Gln Leu Val Gln Ser Gly Pro Glu Leu Lys Lys Pro Gly Glu<br>1               5                   10                  15 | 48 | |
| aca gtc aag atc tcc tgc aag gct tct ggg tat acc ttc aca cac tat<br>Thr Val Lys Ile Ser Cys Lys Ala Ser Gly Tyr Thr Phe Thr His Tyr<br>            20                  25                  30 | 96 | |
| tca atg cac tgg gtg aag cag gct cca gga aag ggt tta aag tgg atg<br>Ser Met His Trp Val Lys Gln Ala Pro Gly Lys Gly Leu Lys Trp Met<br>        35                  40                  45 | 144 | |
| ggc tgg ata aac acc tac act gga gag cca aca tat gct gat gac ttc<br>Gly Trp Ile Asn Thr Tyr Thr Gly Glu Pro Thr Tyr Ala Asp Asp Phe<br>    50                  55                  60 | 192 | |
| aag gga cgg ttt gcc ttc tct ttg gaa acc tct gcc agc act gcc ttt<br>Lys Gly Arg Phe Ala Phe Ser Leu Glu Thr Ser Ala Ser Thr Ala Phe<br>65                  70                  75                  80 | 240 | |
| ttg cag atc aac aac ctc aaa aat gag gac acg gct aca tat ttc tgt<br>Leu Gln Ile Asn Asn Leu Lys Asn Glu Asp Thr Ala Thr Tyr Phe Cys<br>            85                  90                  95 | 288 | |
| gca acc tac tat agg tac gaa aga gac ttt gac tac tgg ggc caa ggc<br>Ala Thr Tyr Tyr Arg Tyr Glu Arg Asp Phe Asp Tyr Trp Gly Gln Gly<br>        100                 105                 110 | 336 | |
| acc act ctc aca gtc tcc tca gcc aaa aca aca gcc cca tcg gtc tat<br>Thr Thr Leu Thr Val Ser Ser Ala Lys Thr Thr Ala Pro Ser Val Tyr<br>    115                 120                 125 | 384 | |
| cca ctg gcc cct gtg tgt gga gat aca act ggc tcc tcg gtg act cta<br>Pro Leu Ala Pro Val Cys Gly Asp Thr Thr Gly Ser Ser Val Thr Leu<br>130                 135                 140 | 432 | |
| gga tgc ctg gtc aag ggt tat ttc cct gag cca gtg acc ttg acc tgg<br>Gly Cys Leu Val Lys Gly Tyr Phe Pro Glu Pro Val Thr Leu Thr Trp<br>145                 150                 155                 160 | 480 | |
| aac tct gga tcc ctg tcc agt ggt gtg cac acc ttc cca gct gtc ctg<br>Asn Ser Gly Ser Leu Ser Ser Gly Val His Thr Phe Pro Ala Val Leu<br>            165                 170                 175 | 528 | |
| cag tct gac ctc tac acc ctc agc agc tca gtg act gta acc tcg agc<br>Gln Ser Asp Leu Tyr Thr Leu Ser Ser Ser Val Thr Val Thr Ser Ser<br>        180                 185                 190 | 576 | |
| acc tgg ccc agc cag tcc atc acc tgc aat gtg gcc cac ccg gca agc<br>Thr Trp Pro Ser Gln Ser Ile Thr Cys Asn Val Ala His Pro Ala Ser<br>    195                 200                 205 | 624 | |
| agc acc aag gta gac aag aaa att gag ccc aga ggg ccc aca atc aag<br>Ser Thr Lys Val Asp Lys Lys Ile Glu Pro Arg Gly Pro Thr Ile Lys<br>210                 215                 220 | 672 | |
| ccc tgt cct cca tgc aaa tgc cca gca cct aac ctc ttg ggt gga cca<br>Pro Cys Pro Pro Cys Lys Cys Pro Ala Pro Asn Leu Leu Gly Gly Pro<br>225                 230                 235                 240 | 720 | |
| tcc gtc ttc atc ttc cct cca aag atc aag gat gta ctc atg atc tcc<br>Ser Val Phe Ile Phe Pro Pro Lys Ile Lys Asp Val Leu Met Ile Ser<br>            245                 250                 255 | 768 | |
| ctg agc ccc ata gtc aca tgt gtg gtg gtg gat gtg agc gag gat gac<br>Leu Ser Pro Ile Val Thr Cys Val Val Val Asp Val Ser Glu Asp Asp<br>        260                 265                 270 | 816 | |
| cca gat gtc cag atc agc tgg ttt gtg aac aac gtg gaa gta cac aca<br>Pro Asp Val Gln Ile Ser Trp Phe Val Asn Asn Val Glu Val His Thr<br>    275                 280                 285 | 864 | |
| gct cag aca caa acc cat aga gag gat tac aac agt act ctc cgg gtg<br>Ala Gln Thr Gln Thr His Arg Glu Asp Tyr Asn Ser Thr Leu Arg Val<br>290                 295                 300 | 912 | |

-continued

```
gtc agt gcc ctc ccc atc cag cac cag gac tgg atg agt ggc aag gag    960
Val Ser Ala Leu Pro Ile Gln His Gln Asp Trp Met Ser Gly Lys Glu
305                 310                 315                 320 ttc aaa tgc aag gtc aac aac aaa gac ctc cca gcg ccc atc gag aga   1008
Phe Lys Cys Lys Val Asn Asn Lys Asp Leu Pro Ala Pro Ile Glu Arg
                325                 330                 335 acc atc tca aaa ccc aaa ggg tca gta aga gct cca cag gta tat gtc   1056
Thr Ile Ser Lys Pro Lys Gly Ser Val Arg Ala Pro Gln Val Tyr Val
            340                 345                 350 ttg cct cca cca gaa gaa gag atg act aag aaa cag gtc act ctg acc   1104
Leu Pro Pro Pro Glu Glu Glu Met Thr Lys Lys Gln Val Thr Leu Thr
        355                 360                 365 tgc atg gtc aca gac ttc atg cct gaa gac att tac gtg gag tgg acc   1152
Cys Met Val Thr Asp Phe Met Pro Glu Asp Ile Tyr Val Glu Trp Thr
370                 375                 380 aac aac ggg aaa aca gag cta aac tac aag aac act gaa cca gtc ctg   1200
Asn Asn Gly Lys Thr Glu Leu Asn Tyr Lys Asn Thr Glu Pro Val Leu
385                 390                 395                 400 gac tct gat ggt tct tac ttc atg tac agc aag ctg aga gtg gaa aag   1248
Asp Ser Asp Gly Ser Tyr Phe Met Tyr Ser Lys Leu Arg Val Glu Lys
                405                 410                 415 aag aac tgg gtg gaa aga aat agc tac tcc tgt tca gtg gtc cac gag   1296
Lys Asn Trp Val Glu Arg Asn Ser Tyr Ser Cys Ser Val Val His Glu
            420                 425                 430 ggt ctg cac aat cac cac acg act aag agc ttc tcc cgg act ccg ggt   1344
Gly Leu His Asn His His Thr Thr Lys Ser Phe Ser Arg Thr Pro Gly
        435                 440                 445 aaa tga                                                            1350
Lys

<210> SEQ ID NO 35
<211> LENGTH: 449
<212> TYPE: PRT
<213> ORGANISM: Mus musculus

<400> SEQUENCE: 35

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr His Tyr
            20                  25                  30

Ser Met His Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Phe
65                  70                  75                  80

Leu Gln Ile Asn Asn Leu Lys Asn Glu Asp Thr Ala Thr Tyr Phe Cys
                85                  90                  95

Ala Thr Tyr Tyr Arg Tyr Glu Arg Asp Phe Asp Tyr Trp Gly Gln Gly
            100                 105                 110

Thr Thr Leu Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
```

```
                    165                 170                 175
Gln Ser Asp Leu Tyr Thr Leu Ser Ser Ser Val Thr Val Thr Ser Ser
                180                 185                 190

Thr Trp Pro Ser Gln Ser Ile Thr Cys Asn Val Ala His Pro Ala Ser
            195                 200                 205

Ser Thr Lys Val Asp Lys Lys Ile Glu Pro Arg Gly Pro Thr Ile Lys
        210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
        355                 360                 365

Cys Met Val Thr Asp Phe Met Pro Glu Asp Ile Tyr Val Glu Trp Thr
370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
        435                 440                 445

Lys
```

<210> SEQ ID NO 36
<211> LENGTH: 660
<212> TYPE: DNA
<213> ORGANISM: Mus musculus
<220> FEATURE:
<221> NAME/KEY: CDS
<222> LOCATION: (1)..(660)

<400> SEQUENCE: 36

```
gat gtt ttg atg acc caa agt cca ctc tcc ctg cct gtc agt ctt gga    48
Asp Val Leu Met Thr Gln Ser Pro Leu Ser Leu Pro Val Ser Leu Gly
1               5                   10                  15 gat caa gcc tcc atc tct tgc aga tct agt cag agc att gta cat agt    96
Asp Gln Ala Ser Ile Ser Cys Arg Ser Ser Gln Ser Ile Val His Ser
            20                  25                  30 aat gga aac acc tat tta gaa tgg tac ctg cag aaa cca ggc cag tct   144
Asn Gly Asn Thr Tyr Leu Glu Trp Tyr Leu Gln Lys Pro Gly Gln Ser
        35                  40                  45 cca aag ctc ctg atc tac aaa gtt tcc aac cga ttt tct ggg gtc cca   192
```

```
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc agg atc      240
Asp Arg Phe Ser Gly Ser Gly Ser Gly Thr Asp Phe Thr Leu Arg Ile
65                  70                  75                  80 agc aga gtg gag gct gag gat ctg gga gtt tat tac tgc ttt caa ggt      288
Ser Arg Val Glu Ala Glu Asp Leu Gly Val Tyr Tyr Cys Phe Gln Gly
                85                  90                  95 tca cat gtt ccg tac acg ttc gga ggg ggg acc aag ctg gaa ata aaa      336
Ser His Val Pro Tyr Thr Phe Gly Gly Gly Thr Lys Leu Glu Ile Lys
                100                 105                 110 cgg gct gat gct gca cca act gta tcc atc ttc cca cca tcc agt gag      384
Arg Ala Asp Ala Ala Pro Thr Val Ser Ile Phe Pro Pro Ser Ser Glu
        115                 120                 125 cag tta aca tct gga ggt gcc tca gtc gtg tgc ttc ttg aac aac ttc      432
Gln Leu Thr Ser Gly Gly Ala Ser Val Val Cys Phe Leu Asn Asn Phe
        130                 135                 140 tac ccc aaa gac atc aat gtc aag tgg aag att gat ggc agt gaa cga      480
Tyr Pro Lys Asp Ile Asn Val Lys Trp Lys Ile Asp Gly Ser Glu Arg
145                 150                 155                 160 caa aat ggc gtc ctg aac agt tgg act gat cag gac agc aaa gac agc      528
Gln Asn Gly Val Leu Asn Ser Trp Thr Asp Gln Asp Ser Lys Asp Ser
                165                 170                 175 acc tac agc atg agc agc acc ctc acg ttg acc aag gac gag tat gaa      576
Thr Tyr Ser Met Ser Ser Thr Leu Thr Leu Thr Lys Asp Glu Tyr Glu
                180                 185                 190 cga cat aac agc tat acc tgt gag gcc act cac aag aca tca act tca      624
Arg His Asn Ser Tyr Thr Cys Glu Ala Thr His Lys Thr Ser Thr Ser
        195                 200                 205 ccc att gtc aag agc ttc aac agg aat gag tgt taa                      660
Pro Ile Val Lys Ser Phe Asn Arg Asn Glu Cys
        210                 215

<210> SEQ ID NO 37
<211> LENGTH: 219
<212> TYPE: PRT
<213> ORGANISM: Mus musculus

<400> SEQUENCE: 37

Asp Val Leu Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
                100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
        130                 135                 140

Tyr Pro Lys Asp Ile Asn Val Lys Trp Lys Ile Asp Gly Ser Glu Arg
```

```
                          145                 150                 155                 160
                    Gln Asn Gly Val Leu Asn Ser Trp Thr Asp Gln Asp Ser Lys Asp Ser
                                    165                 170                 175

Thr Tyr Ser Met Ser Ser Thr Leu Thr Leu Thr Lys Asp Glu Tyr Glu
                                    180                 185                 190

Arg His Asn Ser Tyr Thr Cys Glu Ala Thr His Lys Thr Ser Thr Ser
                                    195                 200                 205

Pro Ile Val Lys Ser Phe Asn Arg Asn Glu Cys
                                    210                 215

<210> SEQ ID NO 38
<211> LENGTH: 1350
<212> TYPE: DNA
<213> ORGANISM: Mus musculus
<220> FEATURE:
<221> NAME/KEY: CDS
<222> LOCATION: (1)..(1350)

<400> SEQUENCE: 38 cag atc cag ttg gtg cag tct gga cct gag ctg aag aag cct gga gag     48
Gln Ile Gln Leu Val Gln Ser Gly Pro Glu Leu Lys Lys Pro Gly Glu
1               5                   10                  15 aca gtc aag atc tcc tgc aag gct tct ggg tat acc ttc ata gac tat     96
Thr Val Lys Ile Ser Cys Lys Ala Ser Gly Tyr Thr Phe Ile Asp Tyr
            20                  25                  30 tca atg cac tgg gtg aag cag gct cca gga aag ggt tta aag tgg atg    144
Ser Met His Trp Val Lys Gln Ala Pro Gly Lys Gly Leu Lys Trp Met
        35                  40                  45 ggc tgg ata aac acc tac act gga gag cca aca tat tct gat gac ttc    192
Gly Trp Ile Asn Thr Tyr Thr Gly Glu Pro Thr Tyr Ser Asp Asp Phe
    50                  55                  60 aag gga cgg ttt gcc ttc tct ttg gaa acc tct gcc agc act gcc tat    240
Lys Gly Arg Phe Ala Phe Ser Leu Glu Thr Ser Ala Ser Thr Ala Tyr
65                  70                  75                  80 ttg cag atc agc aac ctc aaa aat gag gac acg gct tca tat ttc tgt    288
Leu Gln Ile Ser Asn Leu Lys Asn Glu Asp Thr Ala Ser Tyr Phe Cys
                85                  90                  95 gca acc tac tat agg tac gaa aga gac ttt gac tac tgg ggc caa ggc    336
Ala Thr Tyr Tyr Arg Tyr Glu Arg Asp Phe Asp Tyr Trp Gly Gln Gly
            100                 105                 110 acc act ctc aca gtc tcc tca gcc aaa aca aca gcc cca tcg gtc tat    384
Thr Thr Leu Thr Val Ser Ser Ala Lys Thr Thr Ala Pro Ser Val Tyr
        115                 120                 125 cca ctg gcc cct gtg tgt gga gat aca act ggc tcc tcg gtg act cta    432
Pro Leu Ala Pro Val Cys Gly Asp Thr Thr Gly Ser Ser Val Thr Leu
    130                 135                 140 gga tgc ctg gtc aag ggt tat ttc cct gag cca gtg acc ttg acc tgg    480
Gly Cys Leu Val Lys Gly Tyr Phe Pro Glu Pro Val Thr Leu Thr Trp
145                 150                 155                 160 aac tct gga tcc ctg tcc agt ggt gtg cac acc ttc cca gct gtc ctg    528
Asn Ser Gly Ser Leu Ser Ser Gly Val His Thr Phe Pro Ala Val Leu
                165                 170                 175 cag tct gac ctc tac acc ctc agc agc tca gtg act gta acc tcg agc    576
Gln Ser Asp Leu Tyr Thr Leu Ser Ser Ser Val Thr Val Thr Ser Ser
            180                 185                 190 acc tgg ccc agc cag tcc atc acc tgc aat gtg gcc cac ccg gca agc    624
Thr Trp Pro Ser Gln Ser Ile Thr Cys Asn Val Ala His Pro Ala Ser
        195                 200                 205 agc acc aag gtg gac aag aaa att gag ccc aga ggg ccc aca atc aag    672
Ser Thr Lys Val Asp Lys Lys Ile Glu Pro Arg Gly Pro Thr Ile Lys
```

```
            210                 215                 220
ccc tgt cct cca tgc aaa tgc cca gca cct aac ctc ttg ggt gga cca      720
Pro Cys Pro Pro Cys Lys Cys Pro Ala Pro Asn Leu Leu Gly Gly Pro
225                 230                 235                 240 tcc gtc ttc atc ttc cct cca aag atc aag gat gta ctc atg atc tcc      768
Ser Val Phe Ile Phe Pro Pro Lys Ile Lys Asp Val Leu Met Ile Ser
                245                 250                 255 ctg agc ccc ata gtc aca tgt gtg gtg gtg gac gtg agc gag gat gac      816
Leu Ser Pro Ile Val Thr Cys Val Val Val Asp Val Ser Glu Asp Asp
            260                 265                 270 cca gat gtc cag atc agc tgg ttt gtg aac aac gtg gaa gta cac aca      864
Pro Asp Val Gln Ile Ser Trp Phe Val Asn Asn Val Glu Val His Thr
        275                 280                 285 gct cag aca caa acc cat aga gag gat tac aac agt act ctc cgg gtg      912
Ala Gln Thr Gln Thr His Arg Glu Asp Tyr Asn Ser Thr Leu Arg Val
    290                 295                 300 gtc agt gcc ctc ccc atc cag cac cag gac tgg atg agt ggc aag gag      960
Val Ser Ala Leu Pro Ile Gln His Gln Asp Trp Met Ser Gly Lys Glu
305                 310                 315                 320 ttc aaa tgc aag gtc aac aac aaa gac ctc cca gcg ccc atc gag aga     1008
Phe Lys Cys Lys Val Asn Asn Lys Asp Leu Pro Ala Pro Ile Glu Arg
                325                 330                 335 acc atc tca aaa ccc aaa ggg tca gta aga gct cca cag gta tat gtc     1056
Thr Ile Ser Lys Pro Lys Gly Ser Val Arg Ala Pro Gln Val Tyr Val
            340                 345                 350 ttg cct cca cca gaa gaa gag atg act aag aaa cag gtc act ctg acc     1104
Leu Pro Pro Pro Glu Glu Glu Met Thr Lys Lys Gln Val Thr Leu Thr
        355                 360                 365 tgc atg gtc aca gac ttc atg cct gaa gac att tac gtg gag tgg acc     1152
Cys Met Val Thr Asp Phe Met Pro Glu Asp Ile Tyr Val Glu Trp Thr
    370                 375                 380 aac aac ggg aaa aca gag cta aac tac aag aac act gaa cca gtc ctg     1200
Asn Asn Gly Lys Thr Glu Leu Asn Tyr Lys Asn Thr Glu Pro Val Leu
385                 390                 395                 400 gac tct gat ggt tct tac ttc atg tac agc aag ctg aga gtg gaa aag     1248
Asp Ser Asp Gly Ser Tyr Phe Met Tyr Ser Lys Leu Arg Val Glu Lys
                405                 410                 415 aag aac tgg gtg gaa aga aat agc tac tcc tgt tca gtg gtc cac gag     1296
Lys Asn Trp Val Glu Arg Asn Ser Tyr Ser Cys Ser Val Val His Glu
            420                 425                 430 ggt ctg cac aat cac cac acg act aag agc ttc tcc cgg act ccg ggt     1344
Gly Leu His Asn His His Thr Thr Lys Ser Phe Ser Arg Thr Pro Gly
        435                 440                 445 aaa tga                                                             1350
Lys

<210> SEQ ID NO 39
<211> LENGTH: 449
<212> TYPE: PRT
<213> ORGANISM: Mus musculus

<400> SEQUENCE: 39

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Ile Asp Tyr
                20                  25                  30

Ser Met His Trp Val Lys Gln Ala Pro Gly Lys Gly Leu Lys Trp Met
            35                  40                  45

Gly Trp Ile Asn Thr Tyr Thr Gly Glu Pro Thr Tyr Ser Asp Asp Phe
```

Lys Gly Arg Phe Ala Phe Ser Leu Glu Thr Ser Ala Ser Thr Ala Tyr
65                  70                  75                  80

Leu Gln Ile Ser Asn Leu Lys Asn Glu Asp Thr Ala Ser Tyr Phe Cys
                85                  90                  95

Ala Thr Tyr Tyr Arg Tyr Glu Arg Asp Phe Asp Tyr Trp Gly Gln Gly
            100                 105                 110

Thr Thr Leu Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
        355                 360                 365

Cys Met Val Thr Asp Phe Met Pro Glu Asp Ile Tyr Val Glu Trp Thr
    370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
        435                 440                 445

Lys

<210> SEQ ID NO 40
<211> LENGTH: 660

<212> TYPE: DNA
<213> ORGANISM: Mus musculus
<220> FEATURE:
<221> NAME/KEY: CDS
<222> LOCATION: (1)..(660)

<400> SEQUENCE: 40

```
gat gtt ttg atg acc caa act cca ctc tcc ctg cct gtc agt ctt gga      48
Asp Val Leu Met Thr Gln Thr Pro Leu Ser Leu Pro Val Ser Leu Gly
1               5                   10                  15 gat caa gcc tcc atc tct tgc aga tct agt cag agc att gta cat agt      96
Asp Gln Ala Ser Ile Ser Cys Arg Ser Ser Gln Ser Ile Val His Ser
            20                  25                  30 agt gga atc acc tat tta gaa tgg tac ctg cag aaa cca ggc cag tct     144
Ser Gly Ile Thr Tyr Leu Glu Trp Tyr Leu Gln Lys Pro Gly Gln Ser
        35                  40                  45 cca aag ctc ctg atc tac aaa gtt tcc aac cga ttt tct ggg gtc cca     192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc     240
Asp Arg Phe Ser Gly Ser Gly Ser Gly Thr Asp Phe Thr Leu Lys Ile
65                  70                  75                  80 agc aga gtg gag gct gag gat ctg gga gtt tat tac tgc ttt caa ggt     288
Ser Arg Val Glu Ala Glu Asp Leu Gly Val Tyr Tyr Cys Phe Gln Gly
                85                  90                  95 tca cat gtt ccg tac acg ttc gga ggg ggg acc aag ctg gaa ata aaa     336
Ser His Val Pro Tyr Thr Phe Gly Gly Gly Thr Lys Leu Glu Ile Lys
            100                 105                 110 cgg gct gat gct gca cca act gta tcc atc ttc cca cca tcc agt gag     384
Arg Ala Asp Ala Ala Pro Thr Val Ser Ile Phe Pro Pro Ser Ser Glu
        115                 120                 125 cag tta aca tct gga ggt gcc tca gtc gtg tgc ttc ttg aac aac ttc     432
Gln Leu Thr Ser Gly Gly Ala Ser Val Val Cys Phe Leu Asn Asn Phe
    130                 135                 140 tac ccc aaa gac atc aat gtc aag tgg aag att gat ggc agt gaa cga     480
Tyr Pro Lys Asp Ile Asn Val Lys Trp Lys Ile Asp Gly Ser Glu Arg
145                 150                 155                 160 caa aat ggc gtc ctg aac agt tgg act gat cag gac agc aaa gac agc     528
Gln Asn Gly Val Leu Asn Ser Trp Thr Asp Gln Asp Ser Lys Asp Ser
                165                 170                 175 acc tac agc atg agc agc acc ctc acg ttg acc aag gac gag tat gaa     576
Thr Tyr Ser Met Ser Ser Thr Leu Thr Leu Thr Lys Asp Glu Tyr Glu
            180                 185                 190 cga cat aac agc tat acc tgt gag gcc act cac aag aca tca act tca     624
Arg His Asn Ser Tyr Thr Cys Glu Ala Thr His Lys Thr Ser Thr Ser
        195                 200                 205 ccc att gtc aag agc ttc aac agg aat gag tgt taa                     660
Pro Ile Val Lys Ser Phe Asn Arg Asn Glu Cys
    210                 215
```

<210> SEQ ID NO 41
<211> LENGTH: 219
<212> TYPE: PRT
<213> ORGANISM: Mus musculus

<400> SEQUENCE: 41

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Ser Gly Ile Thr Tyr Leu Glu Trp Tyr Leu Gln Lys Pro Gly Gln Ser
```

```
            35                  40                  45
Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Tyr Thr Phe Gly Gly Gly Thr Lys Leu Glu Ile Lys
                100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
                180                 185                 190

Arg His Asn Ser Tyr Thr Cys Glu Ala Thr His Lys Thr Ser Thr Ser
            195                 200                 205

Pro Ile Val Lys Ser Phe Asn Arg Asn Glu Cys
        210                 215

<210> SEQ ID NO 42
<211> LENGTH: 357
<212> TYPE: DNA
<213> ORGANISM: Mus musculus
<220> FEATURE:
<221> NAME/KEY: CDS
<222> LOCATION: (1)..(357)

<400> SEQUENCE: 42 cag atc cag ttg gtg cag tct gga cct gag ctg aag aag cct gga gag      48
Gln Ile Gln Leu Val Gln Ser Gly Pro Glu Leu Lys Lys Pro Gly Glu
 1               5                  10                  15 aca gtc aag atc tcc tgc aag gct tct ggg tat acc ttc aca cac tat      96
Thr Val Lys Ile Ser Cys Lys Ala Ser Gly Tyr Thr Phe Thr His Tyr
             20                  25                  30 tca atg cac tgg gtg aag cag gct cca gga aag ggt tta aag tgg atg     144
Ser Met His Trp Val Lys Gln Ala Pro Gly Lys Gly Leu Lys Trp Met
         35                  40                  45 ggc tgg ata aac acc tac act gga gag cca aca tat gct gat gac ttc     192
Gly Trp Ile Asn Thr Tyr Thr Gly Glu Pro Thr Tyr Ala Asp Asp Phe
     50                  55                  60 aag gga cgg ttt gcc ttc tct ttg gaa acc tct gcc agc act gcc ttt     240
Lys Gly Arg Phe Ala Phe Ser Leu Glu Thr Ser Ala Ser Thr Ala Phe
 65                  70                  75                  80 ttg cag atc aac aac ctc aaa aat gag gac acg gct aca tat ttc tgt     288
Leu Gln Ile Asn Asn Leu Lys Asn Glu Asp Thr Ala Thr Tyr Phe Cys
             85                  90                  95 gca acc tac tat agg tac gaa aga gac ttt gac tac tgg ggc caa ggc     336
Ala Thr Tyr Tyr Arg Tyr Glu Arg Asp Phe Asp Tyr Trp Gly Gln Gly
            100                 105                 110 acc act ctc aca gtc tcc tca                                         357
Thr Thr Leu Thr Val Ser Ser
        115
```

-continued

```
<210> SEQ ID NO 43
<211> LENGTH: 119
<212> TYPE: PRT
<213> ORGANISM: Mus musculus

<400> SEQUENCE: 43

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr His Tyr
            20                  25                  30

Ser Met His Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Phe
65                  70                  75                  80

Leu Gln Ile Asn Asn Leu Lys Asn Glu Asp Thr Ala Thr Tyr Phe Cys
                85                  90                  95

Ala Thr Tyr Tyr Arg Tyr Glu Arg Asp Phe Asp Tyr Trp Gly Gln Gly
            100                 105                 110

Thr Thr Leu Thr Val Ser Ser
        115

<210> SEQ ID NO 44
<211> LENGTH: 993
<212> TYPE: DNA
<213> ORGANISM: Mus musculus
<220> FEATURE:
<221> NAME/KEY: CDS
<222> LOCATION: (1)..(993)

<400> SEQUENCE: 44 gcc aaa aca aca gcc cca tcg gtc tat cca ctg gcc cct gtg tgt gga        48
Ala Lys Thr Thr Ala Pro Ser Val Tyr Pro Leu Ala Pro Val Cys Gly
1               5                   10                  15 gat aca act ggc tcc tcg gtg act cta gga tgc ctg gtc aag ggt tat        96
Asp Thr Thr Gly Ser Ser Val Thr Leu Gly Cys Leu Val Lys Gly Tyr
            20                  25                  30 ttc cct gag cca gtg acc ttg acc tgg aac tct gga tcc ctg tcc agt       144
Phe Pro Glu Pro Val Thr Leu Thr Trp Asn Ser Gly Ser Leu Ser Ser
        35                  40                  45 ggt gtg cac acc ttc cca gct gtc ctg cag tct gac ctc tac acc ctc       192
Gly Val His Thr Phe Pro Ala Val Leu Gln Ser Asp Leu Tyr Thr Leu
    50                  55                  60 agc agc tca gtg act gta acc tcg agc acc tgg ccc agc cag tcc atc       240
Ser Ser Ser Val Thr Val Thr Ser Ser Thr Trp Pro Ser Gln Ser Ile
65                  70                  75                  80 acc tgc aat gtg gcc cac ccg gca agc agc acc aag gta gac aag aaa       288
Thr Cys Asn Val Ala His Pro Ala Ser Ser Thr Lys Val Asp Lys Lys
                85                  90                  95 att gag ccc aga ggg ccc aca atc aag ccc tgt cct cca tgc aaa tgc       336
Ile Glu Pro Arg Gly Pro Thr Ile Lys Pro Cys Pro Pro Cys Lys Cys
            100                 105                 110 cca gca cct aac ctc ttg ggt gga cca tcc gtc ttc atc ttc cct cca       384
Pro Ala Pro Asn Leu Leu Gly Gly Pro Ser Val Phe Ile Phe Pro Pro
        115                 120                 125 aag atc aag gat gta ctc atg atc tcc ctg agc ccc ata gtc aca tgt       432
Lys Ile Lys Asp Val Leu Met Ile Ser Leu Ser Pro Ile Val Thr Cys
    130                 135                 140 gtg gtg gtg gat gtg agc gag gat gac cca gat gtc cag atc agc tgg       480
```

```
Val Val Val Asp Val Ser Glu Asp Pro Asp Val Gln Ile Ser Trp
145                 150                 155                 160 ttt gtg aac aac gtg gaa gta cac aca gct cag aca caa acc cat aga     528
Phe Val Asn Asn Val Glu Val His Thr Ala Gln Thr Gln Thr His Arg
                    165                 170                 175 gag gat tac aac agt act ctc cgg gtg gtc agt gcc ctc ccc atc cag     576
Glu Asp Tyr Asn Ser Thr Leu Arg Val Val Ser Ala Leu Pro Ile Gln
                180                 185                 190 cac cag gac tgg atg agt ggc aag gag ttc aaa tgc aag gtc aac aac     624
His Gln Asp Trp Met Ser Gly Lys Glu Phe Lys Cys Lys Val Asn Asn
            195                 200                 205 aaa gac ctc cca gcg ccc atc gag aga acc atc tca aaa ccc aaa ggg     672
Lys Asp Leu Pro Ala Pro Ile Glu Arg Thr Ile Ser Lys Pro Lys Gly
210                 215                 220 tca gta aga gct cca cag gta tat gtc ttg cct cca cca gaa gaa gag     720
Ser Val Arg Ala Pro Gln Val Tyr Val Leu Pro Pro Pro Glu Glu Glu
225                 230                 235                 240 atg act aag aaa cag gtc act ctg acc tgc atg gtc aca gac ttc atg     768
Met Thr Lys Lys Gln Val Thr Leu Thr Cys Met Val Thr Asp Phe Met
                245                 250                 255 cct gaa gac att tac gtg gag tgg acc aac aac ggg aaa aca gag cta     816
Pro Glu Asp Ile Tyr Val Glu Trp Thr Asn Asn Gly Lys Thr Glu Leu
            260                 265                 270 aac tac aag aac act gaa cca gtc ctg gac tct gat ggt tct tac ttc     864
Asn Tyr Lys Asn Thr Glu Pro Val Leu Asp Ser Asp Gly Ser Tyr Phe
        275                 280                 285 atg tac agc aag ctg aga gtg gaa aag aag aac tgg gtg gaa aga aat     912
Met Tyr Ser Lys Leu Arg Val Glu Lys Lys Asn Trp Val Glu Arg Asn
290                 295                 300 agc tac tcc tgt tca gtg gtc cac gag ggt ctg cac aat cac cac acg     960
Ser Tyr Ser Cys Ser Val Val His Glu Gly Leu His Asn His His Thr
305                 310                 315                 320 act aag agc ttc tcc cgg act ccg ggt aaa tga                         993
Thr Lys Ser Phe Ser Arg Thr Pro Gly Lys
                325                 330

<210> SEQ ID NO 45
<211> LENGTH: 330
<212> TYPE: PRT
<213> ORGANISM: Mus musculus

<400> SEQUENCE: 45

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125
```

```
Lys Ile Lys Asp Val Leu Met Ile Ser Leu Ser Pro Ile Val Thr Cys
        130                 135                 140

Val Val Val Asp Val Ser Glu Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
                180                 185                 190

His Gln Asp Trp Met Ser Gly Lys Glu Phe Lys Cys Lys Val Asn Asn
            195                 200                 205

Lys Asp Leu Pro Ala Pro Ile Glu Arg Thr Ile Ser Lys Pro Lys Gly
210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 46
<211> LENGTH: 336
<212> TYPE: DNA
<213> ORGANISM: Mus musculus
<220> FEATURE:
<221> NAME/KEY: CDS
<222> LOCATION: (1)..(336)

<400> SEQUENCE: 46 gat gtt ttg atg acc caa agt cca ctc tcc ctg cct gtc agt ctt gga     48
Asp Val Leu Met Thr Gln Ser Pro Leu Ser Leu Pro Val Ser Leu Gly
1               5                   10                  15 gat caa gcc tcc atc tct tgc aga tct agt cag agc att gta cat agt     96
Asp Gln Ala Ser Ile Ser Cys Arg Ser Ser Gln Ser Ile Val His Ser
            20                  25                  30 aat gga aac acc tat tta gaa tgg tac ctg cag aaa cca ggc cag tct    144
Asn Gly Asn Thr Tyr Leu Glu Trp Tyr Leu Gln Lys Pro Gly Gln Ser
        35                  40                  45 cca aag ctc ctg atc tac aaa gtt tcc aac cga ttt tct ggg gtc cca    192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc agg atc    240
Asp Arg Phe Ser Gly Ser Gly Ser Gly Thr Asp Phe Thr Leu Arg Ile
65                  70                  75                  80 agc aga gtg gag gct gag gat ctg gga gtt tat tac tgc ttt caa ggt    288
Ser Arg Val Glu Ala Glu Asp Leu Gly Val Tyr Tyr Cys Phe Gln Gly
                85                  90                  95 tca cat gtt ccg tac acg ttc gga ggg ggg acc aag ctg gaa ata aaa    336
Ser His Val Pro Tyr Thr Phe Gly Gly Gly Thr Lys Leu Glu Ile Lys
            100                 105                 110
```

<210> SEQ ID NO 47
<211> LENGTH: 112
<212> TYPE: PRT
<213> ORGANISM: Mus musculus

<400> SEQUENCE: 47

Asp Val Leu Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 48
<211> LENGTH: 324
<212> TYPE: DNA
<213> ORGANISM: Mus musculus
<220> FEATURE:
<221> NAME/KEY: CDS
<222> LOCATION: (1)..(324)

<400> SEQUENCE: 48 cgg gct gat gct gca cca act gta tcc atc ttc cca cca tcc agt gag     48
Arg Ala Asp Ala Ala Pro Thr Val Ser Ile Phe Pro Pro Ser Ser Glu
1               5                   10                  15 cag tta aca tct gga ggt gcc tca gtc gtg tgc ttc ttg aac aac ttc     96
Gln Leu Thr Ser Gly Gly Ala Ser Val Val Cys Phe Leu Asn Asn Phe
            20                  25                  30 tac ccc aaa gac atc aat gtc aag tgg aag att gat ggc agt gaa cga    144
Tyr Pro Lys Asp Ile Asn Val Lys Trp Lys Ile Asp Gly Ser Glu Arg
        35                  40                  45 caa aat ggc gtc ctg aac agt tgg act gat cag gac agc aaa gac agc    192
Gln Asn Gly Val Leu Asn Ser Trp Thr Asp Gln Asp Ser Lys Asp Ser
    50                  55                  60 acc tac agc atg agc agc acc ctc acg ttg acc aag gac gag tat gaa    240
Thr Tyr Ser Met Ser Ser Thr Leu Thr Leu Thr Lys Asp Glu Tyr Glu
65                  70                  75                  80 cga cat aac agc tat acc tgt gag gcc act cac aag aca tca act tca    288
Arg His Asn Ser Tyr Thr Cys Glu Ala Thr His Lys Thr Ser Thr Ser
                85                  90                  95 ccc att gtc aag agc ttc aac agg aat gag tgt taa                    324
Pro Ile Val Lys Ser Phe Asn Arg Asn Glu Cys
            100                 105

<210> SEQ ID NO 49
<211> LENGTH: 107
<212> TYPE: PRT
<213> ORGANISM: Mus musculus

<400> SEQUENCE: 49

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe

```
                 20                  25                  30

Tyr Pro Lys Asp Ile Asn Val Lys Trp Lys Ile Asp Gly Ser Glu Arg
             35                  40                  45

Gln Asn Gly Val Leu Asn Ser Trp Thr Asp Gln Asp Ser Lys Asp Ser
         50                  55                  60

Thr Tyr Ser Met Ser Ser Thr Leu Thr Leu Thr Lys Asp Glu Tyr Glu
 65                  70                  75                  80

Arg His Asn Ser Tyr Thr Cys Glu Ala Thr His Lys Thr Ser Thr Ser
                 85                  90                  95

Pro Ile Val Lys Ser Phe Asn Arg Asn Glu Cys
             100                 105

<210> SEQ ID NO 50
<211> LENGTH: 357
<212> TYPE: DNA
<213> ORGANISM: Mus musculus
<220> FEATURE:
<221> NAME/KEY: CDS
<222> LOCATION: (1)..(357)

<400> SEQUENCE: 50 cag atc cag ttg gtg cag tct gga cct gag ctg aag aag cct gga gag      48
Gln Ile Gln Leu Val Gln Ser Gly Pro Glu Leu Lys Lys Pro Gly Glu
 1               5                  10                  15 aca gtc aag atc tcc tgc aag gct tct ggg tat acc ttc ata gac tat      96
Thr Val Lys Ile Ser Cys Lys Ala Ser Gly Tyr Thr Phe Ile Asp Tyr
             20                  25                  30 tca atg cac tgg gtg aag cag gct cca gga aag ggt tta aag tgg atg     144
Ser Met His Trp Val Lys Gln Ala Pro Gly Lys Gly Leu Lys Trp Met
         35                  40                  45 ggc tgg ata aac acc tac act gga gag cca aca tat tct gat gac ttc     192
Gly Trp Ile Asn Thr Tyr Thr Gly Glu Pro Thr Tyr Ser Asp Asp Phe
     50                  55                  60 aag gga cgg ttt gcc ttc tct ttg gaa acc tct gcc agc act gcc tat     240
Lys Gly Arg Phe Ala Phe Ser Leu Glu Thr Ser Ala Ser Thr Ala Tyr
 65                  70                  75                  80 ttg cag atc agc aac ctc aaa aat gag gac acg gct tca tat ttc tgt     288
Leu Gln Ile Ser Asn Leu Lys Asn Glu Asp Thr Ala Ser Tyr Phe Cys
                 85                  90                  95 gca acc tac tat agg tac gaa aga gac ttt gac tac tgg ggc caa ggc     336
Ala Thr Tyr Tyr Arg Tyr Glu Arg Asp Phe Asp Tyr Trp Gly Gln Gly
             100                 105                 110 acc act ctc aca gtc tcc tca                                          357
Thr Thr Leu Thr Val Ser Ser
        115

<210> SEQ ID NO 51
<211> LENGTH: 119
<212> TYPE: PRT
<213> ORGANISM: Mus musculus

<400> SEQUENCE: 51

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Ile Asp Tyr
             20                  25                  30

Ser Met His Trp Val Lys Gln Ala Pro Gly Lys Gly Leu Lys Trp Met
         35                  40                  45

Gly Trp Ile Asn Thr Tyr Thr Gly Glu Pro Thr Tyr Ser Asp Asp Phe
     50                  55                  60
```

```
Lys Gly Arg Phe Ala Phe Ser Leu Glu Thr Ser Ala Ser Thr Ala Tyr
 65                  70                  75                  80

Leu Gln Ile Ser Asn Leu Lys Asn Glu Asp Thr Ala Ser Tyr Phe Cys
             85                  90                  95

Ala Thr Tyr Tyr Arg Tyr Glu Arg Asp Phe Asp Tyr Trp Gly Gln Gly
            100                 105                 110

Thr Thr Leu Thr Val Ser Ser
        115

<210> SEQ ID NO 52
<211> LENGTH: 993
<212> TYPE: DNA
<213> ORGANISM: Mus musculus
<220> FEATURE:
<221> NAME/KEY: CDS
<222> LOCATION: (1)..(993)

<400> SEQUENCE: 52 gcc aaa aca aca gcc cca tcg gtc tat cca ctg gcc cct gtg tgt gga      48
Ala Lys Thr Thr Ala Pro Ser Val Tyr Pro Leu Ala Pro Val Cys Gly
 1               5                  10                  15 gat aca act ggc tcc tcg gtg act cta gga tgc ctg gtc aag ggt tat      96
Asp Thr Thr Gly Ser Ser Val Thr Leu Gly Cys Leu Val Lys Gly Tyr
            20                  25                  30 ttc cct gag cca gtg acc ttg acc tgg aac tct gga tcc ctg tcc agt     144
Phe Pro Glu Pro Val Thr Leu Thr Trp Asn Ser Gly Ser Leu Ser Ser
        35                  40                  45 ggt gtg cac acc ttc cca gct gtc ctg cag tct gac ctc tac acc ctc     192
Gly Val His Thr Phe Pro Ala Val Leu Gln Ser Asp Leu Tyr Thr Leu
    50                  55                  60 agc agc tca gtg act gta acc tcg agc acc tgg ccc agc cag tcc atc     240
Ser Ser Ser Val Thr Val Thr Ser Ser Thr Trp Pro Ser Gln Ser Ile
 65                  70                  75                  80 acc tgc aat gtg gcc cac ccg gca agc agc acc aag gtg gac aag aaa     288
Thr Cys Asn Val Ala His Pro Ala Ser Ser Thr Lys Val Asp Lys Lys
             85                  90                  95 att gag ccc aga ggg ccc aca atc aag ccc tgt cct cca tgc aaa tgc     336
Ile Glu Pro Arg Gly Pro Thr Ile Lys Pro Cys Pro Pro Cys Lys Cys
            100                 105                 110 cca gca cct aac ctc ttg ggt gga cca tcc gtc ttc atc ttc cct cca     384
Pro Ala Pro Asn Leu Leu Gly Gly Pro Ser Val Phe Ile Phe Pro Pro
        115                 120                 125 aag atc aag gat gta ctc atg atc tcc ctg agc ccc ata gtc aca tgt     432
Lys Ile Lys Asp Val Leu Met Ile Ser Leu Ser Pro Ile Val Thr Cys
    130                 135                 140 gtg gtg gtg gac gtg agc gag gat gac cca gat gtc cag atc agc tgg     480
Val Val Val Asp Val Ser Glu Asp Asp Pro Asp Val Gln Ile Ser Trp
145                 150                 155                 160 ttt gtg aac aac gtg gaa gta cac aca gct cag aca caa acc cat aga     528
Phe Val Asn Asn Val Glu Val His Thr Ala Gln Thr Gln Thr His Arg
                165                 170                 175 gag gat tac aac agt act ctc cgg gtg gtc agt gcc ctc ccc atc cag     576
Glu Asp Tyr Asn Ser Thr Leu Arg Val Val Ser Ala Leu Pro Ile Gln
            180                 185                 190 cac cag gac tgg atg agt ggc aag gag ttc aaa tgc aag gtc aac aac     624
His Gln Asp Trp Met Ser Gly Lys Glu Phe Lys Cys Lys Val Asn Asn
        195                 200                 205 aaa gac ctc cca gcg ccc atc gag aga acc atc tca aaa ccc aaa ggg     672
Lys Asp Leu Pro Ala Pro Ile Glu Arg Thr Ile Ser Lys Pro Lys Gly
    210                 215                 220
```

```
tca gta aga gct cca cag gta tat gtc ttg cct cca cca gaa gaa gag    720
Ser Val Arg Ala Pro Gln Val Tyr Val Leu Pro Pro Pro Glu Glu Glu
225             230                 235                 240 atg act aag aaa cag gtc act ctg acc tgc atg gtc aca gac ttc atg    768
Met Thr Lys Lys Gln Val Thr Leu Thr Cys Met Val Thr Asp Phe Met
                245                 250                 255 cct gaa gac att tac gtg gag tgg acc aac aac ggg aaa aca gag cta    816
Pro Glu Asp Ile Tyr Val Glu Trp Thr Asn Asn Gly Lys Thr Glu Leu
            260                 265                 270 aac tac aag aac act gaa cca gtc ctg gac tct gat ggt tct tac ttc    864
Asn Tyr Lys Asn Thr Glu Pro Val Leu Asp Ser Asp Gly Ser Tyr Phe
        275                 280                 285 atg tac agc aag ctg aga gtg gaa aag aag aac tgg gtg gaa aga aat    912
Met Tyr Ser Lys Leu Arg Val Glu Lys Lys Asn Trp Val Glu Arg Asn
    290                 295                 300 agc tac tcc tgt tca gtg gtc cac gag ggt ctg cac aat cac cac acg    960
Ser Tyr Ser Cys Ser Val Val His Glu Gly Leu His Asn His His Thr
305                 310                 315                 320 act aag agc ttc tcc cgg act ccg ggt aaa tga                        993
Thr Lys Ser Phe Ser Arg Thr Pro Gly Lys
                325                 330
```

<210> SEQ ID NO 53
<211> LENGTH: 330
<212> TYPE: PRT
<213> ORGANISM: Mus musculus

<400> SEQUENCE: 53

```
Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220
```

```
Ser Val Arg Ala Pro Gln Val Tyr Val Leu Pro Pro Glu Glu Glu
225                 230                 235                 240

Met Thr Lys Lys Gln Val Thr Leu Thr Cys Met Val Thr Asp Phe Met
            245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
            275                 280                 285

Met Tyr Ser Lys Leu Arg Val Glu Lys Lys Asn Trp Val Glu Arg Asn
            290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
            325                 330

<210> SEQ ID NO 54
<211> LENGTH: 336
<212> TYPE: DNA
<213> ORGANISM: Mus musculus
<220> FEATURE:
<221> NAME/KEY: CDS
<222> LOCATION: (1)..(336)

<400> SEQUENCE: 54 gat gtt ttg atg acc caa act cca ctc tcc ctg cct gtc agt ctt gga      48
Asp Val Leu Met Thr Gln Thr Pro Leu Ser Leu Pro Val Ser Leu Gly
1               5                   10                  15 gat caa gcc tcc atc tct tgc aga tct agt cag agc att gta cat agt      96
Asp Gln Ala Ser Ile Ser Cys Arg Ser Ser Gln Ser Ile Val His Ser
                20                  25                  30 agt gga atc acc tat tta gaa tgg tac ctg cag aaa cca ggc cag tct     144
Ser Gly Ile Thr Tyr Leu Glu Trp Tyr Leu Gln Lys Pro Gly Gln Ser
            35                  40                  45 cca aag ctc ctg atc tac aaa gtt tcc aac cga ttt tct ggg gtc cca     192
Pro Lys Leu Leu Ile Tyr Lys Val Ser Asn Arg Phe Ser Gly Val Pro
        50                  55                  60 gac agg ttc agt ggc agt gga tca ggg aca gat ttc aca ctc aag atc     240
Asp Arg Phe Ser Gly Ser Gly Ser Gly Thr Asp Phe Thr Leu Lys Ile
65                  70                  75                  80 agc aga gtg gag gct gag gat ctg gga gtt tat tac tgc ttt caa ggt     288
Ser Arg Val Glu Ala Glu Asp Leu Gly Val Tyr Tyr Cys Phe Gln Gly
                85                  90                  95 tca cat gtt ccg tac acg ttc gga ggg ggg acc aag ctg gaa ata aaa     336
Ser His Val Pro Tyr Thr Phe Gly Gly Gly Thr Lys Leu Glu Ile Lys
            100                 105                 110

<210> SEQ ID NO 55
<211> LENGTH: 112
<212> TYPE: PRT
<213> ORGANISM: Mus musculus

<400> SEQUENCE: 55

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Ser Gly Ile Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Tyr Thr Phe Gly Gly Gly Thr Lys Leu Glu Ile Lys
            100                 105                 110
```

<210> SEQ ID NO 56
<211> LENGTH: 324
<212> TYPE: DNA
<213> ORGANISM: Mus musculus
<220> FEATURE:
<221> NAME/KEY: CDS
<222> LOCATION: (1)..(324)

<400> SEQUENCE: 56

```
cgg gct gat gct gca cca act gta tcc atc ttc cca cca tcc agt gag        48
Arg Ala Asp Ala Ala Pro Thr Val Ser Ile Phe Pro Pro Ser Ser Glu
  1               5                  10                  15 cag tta aca tct gga ggt gcc tca gtc gtg tgc ttc ttg aac aac ttc        96
Gln Leu Thr Ser Gly Gly Ala Ser Val Val Cys Phe Leu Asn Asn Phe
             20                  25                  30 tac ccc aaa gac atc aat gtc aag tgg aag att gat ggc agt gaa cga      144
Tyr Pro Lys Asp Ile Asn Val Lys Trp Lys Ile Asp Gly Ser Glu Arg
         35                  40                  45 caa aat ggc gtc ctg aac agt tgg act gat cag gac agc aaa gac agc      192
Gln Asn Gly Val Leu Asn Ser Trp Thr Asp Gln Asp Ser Lys Asp Ser
     50                  55                  60 acc tac agc atg agc agc acc ctc acg ttg acc aag gac gag tat gaa      240
Thr Tyr Ser Met Ser Ser Thr Leu Thr Leu Thr Lys Asp Glu Tyr Glu
 65                  70                  75                  80 cga cat aac agc tat acc tgt gag gcc act cac aag aca tca act tca      288
Arg His Asn Ser Tyr Thr Cys Glu Ala Thr His Lys Thr Ser Thr Ser
                 85                  90                  95 ccc att gtc aag agc ttc aac agg aat gag tgt taa                      324
Pro Ile Val Lys Ser Phe Asn Arg Asn Glu Cys
            100                 105
```

<210> SEQ ID NO 57
<211> LENGTH: 107
<212> TYPE: PRT
<213> ORGANISM: Mus musculus

<400> SEQUENCE: 57

```
Arg Ala Asp Ala Ala Pro Thr Val Ser Ile Phe Pro Pro Ser Ser Glu
  1               5                  10                  15

Gln Leu Thr Ser Gly Gly Ala Ser Val Val Cys Phe Leu Asn Asn Phe
             20                  25                  30

Tyr Pro Lys Asp Ile Asn Val Lys Trp Lys Ile Asp Gly Ser Glu Arg
         35                  40                  45

Gln Asn Gly Val Leu Asn Ser Trp Thr Asp Gln Asp Ser Lys Asp Ser
     50                  55                  60

Thr Tyr Ser Met Ser Ser Thr Leu Thr Leu Thr Lys Asp Glu Tyr Glu
 65                  70                  75                  80

Arg His Asn Ser Tyr Thr Cys Glu Ala Thr His Lys Thr Ser Thr Ser
                 85                  90                  95

Pro Ile Val Lys Ser Phe Asn Arg Asn Glu Cys
            100                 105
```

```
<210> SEQ ID NO 58
<211> LENGTH: 30
<212> TYPE: DNA
<213> ORGANISM: Mus musculus
<220> FEATURE:
<221> NAME/KEY: CDS
<222> LOCATION: (1)..(30)

<400> SEQUENCE: 58 ggg tat acc ttc aca cac tat tca atg cac                    30
Gly Tyr Thr Phe Thr His Tyr Ser Met His
1               5                   10

<210> SEQ ID NO 59
<211> LENGTH: 10
<212> TYPE: PRT
<213> ORGANISM: Mus musculus

<400> SEQUENCE: 59

Gly Tyr Thr Phe Thr His Tyr Ser Met His
1               5                   10

<210> SEQ ID NO 60
<211> LENGTH: 51
<212> TYPE: DNA
<213> ORGANISM: Mus musculus
<220> FEATURE:
<221> NAME/KEY: CDS
<222> LOCATION: (1)..(51)

<400> SEQUENCE: 60 tgg ata aac acc tac act gga gag cca aca tat gct gat gac ttc aag    48
Trp Ile Asn Thr Tyr Thr Gly Glu Pro Thr Tyr Ala Asp Asp Phe Lys
1               5                   10                  15 gga                                                         51
Gly

<210> SEQ ID NO 61
<211> LENGTH: 17
<212> TYPE: PRT
<213> ORGANISM: Mus musculus

<400> SEQUENCE: 61

Trp Ile Asn Thr Tyr Thr Gly Glu Pro Thr Tyr Ala Asp Asp Phe Lys
1               5                   10                  15

Gly

<210> SEQ ID NO 62
<211> LENGTH: 30
<212> TYPE: DNA
<213> ORGANISM: Mus musculus
<220> FEATURE:
<221> NAME/KEY: CDS
<222> LOCATION: (1)..(30)

<400> SEQUENCE: 62 tac tat agg tac gaa aga gac ttt gac tac                    30
Tyr Tyr Arg Tyr Glu Arg Asp Phe Asp Tyr
1               5                   10

<210> SEQ ID NO 63
<211> LENGTH: 10
<212> TYPE: PRT
<213> ORGANISM: Mus musculus

<400> SEQUENCE: 63
```

```
Tyr Tyr Arg Tyr Glu Arg Asp Phe Asp Tyr
1               5                   10
```

<210> SEQ ID NO 64
<211> LENGTH: 48
<212> TYPE: DNA
<213> ORGANISM: Mus musculus
<220> FEATURE:
<221> NAME/KEY: CDS
<222> LOCATION: (1)..(48)

<400> SEQUENCE: 64

```
aga tct agt cag agc att gta cat agt aat gga aac acc tat tta gaa    48
Arg Ser Ser Gln Ser Ile Val His Ser Asn Gly Asn Thr Tyr Leu Glu
1               5                   10                  15
```

<210> SEQ ID NO 65
<211> LENGTH: 16
<212> TYPE: PRT
<213> ORGANISM: Mus musculus

<400> SEQUENCE: 65

```
Arg Ser Ser Gln Ser Ile Val His Ser Asn Gly Asn Thr Tyr Leu Glu
1               5                   10                  15
```

<210> SEQ ID NO 66
<211> LENGTH: 21
<212> TYPE: DNA
<213> ORGANISM: Mus musculus
<220> FEATURE:
<221> NAME/KEY: CDS
<222> LOCATION: (1)..(21)

<400> SEQUENCE: 66

```
aaa gtt tcc aac cga ttt tct                                        21
Lys Val Ser Asn Arg Phe Ser
1               5
```

<210> SEQ ID NO 67
<211> LENGTH: 7
<212> TYPE: PRT
<213> ORGANISM: Mus musculus

<400> SEQUENCE: 67

```
Lys Val Ser Asn Arg Phe Ser
1               5
```

<210> SEQ ID NO 68
<211> LENGTH: 27
<212> TYPE: DNA
<213> ORGANISM: Mus musculus
<220> FEATURE:
<221> NAME/KEY: CDS
<222> LOCATION: (1)..(27)

<400> SEQUENCE: 68

```
ttt caa ggt tca cat gtt ccg tac acg                                27
Phe Gln Gly Ser His Val Pro Tyr Thr
1               5
```

<210> SEQ ID NO 69
<211> LENGTH: 9
<212> TYPE: PRT
<213> ORGANISM: Mus musculus

<400> SEQUENCE: 69

Phe Gln Gly Ser His Val Pro Tyr Thr

<210> SEQ ID NO 70
<211> LENGTH: 30
<212> TYPE: DNA
<213> ORGANISM: Mus musculus
<220> FEATURE:
<221> NAME/KEY: CDS
<222> LOCATION: (1)..(30)

<400> SEQUENCE: 70

```
ggg tat acc ttc ata gac tat tca atg cac                          30
Gly Tyr Thr Phe Ile Asp Tyr Ser Met His
1               5                   10
```

<210> SEQ ID NO 71
<211> LENGTH: 10
<212> TYPE: PRT
<213> ORGANISM: Mus musculus

<400> SEQUENCE: 71

```
Gly Tyr Thr Phe Ile Asp Tyr Ser Met His
1               5                   10
```

<210> SEQ ID NO 72
<211> LENGTH: 51
<212> TYPE: DNA
<213> ORGANISM: Mus musculus
<220> FEATURE:
<221> NAME/KEY: CDS
<222> LOCATION: (1)..(51)

<400> SEQUENCE: 72

```
tgg ata aac acc tac act gga gag cca aca tat tct gat gac ttc aag    48
Trp Ile Asn Thr Tyr Thr Gly Glu Pro Thr Tyr Ser Asp Asp Phe Lys
1               5                   10                  15 gga                                                                51
Gly
```

<210> SEQ ID NO 73
<211> LENGTH: 17
<212> TYPE: PRT
<213> ORGANISM: Mus musculus

<400> SEQUENCE: 73

```
Trp Ile Asn Thr Tyr Thr Gly Glu Pro Thr Tyr Ser Asp Asp Phe Lys
1               5                   10                  15

Gly
```

<210> SEQ ID NO 74
<211> LENGTH: 30
<212> TYPE: DNA
<213> ORGANISM: Mus musculus
<220> FEATURE:
<221> NAME/KEY: CDS
<222> LOCATION: (1)..(30)

<400> SEQUENCE: 74

```
tac tat agg tac gaa aga gac ttt gac tac                          30
Tyr Tyr Arg Tyr Glu Arg Asp Phe Asp Tyr
1               5                   10
```

<210> SEQ ID NO 75
<211> LENGTH: 10
<212> TYPE: PRT
<213> ORGANISM: Mus musculus

<400> SEQUENCE: 75

Tyr Tyr Arg Tyr Glu Arg Asp Phe Asp Tyr
1               5                   10

<210> SEQ ID NO 76
<211> LENGTH: 48
<212> TYPE: DNA
<213> ORGANISM: Mus musculus
<220> FEATURE:
<221> NAME/KEY: CDS
<222> LOCATION: (1)..(48)

<400> SEQUENCE: 76 aga tct agt cag agc att gta cat agt agt gga atc acc tat tta gaa    48
Arg Ser Ser Gln Ser Ile Val His Ser Ser Gly Ile Thr Tyr Leu Glu
1               5                   10                  15

<210> SEQ ID NO 77
<211> LENGTH: 16
<212> TYPE: PRT
<213> ORGANISM: Mus musculus

<400> SEQUENCE: 77

Arg Ser Ser Gln Ser Ile Val His Ser Ser Gly Ile Thr Tyr Leu Glu
1               5                   10                  15

<210> SEQ ID NO 78
<211> LENGTH: 21
<212> TYPE: DNA
<213> ORGANISM: Mus musculus
<220> FEATURE:
<221> NAME/KEY: CDS
<222> LOCATION: (1)..(21)

<400> SEQUENCE: 78 aaa gtt tcc aac cga ttt tct                                        21
Lys Val Ser Asn Arg Phe Ser
1               5

<210> SEQ ID NO 79
<211> LENGTH: 7
<212> TYPE: PRT
<213> ORGANISM: Mus musculus

<400> SEQUENCE: 79

Lys Val Ser Asn Arg Phe Ser
1               5

<210> SEQ ID NO 80
<211> LENGTH: 27
<212> TYPE: DNA
<213> ORGANISM: Mus musculus
<220> FEATURE:
<221> NAME/KEY: CDS
<222> LOCATION: (1)..(27)

<400> SEQUENCE: 80 ttt caa ggt tca cat gtt ccg tac acg                                27
Phe Gln Gly Ser His Val Pro Tyr Thr
1               5

<210> SEQ ID NO 81
<211> LENGTH: 9
<212> TYPE: PRT
<213> ORGANISM: Mus musculus

<400> SEQUENCE: 81

Phe Gln Gly Ser His Val Pro Tyr Thr
1               5

<210> SEQ ID NO 82
<211> LENGTH: 32
<212> TYPE: DNA
<213> ORGANISM: Artificial Sequence
<220> FEATURE:
<223> OTHER INFORMATION: primer N1

<400> SEQUENCE: 82
attaggatcc gagcttccgt actgccagtg tc                                  32

<210> SEQ ID NO 83
<211> LENGTH: 28
<212> TYPE: DNA
<213> ORGANISM: Artificial
<220> FEATURE:
<223> OTHER INFORMATION: primer N2

<400> SEQUENCE: 83
attaggatcc gccccccaag gtgaggct                                       28

<210> SEQ ID NO 84
<211> LENGTH: 34
<212> TYPE: DNA
<213> ORGANISM: Artificial
<220> FEATURE:
<223> OTHER INFORMATION: primer N3

<400> SEQUENCE: 84
attaggatcc ggtcacttac cgcaagaagg gaga                                34

<210> SEQ ID NO 85
<211> LENGTH: 32
<212> TYPE: DNA
<213> ORGANISM: Artificial
<220> FEATURE:
<223> OTHER INFORMATION: primer N4

<400> SEQUENCE: 85
attaggatcc ggtccaggtg caggcactga cg                                  32

<210> SEQ ID NO 86
<211> LENGTH: 31
<212> TYPE: DNA
<213> ORGANISM: Artificial
<220> FEATURE:
<223> OTHER INFORMATION: primer C1

<400> SEQUENCE: 86
aattaagctt gccgccaatc accgccaagt t                                   31

<210> SEQ ID NO 87
<211> LENGTH: 32
<212> TYPE: DNA
<213> ORGANISM: Artificial
<220> FEATURE:
<223> OTHER INFORMATION: primer C2

<400> SEQUENCE: 87
aattaagctt gttgccagat ccctccgggg ac                                  32

<210> SEQ ID NO 88

```
<210> SEQ ID NO 88
<211> LENGTH: 29
<212> TYPE: DNA
<213> ORGANISM: Artificial
<220> FEATURE:
<223> OTHER INFORMATION: primer C3

<400> SEQUENCE: 88
aattaagctt caggtaggtg gtgtctggg                                           29

<210> SEQ ID NO 89
<211> LENGTH: 30
<212> TYPE: DNA
<213> ORGANISM: Artificial
<220> FEATURE:
<223> OTHER INFORMATION: primer C4

<400> SEQUENCE: 89
aattaagctt ctcgtacttc cacactcggc                                          30

<210> SEQ ID NO 90
<211> LENGTH: 720
<212> TYPE: DNA
<213> ORGANISM: Artificial
<220> FEATURE:
<223> OTHER INFORMATION: hSH-348-T1L
<220> FEATURE:
<221> NAME/KEY: CDS
<222> LOCATION: (1)..(720)
<220> FEATURE:
<221> NAME/KEY: sig_peptide
<222> LOCATION: (1)..(60)

<400> SEQUENCE: 90
```

| | | | | | | | | | | | | | | | | |
|---|---|---|---|---|---|---|---|---|---|---|---|---|---|---|---|---|
| atg | gtg | ctg | cag | acc | cag | gtg | ttc | atc | tcc | ctg | ctg | ctg | tgg | atc | tcc | 48 |
| Met | Val | Leu | Gln | Thr | Gln | Val | Phe | Ile | Ser | Leu | Leu | Leu | Trp | Ile | Ser | |
| 1 | | | | 5 | | | | | 10 | | | | | 15 | | |
| ggc | gca | tat | ggc | gac | ata | gtg | atg | acc | cag | agc | ccc | ctg | agc | ctg | ccc | 96 |
| Gly | Ala | Tyr | Gly | Asp | Ile | Val | Met | Thr | Gln | Ser | Pro | Leu | Ser | Leu | Pro | |
| | | | 20 | | | | | 25 | | | | | 30 | | | |
| gtg | acc | ccc | ggc | gag | ccc | gcc | tcc | atc | agc | tgc | cgg | agc | agc | cag | agc | 144 |
| Val | Thr | Pro | Gly | Glu | Pro | Ala | Ser | Ile | Ser | Cys | Arg | Ser | Ser | Gln | Ser | |
| | 35 | | | | | 40 | | | | | 45 | | | | | |
| atc | gtg | cac | agc | aac | ggc | aac | acc | tac | ctg | gag | tgg | tac | ctg | cag | aag | 192 |
| Ile | Val | His | Ser | Asn | Gly | Asn | Thr | Tyr | Leu | Glu | Trp | Tyr | Leu | Gln | Lys | |
| 50 | | | | | 55 | | | | | 60 | | | | | | |
| ccc | ggc | cag | agc | ccc | cag | ctg | ctg | atc | tac | aag | gtg | agc | aac | cgg | ttc | 240 |
| Pro | Gly | Gln | Ser | Pro | Gln | Leu | Leu | Ile | Tyr | Lys | Val | Ser | Asn | Arg | Phe | |
| 65 | | | | | 70 | | | | | 75 | | | | | 80 | |
| agc | ggc | gtg | ccc | gac | cgg | ttc | agc | ggc | agc | ggc | agc | ggc | acc | gac | ttc | 288 |
| Ser | Gly | Val | Pro | Asp | Arg | Phe | Ser | Gly | Ser | Gly | Ser | Gly | Thr | Asp | Phe | |
| | | | | 85 | | | | | 90 | | | | | 95 | | |
| acc | ctg | aag | atc | agc | cgg | gtg | gag | gcc | gag | gac | gtg | ggc | gtg | tac | tac | 336 |
| Thr | Leu | Lys | Ile | Ser | Arg | Val | Glu | Ala | Glu | Asp | Val | Gly | Val | Tyr | Tyr | |
| | | | 100 | | | | | 105 | | | | | 110 | | | |
| tgc | ttc | cag | ggc | tcc | cac | gtg | ccc | tac | acc | ttc | ggc | cag | ggc | acc | aag | 384 |
| Cys | Phe | Gln | Gly | Ser | His | Val | Pro | Tyr | Thr | Phe | Gly | Gln | Gly | Thr | Lys | |
| | | 115 | | | | | 120 | | | | | 125 | | | | |
| gtg | gag | atc | aag | cgt | acg | gtg | gcc | gcc | ccc | tcc | gtg | ttc | atc | ttc | ccc | 432 |
| Val | Glu | Ile | Lys | Arg | Thr | Val | Ala | Ala | Pro | Ser | Val | Phe | Ile | Phe | Pro | |
| | 130 | | | | | 135 | | | | | 140 | | | | | |
| ccc | tcc | gac | gag | cag | ctg | aag | tcc | ggc | acc | gcc | tcc | gtg | gtg | tgc | ctg | 480 |
| Pro | Ser | Asp | Glu | Gln | Leu | Lys | Ser | Gly | Thr | Ala | Ser | Val | Val | Cys | Leu | |
| 145 | | | | | 150 | | | | | 155 | | | | | 160 | |
| ctg | aat | aac | ttc | tac | ccc | aga | gag | gcc | aag | gtg | cag | tgg | aag | gtg | gac | 528 |

```
Leu Asn Asn Phe Tyr Pro Arg Glu Ala Lys Val Gln Trp Lys Val Asp
                165                 170                 175 aac gcc ctg cag tcc ggg aac tcc cag gag agc gtg acc gag cag gac      576
Asn Ala Leu Gln Ser Gly Asn Ser Gln Glu Ser Val Thr Glu Gln Asp
            180                 185                 190 agc aag gac agc acc tac agc ctg agc agc acc ctg acc ctg agc aaa      624
Ser Lys Asp Ser Thr Tyr Ser Leu Ser Ser Thr Leu Thr Leu Ser Lys
        195                 200                 205 gcc gac tac gag aag cac aag gtg tac gcc tgc gag gtg acc cac cag      672
Ala Asp Tyr Glu Lys His Lys Val Tyr Ala Cys Glu Val Thr His Gln
    210                 215                 220 ggc ctg agc tcc ccc gtc acc aag agc ttc aac agg ggg gag tgt tag      720
Gly Leu Ser Ser Pro Val Thr Lys Ser Phe Asn Arg Gly Glu Cys
225                 230                 235

<210> SEQ ID NO 91
<211> LENGTH: 239
<212> TYPE: PRT
<213> ORGANISM: Artificial
<220> FEATURE:
<223> OTHER INFORMATION: Synthetic Construct

<400> SEQUENCE: 91

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Leu Ser Leu Pro
            20                  25                  30

Val Thr Pro Gly Glu Pro Ala Ser Ile Ser Cys Arg Ser Ser Gln Ser
        35                  40                  45

Ile Val His Ser Asn Gly Asn Thr Tyr Leu Glu Trp Tyr Leu Gln Lys
    50                  55                  60

Pro Gly Gln Ser Pro Gln Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Phe Gln Gly Ser His Val Pro Tyr Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 92
<211> LENGTH: 48
<212> TYPE: DNA
<213> ORGANISM: Artificial
```

<220> FEATURE:
<223> OTHER INFORMATION: hSH348-1-T1L CDRL1
<220> FEATURE:
<221> NAME/KEY: CDS
<222> LOCATION: (1)..(48)

<400> SEQUENCE: 92

```
cgg agc agc cag agc atc gtg cac agc aac ggc aac acc tac ctg gag      48
Arg Ser Ser Gln Ser Ile Val His Ser Asn Gly Asn Thr Tyr Leu Glu
1               5                   10                  15
```

<210> SEQ ID NO 93
<211> LENGTH: 16
<212> TYPE: PRT
<213> ORGANISM: Artificial
<220> FEATURE:
<223> OTHER INFORMATION: Synthetic Construct

<400> SEQUENCE: 93

```
Arg Ser Ser Gln Ser Ile Val His Ser Asn Gly Asn Thr Tyr Leu Glu
1               5                   10                  15
```

<210> SEQ ID NO 94
<211> LENGTH: 21
<212> TYPE: DNA
<213> ORGANISM: Artificial
<220> FEATURE:
<223> OTHER INFORMATION: hSH348-1-T1L CDRL2
<220> FEATURE:
<221> NAME/KEY: CDS
<222> LOCATION: (1)..(21)

<400> SEQUENCE: 94

```
aag gtg agc aac cgg ttc agc                                          21
Lys Val Ser Asn Arg Phe Ser
1               5
```

<210> SEQ ID NO 95
<211> LENGTH: 7
<212> TYPE: PRT
<213> ORGANISM: Artificial
<220> FEATURE:
<223> OTHER INFORMATION: Synthetic Construct

<400> SEQUENCE: 95

```
Lys Val Ser Asn Arg Phe Ser
1               5
```

<210> SEQ ID NO 96
<211> LENGTH: 24
<212> TYPE: DNA
<213> ORGANISM: Artificial
<220> FEATURE:
<223> OTHER INFORMATION: hSH348-1-T1L CDRL3
<220> FEATURE:
<221> NAME/KEY: CDS
<222> LOCATION: (1)..(24)

<400> SEQUENCE: 96

```
ttc cag ggc tcc cac gtg ccc tac                                      24
Phe Gln Gly Ser His Val Pro Tyr
1               5
```

<210> SEQ ID NO 97
<211> LENGTH: 8
<212> TYPE: PRT
<213> ORGANISM: Artificial
<220> FEATURE:
<223> OTHER INFORMATION: Synthetic Construct

```
<400> SEQUENCE: 97

Phe Gln Gly Ser His Val Pro Tyr
1               5

<210> SEQ ID NO 98
<211> LENGTH: 720
<212> TYPE: DNA
<213> ORGANISM: Artificial
<220> FEATURE:
<223> OTHER INFORMATION: hSH348-1-T3L
<220> FEATURE:
<221> NAME/KEY: CDS
<222> LOCATION: (1)..(720)
<220> FEATURE:
<221> NAME/KEY: sig_peptide
<222> LOCATION: (1)..(60)

<400> SEQUENCE: 98 atg gtg ctg cag acc cag gtg ttc atc tcc ctg ctg ctg tgg atc tcc    48
Met Val Leu Gln Thr Gln Val Phe Ile Ser Leu Leu Leu Trp Ile Ser
1               5                   10                  15 ggc gca tat ggc gac gtg ctg atg acc cag agc ccc ctg agc ctg ccc    96
Gly Ala Tyr Gly Asp Val Leu Met Thr Gln Ser Pro Leu Ser Leu Pro
            20                  25                  30 gtg acc ccc ggc gag ccc gcc tcc atc agc tgc cgg agc agc cag agc   144
Val Thr Pro Gly Glu Pro Ala Ser Ile Ser Cys Arg Ser Ser Gln Ser
        35                  40                  45 atc gtg cac agc aac ggc aac acc tac ctg gag tgg tac ctg cag aag   192
Ile Val His Ser Asn Gly Asn Thr Tyr Leu Glu Trp Tyr Leu Gln Lys
    50                  55                  60 ccc ggc cag agc ccc cag ctg ctg atc tac aag gtg agc aac cgg ttc   240
Pro Gly Gln Ser Pro Gln Leu Leu Ile Tyr Lys Val Ser Asn Arg Phe
65                  70                  75                  80 agc ggc gtg ccc gac cgg ttc agc ggc agc ggc agc ggc acc gac ttc   288
Ser Gly Val Pro Asp Arg Phe Ser Gly Ser Gly Ser Gly Thr Asp Phe
                85                  90                  95 acc ctg aag atc agc cgg gtg gag gcc gag gac gtg ggc gtg tac tac   336
Thr Leu Lys Ile Ser Arg Val Glu Ala Glu Asp Val Gly Val Tyr Tyr
            100                 105                 110 tgc ttc cag ggc tcc cac gtg ccc tac acc ttc ggc cag ggc acc aag   384
Cys Phe Gln Gly Ser His Val Pro Tyr Thr Phe Gly Gln Gly Thr Lys
        115                 120                 125 gtg gag atc aag cgt acg gtg gcc gcc ccc tcc gtg ttc atc ttc ccc   432
Val Glu Ile Lys Arg Thr Val Ala Ala Pro Ser Val Phe Ile Phe Pro
    130                 135                 140 ccc tcc gac gag cag ctg aag tcc ggc acc gcc tcc gtg gtg tgc ctg   480
Pro Ser Asp Glu Gln Leu Lys Ser Gly Thr Ala Ser Val Val Cys Leu
145                 150                 155                 160 ctg aat aac ttc tac ccc aga gag gcc aag gtg cag tgg aag gtg gac   528
Leu Asn Asn Phe Tyr Pro Arg Glu Ala Lys Val Gln Trp Lys Val Asp
                165                 170                 175 aac gcc ctg cag tcc ggg aac tcc cag gag agc gtg acc gag cag gac   576
Asn Ala Leu Gln Ser Gly Asn Ser Gln Glu Ser Val Thr Glu Gln Asp
            180                 185                 190 agc aag gac agc acc tac agc ctg agc agc acc ctg acc ctg agc aaa   624
Ser Lys Asp Ser Thr Tyr Ser Leu Ser Ser Thr Leu Thr Leu Ser Lys
        195                 200                 205 gcc gac tac gag aag cac aag gtg tac gcc tgc gag gtg acc cac cag   672
Ala Asp Tyr Glu Lys His Lys Val Tyr Ala Cys Glu Val Thr His Gln
    210                 215                 220 ggc ctg agc tcc ccc gtc acc aag agc ttc aac agg ggg gag tgt tag   720
Gly Leu Ser Ser Pro Val Thr Lys Ser Phe Asn Arg Gly Glu Cys
```

Gly Leu Ser Ser Pro Val Thr Lys Ser Phe Asn Arg Gly Glu Cys
225                 230                 235

<210> SEQ ID NO 99
<211> LENGTH: 239
<212> TYPE: PRT
<213> ORGANISM: Artificial
<220> FEATURE:
<223> OTHER INFORMATION: Synthetic Construct

<400> SEQUENCE: 99

Met Val Leu Gln Thr Gln Val Phe Ile Ser Leu Leu Trp Ile Ser
1               5                   10                  15

Gly Ala Tyr Gly Asp Val Leu Met Thr Gln Ser Pro Leu Ser Leu Pro
                20                  25                  30

Val Thr Pro Gly Glu Pro Ala Ser Ile Ser Cys Arg Ser Ser Gln Ser
            35                  40                  45

Ile Val His Ser Asn Gly Asn Thr Tyr Leu Glu Trp Tyr Leu Gln Lys
        50                  55                  60

Pro Gly Gln Ser Pro Gln Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Phe Gln Gly Ser His Val Pro Tyr Thr Phe Gly Gln Gly Thr Lys
        115                 120                 125

Val Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 100
<211> LENGTH: 48
<212> TYPE: DNA
<213> ORGANISM: Artificial
<220> FEATURE:
<223> OTHER INFORMATION: hSH348-1-T3L CDRL1
<220> FEATURE:
<221> NAME/KEY: CDS
<222> LOCATION: (1)..(48)

<400> SEQUENCE: 100 cgg agc agc cag agc atc gtg cac agc aac ggc aac acc tac ctg gag    48
Arg Ser Ser Gln Ser Ile Val His Ser Asn Gly Asn Thr Tyr Leu Glu
1               5                   10                  15

<210> SEQ ID NO 101
<211> LENGTH: 16
<212> TYPE: PRT

```
<213> ORGANISM: Artificial
<220> FEATURE:
<223> OTHER INFORMATION: Synthetic Construct

<400> SEQUENCE: 101

Arg Ser Ser Gln Ser Ile Val His Ser Asn Gly Asn Thr Tyr Leu Glu
1               5                   10                  15

<210> SEQ ID NO 102
<211> LENGTH: 21
<212> TYPE: DNA
<213> ORGANISM: Artificial
<220> FEATURE:
<223> OTHER INFORMATION: hSH348-1-T3L CDRL2
<220> FEATURE:
<221> NAME/KEY: CDS
<222> LOCATION: (1)..(21)

<400> SEQUENCE: 102 aag gtg agc aac cgg ttc agc                                      21
Lys Val Ser Asn Arg Phe Ser
1               5

<210> SEQ ID NO 103
<211> LENGTH: 7
<212> TYPE: PRT
<213> ORGANISM: Artificial
<220> FEATURE:
<223> OTHER INFORMATION: Synthetic Construct

<400> SEQUENCE: 103

Lys Val Ser Asn Arg Phe Ser
1               5

<210> SEQ ID NO 104
<211> LENGTH: 24
<212> TYPE: DNA
<213> ORGANISM: Artificial
<220> FEATURE:
<223> OTHER INFORMATION: hSH348-1-T3L CDRL3
<220> FEATURE:
<221> NAME/KEY: CDS
<222> LOCATION: (1)..(24)

<400> SEQUENCE: 104 ttc cag ggc tcc cac gtg ccc tac                                  24
Phe Gln Gly Ser His Val Pro Tyr
1               5

<210> SEQ ID NO 105
<211> LENGTH: 8
<212> TYPE: PRT
<213> ORGANISM: Artificial
<220> FEATURE:
<223> OTHER INFORMATION: Synthetic Construct

<400> SEQUENCE: 105

Phe Gln Gly Ser His Val Pro Tyr
1               5

<210> SEQ ID NO 106
<211> LENGTH: 1407
<212> TYPE: DNA
<213> ORGANISM: Artificial
<220> FEATURE:
<223> OTHER INFORMATION: hSH348-1-T1H
<220> FEATURE:
<221> NAME/KEY: CDS
<222> LOCATION: (1)..(1407)
```

```
<220> FEATURE:
<221> NAME/KEY: sig_peptide
<222> LOCATION: (1)..(57)

<400> SEQUENCE: 106 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
 1               5                  10                  15 gtg ctg agc cag gtg cag ctg gtg cag agc ggc gcc gag gtg aag aag      96
Val Leu Ser Gln Val Gln Leu Val Gln Ser Gly Ala Glu Val Lys Lys
             20                  25                  30 ccc ggc agc agc gtg aag gtg agc tgc aag gcc agc ggc tac acc ttc     144
Pro Gly Ser Ser Val Lys Val Ser Cys Lys Ala Ser Gly Tyr Thr Phe
         35                  40                  45 acc cac tac agc atg cac tgg gtg cgg cag gcc ccc ggc cag ggc ctg     192
Thr His Tyr Ser Met His Trp Val Arg Gln Ala Pro Gly Gln Gly Leu
     50                  55                  60 gag tgg atg ggc tgg atc aac acc tac acc ggc gag ccc acc tac gcc     240
Glu Trp Met Gly Trp Ile Asn Thr Tyr Thr Gly Glu Pro Thr Tyr Ala
 65                  70                  75                  80 gac gac ttc aag ggc cgg gtg acc atc acc gcc gac acc tcc acc tcc     288
Asp Asp Phe Lys Gly Arg Val Thr Ile Thr Ala Asp Thr Ser Thr Ser
                 85                  90                  95 acc gcc tac ctg gaa ctg agc agc ctg cgg agc gag gac acc gcc gtg     336
Thr Ala Tyr Leu Glu Leu Ser Ser Leu Arg Ser Glu Asp Thr Ala Val
            100                 105                 110 tac tac tgc gcc acc tac tac cgg tac gag cgg gac ttc gac tac tgg     384
Tyr Tyr Cys Ala Thr Tyr Tyr Arg Tyr Glu Arg Asp Phe Asp Tyr Trp
        115                 120                 125 ggc cag ggc acc ctg gtg acc gtg agc tca gcc tcc acc aag ggc cca     432
Gly Gln Gly Thr Leu Val Thr Val Ser Ser Ala Ser Thr Lys Gly Pro
    130                 135                 140 agc gtc ttc ccc ctg gca ccc tcc tcc aag agc acc tct ggc ggc aca     480
Ser Val Phe Pro Leu Ala Pro Ser Ser Lys Ser Thr Ser Gly Gly Thr
145                 150                 155                 160 gcc gcc ctg ggc tgc ctg gtc aag gac tac ttc ccc gaa ccc gtg acc     528
Ala Ala Leu Gly Cys Leu Val Lys Asp Tyr Phe Pro Glu Pro Val Thr
                165                 170                 175 gtg agc tgg aac tca ggc gcc ctg acc agc ggc gtg cac acc ttc ccc     576
Val Ser Trp Asn Ser Gly Ala Leu Thr Ser Gly Val His Thr Phe Pro
            180                 185                 190 gct gtc ctg cag tcc tca gga ctc tac tcc ctc agc agc gtg gtg acc     624
Ala Val Leu Gln Ser Ser Gly Leu Tyr Ser Leu Ser Ser Val Val Thr
        195                 200                 205 gtg ccc tcc agc agc ttg ggc acc cag acc tac atc tgc aac gtg aat     672
Val Pro Ser Ser Ser Leu Gly Thr Gln Thr Tyr Ile Cys Asn Val Asn
    210                 215                 220 cac aag ccc agc aac acc aag gtg gac aag aga gtt gag ccc aaa tct     720
His Lys Pro Ser Asn Thr Lys Val Asp Lys Arg Val Glu Pro Lys Ser
225                 230                 235                 240 tgt gac aaa act cac aca tgc cca ccc tgc cca gca cct gaa ctc ctg     768
Cys Asp Lys Thr His Thr Cys Pro Pro Cys Pro Ala Pro Glu Leu Leu
                245                 250                 255 ggg gga ccc tca gtc ttc ctc ttc ccc cca aaa ccc aag gac acc ctc     816
Gly Gly Pro Ser Val Phe Leu Phe Pro Pro Lys Pro Lys Asp Thr Leu
            260                 265                 270 atg atc tcc cgg acc cct gag gtc aca tgc gtg gtg gtg gac gtg agc     864
Met Ile Ser Arg Thr Pro Glu Val Thr Cys Val Val Val Asp Val Ser
        275                 280                 285 cac gaa gac cct gag gtc aag ttc aac tgg tac gtg gac ggc gtg gag     912
```

```
                                                                         960
gtg cat aat gcc aag aca aag ccc cgg gag gag cag tac aac agc acg
Val His Asn Ala Lys Thr Lys Pro Arg Glu Glu Gln Tyr Asn Ser Thr
305             310                 315                 320

1008
tac cgg gtg gtc agc gtc ctc acc gtc ctg cac cag gac tgg ctg aat
Tyr Arg Val Val Ser Val Leu Thr Val Leu His Gln Asp Trp Leu Asn
                325                 330                 335

1056
ggc aag gag tac aag tgc aag gtc tcc aac aaa gcc ctc cca gcc ccc
Gly Lys Glu Tyr Lys Cys Lys Val Ser Asn Lys Ala Leu Pro Ala Pro
            340                 345                 350

1104
atc gag aaa acc atc tcc aaa gcc aaa ggc cag ccc cgg gaa cca cag
Ile Glu Lys Thr Ile Ser Lys Ala Lys Gly Gln Pro Arg Glu Pro Gln
        355                 360                 365

1152
gtg tac acc ctg ccc cca tcc cgg gag gag atg acc aag aac cag gtc
Val Tyr Thr Leu Pro Pro Ser Arg Glu Glu Met Thr Lys Asn Gln Val
370                 375                 380

1200
agc ctg acc tgc ctg gtc aaa ggc ttc tat ccc agc gac atc gcc gtg
Ser Leu Thr Cys Leu Val Lys Gly Phe Tyr Pro Ser Asp Ile Ala Val
385                 390                 395                 400

1248
gag tgg gag agc aat ggc cag ccc gag aac aac tac aag acc acc cct
Glu Trp Glu Ser Asn Gly Gln Pro Glu Asn Asn Tyr Lys Thr Thr Pro
                405                 410                 415

1296
ccc gtg ctg gac tcc gac ggc tcc ttc ttc ctc tac agc aag ctc acc
Pro Val Leu Asp Ser Asp Gly Ser Phe Phe Leu Tyr Ser Lys Leu Thr
            420                 425                 430

1344
gtg gac aag agc agg tgg cag cag ggc aac gtc ttc tca tgc tcc gtg
Val Asp Lys Ser Arg Trp Gln Gln Gly Asn Val Phe Ser Cys Ser Val
        435                 440                 445

1392
atg cat gag gct ctg cac aac cac tac acc cag aag agc ctc tcc ctg
Met His Glu Ala Leu His Asn His Tyr Thr Gln Lys Ser Leu Ser Leu
450                 455                 460

1407
tct ccc ggc aaa tga
Ser Pro Gly Lys
465

<210> SEQ ID NO 107
<211> LENGTH: 468
<212> TYPE: PRT
<213> ORGANISM: Artificial
<220> FEATURE:
<223> OTHER INFORMATION: Synthetic Construct

<400> SEQUENCE: 107

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr His Tyr Ser Met His Trp Val Arg Gln Ala Pro Gly Gln Gly Leu
    50                  55                  60

Glu Trp Met Gly Trp Ile Asn Thr Tyr Thr Gly Glu Pro Thr Tyr Ala
65                  70                  75                  80

Asp Asp Phe Lys Gly Arg Val Thr Ile Thr Ala Asp Thr Ser Thr Ser
                85                  90                  95

Thr Ala Tyr Leu Glu Leu Ser Ser Leu Arg Ser Glu Asp Thr Ala Val
            100                 105                 110

Tyr Tyr Cys Ala Thr Tyr Tyr Arg Tyr Glu Arg Asp Phe Asp Tyr Trp
```

```
            115                 120                 125
Gly Gln Gly Thr Leu Val Thr Val Ser Ser Ala Ser Thr Lys Gly Pro
        130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
450                 455                 460

Ser Pro Gly Lys
465

<210> SEQ ID NO 108
<211> LENGTH: 15
<212> TYPE: DNA
<213> ORGANISM: Artificial
<220> FEATURE:
<223> OTHER INFORMATION: hSH348-1-T1H CDRH1
<220> FEATURE:
<221> NAME/KEY: CDS
<222> LOCATION: (1)..(15)
```

```
<400> SEQUENCE: 108 cac tac agc atg cac                                          15
His Tyr Ser Met His
1               5

<210> SEQ ID NO 109
<211> LENGTH: 5
<212> TYPE: PRT
<213> ORGANISM: Artificial
<220> FEATURE:
<223> OTHER INFORMATION: Synthetic Construct

<400> SEQUENCE: 109

His Tyr Ser Met His
1               5

<210> SEQ ID NO 110
<211> LENGTH: 51
<212> TYPE: DNA
<213> ORGANISM: Artificial
<220> FEATURE:
<223> OTHER INFORMATION: hSH348-1-T1H_CDRH2
<220> FEATURE:
<221> NAME/KEY: CDS
<222> LOCATION: (1)..(51)

<400> SEQUENCE: 110 tgg atc aac acc tac acc ggc gag ccc acc tac gcc gac gac ttc aag   48
Trp Ile Asn Thr Tyr Thr Gly Glu Pro Thr Tyr Ala Asp Asp Phe Lys
1               5                   10                  15 ggc                                                          51
Gly

<210> SEQ ID NO 111
<211> LENGTH: 17
<212> TYPE: PRT
<213> ORGANISM: Artificial
<220> FEATURE:
<223> OTHER INFORMATION: Synthetic Construct

<400> SEQUENCE: 111

Trp Ile Asn Thr Tyr Thr Gly Glu Pro Thr Tyr Ala Asp Asp Phe Lys
1               5                   10                  15

Gly

<210> SEQ ID NO 112
<211> LENGTH: 30
<212> TYPE: DNA
<213> ORGANISM: Artificial
<220> FEATURE:
<223> OTHER INFORMATION: hSH348-1-T1H CDRH3
<220> FEATURE:
<221> NAME/KEY: CDS
<222> LOCATION: (1)..(30)

<400> SEQUENCE: 112 tac tac cgg tac gag cgg gac ttc gac tac                      30
Tyr Tyr Arg Tyr Glu Arg Asp Phe Asp Tyr
1               5                   10

<210> SEQ ID NO 113
<211> LENGTH: 10
<212> TYPE: PRT
<213> ORGANISM: Artificial
<220> FEATURE:
<223> OTHER INFORMATION: Synthetic Construct
```

<400> SEQUENCE: 113

Tyr Tyr Arg Tyr Glu Arg Asp Phe Asp Tyr
1               5                   10

<210> SEQ ID NO 114
<211> LENGTH: 1407
<212> TYPE: DNA
<213> ORGANISM: Artificial
<220> FEATURE:
<223> OTHER INFORMATION: hSH348-1-T3H
<220> FEATURE:
<221> NAME/KEY: CDS
<222> LOCATION: (1)..(1407)
<220> FEATURE:
<221> NAME/KEY: sig_peptide
<222> LOCATION: (1)..(57)

<400> SEQUENCE: 114

```
atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc cag atc cag ctg gtg cag agc ggc gcc gag gtg aag aag      96
Val Leu Ser Gln Ile Gln Leu Val Gln Ser Gly Ala Glu Val Lys Lys
            20                  25                  30 ccc ggc agc agc gtg aag gtg agc tgc aag gcc agc ggc tac acc ttc     144
Pro Gly Ser Ser Val Lys Val Ser Cys Lys Ala Ser Gly Tyr Thr Phe
        35                  40                  45 acc cac tac agc atg cac tgg gtg cgg cag gcc ccc ggc cag ggc ctg     192
Thr His Tyr Ser Met His Trp Val Arg Gln Ala Pro Gly Gln Gly Leu
    50                  55                  60 aag tgg atg ggc tgg atc aac acc tac acc ggc gag ccc acc tac gcc     240
Lys Trp Met Gly Trp Ile Asn Thr Tyr Thr Gly Glu Pro Thr Tyr Ala
65                  70                  75                  80 gac gac ttc aag ggc cgg ttc gcc ttc agc ctg gac acc tcc acc tcc     288
Asp Asp Phe Lys Gly Arg Phe Ala Phe Ser Leu Asp Thr Ser Thr Ser
                85                  90                  95 acc gcc tac ctg gaa ctg agc agc ctg cgg agc gag gac acc gcc gtg     336
Thr Ala Tyr Leu Glu Leu Ser Ser Leu Arg Ser Glu Asp Thr Ala Val
            100                 105                 110 tac tac tgc gcc acc tac tac cgg tac gag cgg gac ttc gac tac tgg     384
Tyr Tyr Cys Ala Thr Tyr Tyr Arg Tyr Glu Arg Asp Phe Asp Tyr Trp
        115                 120                 125 ggc cag ggc acc ctg gtg acc gtg agc tca gcc tcc acc aag ggc cca     432
Gly Gln Gly Thr Leu Val Thr Val Ser Ser Ala Ser Thr Lys Gly Pro
    130                 135                 140 agc gtc ttc ccc ctg gca ccc tcc tcc aag agc acc tct ggc ggc aca     480
Ser Val Phe Pro Leu Ala Pro Ser Ser Lys Ser Thr Ser Gly Gly Thr
145                 150                 155                 160 gcc gcc ctg ggc tgc ctg gtc aag gac tac ttc ccc gaa ccc gtg acc     528
Ala Ala Leu Gly Cys Leu Val Lys Asp Tyr Phe Pro Glu Pro Val Thr
                165                 170                 175 gtg agc tgg aac tca ggc gcc ctg acc agc ggc gtg cac acc ttc ccc     576
Val Ser Trp Asn Ser Gly Ala Leu Thr Ser Gly Val His Thr Phe Pro
            180                 185                 190 gct gtc ctg cag tcc tca gga ctc tac tcc ctc agc agc gtg gtg acc     624
Ala Val Leu Gln Ser Ser Gly Leu Tyr Ser Leu Ser Ser Val Val Thr
        195                 200                 205 gtg ccc tcc agc agc ttg ggc acc cag acc tac atc tgc aac gtg aat     672
Val Pro Ser Ser Ser Leu Gly Thr Gln Thr Tyr Ile Cys Asn Val Asn
    210                 215                 220 cac aag ccc agc aac acc aag gtg gac aag aga gtt gag ccc aaa tct     720
His Lys Pro Ser Asn Thr Lys Val Asp Lys Arg Val Glu Pro Lys Ser
```

|  |  |  |  |  |  |  |  |  |  |  |  |  |  |  |  |
|---|---|---|---|---|---|---|---|---|---|---|---|---|---|---|---|
| 225 | | | | 230 | | | | 235 | | | | 240 | | | |
| tgt | gac | aaa | act | cac | aca | tgc | cca | ccc | tgc | cca | gca | cct | gaa | ctc | ctg | 768 |
| Cys | Asp | Lys | Thr | His | Thr | Cys | Pro | Pro | Cys | Pro | Ala | Pro | Glu | Leu | Leu |
| | | | 245 | | | | | 250 | | | | | 255 | | |
| ggg | gga | ccc | tca | gtc | ttc | ctc | ttc | ccc | cca | aaa | ccc | aag | gac | acc | ctc | 816 |
| Gly | Gly | Pro | Ser | Val | Phe | Leu | Phe | Pro | Pro | Lys | Pro | Lys | Asp | Thr | Leu |
| | | | 260 | | | | | 265 | | | | | 270 | | |
| atg | atc | tcc | cgg | acc | cct | gag | gtc | aca | tgc | gtg | gtg | gtg | gac | gtg | agc | 864 |
| Met | Ile | Ser | Arg | Thr | Pro | Glu | Val | Thr | Cys | Val | Val | Val | Asp | Val | Ser |
| | | | 275 | | | | | 280 | | | | | 285 | | |
| cac | gaa | gac | cct | gag | gtc | aag | ttc | aac | tgg | tac | gtg | gac | ggc | gtg | gag | 912 |
| His | Glu | Asp | Pro | Glu | Val | Lys | Phe | Asn | Trp | Tyr | Val | Asp | Gly | Val | Glu |
| | 290 | | | | | 295 | | | | | 300 | | | | |
| gtg | cat | aat | gcc | aag | aca | aag | ccc | cgg | gag | gag | cag | tac | aac | agc | acg | 960 |
| Val | His | Asn | Ala | Lys | Thr | Lys | Pro | Arg | Glu | Glu | Gln | Tyr | Asn | Ser | Thr |
| 305 | | | | | 310 | | | | | 315 | | | | | 320 |
| tac | cgg | gtg | gtc | agc | gtc | ctc | acc | gtc | ctg | cac | cag | gac | tgg | ctg | aat | 1008 |
| Tyr | Arg | Val | Val | Ser | Val | Leu | Thr | Val | Leu | His | Gln | Asp | Trp | Leu | Asn |
| | | | | 325 | | | | | 330 | | | | | 335 | |
| ggc | aag | gag | tac | aag | tgc | aag | gtc | tcc | aac | aaa | gcc | ctc | cca | gcc | ccc | 1056 |
| Gly | Lys | Glu | Tyr | Lys | Cys | Lys | Val | Ser | Asn | Lys | Ala | Leu | Pro | Ala | Pro |
| | | | 340 | | | | | 345 | | | | | 350 | | |
| atc | gag | aaa | acc | atc | tcc | aaa | gcc | aaa | ggc | cag | ccc | cgg | gaa | cca | cag | 1104 |
| Ile | Glu | Lys | Thr | Ile | Ser | Lys | Ala | Lys | Gly | Gln | Pro | Arg | Glu | Pro | Gln |
| | | | 355 | | | | | 360 | | | | | 365 | | |
| gtg | tac | acc | ctg | ccc | cca | tcc | cgg | gag | gag | atg | acc | aag | aac | cag | gtc | 1152 |
| Val | Tyr | Thr | Leu | Pro | Pro | Ser | Arg | Glu | Glu | Met | Thr | Lys | Asn | Gln | Val |
| | 370 | | | | | 375 | | | | | 380 | | | | |
| agc | ctg | acc | tgc | ctg | gtc | aaa | ggc | ttc | tat | ccc | agc | gac | atc | gcc | gtg | 1200 |
| Ser | Leu | Thr | Cys | Leu | Val | Lys | Gly | Phe | Tyr | Pro | Ser | Asp | Ile | Ala | Val |
| 385 | | | | | 390 | | | | | 395 | | | | | 400 |
| gag | tgg | gag | agc | aat | ggc | cag | ccc | gag | aac | aac | tac | aag | acc | acc | cct | 1248 |
| Glu | Trp | Glu | Ser | Asn | Gly | Gln | Pro | Glu | Asn | Asn | Tyr | Lys | Thr | Thr | Pro |
| | | | | 405 | | | | | 410 | | | | | 415 | |
| ccc | gtg | ctg | gac | tcc | gac | ggc | tcc | ttc | ttc | ctc | tac | agc | aag | ctc | acc | 1296 |
| Pro | Val | Leu | Asp | Ser | Asp | Gly | Ser | Phe | Phe | Leu | Tyr | Ser | Lys | Leu | Thr |
| | | | 420 | | | | | 425 | | | | | 430 | | |
| gtg | gac | aag | agc | agg | tgg | cag | cag | ggc | aac | gtc | ttc | tca | tgc | tcc | gtg | 1344 |
| Val | Asp | Lys | Ser | Arg | Trp | Gln | Gln | Gly | Asn | Val | Phe | Ser | Cys | Ser | Val |
| | | | 435 | | | | | 440 | | | | | 445 | | |
| atg | cat | gag | gct | ctg | cac | aac | cac | tac | acc | cag | aag | agc | ctc | tcc | ctg | 1392 |
| Met | His | Glu | Ala | Leu | His | Asn | His | Tyr | Thr | Gln | Lys | Ser | Leu | Ser | Leu |
| | 450 | | | | | 455 | | | | | 460 | | | | |
| tct | ccc | ggc | aaa | tga | | | | | | | | | | | | 1407 |
| Ser | Pro | Gly | Lys | | | | | | | | | | | | |
| 465 | | | | | | | | | | | | | | | | |

<210> SEQ ID NO 115
<211> LENGTH: 468
<212> TYPE: PRT
<213> ORGANISM: Artificial
<220> FEATURE:
<223> OTHER INFORMATION: Synthetic Construct

<400> SEQUENCE: 115

Met Lys His Leu Trp Phe Phe Leu Leu Leu Val Ala Ala Pro Arg Trp
1               5                   10                  15

Val Leu Ser Gln Ile Gln Leu Val Gln Ser Gly Ala Glu Val Lys Lys
            20                  25                  30

Pro Gly Ser Ser Val Lys Val Ser Cys Lys Ala Ser Gly Tyr Thr Phe

-continued

```
                35                  40                  45
Thr His Tyr Ser Met His Trp Val Arg Gln Ala Pro Gly Gln Gly Leu
 50                  55                  60

Lys Trp Met Gly Trp Ile Asn Thr Tyr Thr Gly Glu Pro Thr Tyr Ala
 65                  70                  75                  80

Asp Asp Phe Lys Gly Arg Phe Ala Phe Ser Leu Asp Thr Ser Thr Ser
                 85                  90                  95

Thr Ala Tyr Leu Glu Leu Ser Ser Leu Arg Ser Glu Asp Thr Ala Val
            100                 105                 110

Tyr Tyr Cys Ala Thr Tyr Tyr Arg Tyr Glu Arg Asp Phe Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460
```

```
Ser Pro Gly Lys
465

<210> SEQ ID NO 116
<211> LENGTH: 15
<212> TYPE: DNA
<213> ORGANISM: Artificial
<220> FEATURE:
<223> OTHER INFORMATION: hSH348-1-T3H CDRH1
<220> FEATURE:
<221> NAME/KEY: CDS
<222> LOCATION: (1)..(15)

<400> SEQUENCE: 116 cac tac agc atg cac                                                   15
His Tyr Ser Met His
1               5

<210> SEQ ID NO 117
<211> LENGTH: 5
<212> TYPE: PRT
<213> ORGANISM: Artificial
<220> FEATURE:
<223> OTHER INFORMATION: Synthetic Construct

<400> SEQUENCE: 117

His Tyr Ser Met His
1               5

<210> SEQ ID NO 118
<211> LENGTH: 51
<212> TYPE: DNA
<213> ORGANISM: Artificial
<220> FEATURE:
<223> OTHER INFORMATION: hSH348-1-T3H CDRH2
<220> FEATURE:
<221> NAME/KEY: CDS
<222> LOCATION: (1)..(51)

<400> SEQUENCE: 118 tgg atc aac acc tac acc ggc gag ccc acc tac gcc gac gac ttc aag      48
Trp Ile Asn Thr Tyr Thr Gly Glu Pro Thr Tyr Ala Asp Asp Phe Lys
1               5                   10                  15 ggc                                                                  51
Gly

<210> SEQ ID NO 119
<211> LENGTH: 17
<212> TYPE: PRT
<213> ORGANISM: Artificial
<220> FEATURE:
<223> OTHER INFORMATION: Synthetic Construct

<400> SEQUENCE: 119

Trp Ile Asn Thr Tyr Thr Gly Glu Pro Thr Tyr Ala Asp Asp Phe Lys
1               5                   10                  15

Gly

<210> SEQ ID NO 120
<211> LENGTH: 30
<212> TYPE: DNA
<213> ORGANISM: Artificial
<220> FEATURE:
<223> OTHER INFORMATION: hSH348-1-T3H CDRH3
<220> FEATURE:
<221> NAME/KEY: CDS
<222> LOCATION: (1)..(30)
```

<400> SEQUENCE: 120

```
tac tac cgg tac gag cgg gac ttc gac tac                          30
Tyr Tyr Arg Tyr Glu Arg Asp Phe Asp Tyr
1               5                   10
```

<210> SEQ ID NO 121
<211> LENGTH: 10
<212> TYPE: PRT
<213> ORGANISM: Artificial
<220> FEATURE:
<223> OTHER INFORMATION: Synthetic Construct

<400> SEQUENCE: 121

```
Tyr Tyr Arg Tyr Glu Arg Asp Phe Asp Tyr
1               5                   10
```

<210> SEQ ID NO 122
<211> LENGTH: 720
<212> TYPE: DNA
<213> ORGANISM: Artificial
<220> FEATURE:
<223> OTHER INFORMATION: hSH357-1-T1L
<220> FEATURE:
<221> NAME/KEY: CDS
<222> LOCATION: (1)..(720)
<220> FEATURE:
<221> NAME/KEY: sig_peptide
<222> LOCATION: (1)..(60)

<400> SEQUENCE: 122

```
atg gtg ctg cag acc cag gtg ttc atc tcc ctg ctg ctg tgg atc tcc     48
Met Val Leu Gln Thr Gln Val Phe Ile Ser Leu Leu Leu Trp Ile Ser
1               5                   10                  15 ggc gca tat ggc gac ata gtg atg acc cag agc ccc ctg agc ctg ccc     96
Gly Ala Tyr Gly Asp Ile Val Met Thr Gln Ser Pro Leu Ser Leu Pro
                20                  25                  30 gtg acc ccc ggc gag ccc gcc agc atc agc tgc cgg agc agc cag agc    144
Val Thr Pro Gly Glu Pro Ala Ser Ile Ser Cys Arg Ser Ser Gln Ser
            35                  40                  45 atc gtg cac agc agc ggc atc acc tac ctg gag tgg tac ctg cag aag    192
Ile Val His Ser Ser Gly Ile Thr Tyr Leu Glu Trp Tyr Leu Gln Lys
        50                  55                  60 ccc ggc cag agc ccc cag ctg ctg atc tac aag gtg agc aac cgg ttc    240
Pro Gly Gln Ser Pro Gln Leu Leu Ile Tyr Lys Val Ser Asn Arg Phe
65                  70                  75                  80 agc ggc gtg ccc gac cgg ttc agc ggc agc ggc agc ggc acc gac ttc    288
Ser Gly Val Pro Asp Arg Phe Ser Gly Ser Gly Ser Gly Thr Asp Phe
                85                  90                  95 acc ctg aag atc agc cgg gtg gag gcc gag gac gtg ggc gtg tac tac    336
Thr Leu Lys Ile Ser Arg Val Glu Ala Glu Asp Val Gly Val Tyr Tyr
                100                 105                 110 tgc ttc cag ggc agc cac gtg ccc tac acc ttc ggc cag ggc acc aag    384
Cys Phe Gln Gly Ser His Val Pro Tyr Thr Phe Gly Gln Gly Thr Lys
            115                 120                 125 gtg gag atc aag cgt acg gtg gcc gcc ccc tcc gtg ttc atc ttc ccc    432
Val Glu Ile Lys Arg Thr Val Ala Ala Pro Ser Val Phe Ile Phe Pro
        130                 135                 140 ccc tcc gac gag cag ctg aag tcc ggc acc gcc tcc gtg gtg tgc ctg    480
Pro Ser Asp Glu Gln Leu Lys Ser Gly Thr Ala Ser Val Val Cys Leu
145                 150                 155                 160 ctg aat aac ttc tac ccc aga gag gcc aag gtg cag tgg aag gtg gac    528
Leu Asn Asn Phe Tyr Pro Arg Glu Ala Lys Val Gln Trp Lys Val Asp
                165                 170                 175
```

```
aac gcc ctg cag tcc ggg aac tcc cag gag agc gtg acc gag cag gac      576
Asn Ala Leu Gln Ser Gly Asn Ser Gln Glu Ser Val Thr Glu Gln Asp
        180                 185                 190 agc aag gac agc acc tac agc ctg agc agc acc ctg acc ctg agc aaa      624
Ser Lys Asp Ser Thr Tyr Ser Leu Ser Ser Thr Leu Thr Leu Ser Lys
    195                 200                 205 gcc gac tac gag aag cac aag gtg tac gcc tgc gag gtg acc cac cag      672
Ala Asp Tyr Glu Lys His Lys Val Tyr Ala Cys Glu Val Thr His Gln
210                 215                 220 ggc ctg agc tcc ccc gtc acc aag agc ttc aac agg ggg gag tgt tag      720
Gly Leu Ser Ser Pro Val Thr Lys Ser Phe Asn Arg Gly Glu Cys
225                 230                 235

<210> SEQ ID NO 123
<211> LENGTH: 239
<212> TYPE: PRT
<213> ORGANISM: Artificial
<220> FEATURE:
<223> OTHER INFORMATION: Synthetic Construct

<400> SEQUENCE: 123

Met Val Leu Gln Thr Gln Val Phe Ile Ser Leu Leu Trp Ile Ser
1               5                   10                  15

Gly Ala Tyr Gly Asp Ile Val Met Thr Gln Ser Pro Leu Ser Leu Pro
                20                  25                  30

Val Thr Pro Gly Glu Pro Ala Ser Ile Ser Cys Arg Ser Ser Gln Ser
            35                  40                  45

Ile Val His Ser Ser Gly Ile Thr Tyr Leu Glu Trp Tyr Leu Gln Lys
    50                  55                  60

Pro Gly Gln Ser Pro Gln Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Phe Gln Gly Ser His Val Pro Tyr Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 124
<211> LENGTH: 48
<212> TYPE: DNA
<213> ORGANISM: Artificial
<220> FEATURE:
<223> OTHER INFORMATION: hSH357-1-T1L CDRL1
```

```
<220> FEATURE:
<221> NAME/KEY: CDS
<222> LOCATION: (1)..(48)

<400> SEQUENCE: 124 cgg agc agc cag agc atc gtg cac agc agc ggc atc acc tac ctg gag    48
Arg Ser Ser Gln Ser Ile Val His Ser Ser Gly Ile Thr Tyr Leu Glu
1               5                   10                  15

<210> SEQ ID NO 125
<211> LENGTH: 16
<212> TYPE: PRT
<213> ORGANISM: Artificial
<220> FEATURE:
<223> OTHER INFORMATION: Synthetic Construct

<400> SEQUENCE: 125

Arg Ser Ser Gln Ser Ile Val His Ser Ser Gly Ile Thr Tyr Leu Glu
1               5                   10                  15

<210> SEQ ID NO 126
<211> LENGTH: 21
<212> TYPE: DNA
<213> ORGANISM: Artificial
<220> FEATURE:
<223> OTHER INFORMATION: hSH357-1-T1L CDRL2
<220> FEATURE:
<221> NAME/KEY: CDS
<222> LOCATION: (1)..(21)

<400> SEQUENCE: 126 aag gtg agc aac cgg ttc agc                                        21
Lys Val Ser Asn Arg Phe Ser
1               5

<210> SEQ ID NO 127
<211> LENGTH: 7
<212> TYPE: PRT
<213> ORGANISM: Artificial
<220> FEATURE:
<223> OTHER INFORMATION: Synthetic Construct

<400> SEQUENCE: 127

Lys Val Ser Asn Arg Phe Ser
1               5

<210> SEQ ID NO 128
<211> LENGTH: 24
<212> TYPE: DNA
<213> ORGANISM: Artificial
<220> FEATURE:
<223> OTHER INFORMATION: hSH357-1-T1L_CDRL3
<220> FEATURE:
<221> NAME/KEY: CDS
<222> LOCATION: (1)..(24)

<400> SEQUENCE: 128 ttc cag ggc agc cac gtg ccc tac                                    24
Phe Gln Gly Ser His Val Pro Tyr
1               5

<210> SEQ ID NO 129
<211> LENGTH: 8
<212> TYPE: PRT
<213> ORGANISM: Artificial
<220> FEATURE:
<223> OTHER INFORMATION: Synthetic Construct

<400> SEQUENCE: 129
```

```
Phe Gln Gly Ser His Val Pro Tyr
1               5
```

```
<210> SEQ ID NO 130
<211> LENGTH: 720
<212> TYPE: DNA
<213> ORGANISM: Artificial
<220> FEATURE:
<223> OTHER INFORMATION: hSH357-1-T3L
<220> FEATURE:
<221> NAME/KEY: CDS
<222> LOCATION: (1)..(720)
<220> FEATURE:
<221> NAME/KEY: sig_peptide
<222> LOCATION: (1)..(60)

<400> SEQUENCE: 130 atg gtg ctg cag acc cag gtg ttc atc tcc ctg ctg ctg tgg atc tcc    48
Met Val Leu Gln Thr Gln Val Phe Ile Ser Leu Leu Leu Trp Ile Ser
1               5                   10                  15 ggc gca tat ggc gac gtg ctg atg acc cag agc ccc ctg agc ctg ccc    96
Gly Ala Tyr Gly Asp Val Leu Met Thr Gln Ser Pro Leu Ser Leu Pro
            20                  25                  30 gtg acc ccc ggc gag ccc gcc agc atc agc tgc cgg agc agc cag agc   144
Val Thr Pro Gly Glu Pro Ala Ser Ile Ser Cys Arg Ser Ser Gln Ser
        35                  40                  45 atc gtg cac agc agc ggc atc acc tac ctg gag tgg tac ctg cag aag   192
Ile Val His Ser Ser Gly Ile Thr Tyr Leu Glu Trp Tyr Leu Gln Lys
    50                  55                  60 ccc ggc cag agc ccc cag ctg ctg atc tac aag gtg agc aac cgg ttc   240
Pro Gly Gln Ser Pro Gln Leu Leu Ile Tyr Lys Val Ser Asn Arg Phe
65                  70                  75                  80 agc ggc gtg ccc gac cgg ttc agc ggc agc ggc agc ggc acc gac ttc   288
Ser Gly Val Pro Asp Arg Phe Ser Gly Ser Gly Ser Gly Thr Asp Phe
                85                  90                  95 acc ctg aag atc agc cgg gtg gag gcc gag gac gtg ggc gtg tac tac   336
Thr Leu Lys Ile Ser Arg Val Glu Ala Glu Asp Val Gly Val Tyr Tyr
            100                 105                 110 tgc ttc cag ggc agc cac gtg ccc tac acc ttc ggc cag ggc acc aag   384
Cys Phe Gln Gly Ser His Val Pro Tyr Thr Phe Gly Gln Gly Thr Lys
        115                 120                 125 gtg gag atc aag cgt acg gtg gcc gcc ccc tcc gtg ttc atc ttc ccc   432
Val Glu Ile Lys Arg Thr Val Ala Ala Pro Ser Val Phe Ile Phe Pro
    130                 135                 140 ccc tcc gac gag cag ctg aag tcc ggc acc gcc tcc gtg gtg tgc ctg   480
Pro Ser Asp Glu Gln Leu Lys Ser Gly Thr Ala Ser Val Val Cys Leu
145                 150                 155                 160 ctg aat aac ttc tac ccc aga gag gcc aag gtg cag tgg aag gtg gac   528
Leu Asn Asn Phe Tyr Pro Arg Glu Ala Lys Val Gln Trp Lys Val Asp
                165                 170                 175 aac gcc ctg cag tcc ggg aac tcc cag gag agc gtg acc gag cag gac   576
Asn Ala Leu Gln Ser Gly Asn Ser Gln Glu Ser Val Thr Glu Gln Asp
            180                 185                 190 agc aag gac agc acc tac agc ctg agc agc acc ctg acc ctg agc aaa   624
Ser Lys Asp Ser Thr Tyr Ser Leu Ser Ser Thr Leu Thr Leu Ser Lys
        195                 200                 205 gcc gac tac gag aag cac aag gtg tac gcc tgc gag gtg acc cac cag   672
Ala Asp Tyr Glu Lys His Lys Val Tyr Ala Cys Glu Val Thr His Gln
    210                 215                 220 ggc ctg agc tcc ccc gtc acc aag agc ttc aac agg ggg gag tgt tag   720
Gly Leu Ser Ser Pro Val Thr Lys Ser Phe Asn Arg Gly Glu Cys
225                 230                 235
```

<210> SEQ ID NO 131
<211> LENGTH: 239
<212> TYPE: PRT
<213> ORGANISM: Artificial
<220> FEATURE:
<223> OTHER INFORMATION: Synthetic Construct

<400> SEQUENCE: 131

Met Val Leu Gln Thr Gln Val Phe Ile Ser Leu Leu Trp Ile Ser
1               5                   10                  15

Gly Ala Tyr Gly Asp Val Leu Met Thr Gln Ser Pro Leu Ser Leu Pro
            20                  25                  30

Val Thr Pro Gly Glu Pro Ala Ser Ile Ser Cys Arg Ser Ser Gln Ser
        35                  40                  45

Ile Val His Ser Ser Gly Ile Thr Tyr Leu Glu Trp Tyr Leu Gln Lys
    50                  55                  60

Pro Gly Gln Ser Pro Gln Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Phe Gln Gly Ser His Val Pro Tyr Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 132
<211> LENGTH: 48
<212> TYPE: DNA
<213> ORGANISM: Artificial
<220> FEATURE:
<223> OTHER INFORMATION: hSH357-1-T3L CDRL1
<220> FEATURE:
<221> NAME/KEY: CDS
<222> LOCATION: (1)..(48)

<400> SEQUENCE: 132 cgg agc agc cag agc atc gtg cac agc agc ggc atc acc tac ctg gag    48
Arg Ser Ser Gln Ser Ile Val His Ser Ser Gly Ile Thr Tyr Leu Glu
1               5                   10                  15

<210> SEQ ID NO 133
<211> LENGTH: 16
<212> TYPE: PRT
<213> ORGANISM: Artificial
<220> FEATURE:

<223> OTHER INFORMATION: Synthetic Construct

<400> SEQUENCE: 133

Arg Ser Ser Gln Ser Ile Val His Ser Ser Gly Ile Thr Tyr Leu Glu
1               5                   10                  15

<210> SEQ ID NO 134
<211> LENGTH: 21
<212> TYPE: DNA
<213> ORGANISM: Artificial
<220> FEATURE:
<223> OTHER INFORMATION: hSH357-1-T3L CDRL2
<220> FEATURE:
<221> NAME/KEY: CDS
<222> LOCATION: (1)..(21)

<400> SEQUENCE: 134 aag gtg agc aac cgg ttc agc                                      21
Lys Val Ser Asn Arg Phe Ser
1               5

<210> SEQ ID NO 135
<211> LENGTH: 7
<212> TYPE: PRT
<213> ORGANISM: Artificial
<220> FEATURE:
<223> OTHER INFORMATION: Synthetic Construct

<400> SEQUENCE: 135

Lys Val Ser Asn Arg Phe Ser
1               5

<210> SEQ ID NO 136
<211> LENGTH: 24
<212> TYPE: DNA
<213> ORGANISM: Artificial
<220> FEATURE:
<223> OTHER INFORMATION: hSH357-1-T3L CDRL3
<220> FEATURE:
<221> NAME/KEY: CDS
<222> LOCATION: (1)..(24)

<400> SEQUENCE: 136 ttc cag ggc agc cac gtg ccc tac                                  24
Phe Gln Gly Ser His Val Pro Tyr
1               5

<210> SEQ ID NO 137
<211> LENGTH: 8
<212> TYPE: PRT
<213> ORGANISM: Artificial
<220> FEATURE:
<223> OTHER INFORMATION: Synthetic Construct

<400> SEQUENCE: 137

Phe Gln Gly Ser His Val Pro Tyr
1               5

<210> SEQ ID NO 138
<211> LENGTH: 1407
<212> TYPE: DNA
<213> ORGANISM: Artificial
<220> FEATURE:
<223> OTHER INFORMATION: hSH357-1-T1H
<220> FEATURE:
<221> NAME/KEY: CDS
<222> LOCATION: (1)..(1407)
<220> FEATURE:
<221> NAME/KEY: sig_peptide

<222> LOCATION: (1)..(57)

<400> SEQUENCE: 138

```
atg aaa cac ctg tgg ttc ttc ctc ctg ctg gtg gca gct ccc aga tgg         48
Met Lys His Leu Trp Phe Phe Leu Leu Leu Val Ala Ala Pro Arg Trp
1               5                   10                  15 gtg ctg agc cag gtg cag ctg gtg cag tcc ggc gcc gag gtg aag aag         96
Val Leu Ser Gln Val Gln Leu Val Gln Ser Gly Ala Glu Val Lys Lys
            20                  25                  30 ccc ggc gcc tcc gtg aag gtg tcc tgt aag gcc tcc ggc tac acc ttc        144
Pro Gly Ala Ser Val Lys Val Ser Cys Lys Ala Ser Gly Tyr Thr Phe
        35                  40                  45 atc gac tac tcc atg cac tgg gtg agg cag gcc ccc ggc cag ggc ctg        192
Ile Asp Tyr Ser Met His Trp Val Arg Gln Ala Pro Gly Gln Gly Leu
    50                  55                  60 gag tgg atg ggc tgg atc aac acc tac acc ggc gag ccc acc tac tcc        240
Glu Trp Met Gly Trp Ile Asn Thr Tyr Thr Gly Glu Pro Thr Tyr Ser
65                  70                  75                  80 gac gac ttc aag ggc agg gtg acc atc acc gcc gac acc tcc acc agc        288
Asp Asp Phe Lys Gly Arg Val Thr Ile Thr Ala Asp Thr Ser Thr Ser
                85                  90                  95 acc gcc tac ctg gag ctg tcc tcc ctg agg tcc gag gac acc gcc gtg        336
Thr Ala Tyr Leu Glu Leu Ser Ser Leu Arg Ser Glu Asp Thr Ala Val
            100                 105                 110 tac tac tgt gcc acc tac tac agg tac gag agg gac ttc gac tac tgg        384
Tyr Tyr Cys Ala Thr Tyr Tyr Arg Tyr Glu Arg Asp Phe Asp Tyr Trp
        115                 120                 125 ggc cag ggc acc ctg gtg acg gtg agc tca gcc tcc acc aag ggc cca        432
Gly Gln Gly Thr Leu Val Thr Val Ser Ser Ala Ser Thr Lys Gly Pro
    130                 135                 140 agc gtc ttc ccc ctg gca ccc tcc tcc aag agc acc tct ggc ggc aca        480
Ser Val Phe Pro Leu Ala Pro Ser Ser Lys Ser Thr Ser Gly Gly Thr
145                 150                 155                 160 gcc gcc ctg ggc tgc ctg gtc aag gac tac ttc ccc gaa ccc gtg acc        528
Ala Ala Leu Gly Cys Leu Val Lys Asp Tyr Phe Pro Glu Pro Val Thr
                165                 170                 175 gtg agc tgg aac tca ggc gcc ctg acc agc ggc gtg cac acc ttc ccc        576
Val Ser Trp Asn Ser Gly Ala Leu Thr Ser Gly Val His Thr Phe Pro
            180                 185                 190 gct gtc ctg cag tcc tca gga ctc tac tcc ctc agc agc gtg gtg acc        624
Ala Val Leu Gln Ser Ser Gly Leu Tyr Ser Leu Ser Ser Val Val Thr
        195                 200                 205 gtg ccc tcc agc agc ttg ggc acc cag acc tac atc tgc aac gtg aat        672
Val Pro Ser Ser Ser Leu Gly Thr Gln Thr Tyr Ile Cys Asn Val Asn
    210                 215                 220 cac aag ccc agc aac acc aag gtg gac aag aga gtt gag ccc aaa tct        720
His Lys Pro Ser Asn Thr Lys Val Asp Lys Arg Val Glu Pro Lys Ser
225                 230                 235                 240 tgt gac aaa act cac aca tgc cca ccc tgc cca gca cct gaa ctc ctg        768
Cys Asp Lys Thr His Thr Cys Pro Pro Cys Pro Ala Pro Glu Leu Leu
                245                 250                 255 ggg gga ccc tca gtc ttc ctc ttc ccc cca aaa ccc aag gac acc ctc        816
Gly Gly Pro Ser Val Phe Leu Phe Pro Pro Lys Pro Lys Asp Thr Leu
            260                 265                 270 atg atc tcc cgg acc cct gag gtc aca tgc gtg gtg gtg gac gtg agc        864
Met Ile Ser Arg Thr Pro Glu Val Thr Cys Val Val Val Asp Val Ser
        275                 280                 285 cac gaa gac cct gag gtc aag ttc aac tgg tac gtg gac ggc gtg gag        912
His Glu Asp Pro Glu Val Lys Phe Asn Trp Tyr Val Asp Gly Val Glu
    290                 295                 300
```

```
gtg cat aat gcc aag aca aag ccc cgg gag gag cag tac aac agc acg      960
Val His Asn Ala Lys Thr Lys Pro Arg Glu Glu Gln Tyr Asn Ser Thr
305                 310                 315                 320 tac cgg gtg gtc agc gtc ctc acc gtc ctg cac cag gac tgg ctg aat     1008
Tyr Arg Val Val Ser Val Leu Thr Val Leu His Gln Asp Trp Leu Asn
                325                 330                 335 ggc aag gag tac aag tgc aag gtc tcc aac aaa gcc ctc cca gcc ccc     1056
Gly Lys Glu Tyr Lys Cys Lys Val Ser Asn Lys Ala Leu Pro Ala Pro
            340                 345                 350 atc gag aaa acc atc tcc aaa gcc aaa ggc cag ccc cgg gaa cca cag     1104
Ile Glu Lys Thr Ile Ser Lys Ala Lys Gly Gln Pro Arg Glu Pro Gln
        355                 360                 365 gtg tac acc ctg ccc cca tcc cgg gag gag atg acc aag aac cag gtc     1152
Val Tyr Thr Leu Pro Pro Ser Arg Glu Glu Met Thr Lys Asn Gln Val
    370                 375                 380 agc ctg acc tgc ctg gtc aaa ggc ttc tat ccc agc gac atc gcc gtg     1200
Ser Leu Thr Cys Leu Val Lys Gly Phe Tyr Pro Ser Asp Ile Ala Val
385                 390                 395                 400 gag tgg gag agc aat ggc cag ccc gag aac aac tac aag acc acc cct     1248
Glu Trp Glu Ser Asn Gly Gln Pro Glu Asn Asn Tyr Lys Thr Thr Pro
                405                 410                 415 ccc gtg ctg gac tcc gac ggc tcc ttc ttc ctc tac agc aag ctc acc     1296
Pro Val Leu Asp Ser Asp Gly Ser Phe Phe Leu Tyr Ser Lys Leu Thr
            420                 425                 430 gtg gac aag agc agg tgg cag cag ggc aac gtc ttc tca tgc tcc gtg     1344
Val Asp Lys Ser Arg Trp Gln Gln Gly Asn Val Phe Ser Cys Ser Val
        435                 440                 445 atg cat gag gct ctg cac aac cac tac acc cag aag agc ctc tcc ctg     1392
Met His Glu Ala Leu His Asn His Tyr Thr Gln Lys Ser Leu Ser Leu
    450                 455                 460 tct ccc ggc aaa tga                                                 1407
Ser Pro Gly Lys
465

<210> SEQ ID NO 139
<211> LENGTH: 468
<212> TYPE: PRT
<213> ORGANISM: Artificial
<220> FEATURE:
<223> OTHER INFORMATION: Synthetic Construct

<400> SEQUENCE: 139

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Ile Asp Tyr Ser Met His Trp Val Arg Gln Ala Pro Gly Gln Gly Leu
    50                  55                  60

Glu Trp Met Gly Trp Ile Asn Thr Tyr Thr Gly Glu Pro Thr Tyr Ser
65                  70                  75                  80

Asp Asp Phe Lys Gly Arg Val Thr Ile Thr Ala Asp Thr Ser Thr Ser
                85                  90                  95

Thr Ala Tyr Leu Glu Leu Ser Ser Leu Arg Ser Glu Asp Thr Ala Val
            100                 105                 110

Tyr Tyr Cys Ala Thr Tyr Tyr Arg Tyr Glu Arg Asp Phe Asp Tyr Trp
        115                 120                 125
```

Gly Gln Gly Thr Leu Val Thr Val Ser Ser Ala Ser Thr Lys Gly Pro
            130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
450                 455                 460

Ser Pro Gly Lys
465

<210> SEQ ID NO 140
<211> LENGTH: 18
<212> TYPE: DNA
<213> ORGANISM: Artificial
<220> FEATURE:
<223> OTHER INFORMATION: hSH357-1-T1H CDRH1
<220> FEATURE:
<221> NAME/KEY: CDS
<222> LOCATION: (1)..(18)

<400> SEQUENCE: 140

```
atc gac tac tcc atg cac                                              18
Ile Asp Tyr Ser Met His
1               5

<210> SEQ ID NO 141
<211> LENGTH: 6
<212> TYPE: PRT
<213> ORGANISM: Artificial
<220> FEATURE:
<223> OTHER INFORMATION: Synthetic Construct

<400> SEQUENCE: 141

Ile Asp Tyr Ser Met His
1               5

<210> SEQ ID NO 142
<211> LENGTH: 51
<212> TYPE: DNA
<213> ORGANISM: Artificial
<220> FEATURE:
<223> OTHER INFORMATION: hSH357-1-T1H CDRH2
<220> FEATURE:
<221> NAME/KEY: CDS
<222> LOCATION: (1)..(51)

<400> SEQUENCE: 142 tgg atc aac acc tac acc ggc gag ccc acc tac tcc gac gac ttc aag    48
Trp Ile Asn Thr Tyr Thr Gly Glu Pro Thr Tyr Ser Asp Asp Phe Lys
1               5                   10                  15 ggc                                                                  51
Gly

<210> SEQ ID NO 143
<211> LENGTH: 17
<212> TYPE: PRT
<213> ORGANISM: Artificial
<220> FEATURE:
<223> OTHER INFORMATION: Synthetic Construct

<400> SEQUENCE: 143

Trp Ile Asn Thr Tyr Thr Gly Glu Pro Thr Tyr Ser Asp Asp Phe Lys
1               5                   10                  15

Gly

<210> SEQ ID NO 144
<211> LENGTH: 30
<212> TYPE: DNA
<213> ORGANISM: Artificial
<220> FEATURE:
<223> OTHER INFORMATION: hSH357-1-T1H CDRH3
<220> FEATURE:
<221> NAME/KEY: CDS
<222> LOCATION: (1)..(30)

<400> SEQUENCE: 144 tac tac agg tac gag agg gac ttc gac tac                             30
Tyr Tyr Arg Tyr Glu Arg Asp Phe Asp Tyr
1               5                   10

<210> SEQ ID NO 145
<211> LENGTH: 10
<212> TYPE: PRT
<213> ORGANISM: Artificial
<220> FEATURE:
<223> OTHER INFORMATION: Synthetic Construct

<400> SEQUENCE: 145
```

Tyr Tyr Arg Tyr Glu Arg Asp Phe Asp Tyr
1               5                   10

<210> SEQ ID NO 146
<211> LENGTH: 1407
<212> TYPE: DNA
<213> ORGANISM: Artificial
<220> FEATURE:
<223> OTHER INFORMATION: hSH357-1-T3H
<220> FEATURE:
<221> NAME/KEY: CDS
<222> LOCATION: (1)..(1407)
<220> FEATURE:
<221> NAME/KEY: sig_peptide
<222> LOCATION: (1)..(57)

<400> SEQUENCE: 146

| | | |
|---|---|---|
| atg aaa cac ctg tgg ttc ttc ctc ctg ctg gtg gca gct ccc aga tgg<br>Met Lys His Leu Trp Phe Phe Leu Leu Leu Val Ala Ala Pro Arg Trp<br>1               5                   10                  15 | 48 |
| gtg ctg agc cag atc cag ctg gtg cag tcc ggc gcc gag gtg aag aag<br>Val Leu Ser Gln Ile Gln Leu Val Gln Ser Gly Ala Glu Val Lys Lys<br>            20                  25                  30 | 96 |
| ccc ggc gcc tcc gtg aag gtg tcc tgt aag gcc tcc ggc tac acc ttc<br>Pro Gly Ala Ser Val Lys Val Ser Cys Lys Ala Ser Gly Tyr Thr Phe<br>        35                  40                  45 | 144 |
| atc gac tac tcc atg cac tgg gtg agg cag gcc ccc ggc cag ggc ctg<br>Ile Asp Tyr Ser Met His Trp Val Arg Gln Ala Pro Gly Gln Gly Leu<br>    50                  55                  60 | 192 |
| aag tgg atg ggc tgg atc aac acc tac acc ggc gag ccc acc tac tcc<br>Lys Trp Met Gly Trp Ile Asn Thr Tyr Thr Gly Glu Pro Thr Tyr Ser<br>65                  70                  75                  80 | 240 |
| gac gac ttc aag ggc agg ttc gcc ttc tcc ctg gac acc tcc acc agc<br>Asp Asp Phe Lys Gly Arg Phe Ala Phe Ser Leu Asp Thr Ser Thr Ser<br>                85                  90                  95 | 288 |
| acc gcc tac ctg gag ctg tcc tcc ctg agg tcc gag gac acc gcc gtg<br>Thr Ala Tyr Leu Glu Leu Ser Ser Leu Arg Ser Glu Asp Thr Ala Val<br>            100                 105                 110 | 336 |
| tac tac tgt gcc acc tac tac agg tac gag agg gac ttc gac tac tgg<br>Tyr Tyr Cys Ala Thr Tyr Tyr Arg Tyr Glu Arg Asp Phe Asp Tyr Trp<br>        115                 120                 125 | 384 |
| ggc cag ggc acc ctg gtg acg gtg agc tca gcc tcc acc aag ggc cca<br>Gly Gln Gly Thr Leu Val Thr Val Ser Ser Ala Ser Thr Lys Gly Pro<br>    130                 135                 140 | 432 |
| agc gtc ttc ccc ctg gca ccc tcc tcc aag agc acc tct ggc ggc aca<br>Ser Val Phe Pro Leu Ala Pro Ser Ser Lys Ser Thr Ser Gly Gly Thr<br>145                 150                 155                 160 | 480 |
| gcc gcc ctg ggc tgc ctg gtc aag gac tac ttc ccc gaa ccc gtg acc<br>Ala Ala Leu Gly Cys Leu Val Lys Asp Tyr Phe Pro Glu Pro Val Thr<br>                165                 170                 175 | 528 |
| gtg agc tgg aac tca ggc gcc ctg acc agc ggc gtg cac acc ttc ccc<br>Val Ser Trp Asn Ser Gly Ala Leu Thr Ser Gly Val His Thr Phe Pro<br>            180                 185                 190 | 576 |
| gct gtc ctg cag tcc tca gga ctc tac tcc ctc agc agc gtg gtg acc<br>Ala Val Leu Gln Ser Ser Gly Leu Tyr Ser Leu Ser Ser Val Val Thr<br>        195                 200                 205 | 624 |
| gtg ccc tcc agc agc ttg ggc acc cag acc tac atc tgc aac gtg aat<br>Val Pro Ser Ser Ser Leu Gly Thr Gln Thr Tyr Ile Cys Asn Val Asn<br>    210                 215                 220 | 672 |
| cac aag ccc agc aac acc aag gtg gac aag aga gtt gag ccc aaa tct<br>His Lys Pro Ser Asn Thr Lys Val Asp Lys Arg Val Glu Pro Lys Ser<br>225                 230                 235                 240 | 720 |

```
tgt gac aaa act cac aca tgc cca ccc tgc cca gca cct gaa ctc ctg      768
Cys Asp Lys Thr His Thr Cys Pro Pro Cys Pro Ala Pro Glu Leu Leu
            245                 250                 255 ggg gga ccc tca gtc ttc ctc ttc ccc cca aaa ccc aag gac acc ctc      816
Gly Gly Pro Ser Val Phe Leu Phe Pro Pro Lys Pro Lys Asp Thr Leu
            260                 265                 270 atg atc tcc cgg acc cct gag gtc aca tgc gtg gtg gtg gac gtg agc      864
Met Ile Ser Arg Thr Pro Glu Val Thr Cys Val Val Val Asp Val Ser
            275                 280                 285 cac gaa gac cct gag gtc aag ttc aac tgg tac gtg gac ggc gtg gag      912
His Glu Asp Pro Glu Val Lys Phe Asn Trp Tyr Val Asp Gly Val Glu
            290                 295                 300 gtg cat aat gcc aag aca aag ccc cgg gag gag cag tac aac agc acg      960
Val His Asn Ala Lys Thr Lys Pro Arg Glu Glu Gln Tyr Asn Ser Thr
305                 310                 315                 320 tac cgg gtg gtc agc gtc ctc acc gtc ctg cac cag gac tgg ctg aat     1008
Tyr Arg Val Val Ser Val Leu Thr Val Leu His Gln Asp Trp Leu Asn
            325                 330                 335 ggc aag gag tac aag tgc aag gtc tcc aac aaa gcc ctc cca gcc ccc     1056
Gly Lys Glu Tyr Lys Cys Lys Val Ser Asn Lys Ala Leu Pro Ala Pro
            340                 345                 350 atc gag aaa acc atc tcc aaa gcc aaa ggc cag ccc cgg gaa cca cag     1104
Ile Glu Lys Thr Ile Ser Lys Ala Lys Gly Gln Pro Arg Glu Pro Gln
            355                 360                 365 gtg tac acc ctg ccc cca tcc cgg gag gag atg acc aag aac cag gtc     1152
Val Tyr Thr Leu Pro Pro Ser Arg Glu Glu Met Thr Lys Asn Gln Val
            370                 375                 380 agc ctg acc tgc ctg gtc aaa ggc ttc tat ccc agc gac atc gcc gtg     1200
Ser Leu Thr Cys Leu Val Lys Gly Phe Tyr Pro Ser Asp Ile Ala Val
385                 390                 395                 400 gag tgg gag agc aat ggc cag ccc gag aac aac tac aag acc acc cct     1248
Glu Trp Glu Ser Asn Gly Gln Pro Glu Asn Asn Tyr Lys Thr Thr Pro
            405                 410                 415 ccc gtg ctg gac tcc gac ggc tcc ttc ttc ctc tac agc aag ctc acc     1296
Pro Val Leu Asp Ser Asp Gly Ser Phe Phe Leu Tyr Ser Lys Leu Thr
            420                 425                 430 gtg gac aag agc agg tgg cag cag ggc aac gtc ttc tca tgc tcc gtg     1344
Val Asp Lys Ser Arg Trp Gln Gln Gly Asn Val Phe Ser Cys Ser Val
            435                 440                 445 atg cat gag gct ctg cac aac cac tac acc cag aag agc ctc tcc ctg     1392
Met His Glu Ala Leu His Asn His Tyr Thr Gln Lys Ser Leu Ser Leu
            450                 455                 460 tct ccc ggc aaa tga                                                 1407
Ser Pro Gly Lys
465

<210> SEQ ID NO 147
<211> LENGTH: 468
<212> TYPE: PRT
<213> ORGANISM: Artificial
<220> FEATURE:
<223> OTHER INFORMATION: Synthetic Construct

<400> SEQUENCE: 147

Met Lys His Leu Trp Phe Phe Leu Leu Leu Val Ala Ala Pro Arg Trp
1               5                   10                  15

Val Leu Ser Gln Ile Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45
```

```
Ile Asp Tyr Ser Met His Trp Val Arg Gln Ala Pro Gly Gln Gly Leu
 50                  55                  60

Lys Trp Met Gly Trp Ile Asn Thr Tyr Thr Gly Glu Pro Thr Tyr Ser
 65                  70                  75                  80

Asp Asp Phe Lys Gly Arg Phe Ala Phe Ser Leu Asp Thr Ser Thr Ser
                 85                  90                  95

Thr Ala Tyr Leu Glu Leu Ser Ser Leu Arg Ser Glu Asp Thr Ala Val
                100                 105                 110

Tyr Tyr Cys Ala Thr Tyr Tyr Arg Tyr Glu Arg Asp Phe Asp Tyr Trp
                115                 120                 125

Gly Gln Gly Thr Leu Val Thr Val Ser Ser Ala Ser Thr Lys Gly Pro
130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
                195                 200                 205

Val Pro Ser Ser Ser Leu Gly Thr Gln Thr Tyr Ile Cys Asn Val Asn
210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
                275                 280                 285

His Glu Asp Pro Glu Val Lys Phe Asn Trp Tyr Val Asp Gly Val Glu
290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
                355                 360                 365

Val Tyr Thr Leu Pro Pro Ser Arg Glu Glu Met Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
                435                 440                 445

Met His Glu Ala Leu His Asn His Tyr Thr Gln Lys Ser Leu Ser Leu
450                 455                 460

Ser Pro Gly Lys
```

```
<210> SEQ ID NO 148
<211> LENGTH: 18
<212> TYPE: DNA
<213> ORGANISM: Artificial
<220> FEATURE:
<223> OTHER INFORMATION: hSH357-1-T3H CDRH1
<220> FEATURE:
<221> NAME/KEY: CDS
<222> LOCATION: (1)..(18)

<400> SEQUENCE: 148 atc gac tac tcc atg cac                             18
Ile Asp Tyr Ser Met His
1               5

<210> SEQ ID NO 149
<211> LENGTH: 6
<212> TYPE: PRT
<213> ORGANISM: Artificial
<220> FEATURE:
<223> OTHER INFORMATION: Synthetic Construct

<400> SEQUENCE: 149

Ile Asp Tyr Ser Met His
1               5

<210> SEQ ID NO 150
<211> LENGTH: 51
<212> TYPE: DNA
<213> ORGANISM: Artificial
<220> FEATURE:
<223> OTHER INFORMATION: hSH357-1-T3H CDRH2
<220> FEATURE:
<221> NAME/KEY: CDS
<222> LOCATION: (1)..(51)

<400> SEQUENCE: 150 tgg atc aac acc tac acc ggc gag ccc acc tac tcc gac gac ttc aag    48
Trp Ile Asn Thr Tyr Thr Gly Glu Pro Thr Tyr Ser Asp Asp Phe Lys
1               5                   10                  15 ggc                                                 51
Gly

<210> SEQ ID NO 151
<211> LENGTH: 17
<212> TYPE: PRT
<213> ORGANISM: Artificial
<220> FEATURE:
<223> OTHER INFORMATION: Synthetic Construct

<400> SEQUENCE: 151

Trp Ile Asn Thr Tyr Thr Gly Glu Pro Thr Tyr Ser Asp Asp Phe Lys
1               5                   10                  15
Gly

<210> SEQ ID NO 152
<211> LENGTH: 30
<212> TYPE: DNA
<213> ORGANISM: Artificial
<220> FEATURE:
<223> OTHER INFORMATION: hSH357-1-T3H CDRH3
<220> FEATURE:
<221> NAME/KEY: CDS
<222> LOCATION: (1)..(30)

<400> SEQUENCE: 152
```

```
tac tac agg tac gag agg gac ttc gac tac                              30
Tyr Tyr Arg Tyr Glu Arg Asp Phe Asp Tyr
1               5                   10
```

<210> SEQ ID NO 153
<211> LENGTH: 10
<212> TYPE: PRT
<213> ORGANISM: Artificial
<220> FEATURE:
<223> OTHER INFORMATION: Synthetic Construct

<400> SEQUENCE: 153

```
Tyr Tyr Arg Tyr Glu Arg Asp Phe Asp Tyr
1               5                   10
```

<210> SEQ ID NO 154
<211> LENGTH: 520
<212> TYPE: DNA
<213> ORGANISM: Artificial
<220> FEATURE:
<223> OTHER INFORMATION: IgGL constant+signal

<400> SEQUENCE: 154

```
ctaggtaagc ttggtaccac ccaagctggc taggtaagct tgctagcgcc accatggtgc    60
tgcagaccca ggtgttcatc tccctgctgc tgtggatctc cggcgcatat ggcgatatcg   120
tgatgattaa acgtacggtg ccgcccccct ccgtgttcat cttcccccc tccgacgagc    180
agctgaagtc cggcaccgcc tccgtggtgt gcctgctgaa taacttctac cccagagagg   240
ccaaggtgca gtggaaggtg gacaacgccc tgcagtccgg gaactcccag agagcgtga    300
ccgagcagga cagcaaggac agcacctaca gcctgagcag cacctgacc ctgagcaaag    360
ccgactacga gaagcacaag gtgtacgcct gcgaggtgac ccaccagggc ctgagctccc   420
ccgtcaccaa gagcttcaac aggggggagt gttagggcc cgtttaaacg gtggcatcc    480
ctgtgacccc tccccagtgc ctctcctggc cctggaagtt                         520
```

<210> SEQ ID NO 155
<211> LENGTH: 1140
<212> TYPE: DNA
<213> ORGANISM: Artificial
<220> FEATURE:
<223> OTHER INFORMATION: IgGH constant+signal

<400> SEQUENCE: 155

```
ttggtaccac ccaagctggc taggtaagct tgctagcgcc accatgaaac acctgtggtt    60
cttcctcctg ctggtggcag ctcccagatg ggtgctgagc caggtgcaat gtgcaggcg   120
gttagctcag cctccaccaa gggcccaagc gtcttccccc tggcaccctc ctccaagagc   180
acctctggcg gcacagccgc cctgggctgc ctggtcaagg actacttccc cgaaccgtg   240
accgtgagct ggaactcagg cgccctgacc agcggcgtgc acaccttccc cgctgtcctg   300
cagtcctcag gactctactc cctcagcagc gtggtgaccg tgcctccag cagcttgggc   360
acccagacct acatctgcaa cgtgaatcac aagcccagca caccaaggt ggacaagaga   420
gttgagccca atcttgtga caaaactcac acatgccac cctgcccagc acctgaactc    480
ctggggggac cctcagtctt cctcttcccc ccaaaaccca aggacaccct catgatctcc   540
cggacccctg aggtcacatg cgtggtggtg gacgtgagcc acgaagaccc tgaggtcaag   600
ttcaactggt acgtgacgg cgtggaggtg cataatgcca agacaaagcc cggggaggag   660
cagtacaaca gcacgtaccg ggtggtcagc gtcctcaccg tcctgcacca ggactggctg   720
```

```
aatggcaagg agtacaagtg caaggtctcc aacaaagccc tcccagcccc catcgagaaa      780
accatctcca aagccaaagg ccagccccgg gaaccacagg tgtacaccct gcccccatcc      840
cgggaggaga tgaccaagaa ccaggtcagc ctgacctgcc tggtcaaagg cttctatccc      900
agcgacatcg ccgtggagtg ggagagcaat ggccagcccg agaacaacta caagaccacc      960
cctcccgtgc tggactccga cggctccttc ttcctctaca gcaagctcac cgtggacaag     1020
agcaggtggc agcagggcaa cgtcttctca tgctccgtga tgcatgaggc tctgcacaac     1080
cactacaccc agaagagcct ctccctgtct cccggcaaat gagatatcgg gcccgtttaa     1140

<210> SEQ ID NO 156
<211> LENGTH: 442
<212> TYPE: DNA
<213> ORGANISM: Artificial
<220> FEATURE:
<223> OTHER INFORMATION: hSH348-1-T1L+signal

<400> SEQUENCE: 156
aggtaagctt gctagcgcca ccatggtgct gcagacccag gtgttcatct ccctgctgct       60
gtggatctcc ggcgcatatg cgacatagt gatgacccag agcccctga gcctgcccgt       120 gacccccggc gagcccgcct ccatcagctg ccggagcagc cagagcatcg tgcacagcaa      180
cggcaacacc tacctggagt ggtacctgca gaagcccggc cagagccccc agctgctgat      240
ctacaaggtg agcaaccggt tcagcggcgt gcccgaccgg ttcagcggca gcggcagcgg      300
caccgacttc accctgaaga tcagccgggt ggaggccgag gacgtgggcg tgtactactg      360
cttccagggc tcccacgtgc cctacacctt cggccagggc accaaggtgg agatcaagcg      420
tacggtggcc gcccctccg tg                                              442

<210> SEQ ID NO 157
<211> LENGTH: 442
<212> TYPE: DNA
<213> ORGANISM: Artificial
<220> FEATURE:
<223> OTHER INFORMATION: hSH348-1-T3L+signal

<400> SEQUENCE: 157
aggtaagctt gctagcgcca ccatggtgct gcagacccag gtgttcatct ccctgctgct       60
gtggatctcc ggcgcatatg cgacgtgct gatgacccag agcccctga gcctgcccgt       120 gacccccggc gagcccgcct ccatcagctg ccggagcagc cagagcatcg tgcacagcaa      180
cggcaacacc tacctggagt ggtacctgca gaagcccggc cagagccccc agctgctgat      240
ctacaaggtg agcaaccggt tcagcggcgt gcccgaccgg ttcagcggca gcggcagcgg      300
caccgacttc accctgaaga tcagccgggt ggaggccgag gacgtgggcg tgtactactg      360
cttccagggc tcccacgtgc cctacacctt cggccagggc accaaggtgg agatcaagcg      420
tacggtggcc gcccctccg tg                                              442

<210> SEQ ID NO 158
<211> LENGTH: 460
<212> TYPE: DNA
<213> ORGANISM: Artificial
<220> FEATURE:
<223> OTHER INFORMATION: hSH348-1-T1H+signal

<400> SEQUENCE: 158
gtaagcttgc tagcgcacca tgaagcacct gtggttcttc ctgctgctgg tggccgcccc       60
```

```
cagatgggtg ctgagccagg tgcagctggt gcagagcggc gccgaggtga agaagcccgg    120
cagcagcgtg aaggtgagct gcaaggccag cggctacacc ttcacccact acagcatgca    180
ctgggtgcgg caggcccccg gccagggcct ggagtggatg ggctggatca acacctacac    240
cggcgagccc acctacgccg acgacttcaa gggccgggtg accatcaccg ccgacacctc    300
cacctccacc gcctacctgg aactgagcag cctgcgcagc gaggacaccg ccgtgtacta    360
ctgcgccacc tactaccggt acgagcggga cttcgactac tggggccagc gcaccctggt    420
gaccgtgagc tcagcctcct ccaccaaggg cccctccgtg                           460
```

```
<210> SEQ ID NO 159
<211> LENGTH: 460
<212> TYPE: DNA
<213> ORGANISM: Artificial
<220> FEATURE:
<223> OTHER INFORMATION: hSH348-1-T3H+signal

<400> SEQUENCE: 159
```

```
gtaagcttgc tagcgcacca tgaagcacct gtggttcttc ctgctgctgg tggccgcccc    60
cagatgggtg ctgagccaga tccagctggt gcagagcggc gccgaggtga agaagcccgg    120
cagcagcgtg aaggtgagct gcaaggccag cggctacacc ttcacccact acagcatgca    180
ctgggtgcgg caggcccccg gccagggcct gaagtggatg ggctggatca acacctacac    240
cggcgagccc acctacgccg acgacttcaa gggccgggtc gccttcagcc tggacacctc    300
cacctccacc gcctacctgg aactgagcag cctgcgcagc gaggacaccg ccgtgtacta    360
ctgcgccacc tactaccggt acgagcggga cttcgactac tggggccagc gcaccctggt    420
gaccgtgagc tcagcctcct ccaccaaggg cccctccgtg                           460
```

```
<210> SEQ ID NO 160
<211> LENGTH: 442
<212> TYPE: DNA
<213> ORGANISM: Artificial
<220> FEATURE:
<223> OTHER INFORMATION: hSH357-1-T1L+signal

<400> SEQUENCE: 160
```

```
aggtaagctt gctagcgcca ccatggtgct gcagacccag gtgttcatct ccctgctgct    60
gtggatctcc ggcgcatatg cgacatagt gatgacccag agcccctga gcctgccgt       120 gacccccggc gagcccgcca gcatcagctg ccggagcagc cagagcatcg tgcacagcag    180
cggcatcacc tacctggagt ggtacctgca gaagcccggc cagagccccc agctgctgat    240
ctacaaggtg agcaaccggt tcagcggcgt gcccgaccgg ttcagcggca gcggcagcgg    300
caccgacttc accctgaaga tcagccgggt ggaggccgag gacgtgggcg tgtactactg    360
cttccagggc agccacgtgc cctacacctt cggccagggc accaaggtgg agatcaagcg    420
tacggtggcc gcccccctcg tg                                              442
```

```
<210> SEQ ID NO 161
<211> LENGTH: 442
<212> TYPE: DNA
<213> ORGANISM: Artificial
<220> FEATURE:
<223> OTHER INFORMATION: hSH357-1-T3L+signal

<400> SEQUENCE: 161
```

```
aggtaagctt gctagcgcca ccatggtgct gcagacccag gtgttcatct ccctgctgct    60
gtggatctcc ggcgcatatg cgacgtgct gatgacccag agcccctga gcctgccgt       120
```

```
gaccccggc gagcccgcca gcatcagctg ccggagcagc cagagcatcg tgcacagcag      180
cggcatcacc tacctggagt ggtacctgca gaagcccggc cagagccccc agctgctgat      240
ctacaaggtg agcaaccggt tcagcggcgt gcccgaccgg ttcagcggca gcggcagcgg      300
caccgacttc accctgaaga tcagcccggt ggaggccgag gacgtgggcg tgtactactg      360
cttccagggc agccacgtgc cctacacctt cggccagggc accaaggtgg agatcaagcg      420
tacggtggcc gccccctccg tg                                               442

<210> SEQ ID NO 162
<211> LENGTH: 460
<212> TYPE: DNA
<213> ORGANISM: Artificial
<220> FEATURE:
<223> OTHER INFORMATION: hSH357-1-T1H+signal

<400> SEQUENCE: 162
gtaagcttgc tagcgcacca tgaagcacct gtggttcttc ctgctgctgg tggccgcccc       60
cagatgggtg ctgagccagg tgcagctggt gcagtccggc gccgaggtga agaagcccgg      120
cgcctccgtg aaggtgtcct gtaaggcctc cggctacacc ttcatcgact actccatgca      180
ctgggtgagg caggcccccg gccagggcct ggagtggatg ggctggatca acacctacac      240
cggcgagccc acctactccg acgacttcaa gggcagggtg accatcaccg ccgacacctc      300
caccagcacc gcctacctgg agctgtcctc cctgaggtcc gaggacaccg ccgtgtacta      360
ctgtgccacc tactacaggt acgagaggga cttcgactac tggggccagg gcaccctggt      420
gacggtgagc tcagcctcct ccaccaaggg cccctccgtg                            460

<210> SEQ ID NO 163
<211> LENGTH: 460
<212> TYPE: DNA
<213> ORGANISM: Artificial
<220> FEATURE:
<223> OTHER INFORMATION: hSH357-1-T3H+signal

<400> SEQUENCE: 163
gtaagcttgc tagcgcacca tgaagcacct gtggttcttc ctgctgctgg tggccgcccc       60
cagatgggtg ctgagccaga tccagctggt gcagtccggc gccgaggtga agaagcccgg      120
cgcctccgtg aaggtgtcct gtaaggcctc cggctacacc ttcatcgact actccatgca      180
ctgggtgagg caggcccccg gccagggcct gaagtggatg ggctggatca acacctacac      240
cggcgagccc acctactccg acgacttcaa gggcaggttc gccttctccc tggacacctc      300
caccagcacc gcctacctgg agctgtcctc cctgaggtcc gaggacaccg ccgtgtacta      360
ctgtgccacc tactacaggt acgagaggga cttcgactac tggggccagg gcaccctggt      420
gacggtgagc tcagcctcct ccaccaaggg cccctccgtg                            460
```

ANTI-EPHA2 ANTIBODY

CROSS-REFERENCES TO RELATED APPLICATIONS

This application is a divisional of U.S. patent application Ser. No. 12/713,041, filed Feb. 25, 2010, which is a continuation-in-part of International Application No. PCT/JP2008/065486, filed Aug. 29, 2008, which claims priority from Japanese Patent Application No. 2007-224007, filed Aug. 30, 2007.

TECHNICAL FIELD

The present invention relates to an antibody having an inhibitory activity against cell malignant transformation and/or tumor cell growth. More specifically, the present invention relates to an antibody against EPHA2 and a pharmaceutical composition comprising the antibody.

STATEMENT REGARDING SEQUENCE LISTING

The sequence listing associated with this application is provided in text format in lieu of a paper copy and is hereby incorporated by reference into the specification. The name of the text file containing the sequence listing is 40515 SEQ Final 2013-05-21.txt. The text file is 233 KB; was created on May 21, 2013; and is being submitted via EFS-Web with the filing of the specification.

BACKGROUND

EPHA2 is a receptor tyrosine kinase that has a molecular weight of 130 kDa and has a single transmembrane domain (Molecular and Cellular Biology, 1990, vol. 10, p. 6316-6324). EPHA2 has a ligand-binding domain and two fibronectin type 3 domains present in the N-terminal extracellular region and a tyrosine kinase domain and a sterile-α-motif (SAM) domain present in the C-terminal intracellular region.

GPI-anchored plasma membrane proteins ephrin-A1 to ephrin-A5 are known as EPHA2 ligands (Annual Review of Neuroscience, 1998, vol. 21, p. 309-345). The ligand binding to EPHA2 activates the tyrosine kinase domain and phosphorylates tyrosine residues present in the EPHA2 intracellular region, resulting in signal transduction within the cell. It has also been reported that EPHA2 bound with the ligand is internalized into the cell through endocytosis and is eventually degraded by a proteasome (Molecular Cancer Research, 2002, vol. 1, p. 79-87).

High expression of EPHA2 has been reported clinically in many cancers, particularly, breast cancer, esophagus cancer, prostate cancer, gastric cancer, non-small cell lung cancer, colon cancer, and glioblastoma multiforme (Cancer Research, 2001, vol. 61, p. 2301-2306; International Journal of Cancer, 2003, vol. 103, p. 657-663; The Prostate, 1999, vol. 41, p. 275-280; American Journal of Pathology, 2003, vol. 163, p. 2271-2276; Cancer Science, 2005, vol. 96, p. 42-47; Clinical Cancer Research, 2003, vol. 9, p. 613-618; Oncology Reports, 2004, vol. 11, p. 605-611; and Molecular Cancer Research, 2005, vol. 3, p. 541-551). It has also been reported that: for esophagus cancer, EPHA2 expression-positive patients tend to have a high frequency of regional lymph node metastasis, a large number of lymph node metastases, and a poor degree of tumor differentiation and a low five-year survival rate (International Journal of Cancer, 2003, vol. 103, p. 657-663); for non-small cell lung cancer, patients highly expressing EPHA2 tend to have a low disease-free survival rate and to have recurrence, particularly of brain metastasis (Clinical Cancer Research, 2003, vol. 9, p. 613-618); and for colon cancer, EPHA2 expression-positive patients tend to have liver metastasis, lymphatic vessel invasion, and lymph node metastasis, and many patients with high clinical stage are EPHA2 expression-positive patients (Oncology Reports, 2004, vol. 11, p. 605-611).

Moreover, it has been reported that by the introduction of EPHA2 genes into cells, non-cancer cells acquire cancer phenotypes such as anchorage-independent growth ability, tubular morphology-forming ability on the extracellular matrix, and in vivo tumor growth ability (Cancer Research, 2001, vol. 61, p. 2301-2306), and cancer cells have enhanced invasiveness through the extracellular matrix (Biochemical and Biophysical Research Communications, 2004, vol. 320, p. 1096-1102; and Oncogene, 2004, vol. 23, p. 1448-1456). In addition, it has been reported that: the invasiveness or anchorage-independent growth of cancer cells and in vivo tumor growth are inhibited by knockdown of EPHA2 expression using siRNA (Oncogene, 2004, vol. 23, p. 1448-1456; and Cancer Research, 2002, vol. 62, p. 2840-2847); and the invasiveness, anchorage-independent growth, and tubular morphology-forming ability of cancer cells are inhibited by activating EPHA2 using fusion proteins of its ligand ephrin-A1 and a human IgG Fc region and inducing EPHA2 degradation through endocytosis (Cancer Research, 2001, vol. 61, p. 2301-2306; Molecular Cancer Research, 2005, vol. 3, p. 541-551; and Biochemical and Biophysical Research Communications, 2004, vol. 320, p. 1096-1102).

On the other hand, EPHA2 has been reported to be expressed not only in cancer cells but also within tumors or in their surrounding blood vessels (Oncogene, 2000, vol. 19, p. 6043-6052). It has been reported that in mice, EPHA2 signals are involved in angiogenesis induced by ephrin-A1, and particularly, EPHA2 expressed in vascular endothelial cells is required for the tube formation or survival of the vascular endothelial cells (Journal of Cell Science, 2004, vol. 117, p. 2037-2049). It has also been reported that fusion proteins of an EPHA2 extracellular region and a human IgG Fc region inhibit angiogenesis in vivo and exhibit an antitumor effect (Oncogene, 2002, vol. 21, p. 7011-7026).

Monoclonal antibodies are useful not only as diagnostic drugs but also as therapeutic drugs. Monoclonal antibodies are actively used particularly in the field of cancer therapy, and monoclonal antibodies against receptor tyrosine kinases such as HER2 and EGFR or against CD20 extracellular regions are used in cancer therapy and exhibit excellent effects (The New England Journal of Medicine, 2007, vol. 357, p. 39-51; Oncogene, 2007, vol. 26, p. 3661-3678; and Oncogene, 2007, vol. 26, p. 3603-3613). The mechanisms of action of the monoclonal antibodies used in cancer therapy include apoptosis induction and inhibition of growth signals. In addition, their immunoresponse-mediated action such as ADCC or CDC is also considered to play a very important role. In actuality, it has been reported that anti-HER2 antibodies (trastuzumab) or anti-CD20 antibodies (rituximab) exhibit a much weaker antitumor effect in xenografts of nude mice deficient in FcγRs necessary for ADCC induction than in nude mice that are not deficient in FcγRs, when these antibodies are administered thereto (Nature Medicine, 2000, vol. 6, p. 443-446). It has also been reported that anti-CD20 antibodies (rituximab) exhibit a weaker antitumor effect in mice depleted of complement by the administration of cobra venom than in mice that are not depleted of complement, when the antibody is administered thereto (Blood, 2004, vol. 103, p. 2738-2743).

For EPHA2, it has been reported that agonistic anti-EPHA2 monoclonal antibodies having an activity of inducing the phosphorylation of EPHA2 tyrosine residues and an activity of inducing EPHA2 degradation, as for the ligands, inhibit the anchorage-independent growth of a breast cancer cell line and the tubular morphology formation thereof on the extracellular matrix (Cancer Research, 2002, vol. 62, p. 2840-2847). It has also been reported that agonistic anti-EPHA2 monoclonal antibodies which recognize an epitope on EPHA2 displayed on cancer cells rather than non-cancer cells and have an activity of inducing the phosphorylation of EPHA2 tyrosine residues and an activity of inducing EPHA2 degradation exhibit an antitumor effect in vivo (Cancer Research, 2003, vol. 63, p. 7907-7912; and the pamphlet of WO 03/094859). On the other hand, Kiewlich et al. have reported that their anti-EPHA2 monoclonal antibodies had an activity of inducing the phosphorylation of EPHA2 tyrosine residues and an activity of inducing EPHA2 degradation but did not exhibit an antitumor effect in vivo (Neoplasia, 2006, vol. 8, p. 18-30).

Moreover, the pamphlet of WO 2006/084226 discloses anti-EPHA2 monoclonal antibodies LUCA19, SG5, LUCA40, and SPL1 obtained by immunizing mice with cancer cells and discloses that, among these antibodies: LUCA19 and SG5 do not influence the phosphorylation of EPHA2 tyrosine residues; LUCA40 inhibits cancer cell growth in vitro; and LUCA19, SG5, and LUCA40 are internalized into cancer cells in the presence of anti-mouse antibody labeled with toxin (saporin). The document has also reported that LUCA40 and SPL1 exhibit an antitumor effect in vivo. However, the presence or absence of the agonistic activities of these antibodies remains to be clarified.

Despite these studies, an epitope for an anti-EPHA2 antibody that exhibits an antitumor effect in vivo is still unknown. No previous document has reported that a particular amino acid sequence in an EPHA2 extracellular region is useful as an epitope for a monoclonal antibody intended for cancer therapy.

Even antibodies against the same antigen differ in their properties depending on differences in epitopes or their sequences. Furthermore, due to this difference in their properties, the antibodies, when administered to humans, would clinically respond in different a manner with respect to drug effectiveness, the frequency of therapeutic response, side effects, the frequency of occurrence of drug resistance, etc.

Thus, a drug having clinically the best properties may also differ depending on the patient. In many cases, such properties are unknown until the drug is actually administered. Thus, it has been strongly required to develop a drug having a novel mechanism of action. It has also been strongly required to develop an antibody against EPHA2 having properties different from those of conventional antibodies.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

BRIEF DESCRIPTION OF THE DRAWINGS

Figure 1A:
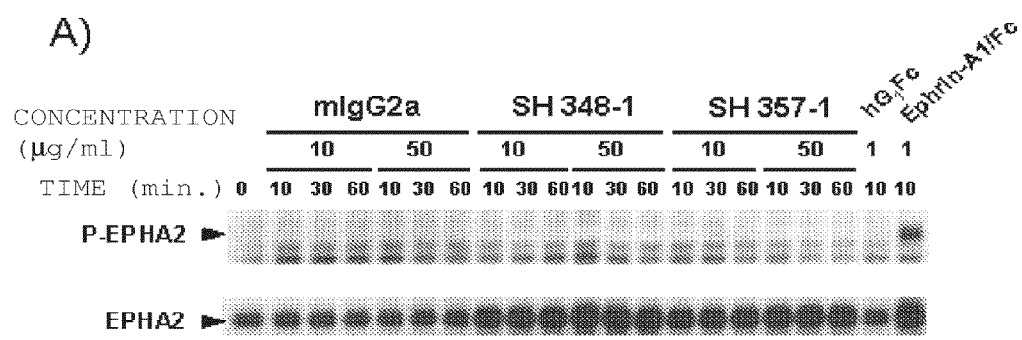
Figure 1B:
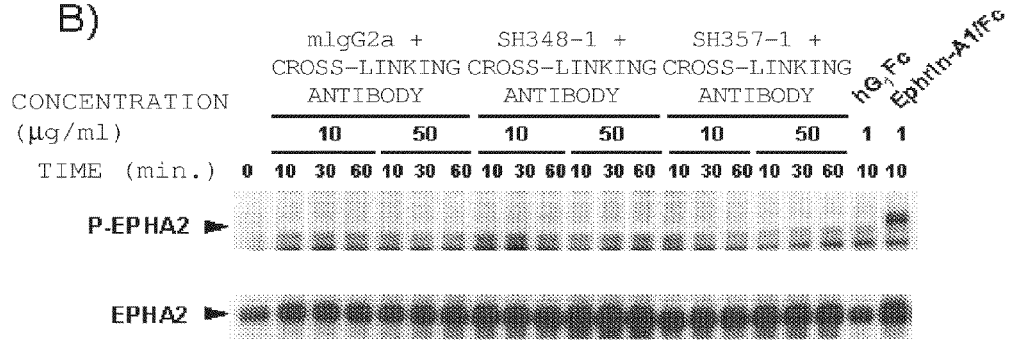
Figure 2A:
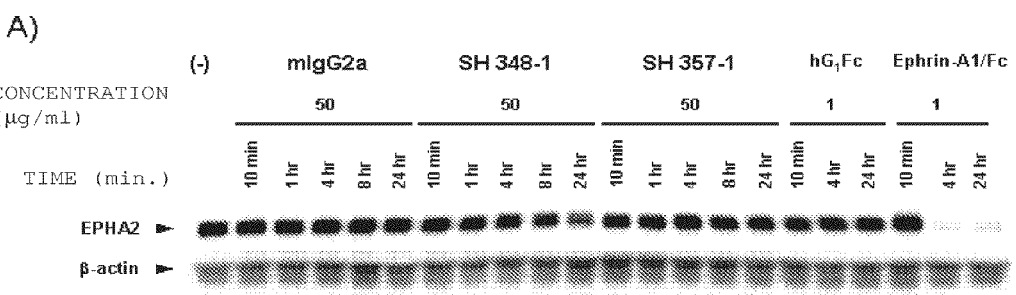
Figure 2B:
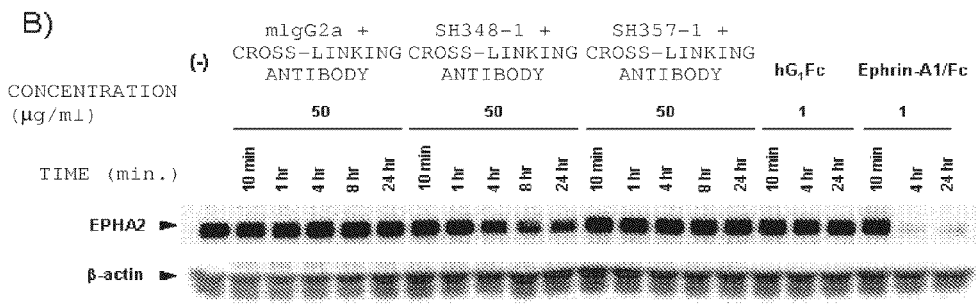
Figure 3A:
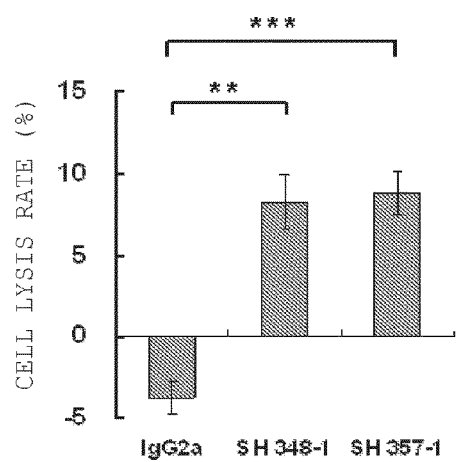
Figure 3B:
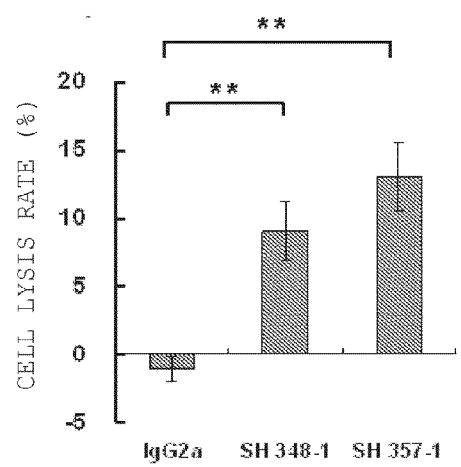
Figure 3C:
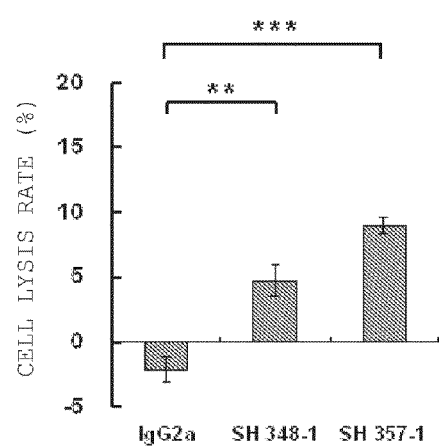
Figure 4A:
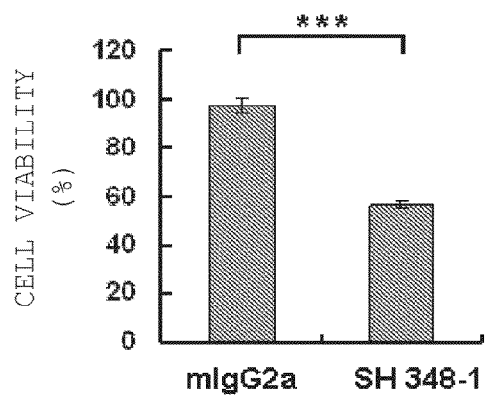
Figure 4B:
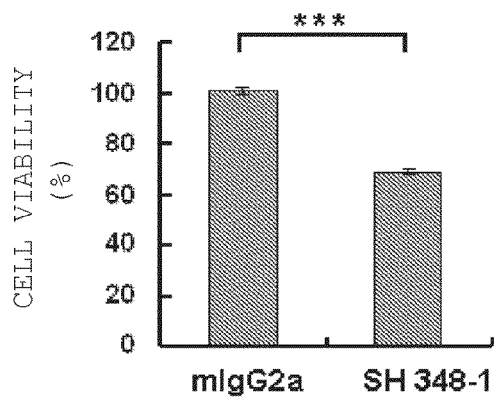
Figure 4C:
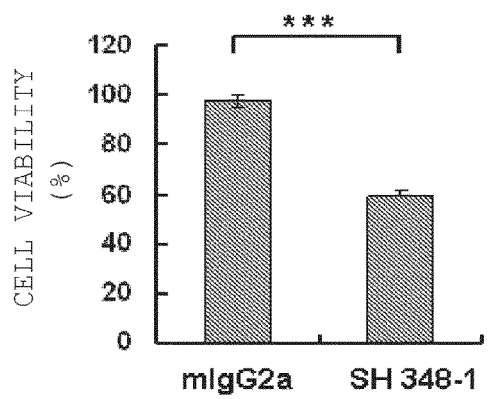
Figure 4D:
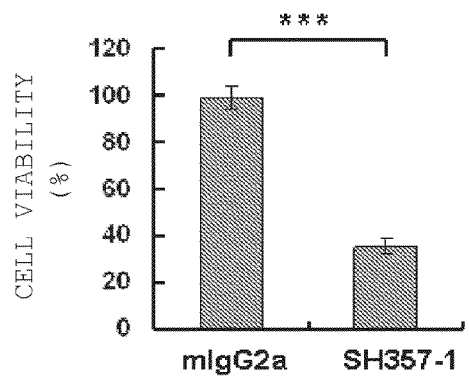
Figure 4E:
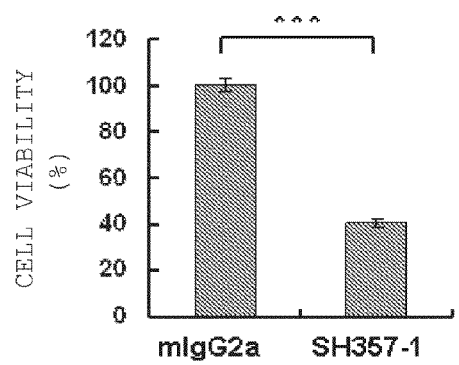
Figure 4F:
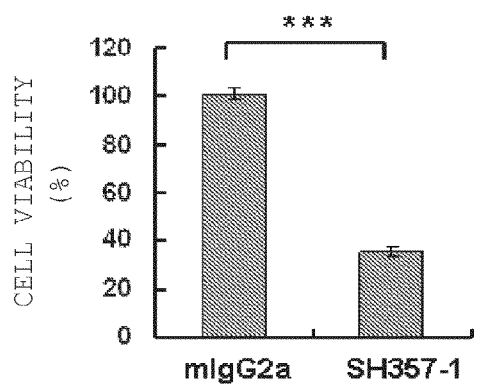
Figure 5A:
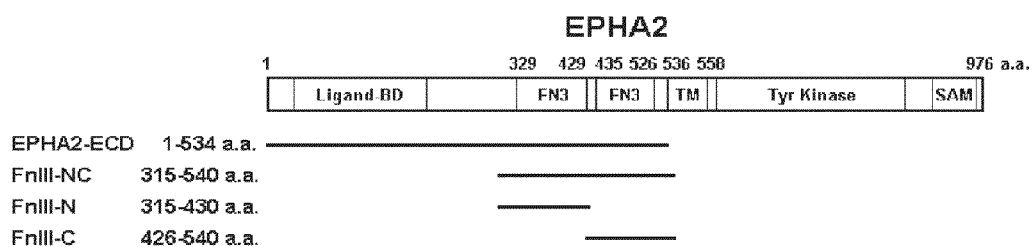
Figure 5B:
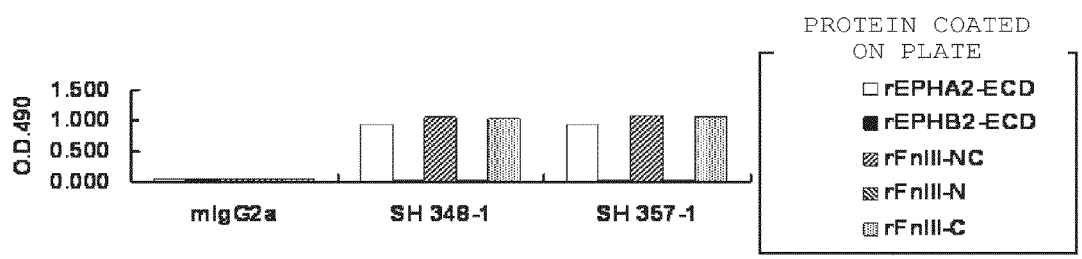
Figure 6A:
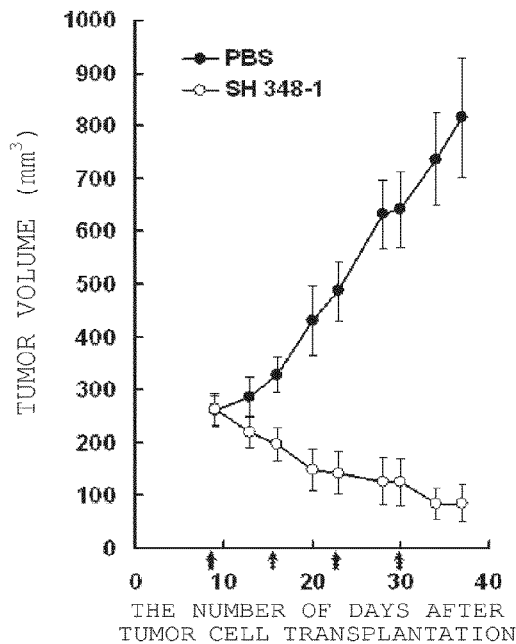
Figure 6B:
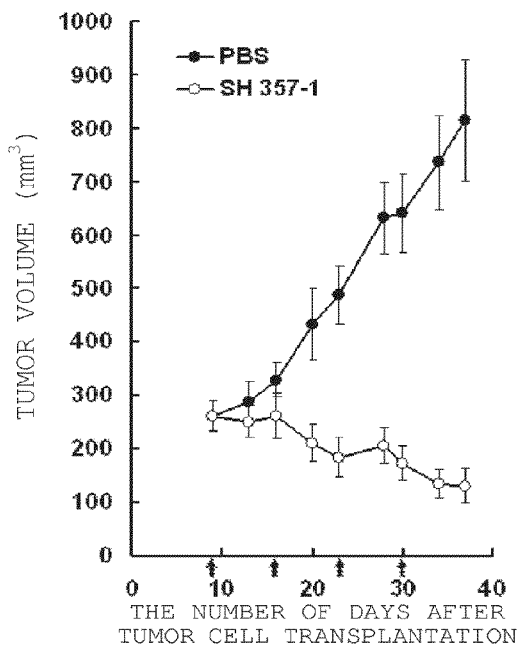
Figure 7A:
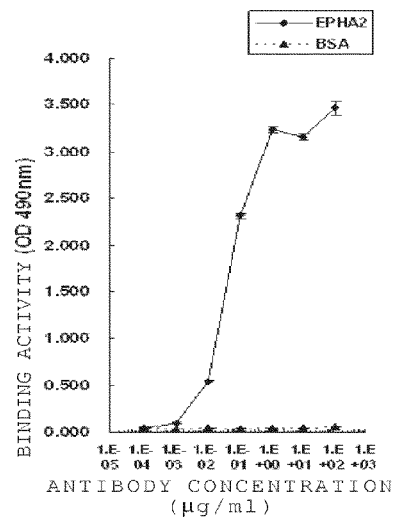
Figure 7B:
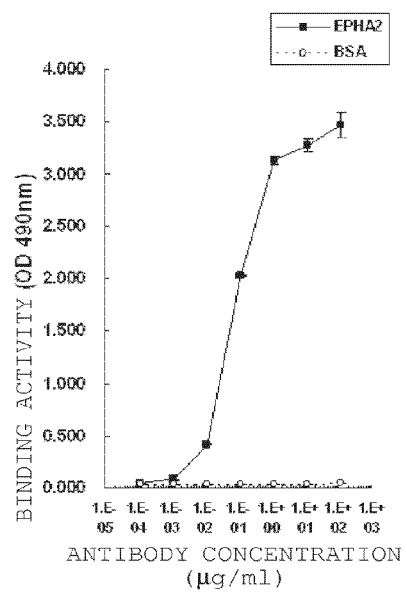
Figure 7C:
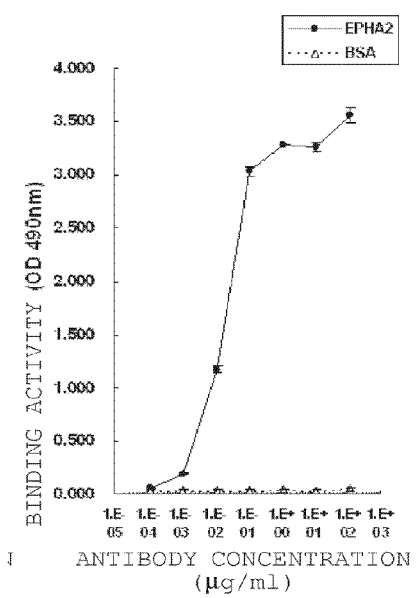
Figure 8:
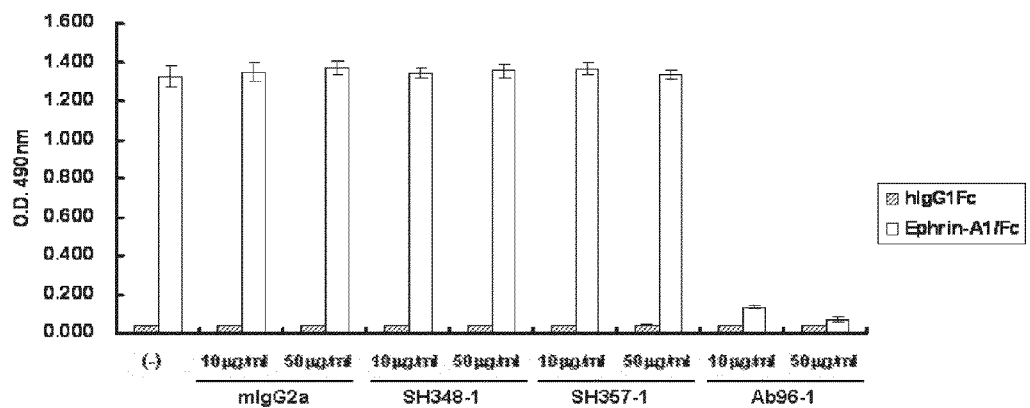
Figure 9:
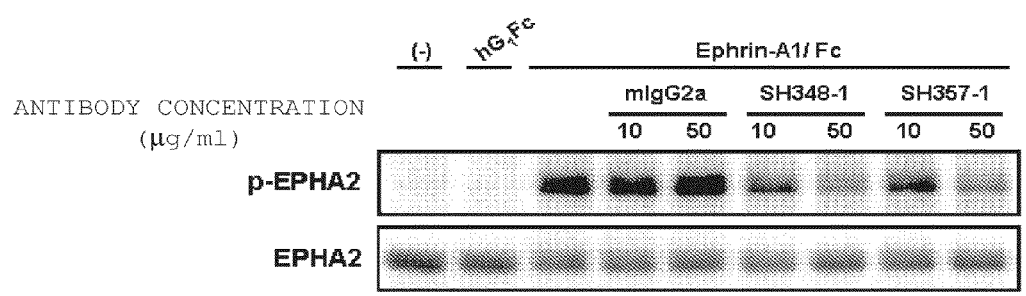
Figure 10:
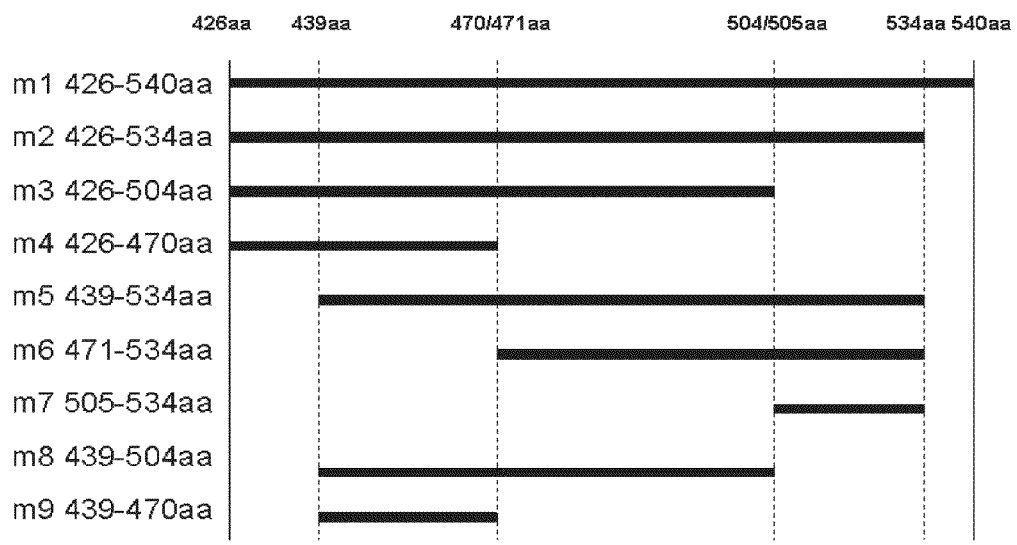
Figure 11A:
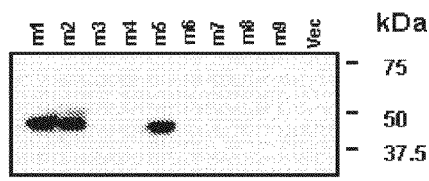
Figure 11B:
Figure 11C:
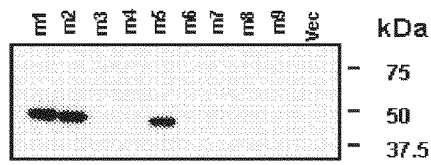
Figure 11D:
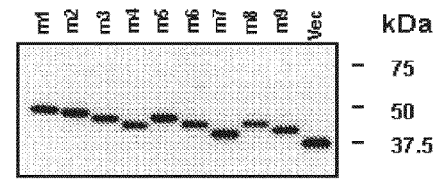
Figure 12A:
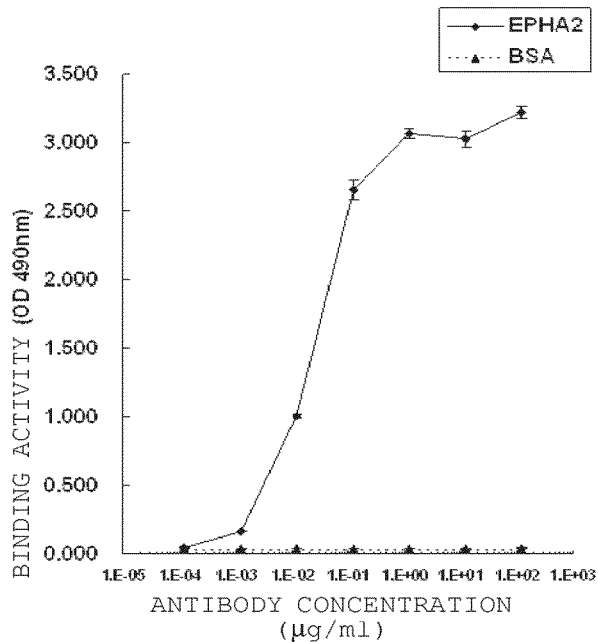
Figure 12B:
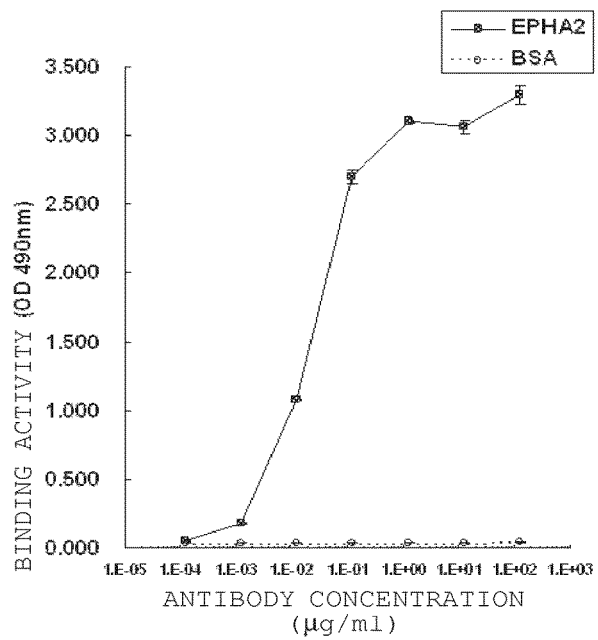
Figure 12C:
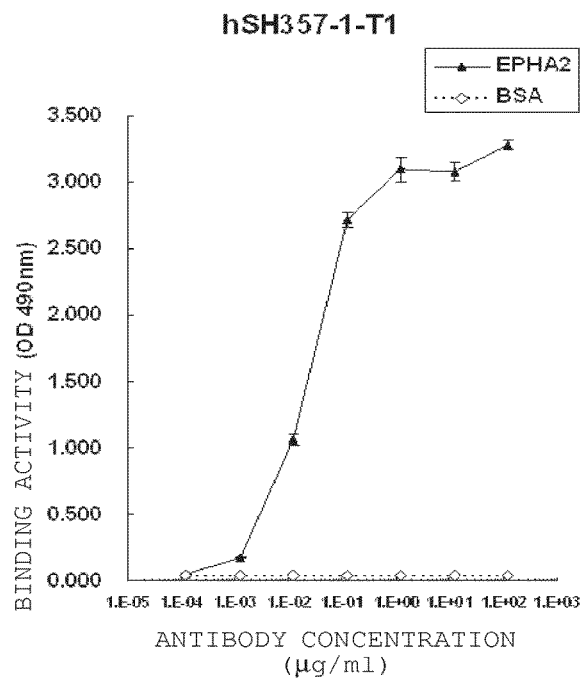
Figure 12D:
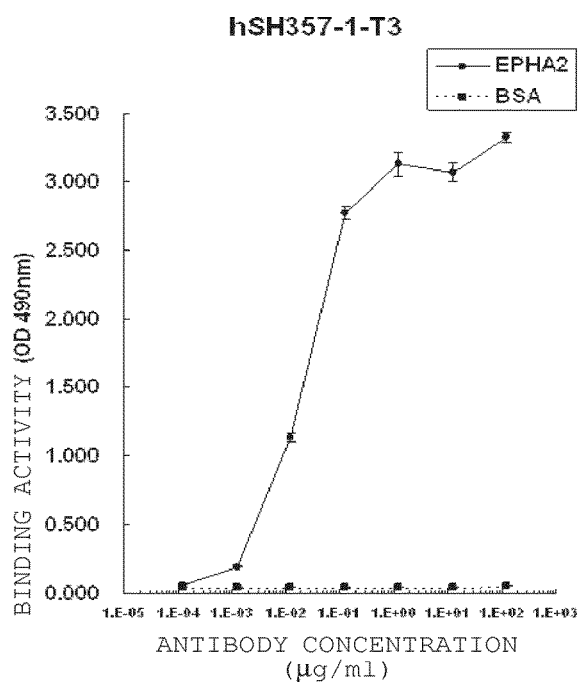
Figure 13A:
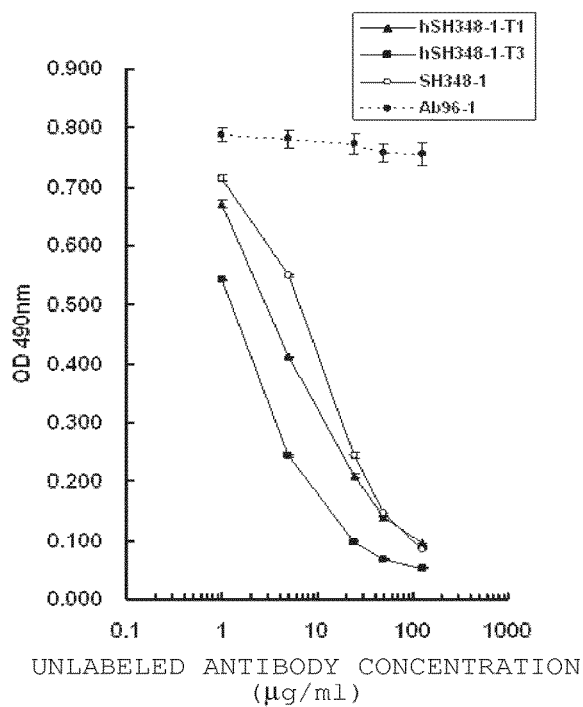
Figure 13B:
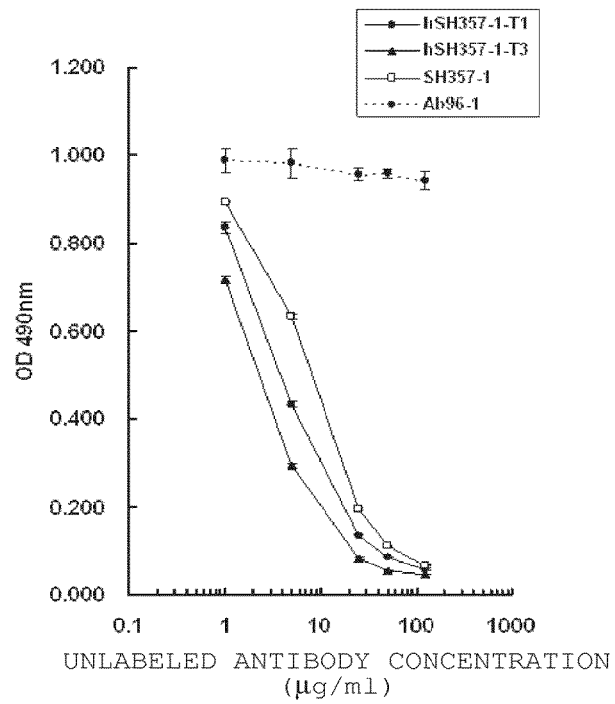
Figure 14A:
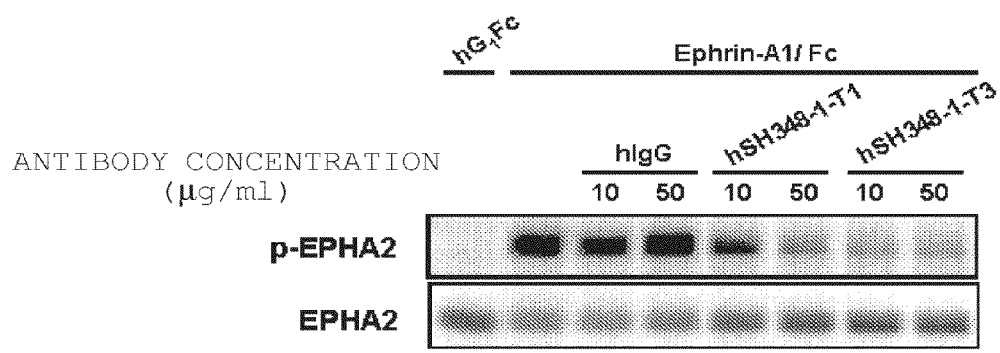
Figure 14B:
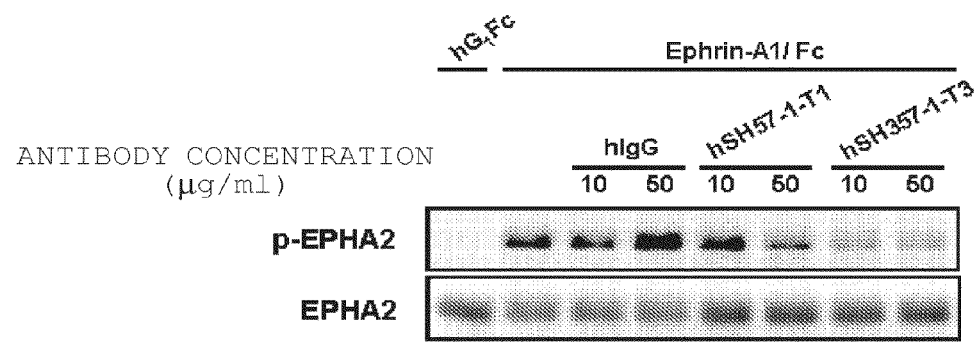

FIGS. 1A and 1B are diagrams of Western blotting results showing the presence or absence of the activity of inducing the phosphorylation of EPHA2 tyrosine residues by an anti-EPHA2 antibody. FIG. 1A) is a diagram showing the results obtained in the absence of a cross-linking antibody, wherein the upper bar shows the results for a 4G10 antibody, and the lower bar shows the results for an anti-EPHA2 antibody (D7). FIG. 1B) is a diagram showing the results obtained in the presence of a cross-linking antibody, wherein the upper bar shows the results of a 4G10 antibody, and the lower bar shows the results of an anti-EPHA2 antibody (D7);

FIGS. 2A and 2B are diagrams of Western blotting results showing the presence or absence of the activity of inducing a decrease in EPHA2 protein level by an anti-EPHA2 antibody. FIG. 2A) is a diagram showing the results obtained in the absence of a cross-linking antibody, wherein the upper bar shows the results for an anti-EPHA2 antibody (D7), and the lower bar shows the results for an anti-β-actin antibody. FIG. 2B) is a diagram showing the results obtained in the presence of a cross-linking antibody, wherein the upper bar shows the results for an anti-EPHA2 antibody (D7), and the lower bar shows the results for an anti-β-actin antibody;

FIGS. 3A through 3C are diagrams showing the presence or absence of the ADCC activity of an anti-EPHA2 antibody against various cell lines. In the diagrams, "" represents $P<0.01$, and "*" represents $P<0.001$. FIG. 3A) is a diagram showing the ADCC activity against MDA-MB-231 cells. FIG. 3B) is a diagram showing the ADCC activity against A549 cells. FIG. 3C) is a diagram showing the ADCC activity against PC-3 cells;

FIGS. 4A through 4F are diagrams showing the presence or absence of the CDC activity of an anti-EPHA2 antibody against various cells. In the diagrams, "***" represents $P<0.001$. FIG. 4A) is a diagram showing the CDC activity of SH348-1 against MDA-MB-231 cells. FIG. 4B) is a diagram showing the CDC activity of SH348-1 against A549 cells. FIG. 4C) is a diagram showing the CDC activity of SH348-1 against PC-3 cells. FIG. 4D) is a diagram showing the CDC activity of SH357-1 against MDA-MB-231 cells. FIG. 4E) is a diagram showing the CDC activity of SH357-1 against A549 cells. FIG. 4F) is a diagram showing the CDC activity of SH357-1 against PC-3 cells;

FIG. 5A) is a diagram showing EPHA2 domain structure prediction and the positions, in EPHA2, of EPHA2-ECD, FNIII-NC, FNIII-N, and FNIII-C which are peptides for epitope determination. In the diagram, Ligand-BD represents a ligand-binding domain, FN3 represents a fibronectin type 3 domain, TM represents a transmembrane region, Trk kinase represents a tyrosine kinase domain, and SAM represents a SAM domain;

FIG. 5B) is a diagram showing the presence or absence of the binding activity of an anti-EPHA2 antibody for EPHA2-ECD, FNIII-NC, FNIII-N, and FNIII-C;

FIG. 6A) is a diagram showing the antitumor activity of SH348-1 against MDA-MB-231 cell-transplanted mice;

FIG. 6B) is a diagram showing the antitumor activity of SH357-1 against MDA-MB-231 cell-transplanted mice. In the diagram, the error bar represents a standard error (n=9);

FIG. 7A) is a diagram showing the binding activity of SH348-1 to an EPHA2 extracellular region polypeptide;

FIG. 7B) is a diagram showing the binding activity of SH357-1 to an EPHA2 extracellular region polypeptide;

FIG. 7C) is a diagram showing the binding activity of Ab96-1 to an EPHA2 extracellular region polypeptide;

FIG. 8 is a diagram showing the ligand binding inhibitory activities of SH348-1, SH357-1, and Ab96-1;

FIG. 9 is a diagram showing that SH348-1 and SH357-1 have an activity of inhibiting the ephrin-A1-dependent phosphorylation of EPHA2 tyrosine residues;

FIG. 10 is a diagram showing the outline of deletion mutants of EPHA2 for epitope identification;

FIG. 11A) is a diagram showing the reactivity of SH348-1 to deletion mutants of EPHA2;

FIG. 11B) is a diagram showing the detection of the deletion mutants of EPHA2 on a PVDF membrane in FIG. 11A);

FIG. 11C) is a diagram showing the reactivity of SH357-1 to deletion mutants of EPHA2;

FIG. 11D) is a diagram showing the detection of the deletion mutants of EPHA2 on a PVDF membrane in FIG. 11C);

FIG. 12A) is a diagram showing the binding activity of hSH348-1-T1 to an EPHA2 extracellular region polypeptide;

FIG. 12B) is a diagram showing the binding activity of hSH348-1-T3 to an EPHA2 extracellular region polypeptide;

FIG. 12C) is a diagram showing the binding activity of hSH357-1-T1 to an EPHA2 extracellular region polypeptide;

FIG. 12D) is a diagram showing the binding activity of hSH357-1-T3 to an EPHA2 extracellular region polypeptide;

FIG. 13A) is a diagram showing the competitive inhibitory activities of hSH348-1-T1 and hSH348-1-T3 against the antigen binding of SH348-1;

FIG. 13B) is a diagram showing the competitive inhibitory activities of hSH357-1-T1 and hSH357-1-T3 against the antigen binding of SH357-1;

FIG. 14A) is a diagram showing the activity of inhibiting the ephrin-A1-dependent phosphorylation of EPHA2 tyrosine residues by hSH348-1-T1 or hSH348-1-T3; and FIG. 14B) is a diagram showing the activity of inhibiting the ephrin-A1-dependent phosphorylation of EPHA2 tyrosine residues by hSH357-1-T1 or hSH357-1-T3.

DETAILED DESCRIPTION

Problems to be Solved by the Invention

An object of the present invention is to provide an antibody against EPHA2.

A further object of the present invention is to provide a pharmaceutical composition and the like comprising an anti-EPHA2 antibody having a therapeutic effect on cancer.

A further object of the present invention is to provide a method for producing the antibody.

A further object of the present invention is to provide a method for inhibiting tumor growth using the antibody, etc.

Means for Solving the Problems

The present inventors have conducted diligent studies to attain the objects and consequently successfully obtained a novel anti-EPHA2 monoclonal antibody which has no activity of inducing the phosphorylation of EPHA2 tyrosine residues and has ADCC and CDC activities against EPHA2-expressing cancer cells. Furthermore, the present inventors have examined an epitope for this antibody and consequently found for the first time that an antibody that binds to a region comprising, of two fibronectin type 3 domains present in EPHA2, the c-terminal domain, has an excellent antitumor activity in vivo. Based on these findings, the present invention has been completed.

Specifically, the present invention comprises:

(1) An antibody which recognizes an epitope recognized by an antibody produced by the hybridoma SH348-1 (FERM BP-10836);

(2) The antibody according to (1), wherein the antibody has the following properties a) to d):
  a) having no ability to phosphorylate EPHA2 tyrosine residues;
  b) having an ADCC activity against EPHA2-expressing cells;
  c) having a CDC activity against EPHA2-expressing cells; and
  d) having an antitumor activity in vivo;

(3) The antibody according to (1), wherein the antibody has the following properties a) to e):
  a) having no ability to phosphorylate EPHA2 tyrosine residues;
  b) exhibiting an effect of decreasing an EPHA2 protein level;
  c) having an ADCC activity against EPHA2-expressing cells;
  d) having a CDC activity against EPHA2-expressing cells; and
  e) having an antitumor activity in vivo;

(4) An antibody which specifically binds to a polypeptide consisting of an amino acid sequence represented by amino acid Nos. 426 to 534 of SEQ ID NO: 8 in the sequence listing;

(5) An antibody which specifically binds to a polypeptide consisting of an amino acid sequence represented by amino acid Nos. 426 to 534 of SEQ ID NO: 8 in the sequence listing and has the following properties a) to d):
  a) having no ability to phosphorylate EPHA2 tyrosine residues;
  b) having an ADCC activity against EPHA2-expressing cells;
  c) having a CDC activity against EPHA2-expressing cells; and
  d) having an antitumor activity in vivo;

(6) An antibody which specifically binds to a peptide consisting of an amino acid sequence represented by amino acid Nos. 426 to 534 of SEQ ID NO: 8 in the sequence listing and has the following properties a) to e):
  a) having no ability to phosphorylate EPHA2 tyrosine residues;
  b) exhibiting an effect of decreasing an EPHA2 protein level;
  c) having an ADCC activity against EPHA2-expressing cells;
  d) having a CDC activity against EPHA2-expressing cells; and
  e) having an antitumor activity in vivo;

(7) The antibody according to any one of (1) to (6), wherein the antibody specifically binds to a peptide consisting of an amino acid sequence represented by amino acid Nos. 439 to 534 of SEQ ID NO: 8 in the sequence listing;

(8) The antibody according to any one of (1) to (7), wherein the antibody inhibits the phosphorylation of EPHA2 tyrosine residues induced by an EPHA2 ligand;

(9) The antibody according to any one of (1) to (7), wherein the antibody does not inhibit EPHA2 ligand binding to EPHA2 but inhibits the phosphorylation of EPHA2 tyrosine residues induced by the ligand;

(10) An antibody which specifically binds to a polypeptide consisting of the amino acid sequence represented by SEQ ID NO: 8 in the sequence listing, wherein the antibody has the amino acid sequences represented by SEQ ID NOs: 59, 61, and 63 in the sequence listing, or amino acid sequences having deletion, substitution, or addition of one or more amino acids in the amino acid sequences, as the complementarity determining regions in the heavy chain variable region and has the amino acid sequences represented by SEQ ID NOs:

65, 67, and 69 in the sequence listing, or amino acid sequences having deletion, substitution, or addition of one or more amino acids in the amino acid sequences, as complementarity determining regions in the light chain variable region;

(11) An antibody which specifically binds to a polypeptide consisting of the amino acid sequence represented by SEQ ID NO: 8 in the sequence listing, characterized by the following 1) and 2):

1) having a heavy chain peptide comprising an amino acid sequence represented by the general formula (I):

-FRH$_1$-CDRH$_1$-FRH$_2$-CDRH$_2$-FRH$_3$-CDRH$_3$-FRH$_4$- (I)

wherein FRH$_1$ represents an arbitrary amino acid sequence consisting of 18 to 30 amino acids; CDRH$_1$ represents the amino acid sequence represented by SEQ ID NO: 59 in the sequence listing or an amino acid sequence having deletion, substitution, or addition of one or more amino acids in the amino acid sequence; FRH$_2$ represents an arbitrary amino acid sequence consisting of 14 amino acids; CDRH$_2$ represents the amino acid sequence represented by SEQ ID NO: 61 in the sequence listing or an amino acid sequence having deletion, substitution, or addition of one or more amino acids in the amino acid sequence; FRH$_3$ represents an arbitrary amino acid sequence consisting of 32 amino acids; CDRH$_3$ represents the amino acid sequence represented by SEQ ID NO: 63 in the sequence listing or an amino acid sequence having deletion, substitution, or addition of one or more amino acids in the amino acid sequence; and FRH$_4$ represents an arbitrary amino acid sequence consisting of 11 amino acids, wherein these amino acids are linked to each other through peptide bonds; and 2) having a light chain polypeptide comprising an amino acid sequence represented by the general formula (II):

-FRL$_1$-CDRL$_1$-FRL$_2$-CDRL$_2$-FRL$_3$-CDRL$_3$-FRL$_4$- (II)

wherein FRL$_1$ represents an arbitrary amino acid sequence consisting of 23 amino acids; CDRL$_1$ represents the amino acid sequence represented by SEQ ID NO: 65 in the sequence listing or an amino acid sequence having deletion, substitution, or addition of one or more amino acids in the amino acid sequence; FRL$_2$ represents an arbitrary amino acid sequence consisting of 15 amino acids; CDRL$_2$ represents the amino acid sequence represented by SEQ ID NO: 67 in the sequence listing or an amino acid sequence having deletion, substitution, or addition of one or more amino acids in the amino acid sequence; FRL$_3$ represents an arbitrary amino acid sequence consisting of 32 amino acids; CDRL$_3$ represents the amino acid sequence represented by SEQ ID NO: 69 in the sequence listing or an amino acid sequence having deletion, substitution, or addition of one or more amino acids in the amino acid sequence; and FRL$_4$ represents an arbitrary amino acid sequence consisting of 10 amino acids, wherein these amino acids are linked to each other through peptide bonds;

(12) An antibody which recognizes an epitope recognized by an antibody produced by the hybridoma SH357-1 (FERM BP-10837);

(13) The antibody according to (12), wherein the antibody has the following properties a) to d):
a) having no ability to phosphorylate EPHA2 tyrosine residues;
b) having an ADCC activity against EPHA2-expressing cells;
c) having a CDC activity against EPHA2-expressing cells; and
d) having an antitumor activity in vivo;

(14) An antibody which specifically binds to a peptide consisting of an amino acid sequence represented by amino acid Nos. 426 to 534 of SEQ ID NO: 8 in the sequence listing and has the following properties a) to e):
a) having no ability to phosphorylate EPHA2 tyrosine residues;
b) exhibiting no effect of decreasing an EPHA2 protein level;
c) having an ADCC activity against EPHA2-expressing cells;
d) having a CDC activity against EPHA2-expressing cells; and
e) having an antitumor activity in vivo;

(15) The antibody according to any one of (12) to (14), wherein the antibody specifically binds to a peptide consisting of an amino acid sequence represented by amino acid Nos. 439 to 534 of SEQ ID NO: 8 in the sequence listing;

(16) The antibody according to any one of (12) to (15), wherein the antibody inhibits the phosphorylation of EPHA2 tyrosine residues induced by an EPHA2 ligand;

(17) The antibody according to any one of (12) to (15), wherein the antibody does not inhibit EPHA2 ligand binding to EPHA2 but inhibits the phosphorylation of EPHA2 tyrosine residues induced by the ligand;

(18) An antibody which specifically binds to a polypeptide consisting of the amino acid sequence represented by SEQ ID NO: 8 in the sequence listing, wherein the antibody has the amino acid sequences represented by SEQ ID NOs: 71, 73, and 75 in the sequence listing, or amino acid sequences having deletion, substitution, or addition of one or more amino acids in the amino acid sequences, as complementarity determining regions in the heavy chain variable region and has the amino acid sequences represented by SEQ ID NOs: 77, 79, and 81 in the sequence listing, or amino acid sequences having deletion, substitution, or addition of one or more amino acids in the amino acid sequences, as complementarity determining regions in the light chain variable region;

(19) An antibody which specifically binds to a polypeptide consisting of the amino acid sequence represented by SEQ ID NO: 8 in the sequence listing, characterized by the following 1) and 2):

1) having a heavy chain peptide comprising an amino acid sequence represented by the general formula (I):

-FRH$_1$-CDRH$_1$-FRH$_2$-CDRH$_2$-FRH$_3$-CDRH$_3$-FRH$_4$- (I)

wherein FRH$_1$ represents an arbitrary amino acid sequence consisting of 18 to 30 amino acids; CDRH$_1$ represents the amino acid sequence represented by SEQ ID NO: 71 in the sequence listing or an amino acid sequence having deletion, substitution, or addition of one or more amino acids in the amino acid sequence; FRH$_2$ represents an arbitrary amino acid sequence consisting of 14 amino acids; CDRH$_2$ represents the amino acid sequence represented by SEQ ID NO: 73 in the sequence listing or an amino acid sequence having deletion, substitution, or addition of one or more amino acids in the amino acid sequence; FRH$_3$ represents an arbitrary amino acid sequence consisting of 32 amino acids; CDRH$_3$ represents the amino acid sequence represented by SEQ ID NO: 75 in the sequence listing or an amino acid sequence having deletion, substitution, or addition of one or more amino acids in the amino acid sequence; and FRH$_4$ represents an arbitrary amino acid sequence consisting of 11 amino acids, wherein these amino acids are linked to each other through peptide bonds; and 2) having a light chain polypeptide comprising an amino acid sequence represented by the general formula (II):

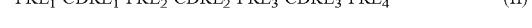
-FRL$_1$-CDRL$_1$-FRL$_2$-CDRL$_2$-FRL$_3$-CDRL$_3$-FRL$_4$- (II)

wherein FRL$_1$ represents an arbitrary amino acid sequence consisting of 23 amino acids; CDRL$_1$ represents the amino acid sequence represented by SEQ ID NO: 77 in the sequence listing or an amino acid sequence having deletion, substitution, or addition of one or more amino acids in the amino acid sequence; FRL$_2$ represents an arbitrary amino acid sequence consisting of 15 amino acids; CDRL$_2$ represents the amino acid sequence represented by SEQ ID NO: 79 in the sequence listing or an amino acid sequence having deletion, substitution, or addition of one or more amino acids in the amino acid sequence; FRL$_3$ represents an arbitrary amino acid sequence consisting of 32 amino acids; CDRL$_3$ represents the amino acid sequence represented by SEQ ID NO: 81 in the sequence listing or an amino acid sequence having deletion, substitution, or addition of one or more amino acids in the amino acid sequence; and FRL$_4$ represents an arbitrary amino acid sequence consisting of 10 amino acids, wherein these amino acids are linked to each other through peptide bonds; (20) The antibody according to any one of (1) to (19), characterized in that the antibody is a humanized antibody;

(21) The antibody according to any one of (1) to (19), characterized in that the antibody is a human antibody;

(22) The antibody according to any one of (1) to (19), characterized in that the antibody is an IgG antibody;

(23) The antibody according to any one of (1) to (9) and (12) to (17), characterized in that the antibody is any selected from Fab, F(ab')2, Fv, scFv, a diabody, a linear antibody, and a multispecific antibody;

(24) An antibody produced by the hybridoma SH348-1 (FERM BP-10836);

(25) An antibody produced by the hybridoma SH357-1 (FERM BP-10837);

(26) An antibody consisting of the following 1) and 2):
1) a heavy chain polypeptide comprising an amino acid sequence represented by amino acid Nos. 1 to 119 of SEQ ID NO: 35 in the sequence listing or a heavy chain polypeptide comprising an amino acid sequence represented by amino acid Nos. 1 to 119 of SEQ ID NO: 39 in the sequence listing; and
2) a light chain polypeptide comprising an amino acid sequence represented by amino acid Nos. 1 to 112 of SEQ ID NO: 37 in the sequence listing or a light chain polypeptide comprising an amino acid sequence represented by amino acid Nos. 1 to 112 of SEQ ID NO: 41 in the sequence listing;

(27) An antibody consisting of the following 1) or 2):
1) a heavy chain polypeptide comprising an amino acid sequence represented by amino acid Nos. 1 to 119 of SEQ ID NO: 35 in the sequence listing and a light chain polypeptide comprising an amino acid sequence represented by amino acid Nos. 1 to 112 of SEQ ID NO: 37 in the sequence listing; and
2) a heavy chain polypeptide comprising an amino acid sequence represented by amino acid Nos. 1 to 119 of SEQ ID NO: 39 in the sequence listing and a light chain polypeptide comprising an amino acid sequence represented by amino acid Nos. 1 to 112 of SEQ ID NO: 41 in the sequence listing;

(28) An antibody consisting of the following 1) and 2):
1) a heavy chain polypeptide comprising the amino acid sequence represented by SEQ ID NO: 35 in the sequence listing or a heavy chain polypeptide comprising the amino acid sequence represented by SEQ ID NO: 39 in the sequence listing; and
2) a light chain polypeptide comprising the amino acid sequence represented by SEQ ID NO: 37 in the sequence listing or a light chain polypeptide comprising the amino acid sequence represented by SEQ ID NO: 41 in the sequence listing;

(29) An antibody consisting of the following 1) or 2):
1) a heavy chain polypeptide comprising the amino acid sequence represented by SEQ ID NO: 35 in the sequence listing and a light chain polypeptide comprising the amino acid sequence represented by SEQ ID NO: 37 in the sequence listing; and
2) a heavy chain polypeptide comprising the amino acid sequence represented by EQ ID NO: 39 in the sequence listing and a light chain polypeptide comprising the amino acid sequence represented by SEQ ID NO: 41 in the sequence listing;

(30) An antibody obtained by humanizing an antibody according to any one of (24) to (29);

(31) An antibody consisting of the following 1) and 2):
1) a heavy chain polypeptide comprising an amino acid sequence represented by amino acid Nos. 20 to 468 of SEQ ID NO: 107 in the sequence listing or a heavy chain polypeptide comprising an amino acid sequence represented by amino acid Nos. 20 to 468 of SEQ ID NO: 115 in the sequence listing; and
2) a light chain polypeptide comprising an amino acid sequence represented by amino acid Nos. 21 to 239 of SEQ ID NO: 91 in the sequence listing or a light chain polypeptide comprising an amino acid sequence represented by amino acid Nos. 21 to 239 of SEQ ID NO: 99 in the sequence listing;

(32) An antibody consisting of the following 1) or 2):
1) a heavy chain polypeptide comprising an amino acid sequence represented by amino acid Nos. 20 to 468 of SEQ ID NO: 107 in the sequence listing and a light chain polypeptide comprising an amino acid sequence represented by amino acid Nos. 21 to 239 of SEQ ID NO: 91 in the sequence listing; and
2) a heavy chain polypeptide comprising an amino acid sequence represented by amino acid Nos. 20 to 468 of SEQ ID NO: 115 in the sequence listing and a light chain polypeptide comprising an amino acid sequence represented by amino acid Nos. 21 to 239 of SEQ ID NO: 99 in the sequence listing;

(33) An antibody consisting of the following 1) and 2):
1) a heavy chain polypeptide comprising an amino acid sequence represented by amino acid Nos. 20 to 468 of SEQ ID NO: 139 in the sequence listing or a heavy chain polypeptide comprising an amino acid sequence represented by amino acid Nos. 20 to 468 of SEQ ID NO: 147 in the sequence listing; and
2) a light chain polypeptide comprising an amino acid sequence represented by amino acid Nos. 21 to 239 of SEQ ID NO: 123 in the sequence listing or a light chain polypeptide comprising an amino acid sequence represented by amino acid Nos. 21 to 239 of SEQ ID NO: 131 in the sequence listing;

(34) An antibody consisting of the following 1) or 2):
1) a heavy chain polypeptide comprising an amino acid sequence represented by amino acid Nos. 20 to 468 of SEQ ID NO: 139 in the sequence listing and a light chain polypeptide comprising an amino acid sequence represented by amino acid Nos. 21 to 239 of SEQ ID NO: 123 in the sequence listing; and
2) a heavy chain polypeptide comprising an amino acid sequence represented by amino acid Nos. 20 to 468 of SEQ ID NO: 147 in the sequence listing and a light chain polypeptide comprising an amino acid sequence represented by amino acid Nos. 21 to 239 of SEQ ID NO: 131 in the sequence listing;

(35) A Fab, F(ab')2, Fv, scFv, a diabody, a linear antibody, or a multispecific antibody derived from antibodies according to any of (24) to (34);

(36) Any one polypeptide selected from the group consisting of the following 1) to 20):

1) a polypeptide comprising an amino acid sequence represented by amino acid Nos. 1 to 119 of SEQ ID NO: 35 in the sequence listing;
2) a polypeptide comprising an amino acid sequence represented by amino acid Nos. 1 to 119 of SEQ ID NO: 39 in the sequence listing;
3) a polypeptide comprising an amino acid sequence represented by amino acid Nos. 1 to 112 of SEQ ID NO: 37 in the sequence listing;
4) a polypeptide comprising an amino acid sequence represented by amino acid Nos. 1 to 112 of SEQ ID NO: 41 in the sequence listing;
5) a polypeptide comprising an amino acid sequence represented by amino acid Nos. 20 to 468 of SEQ ID NO: 107 in the sequence listing;
6) a polypeptide comprising an amino acid sequence represented by amino acid Nos. 20 to 468 of SEQ ID NO: 115 in the sequence listing;
7) a polypeptide comprising an amino acid sequence represented by amino acid Nos. 20 to 138 of SEQ ID NO: 107 in the sequence listing;
8) a polypeptide comprising an amino acid sequence represented by amino acid Nos. 20 to 138 of SEQ ID NO: 115 in the sequence listing;
9) a polypeptide comprising an amino acid sequence represented by amino acid Nos. 21 to 239 of SEQ ID NO: 91 in the sequence listing;
10) a polypeptide comprising an amino acid sequence represented by amino acid Nos. 21 to 239 of SEQ ID NO: 99 in the sequence listing;
11) a polypeptide comprising an amino acid sequence represented by amino acid Nos. 21 to 134 of SEQ ID NO: 91 in the sequence listing;
12) a polypeptide comprising an amino acid sequence represented by amino acid Nos. 21 to 134 of SEQ ID NO: 99 in the sequence listing;
13) a polypeptide comprising an amino acid sequence represented by amino acid Nos. 20 to 468 of SEQ ID NO: 139 in the sequence listing;
14) a polypeptide comprising an amino acid sequence represented by amino acid Nos. 20 to 468 of SEQ ID NO: 147 in the sequence listing;
15) a polypeptide comprising an amino acid sequence represented by amino acid Nos. 20 to 138 of SEQ ID NO: 139 in the sequence listing;
16) a polypeptide comprising an amino acid sequence represented by amino acid Nos. 20 to 138 of SEQ ID NO: 147 in the sequence listing;
17) a polypeptide comprising an amino acid sequence represented by amino acid Nos. 21 to 239 of SEQ ID NO: 123 in the sequence listing;
18) a polypeptide comprising an amino acid sequence represented by amino acid Nos. 21 to 239 of SEQ ID NO: 131 in the sequence listing;
19) a polypeptide comprising an amino acid sequence represented by amino acid Nos. 21 to 134 of SEQ ID NO: 123 in the sequence listing; and
20) a polypeptide comprising an amino acid sequence represented by amino acid Nos. 21 to 134 of SEQ ID NO: 131 in the sequence listing;

(37) The mouse hybridoma SH348-1 (FERM BP-10836);
(38) The mouse hybridoma SH357-1 (FERM BP-10837);
(39) A pharmaceutical composition characterized by comprising at least one antibody selected from the antibodies according to (1) to (35);
(40) A pharmaceutical composition for cancer treatment characterized by comprising at least one antibody selected from the antibodies according to (1) to (35);
(41) A method for inhibiting tumor growth in a mammal, comprising administering any antibody selected from the group consisting of antibodies according to (1) to (35), (39), and (40);
(42) The method for inhibiting tumor growth according to (41), characterized in that the tumor is a tumor expressing EPHA2;
(43) A polynucleotide encoding an antibody or a polypeptide according to any one of (1) to (36);
(44) A host cell transformed with a polynucleotide according to (43); and
(45) A method for producing an antibody using a host cell according to (44).

Advantages of the Invention

According to the present invention, a novel anti-EPHA2 monoclonal antibody has been successfully obtained, which has no activity of inducing the phosphorylation of EPHA2 tyrosine residues and has ADCC and CDC activities against EPHA2-expressing cancer cells. Furthermore, it has been found that the antibody has excellent antitumor activity in vivo.

Furthermore, a pharmaceutical composition for cancer treatment comprising the antibody has been provided.

BEST MODE FOR CARRYING OUT THE INVENTION

1. Definitions

In the present specification, the terms "cancer" and "tumor" are used in the same sense.

In the present specification, the term "gene" is meant to encompass not only DNA but also mRNA thereof, cDNA, and cRNA thereof. Thus, the term "EPHA2 gene" in the present invention encompasses EPHA2 DNA, mRNA, cDNA, and cRNA.

In the present specification, the term "polynucleotide" is used in the same sense as a nucleic acid and also encompasses DNA, RNA, probes, oligonucleotides, and primers.

In the present specification, the terms "polypeptide" and "protein" are used without being differentiated therebetween.

In the present specification, the term "cell" also encompasses cells in individual animal and cultured cells.

In the present specification, the term "cell malignant transformation" means that cells exhibit abnormal growth, for example, lose sensitivity to contact inhibition or exhibit anchorage-independent growth. Cells exhibiting such abnormal growth are referred to as "cancer cells".

In the present specification, a protein having equivalent functions to the cell malignant transformation activity and/or cell growth activity or the like of EPHA2 is also referred to as EPHA2.

In the present specification, the term "phosphorylation of tyrosine residues" means that tyrosine residues contained in the amino acid sequence of a peptide are phosphorylated. Whether or not tyrosine residues are phosphorylated can be examined, for example, based on the affinity of the peptide for an anti-phosphotyrosine antibody (e.g., Anti-Phosphotyrosine, recombinant 4G10 HRP-conjugate (manufactured by Millipore (Upstate), #16-184)). The tyrosine residues can be determined to be phosphorylated, when the peptide binds to the antibody.

In the present specification, the term "ability to phosphorylate EPHA2 tyrosine residues" refers to an ability to phosphorylate tyrosine residues in the amino acid sequence of EPHA2. Whether or not an antibody has the ability to phosphorylate EPHA2 tyrosine residues can be determined, for example, by incubating the antibody and EPHA2 and then examining the presence or absence of the affinity of the EPHA2 for an anti-phosphotyrosine antibody.

In the present specification, the phrase "decreasing an EPHA2 protein expression level" means that an EPHA2 protein level is decreased. Whether or not an antibody has an effect of decreasing an EPHA2 protein level can be examined, for example, by incubating the antibody and EPHA2 and then quantifying the EPHA2 level.

In the present specification, the term "EPHA2 ligand" refers to a substance capable of serving as an EPHA2 ligand. Specific examples thereof can include GPI-anchored plasma membrane proteins ephrin-A1 to ephrin-A5 (Annual Review of Neuroscience, 1998, vol. 21, p. 309-345).

In the present specification, the term "cytotoxicity" refers to any pathologic change in cells and refers not only to direct injury but also to any structural or functional damage to cells such as DNA cleavage, dimerization of bases, chromosomal breakage, damage of mitotic apparatus, and decrease in various enzyme activities.

In the present specification, the term "cytotoxic activity" refers to an activity that causes the cytotoxicity.

In the present specification, ADCC is synonymous with antibody-dependent cellular cytotoxicity and refers to a reaction through which Fcγ receptor-bearing cells adhere via the Fcγ receptors to the Fc portions of antibodies bound with surface antigens in target cells and kill the target cells. An ADCC activity is also referred to as an antibody-dependent cytotoxic activity and refers to an activity that causes the reaction. The ADCC activity can be measured by methods usually performed by those skilled in the art and can be measured, for example, according to a method described in paragraph 3)-2 of Example 3 in the present specification.

In the present specification, the term "CDC" is synonymous with complement-dependent cytotoxicity. A CDC activity refers to an activity that causes complement-dependent cytotoxicity. The CDC activity can be measured by methods usually performed by those skilled in the art and can be measured, for example, according to a method described in paragraph 3)-3 of Example 3 in the present specification.

In the present specification, the phrase "having an antitumor activity in vivo" means having the activity of inhibiting or reducing tumor growth in tumor-bearing animal individuals. Whether or not an anti-EPHA2 antibody "has an antitumor activity in vivo" can be examined by methods usually performed by those skilled in the art and can also be examined, for example, according to the following method: an appropriate dose of the anti-EPHA2 antibody is intraperitoneally administered as a test substance to tumor cell (e.g., MDA-MB-231 cell)-subcutaneously transplanted nude mice (e.g., BALB/cAJc1-nu/nu; obtained from CLEA Japan, Inc.), and the time-dependent change in tumor volume is compared between the nude mice and anti-EPHA2 antibody-unadministered controls. The anti-EPHA2 antibody as a test substance can be determined to "have an antitumor activity in vivo", when the tumor volume is significantly smaller in the mice than in the controls.

Each of the heavy and light chains of an antibody molecule is known to have three complementarity determining regions (CDRs). In the present specification, the complementarity determining regions of an antibody are represented by $CDRH_1$, $CDRH_2$, and $CDRH_3$ for the complementarity determining regions of the heavy chain and by $CDRL_1$, $CDRL_2$, and $CDRL_3$ for the complementarity determining regions of the light chain.

In the present specification, the term "epitope" means an EPHA2 partial peptide having antigenicity and/or immunogenicity in vivo in animals, preferably, mammals, more preferably mice or humans. The epitope as an EPHA2 partial peptide having antigenicity can be determined by methods well known by those skilled in the art, such as by an immunoassay, and can be determined, for example, according to the following method in which various partial structures of EPHA2 are prepared. For the preparation of the partial structures, oligopeptide synthesis techniques known in the art can be used. For example, a series of sequentially shorter polypeptides of appropriate lengths from the C- or N-terminus of EPHA2 is prepared using a gene recombination technique well known by those skilled in the art. Then, the reactivity of the antibody to these polypeptides is studied. A recognition site is roughly determined, and shorter peptides are then synthesized. The reactivity to these peptides can be studied to thereby determine the epitope.

1. Regarding EPHA2

(1) EPHA2 Gene

The nucleotide sequence of the EPHA2 gene and the amino acid sequence thereof are recorded as EPH receptor A2 in GenBank (Accession NOs: NM_004431 and NP_004422, respectively). Moreover, the nucleotide sequence of an open reading frame (ORF) in the EPHA2 gene is described in SEQ ID NO: 1 in the sequence listing. The amino acid sequence thereof is described in SEQ ID NO: 2 in the sequence listing.

In this context, EPHA2 also encompasses proteins which consist of an amino acid sequence derived from the EPHA2 amino acid sequence by the substitution, deletion, or addition of one or more amino acids and have an equivalent biological activity to that of this enzyme.

(2) Cancer Site-Specific Expression of EPHA2 Gene

The EPHA2 gene has been reported to be highly expressed in many cancers, particularly, breast cancer, esophagus cancer, prostate cancer, gastric cancer, non-small cell lung cancer, colon cancer, and glioblastoma multiform.

Specifically, the expression level of EPHA2 in each cell and/or each tissue can be measured to thereby determine the state of malignant transformation and/or cancer cell growth that can be attributed to EPHA2 over-expression in test subjects.

Moreover, a substance that inhibits the expression level and/or activity of EPHA2 has an activity of inhibiting cell malignant transformation and/or cancer cell growth attributed to EPHA2.

Thus, test substances are contacted with EPHA2-expressing cells, and a substance that inhibits the expression level and/or activity of EPHA2 can be selected to thereby screen for an antitumor substance.

In this context, siRNA against EPHA2 inhibits EPHA2 expression and can be used as an antitumor agent. The siRNA against EPHA2 can be produced by: designing, based on the nucleotide sequence of EPHA2 mRNA, RNA consisting of a partial sequence of EPHA2 mRNA (sense RNA) and RNA consisting of a nucleotide sequence complementary to the nucleotide sequence of the RNA (antisense RNA); synthesizing the RNAs by a chemical synthesis method known per se in the art; and hybridizing both the obtained RNAs. It is preferred that a sequence of one or more nucleotides called an overhang sequence should be bound to the 3'-end of each of the sense and antisense RNAs constituting the siRNA. The overhang sequence is not particularly limited as long as it protects the RNA from nuclease. Any sequence of preferably 1 to 10, more preferably 1 to 4, even more preferably 2 nucleotides can be used.

2. Antibody Against EPHA2

(1) Preparation of Antigen

Examples of antigens for obtaining the antibody of the present invention against EPHA2 can include a full-length polypeptide of EPHA2 and partial polypeptides thereof and can more specifically include a full-length polypeptide of EPHA2 and preferably an EPHA2 extracellular region polypeptide (consisting of an amino acid sequence represented by amino acid Nos. 1 to 534 of SEQ ID NO: 8 in the sequence listing), more preferably a partial polypeptide of the EPHA2 extracellular region polypeptide comprising an amino acid sequence represented by amino acid Nos. 426 to 534 of SEQ ID NO: 8 in the sequence listing, even more preferably a partial polypeptide of the EPHA2 extracellular region polypeptide comprising an amino acid sequence represented by amino acid Nos. 439 to 534 of SEQ ID NO: 8 in the sequence listing, and derivatives obtained by adding an arbitrary amino acid sequence or a carrier to these sequences. Further examples thereof can include polypeptides consisting of consecutive partial amino acid sequences of at least 6 amino acids and derivatives obtained by adding an arbitrary amino acid sequence or a carrier to these sequences.

In this context, the EPHA2 full-length polypeptide or the partial polypeptides thereof used as an antigen can be obtained by causing the EPHA2 gene or genes of the partial polypeptides to be expressed in host cells by genetic engineering.

EPHA2 can be directly purified, for use, from human tumor tissues or tumor cells. Moreover, the EPHA2 full-length polypeptide or the partial polypeptides thereof can be synthesized in vitro or obtained by causing host cells by genetic engineering to produce the polypeptide.

In the genetic engineering, specifically, genes encoding EPHA2 or partial polypeptides thereof are incorporated into vectors capable of expressing the EPHA2 or partial polypeptides thereof, and the EPHA2 or partial polypeptides thereof can then be synthesized in a solution containing enzymes, substrates, and energy substances necessary for transcription and translation. Alternatively, host cells of other prokaryotes or eukaryotes can be transformed therewith and caused to express the EPHA2 or partial polypeptides thereof to obtain the desired protein.

cDNA of the partial polypeptide of EPHA2 can be obtained, for example, by a so-called polymerase chain reaction (hereinafter, referred to as "PCR") method in which PCR (see Saiki, R. K., et al. Science (1988) 239, p. 487-489) is performed using EPHA2-expressing cDNA libraries as templates and primers specifically amplifying EPHA2 cDNA or DNA encoding the partial polypeptide.

Examples of in vitro polypeptide synthesis include, but are not limited to, the Rapid Translation System (RTS) manufactured by Roche Diagnostics Corp.

Examples of the host prokaryotic cells include *Escherichia coli* and *Bacillus subtilis*. To transform these host cells with the gene of interest, the host cells are transformed with plasmid vectors comprising a replicon, i.e., a replication origin, and a regulatory sequence derived from a species compatible with the hosts. Moreover, it is preferred that the vectors should have a sequence that can impart phenotypic character (phenotype) selectivity to the transformed cells.

The host eukaryotic cells encompass cells of vertebrates, insects, yeast, and the like. For example, monkey COS cells (Gluzman, Y. Cell (1981) 23, p. 175-182, ATCC CRL-1650), mouse fibroblasts NIH3T3 (ATCC No. CRL-1658), and dihydrofolate reductase-deficient strains (Urlaub, G. and Chasin, L. A., Proc. Natl. Acad. Sci. USA (1980) 77, p. 4126-4220) of Chinese hamster ovarian cells (CHO cells, ATCC CCL-61) are often used as the vertebrate cells, though the vertebrate cells are not limited thereto.

The transformants thus obtained can be cultured according to standard methods and are able within the culture to intracellularly or extracellularly produce the polypeptide of interest.

A medium used in the culture can be selected appropriately according to the adopted host cells from among various media routinely used. For *Escherichia coli*, for example, an LB medium optionally supplemented with an antibiotic (e.g., ampicillin) or IPTG can be used.

The recombinant protein intracellularly or extracellularly produced by the transformants in the culture can be separated and purified by various separation procedures known in the art using the physical properties, chemical properties, or the like of the protein.

The procedures can be exemplified specifically by treatment with usual protein precipitants, ultrafiltration, various liquid chromatography techniques such as molecular sieve chromatography (gel filtration), adsorption chromatography, ion-exchange chromatography, affinity chromatography, and high-performance liquid chromatography (HPLC), dialysis, and combinations thereof.

Moreover, the recombinant protein to be expressed can be linked to 6 histidine residues to thereby efficiently purify the resulting protein on a nickel affinity column.

By combining these methods, the polypeptide of interest can be produced easily in large amounts with high yields and high purity.

The antibody of the present invention can be obtained by immunizing animals with the antigen according to a standard method and collecting antibodies produced in vivo, followed by purification.

Moreover, antibody-producing cells that produce the antibody against EPHA2 are fused with myeloma cells according to a method known in the art (e.g., Kohler and Milstein, Nature (1975) 256, p. 495-497; and Kennet, R. ed., Monoclonal Antibodies, p. 365-367, Plenum Press, N.Y. (1980)) to thereby establish hybridomas, from which monoclonal antibodies can also be obtained.

(2) Production of Anti-EPHA2 Monoclonal Antibody

Examples of antibodies which specifically bind to EPHA2 can include monoclonal antibodies which specifically bind to EPHA2. A method for obtaining the antibodies is as described below.

For monoclonal antibody production, the following process is generally required:

(a) the step of purifying biopolymers used as antigens, (b) the step of immunizing animals with the antigens through injection, then collecting blood from the animals, assaying the antibody titer thereof to determine the timing of splenectomy, and then preparing antibody-producing cells, (c) the step of preparing myeloma cells (hereinafter, referred to as "myelomas"), (d) the step of performing cell fusion between the antibody-producing cells and the myelomas, (e) the step of selecting a hybridoma group that produces the antibody of interest, (f) the step of dividing into single cell clones (cloning), (g) the step of culturing the hybridomas for producing monoclonal antibodies in large amounts or raising hybridoma-transplanted animals, according to circumstances, (h) the step of studying the bioactivities and binding specificities of the monoclonal antibodies thus produced or assaying properties as labeling reagents, etc.

Hereinafter, the method for preparing monoclonal antibodies will be described in detail in line with these steps, though the method for preparing antibodies is not limited thereto. For example, antibody-producing cells other than splenic cells and myelomas can also be used.

(a) Purification of Antigens

EPHA2 or partial polypeptides thereof prepared by the method as described above can be used as antigens.

Moreover, partial peptides of the protein of the present invention, which are chemically synthesized using membrane fractions prepared from EPHA2-expressing recombinant somatic cells or the EPHA2-expressing recombinant somatic cells themselves according to a method well known by those skilled in the art, can also be used as antigens.

(b) Preparation of Antibody-Producing Cells

The antigens obtained in step (a) are mixed with adjuvants well known by those skilled in the art, for example, complete or incomplete Freund's adjuvants, or other auxiliaries such as potassium aluminum sulfate, and experimental animals are immunized with these immunogens. Animals used in hybridoma preparation methods known in the art can be used as the experimental animals without problems. Specifically, for example, mice, rats, goats, sheep, cow, and horses can be used. However, mice or rats are preferably used as the animals to be immunized, from the viewpoint of the easy availability of myeloma cells to be fused with the extracted antibody-producing cells, etc.

Moreover, the lineages of the mice and rats actually used are not particularly limited. For example, mouse lineages such as A, AKR, BALB/c, BDP, BA, CE, C3H, 57BL, C57BR, C57L, DBA, FL, HTH, HT1, LP, NZB, NZW, RF, R III, SJL, SWR, WB, and 129 and rat lineages such as Low, Lewis, Sprague-Dawley, ACI, BN, and Fischer can be used.

These mice and rats can be obtained from, for example, experimental animal growers/distributors such as CLEA Japan, Inc. and Charles River Laboratories Japan, Inc.

Of these lineages, the mouse BALB/c lineage and the rat Low lineage are particularly preferable as the animals to be immunized, in consideration of fusion compatibility with myeloma cells as described later.

Moreover, mice having a reduced biological mechanism for autoantibody removal, i.e., autoimmune disease mice, are also preferably used in consideration of the antigenic homology between humans and mice.

These mice or rats are preferably 5 to 12 weeks old, more preferably 6 to 8 weeks old, at the time of immunization.

For the immunization of the animals with EPHA2 or the recombinant antigens thereof, methods known in the art described in detail in, for example, Weir, D. M., Handbook of Experimental Immunology Vol. I. II. III., Blackwell Scientific Publications, Oxford (1987), and Kabat, E. A. and Mayer, M. M., Experimental Immunochemistry, Charles C. Thomas Publisher Springfield, Ill. (1964) can be used.

Of these immunization methods, a method preferable in the present invention is specifically illustrated as described below.

Specifically, the membrane protein fractions used as antigens or antigen-expressing cells are first administered intradermally or intraperitoneally to the animals.

However, the combined use of both of the administration routes is preferable for enhancing immunization efficiency. Immunization efficiency can be enhanced particularly by performing intradermal administration in early immunizations and performing intraperitoneal administration in later immunizations or only in the last immunization.

The administration schedule of the antigens differs depending on the type of animals to be immunized, the individual differences thereof, etc. The antigens are generally administered at 3 to 6 doses preferably at 2- to 6-week intervals, more preferably at 3 to 4 doses at 2- to 4-week intervals.

Moreover, the dose of the antigens differs depending on the type of animals, the individual differences thereof, etc., and is generally of the order of 0.05 to 5 mg, preferably 0.1 to 0.5 mg.

A booster is performed 1 to 6 weeks later, preferably 2 to 4 weeks later, more preferably 2 to 3 weeks later, from such antigen administration.

In this context, the dose of the antigens in the booster differs depending on the type of animals, the size thereof, etc., and is generally of the order of 0.05 to 5 mg, preferably 0.1 to 0.5 mg, more preferably 0.1 to 0.2 mg, for example, for mice.

1 to 10 days later, preferably 2 to 5 days later, more preferably 2 to 3 days later, from the booster, splenic cells or lymphocytes containing antibody-producing cells are aseptically extracted from the animals to be immunized.

In this procedure, their antibody titers are measured, and animals having a sufficiently increased antibody titer can be used as sources of antibody-producing cells to thereby enhance the efficiency of the subsequent procedures.

Examples of methods for measuring the antibody titers used here can include, but not limited to, RIA and ELISA.

The antibody titer measurement according to the present invention can be performed by procedures as described below, for example, according to ELISA.

First, the purified or partially purified antigens are adsorbed onto the surface of a solid phase such as 96-well plates for ELISA. Furthermore, antigen-unadsorbed solid phase surface is covered with proteins unrelated to the antigens, for example, bovine serum albumin (hereinafter, referred to as "BSA"). The surfaces are washed and then contacted with serially diluted samples (e.g., mouse serum) as primary antibodies such that the antibodies in the samples are bound to the antigens.

Furthermore, enzyme-labeled antibodies against the mouse antibodies are added thereto as secondary antibodies such that the secondary antibodies are bound to the mouse antibodies. After washing, substrates for the enzyme are added thereto, and, for example, the change in absorbance caused by color development based on substrate degradation is measured to thereby calculate antibody titers.

The antibody-producing cells can be separated from these spleen cells or lymphocytes according to methods known in the art (e.g., Kohler et al., Nature (1975) 256, p. 495; Kohler et al., Eur. J. Immunol. (1977) 6, p. 511; Milstein et al., Nature (1977), 266, p. 550; and Walsh, Nature, (1977) 266, p. 495).

For example, for the spleen cells, a general method can be adopted, which involves cutting the cells into strips, filtering them through a stainless mesh, and then separating the antibody-producing cells therefrom by floating in Eagle's minimal essential medium (MEM).

(C) Preparation of Myeloma Cells (Hereinafter, Referred to as "Myelomas")

Myeloma cells used in cell fusion are not particularly limited and can be selected appropriately, for use, from cell strains known in the art. However, HGPRT (hypoxanthine-guanine phosphoribosyl transferase)-deficient strains for which selection methods have been established are preferably used in consideration of convenient hybridoma selection from fused cells.

Specific examples thereof include: mouse-derived X63-Ag8 (X63), NS1-ANS/1 (NS1), P3X63-Ag8.U1 (P3U1), X63-Ag8.653 (X63.653), SP2/0-Ag14 (SP2/0), MPC11-45.6TG1.7 (45.6TG), FO, S149/5XXO, and BU.1; rat-derived 210.RSY3.Ag.1.2.3 (Y3); and human-derived U266AR (SKO-007), GM1500.GTG-A12 (GM1500), UC729-6, LICR-LON-HMy2 (HMy2), and 8226AR/NIP4-1 (NP41).

These HGPRT-deficient strains can be obtained from, for example, American Type Culture Collection (ATCC).

These cell strains are subcultured in an appropriate medium, for example, an 8-azaguanine medium [RPMI-1640 medium supplemented with glutamine, 2-mercaptoethanol, gentamicin, and fetal bovine serum (hereinafter, referred to as "FBS") and further supplemented with 8-azaguanine], an Iscove's Modified Dulbecco's Medium (hereinafter, referred to as "IMDM"), or a Dulbecco's Modified Eagle Medium (hereinafter, referred to as "DMEM") and subcultured in a normal medium [e.g., an ASF104 medium (manufactured by Ajinomoto Co., Inc.) containing 10% FBS] 3 to 4 days before cell fusion. On the day of fusion, $2 \times 10^7$ or more cells are secured.

(d) Cell Fusion

Fusion between the antibody-producing cells and the myeloma cells can be performed appropriately under conditions that do not excessively reduce the cell survival rates, according to methods known in the art (e.g., Weir, D. M., Handbook of Experimental Immunology Vol. I. II. III., Blackwell Scientific Publications, Oxford (1987); and Kabat, E. A. and Mayer, M. M., Experimental Immunochemistry, Charles C. Thomas Publisher Springfield, Ill. (1964)).

For example, a chemical method which involves mixing the antibody-producing cells and the myeloma cells in a high-concentration polymer (e.g., polyethylene glycol) solution and a physical method which uses electric stimulations can be used as such methods.

Of these methods, the chemical method is specifically exemplified as described below.

Specifically, when polyethylene glycol is used as a polymer in the high-concentration polymer solution, the antibody-producing cells and the myeloma cells are mixed in a solution of polyethylene glycol having a molecular weight of 1500 to 6000, preferably 2000 to 4000, at a temperature of 30 to 40° C., preferably 35 to 38° C., for 1 to 10 minutes, preferably 5 to 8 minutes.

(e) Selection of Hybridoma Group

A method for selecting the hybridomas obtained by the cell fusion is not particularly limited, and a HAT (hypoxanthine-aminopterin-thymidine) selection method (Kohler et al., Nature (1975) 256, p. 495; and Milstein et al., Nature (1977) 266, p. 550) is usually used.

This method is effective for obtaining hybridomas using HGPRT-deficient myeloma cell strains that cannot survive in aminopterin.

Specifically, unfused cells and the hybridomas can be cultured in a HAT medium to thereby cause only aminopterin-resistant hybridomas to remain and grow.

(f) Dividing into Single Cell Clones (Cloning)

For example, methods known in the art, such as methylcellulose, soft agarose, and limiting dilution methods can be used as methods for cloning the hybridomas (see e.g., Barbara, B. M. and Stanley, M. S.: Selected Methods in Cellular Immunology, W.H. Freeman and Company, San Francisco (1980)). Of these methods, the limiting dilution method is particularly preferable.

In this method, feeders such as rat fetus-derived fibroblast strains or normal mouse splenic, thymus, or ascites cells are inoculated onto a microplate.

On the other hand, the hybridomas are diluted to 0.2 to 0.5 individuals/0.2 ml in advance in a medium. This solution containing the diluted hybridomas floating therein is added at a concentration of 0.1 ml/well, and the hybridomas can be continuously cultured for approximately 2 weeks while approximately ⅓ of the medium is replaced with a new one at regular intervals (e.g., 3-day intervals), to thereby grow hybridoma clones.

For wells having an observable antibody titer, for example, cloning by the limiting dilution method is repeated 2 to 4 times, and clones whose antibody titer is stably observed can be selected as anti-EPHA2 monoclonal antibody-producing hybridoma strains.

Examples of the hybridoma strains thus cloned can include hybridoma SH348-1 and hybridoma SH357-1. Hybridoma SH348-1 and hybridoma SH357-1 have been deposited on Jun. 8, 2007 with International Patent Organism Depositary, National Institute of Advanced Industrial Science and Technology, (address: Tsukuba Central 6, Higashi 1-1-1, Tsukuba, Ibaraki, Japan). Hybridoma SH348-1 has been designated as SH348-1 with Accession No. FERM BP-10836, and hybridoma SH357-1 has been designated as SH357-1 with Accession No. FERM BP-10837.

In the present specification, an antibody produced by hybridoma SH348-1 is referred to as "SH348-1", and an antibody produced by hybridoma SH357-1 is referred to as "SH357-1".

(g) Preparation of Monoclonal Antibodies by Hybridoma Culture

The hybridomas thus selected can be cultured to thereby efficiently obtain monoclonal antibodies. Prior to the culture, it is preferred that hybridomas producing the monoclonal antibody of interest should be screened.

For this screening, methods known per se in the art can be adopted.

The antibody titer measurement according to the present invention can be performed, for example, by ELISA as described in paragraph (b).

The hybridomas obtained by the method as described above can be cryopreserved in liquid nitrogen or in a freezer at −80° C. or lower.

Moreover, the completely cloned hybridomas can be passaged several times in a HT medium (HAT medium except for aminopterin) and then cultured in a normal medium changed therefrom.

Large-scale culture is performed by rotational culture using large culture bottles or spinner culture.

A supernatant obtained in this large-scale culture can be purified according to methods well known by those skilled in the art, such as gel filtration, to obtain monoclonal antibodies which specifically bind to the protein of the present invention.

Moreover, the hybridomas can be intraperitoneally injected to mice of the same lineage thereas (e.g., BALB/c) or Nu/Nu mice and grown to obtain ascites containing the monoclonal antibody of the present invention in large amounts.

For the intraperitoneal administration, mineral oil such as 2,6,10,14-tetramethyl pentadecane (pristane) is administered beforehand (3 to 7 days before the administration) to obtain ascites in larger amounts.

For example, an immunosuppressive agent is intraperitoneally injected in advance to the mice of the same lineage as the hybridomas to inactivate the T cells. 20 days later, $10^6$ to $10^7$ hybridoma clone cells are allowed to float (0.5 ml) in a serum-free medium, and this solution is intraperitoneally administered to the mice. Ascites are usually collected from the mice when abdominal distention occurs by accumulated ascites.

By this method, monoclonal antibodies are obtained with a concentration approximately 100 times higher than that in the culture solution.

The monoclonal antibodies obtained by the method can be purified by methods described in, for example, Weir, D. M.: Handbook of Experimental Immunology, Vol. I, II, III, Blackwell Scientific Publications, Oxford (1978).

Specific examples thereof include ammonium sulfate precipitation, gel filtration, ion-exchange chromatography, and affinity chromatography.

For the purification, commercially available monoclonal antibody purification kits (e.g., MAbTrap GII Kit; manufactured by Pharmacia Inc.) and the like can also be used as convenient methods.

The monoclonal antibodies thus obtained have high antigen specificity for EPHA2.

(h) Assay of Monoclonal Antibodies

The isotype and subclass of the monoclonal antibodies thus obtained can be determined as described below.

First, examples of identification methods include the Ouchterlony method, ELISA, and RIA.

The Ouchterlony method is convenient but requires a concentration procedure for a low concentration of monoclonal antibodies.

On the other hand, when the ELISA or RIA is used, the culture supernatant is directly reacted with an antigen-adsorbed solid phase, and further, antibodies compatible with various immunoglobulin isotypes and subclasses can be used as secondary antibodies to thereby identify the isotype or subclass of the monoclonal antibodies.

Moreover, commercially available kits for identification (e.g., Mouse Typer Kit; manufactured by Bio-Rad Laboratories, Inc.) and the like can also be used as more convenient methods.

Furthermore, the proteins can be quantified according to a Folin-Lowry method and a calculation method using absorbance at 280 nm [1.4 (OD280)=1 mg/ml immunoglobulin].

(3) Other Antibodies

The antibody of the present invention encompasses the monoclonal antibody against EPHA2 as well as genetic recombinant antibodies artificially modified for the purpose of, for example, reducing xenoantigenicity against humans, for example, chimeric, humanized, and human antibodies. These antibodies can be produced according to known methods.

Examples of the chimeric antibody include an antibody having variable and constant regions derived from species different from each other and specifically include a chimeric antibody comprising mouse-derived variable regions and human-derived constant regions joined together (see Proc. Natl. Acad. Sci. U.S.A., 81, 6851-6855, (1984)).

Examples of the humanized antibody can include an antibody comprising a human-derived antibody with complementarity determining regions (CDRs) replaced with those of another species (see Nature (1986) 321, p. 522-525) and an antibody comprising a human antibody with CDR sequences and some framework amino acid residues replaced with those of another species by CDR grafting (see WO 90/07861 and U.S. Pat. No. 6,972,323).

Further examples of the antibody of the present invention can include an anti-human antibody. The anti-EPHA2 human antibody means a human antibody having only the gene sequence of a human chromosome-derived antibody. The anti-EPHA2 human antibody can be obtained by methods using human antibody-producing mice having a human chromosome fragment containing genes of human antibody H and L chains (see e.g., Tomizuka, K. et al., Nature Genetics (1997) 16, p. 133-143; Kuroiwa, Y. et al., Nucl. Acids Res. (1998) 26, p. 3447-3448; Yoshida, H. et al., Animal Cell Technology: Basic and Applied Aspects vol. 10, p. 69-73 (Kitagawa, Y., Matsuda, T. and Iijima, S. eds.), Kluwer Academic Publishers, 1999; and Tomizuka, K. et al., Proc. Natl. Acad. Sci. USA (2000) 97, p. 722-727).

For such transgenic animals, specifically, genetic recombinant animals in which loci of endogenous immunoglobulin heavy and light chains in non-human mammals are broken and loci of human immunoglobulin heavy and light chains are introduced instead via yeast artificial chromosome (YAC) vectors or the like can be created by preparing knockout animals and transgenic animals and crossing these animals.

Moreover, eukaryotic cells are transformed with cDNA encoding each of such human antibody heavy and light chains, preferably vectors containing the cDNA, by gene recombination techniques, and transformed cells producing genetic recombinant human monoclonal antibodies can also be cultured to thereby obtain these antibodies from the culture supernatant.

In this context, for example, eukaryotic cells, preferably mammalian cells such as CHO cells, lymphocytes, and myelomas can be used as hosts.

Moreover, methods for obtaining phage-displayed human antibodies selected from human antibody libraries are also known (see e.g., Wormstone, I. M. et al., Investigative Ophthalmology & Visual Science. (2002) 43 (7), p. 2301-2308; Carmen, S. et al., Briefings in Functional Genomics and Proteomics (2002), 1 (2), p. 189-203; and Siriwardena, D. et al., Ophthalmology (2002) 109 (3), p. 427-431).

For example, a phage display method can be used, which involves causing human antibody variable regions to be expressed as a single-chain antibody (scFv) on phage surface and selecting phages binding to antigens (Nature Biotechnology (2005), 23, (9), p. 1105-1116).

Likewise, another phage display method can also be used, which involves causing human antibody Fab (antigen-binding fragment) to be expressed on the surface of phage and selecting phages binding to antigens (WO 97/08320 and WO 01/05950).

Genes of the phages selected based on antigen binding can be analyzed to thereby determine DNA sequences encoding human antibody variable regions binding to the antigens.

When the DNA sequence of scFv or Fab binding to the antigens is clarified, CDR sequences are extracted therefrom, and expression vectors having the sequences can be prepared and introduced into appropriate hosts, followed by gene expression to obtain human antibodies (WO 92/01047, WO 92/20791, WO 93/06213, WO 93/11236, WO 93/19172, WO 95/01438, WO 95/15388, Annu Rev. Immunol (1994) 12, p. 433-455, and Nature Biotechnology (2005) 23 (9), p. 1105-1116).

The antibody genes can be temporarily isolated and then introduced into appropriate hosts to prepare antibodies. In such a case, appropriate hosts and expression vectors can be combined for use.

When eukaryotic cells are used as hosts, animal cells, plant cells, and eukaryotic microorganisms can be used.

Examples of the animal cells can include (1) mammalian cells, for example, monkey COS cells (Gluzman, Y. Cell (1981) 23, p. 175-182, ATCC CRL-1650), mouse fibroblasts NIH3T3 (ATCC No. CRL-1658), and dihydrofolate reductase-deficient strains (Urlaub, G. and Chasin, L. A. Proc. Natl. Acad. Sci. U.S.A. (1980) 77, p. 4126-4220) of Chinese hamster ovarian cells (CHO cells, ATCC CCL-61).

Moreover, these hosts can also be modified, for use, to express antibodies having a modified sugar chain structure and an enhanced ADCC activity (antibody-dependent cytotoxic activity) or CDC activity. Examples of such hosts can include CHO cells comprising genes incorporated therein which encode antibody molecules producing antibody compositions in which sugar chains having fucose-unbound N-acetylglucosamine at the reducing ends thereof occupy 20% or more of complex-type N-glycoside linked sugar chains binding to antibody Fc regions (see WO 02/31140).

When prokaryotic cells are used, examples thereof can include *Escherichia coli* and *Bacillus subtilis*.

The antibody gene of interest is introduced into these cells by transformation, and the transformed cells are cultured in vitro to obtain antibodies.

The isotype of the antibody of the present invention is not limited, and examples thereof include IgG (IgG1, IgG2, IgG3, or IgG4), IgM, IgA (IgA1 or IgA2), IgD, and IgE and can preferably include IgG and IgM.

Moreover, the antibody of the present invention may be an antibody fragment having the antigen-binding site of the antibody or a modified form thereof.

Examples of the antibody fragment include Fab, F(ab')2, Fv, single-chain Fv (scFv) comprising heavy and light chain Fvs linked via an appropriate linker, a diabody, a linear antibody, and a multispecific antibody formed by antibody fragments.

Furthermore the antibody of the present invention may be a multispecific antibody having specificity for at least two different antigens.

Such a molecule usually binds two antigens (i.e., a bispecific antibody). The "multispecific antibody" according to the present invention encompasses antibodies having specificity for more (e.g., three) antigens.

The multispecific antibody used as the antibody of the present invention may be a full-length antibody or a fragment of such an antibody (e.g., a F(ab')2 bispecific antibody). The bispecific antibody can be prepared by binding heavy and light chains (HL pairs) of two antibodies or can also be prepared by fusing hybridomas producing monoclonal antibodies different from each other to prepare bispecific antibody-producing fused cells (Millstein et al., Nature (1983) 305, p. 537-539).

The antibody of the present invention may be a single-chain antibody (also referred to as scFv). The single-chain antibody is obtained by linking antibody heavy and light chain V regions via a polypeptide linker (Pluckthun, The Pharmacology of Monoclonal Antibodies, 113 (Rosenberg and Moore ed., Springer Verlag, New York, p. 269-315 (1994)); and Nature Biotechnology (2005), 23, p. 1126-1136).

Methods for preparing the single-chain antibody are well known in the art (see e.g., U.S. Pat. Nos. 4,946,778, 5,260,203, 5,091,513, and 5,455,030). In this scFv, the heavy and light chain V regions are linked via a linker that does not form a conjugate, preferably a polypeptide linker (Huston, J. S. et al., Proc. Natl. Acad. Sci. U.S.A. (1988), 85, p. 5879-5883). The heavy and light chain V regions in the scFv may be derived from the same antibodies or may be derived from different antibodies.

For example, an arbitrary single-chain peptide of 12 to 19 residues is used as the peptide linker for linking the V regions.

DNA encoding the scFv is obtained by: amplifying, as templates, the full-length sequences or partial sequences (encoding the desired amino acid sequences) of DNA encoding the heavy chain or heavy chain V region of the antibody and DNA encoding the light chain or light chain V region thereof, by a PCR method using primer pairs designed for both ends thereof; and subsequently further amplifying DNA encoding the peptide linker portion in combination with a primer pair designed to respectively link both ends of the linker sequence to the heavy and light chain sequences.

Moreover, once the DNA encoding the scFv is prepared, expression vectors containing the DNA and hosts transformed with the expression vectors can be obtained according to standard methods. Moreover, by use of the hosts, the scFv can be obtained according to standard methods.

For these antibody fragments, their genes are obtained and expressed in the same way as above, and the hosts can be allowed to produce the antibody fragments.

The antibody of the present invention may be a polyclonal antibody, which is a mixture of a plurality of anti-EPHA2 antibodies differing in amino acid sequences. One example of the polyclonal antibody can include a mixture of a plurality of antibodies differing in CDRs. A mixture of cells producing antibodies different from each other is cultured, and antibodies purified from the culture can be used as such polyclonal antibodies (see WO 2004/061104).

Antibodies obtained by binding the antibody of the present invention with various molecules such as polyethylene glycol (PEG) can also be used as the modified form of the antibody.

Furthermore, the antibody of the present invention may be a conjugate of these antibodies formed with other drugs (immunoconjugate). Examples of such an antibody can include conjugates obtained by binding these antibodies to radioactive materials or compounds having a pharmacological effect (Nature Biotechnology (2005) 23, p. 1137-1146).

The obtained antibodies can be purified until homogeneous. In the antibody separation and purification, any separation/purification method used for usual proteins can be used.

The antibodies can be separated and purified by appropriately selecting and combining, for example, using chromatography columns, filters, ultrafiltration, salting-out, dialysis, polyacrylamide gel electrophoresis for preparation, and isoelectric focusing (Strategies for Protein Purification and Characterization: A Laboratory Course Manual, Daniel R. Marshak et al. eds., Cold Spring Harbor Laboratory Press (1996); and Antibodies: A Laboratory Manual. Ed Harlow and David Lane, Cold Spring Harbor Laboratory (1988)), though the separation/purification method is not limited thereto.

Examples of chromatography include affinity chromatography, ion-exchange chromatography, hydrophobic chromatography, gel filtration, reverse-phase chromatography, and adsorption chromatography.

These chromatography techniques can be performed using liquid-phase chromatography such as HPLC or FPLC.

Examples of columns used in the affinity chromatography include protein A and protein G columns.

Examples of columns based on the protein A column include Hyper D, POROS, Sepharose F.F. (Pharmacia Inc.).

Moreover, the antibodies can also be purified through their affinity for antigens using an antigen-immobilized carrier.

3. Properties of Antibody of the Present Invention

The anti-EPHA2 antibody of the present invention obtained by the method has the following properties:

(1) one antibody of the present invention has the following properties a) to e):

a) having no ability to phosphorylate EPHA2 tyrosine residues;

b) having an ADCC activity against EPHA2-expressing cells;

c) having a CDC activity against EPHA2-expressing cells;

d) having an antitumor activity in vivo; and e) specifically binding to a polypeptide consisting of an amino acid sequence represented by amino acid Nos. 426 to 534 of SEQ ID NO: 8 in the sequence listing.

Examples of the antibody having such properties can include any one antibody selected from the group consisting of the following 1) to 8):

1) SH348-1, 2) an antibody which recognizes an epitope recognized by an antibody produced by hybridoma SH348-1 (FERM BP-10836), 3) an antibody which has the amino acid sequences represented by SEQ ID NOs: 59, 61, and 63 in the sequence listing as complementarity determining regions in the heavy chain variable region and has the amino acid sequences represented by SEQ ID NOs: 65, 67, and 69 in the sequence listing as complementarity determining regions in the light chain variable region, 4) an antibody characterized by the following i) and ii):

i) having a heavy chain peptide comprising an amino acid sequence represented by the general formula (I):

-FRH$_1$-CDRH$_1$-FRH$_2$-CDRH$_2$-FRH$_3$-CDRH$_3$-FRH$_4$-   (I)

wherein FRH$_1$ represents an arbitrary amino acid sequence consisting of 18 to 30 amino acids; CDRH$_1$ represents the amino acid sequence represented by SEQ ID NO: 59 in the sequence listing; FRH$_2$ represents an arbitrary amino acid sequence consisting of 14 amino acids; CDRH$_2$ represents the amino acid sequence represented by SEQ ID NO: 61 in the sequence listing; FRH$_3$ represents an arbitrary amino acid sequence consisting of 32 amino acids; CDRH$_3$ represents the amino acid sequence represented by SEQ ID NO: 63 in the sequence listing; and FRH$_4$ represents an arbitrary amino acid sequence consisting of 11 amino acids, wherein these amino acids are linked to each other through peptide bonds; and ii) having a light chain polypeptide comprising an amino acid sequence represented by the general formula (II):

-FRL$_1$-CDRL$_1$-FRL$_2$-CDRL$_2$-FRL$_3$-CDRL$_3$-FRL$_4$-   (II)

wherein FRL$_1$ represents an arbitrary amino acid sequence consisting of 23 amino acids; CDRL$_1$ represents the amino acid sequence represented by SEQ ID NO: 65 in the sequence listing; FRL$_2$ represents an arbitrary amino acid sequence consisting of 15 amino acids; CDRL$_2$ represents the amino acid sequence represented by SEQ ID NO: 67 in the sequence listing; FRL$_3$ represents an arbitrary amino acid sequence consisting of 32 amino acids; CDRL$_3$ represents the amino acid sequence represented by SEQ ID NO: 69 in the sequence listing; and FRL$_4$ represents an arbitrary amino acid sequence consisting of 10 amino acids, wherein these amino acids are linked to each other through peptide bonds.

5) SH357-1, 6) an antibody which recognizes an epitope recognized by an antibody produced by hybridoma SH357-1 (FERM BP-10837), 7) an antibody which has the amino acid sequences represented by SEQ ID NOs: 71, 73, and 75 in the sequence listing as complementarity determining regions in the heavy chain variable region and has the amino acid sequences represented by SEQ ID NOs: 77, 79, and 81 in the sequence listing as complementarity determining regions in the light chain variable region, 8) an antibody according to any one of (5) to (7), characterized by the following i) and ii):

i) having a heavy chain peptide comprising an amino acid sequence represented by the general formula (I):

-FRH$_1$-CDRH$_1$-FRH$_2$-CDRH$_2$-FRH$_3$-CDRH$_3$-FRH$_4$-   (I)

wherein FRH$_1$ represents an arbitrary amino acid sequence consisting of 18 to 30 amino acids sequences; CDRH$_1$ represents the amino acid sequence represented by SEQ ID NO: 71 in the sequence listing; FRH$_2$ represents an arbitrary amino acid sequence consisting of 14 amino acids; CDRH$_2$ represents the amino acid sequence represented by SEQ ID NO: 73 in the sequence listing; FRH$_3$ represents an arbitrary amino acid sequence consisting of 32 amino acids; CDRH$_3$ represents the amino acid sequence represented by SEQ ID NO: 75 in the sequence listing; and FRH$_4$ represents an arbitrary amino acid sequence consisting of 11 amino acids, wherein these amino acids are linked to each other through peptide bonds; and ii) having a light chain polypeptide comprising an amino acid sequence represented by the general formula (II):

-FRL$_1$-CDRL$_1$-FRL$_2$-CDRL$_2$-FRL$_3$-CDRL$_3$-FRL$_4$-   (II)

wherein FRL$_1$ represents an arbitrary amino acid sequence consisting of 23 amino acids; CDRL$_1$ represents the amino acid sequence represented by SEQ ID NO: 77 in the sequence listing; FRL$_2$ represents an arbitrary amino acid sequence consisting of 15 amino acids; CDRL$_2$ represents the amino acid sequence represented by SEQ ID NO: 79 in the sequence listing; FRL$_3$ represents an arbitrary amino acid sequence consisting of 32 amino acids; CDRL$_3$ represents the amino acid sequence represented by SEQ ID NO: 81 in the sequence listing; and FRL$_4$ represents an arbitrary amino acid sequence consisting of 10 amino acids, wherein these amino acids are linked to each other through peptide bonds.

(2) another antibody of the present invention has the following properties a) to f):

a) having no ability to phosphorylate EPHA2 tyrosine residues;

b) exhibiting an effect of decreasing an EPHA2 protein level;

c) having an ADCC activity against EPHA2-expressing cells;

d) having a CDC activity against EPHA2-expressing cells;

e) having an antitumor activity in vivo; and f) specifically binding to a polypeptide consisting of an amino acid sequence represented by amino acid Nos. 426 to 534 of SEQ ID NO: 8 in the sequence listing.

Examples of the antibody having such properties can include any one antibody selected from the group consisting of the following 1) to 4):

1) SH348-1, 2) an antibody which recognizes an epitope recognized by an antibody produced by hybridoma SH348-1 (FERM BP-10836), 3) an antibody which has the amino acid sequences represented by SEQ ID NOs: 59, 61, and 63 in the sequence listing as complementarity determining regions in the heavy chain variable region and has the amino acid sequences represented by SEQ ID NOs: 65, 67, and 69 in the sequence listing as complementarity determining regions in the light chain variable region, 4) an antibody characterized by the following i) and ii):

i) having a heavy chain peptide comprising an amino acid sequence represented by the general formula (I):

-FRH$_1$-CDRH$_1$-FRH$_2$-CDRH$_2$-FRH$_3$-CDRH$_3$-FRH$_4$-   (I)

wherein FRH$_1$ represents an arbitrary amino acid sequence consisting of 18 to 30 amino acids; CDRH$_1$ represents the amino acid sequence represented by SEQ ID NO: 59 in the sequence listing; FRH$_2$ represents an arbitrary amino acid sequence consisting of 14 amino acids; CDRH$_2$ represents the amino acid sequence represented by SEQ ID NO: 61 in the sequence listing; FRH$_3$ represents an arbitrary amino acid sequence consisting of 32 amino acids; CDRH$_3$ represents the amino acid sequence represented by SEQ ID NO: 63 in the sequence listing; and FRH$_4$ represents an arbitrary amino acid sequence consisting of 11 amino acids, wherein these amino acids are linked to each other through peptide bonds; and ii) having a light chain polypeptide comprising an amino acid sequence represented by the general formula (II):

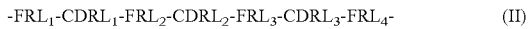

-FRL$_1$-CDRL$_1$-FRL$_2$-CDRL$_2$-FRL$_3$-CDRL$_3$-FRL$_4$-    (II)

wherein FRL$_1$ represents an arbitrary amino acid sequence consisting of 23 amino acids; CDRL$_1$ represents the amino acid sequence represented by SEQ ID NO: 65 in the sequence listing; FRL$_2$ represents an arbitrary amino acid sequence consisting of 15 amino acids; CDRL$_2$ represents the amino acid sequence represented by SEQ ID NO: 67 in the sequence listing; FRL$_3$ represents an arbitrary amino acid sequence consisting of 32 amino acids; CDRL$_3$ represents the amino acid sequence represented by SEQ ID NO: 69 in the sequence listing; and FRL$_4$ represents an arbitrary amino acid sequence consisting of 10 amino acids, wherein these amino acids are linked to each other through peptide bonds.

(3) another antibody of the present invention has the following properties a) to e):

a) having no ability to phosphorylate EPHA2 tyrosine residues;

b) exhibiting no effect of decreasing an EPHA2 protein level;

c) having an ADCC activity;

d) having a CDC activity;

e) having an antitumor activity in vivo; and f) specifically binding to a polypeptide consisting of an amino acid sequence represented by amino acid Nos. 426 to 534 of SEQ ID NO: 8 in the sequence listing.

Examples of the antibody having such properties can include any one antibody selected from the group consisting of the following 1) to 4):

1) SH357-1, 2) an antibody which recognizes an epitope recognized by an antibody produced by hybridoma SH357-1 (FERM BP-10836), 3) an antibody which has the amino acid sequences represented by SEQ ID NOs: 71, 73, and 75 in the sequence listing as complementarity determining regions in the heavy chain variable region and has the amino acid sequences represented by SEQ ID NOs: 77, 79, and 81 in the sequence listing as complementarity determining regions in the light chain variable region, 4) an antibody having the following properties i) and ii):

i) having a heavy chain peptide comprising an amino acid sequence represented by the general formula (I):

-FRH$_1$-CDRH$_1$-FRH$_2$-CDRH$_2$-FRH$_3$-CDRH$_3$-FRH$_4$-    (I)

wherein FRH$_1$ represents an arbitrary amino acid sequence consisting of 18 to 30 amino acids; CDRH$_1$ represents the amino acid sequence represented by SEQ ID NO: 71 in the sequence listing; FRH$_2$ represents an arbitrary amino acid sequence consisting of 14 amino acids; CDRH$_2$ represents the amino acid sequence represented by SEQ ID NO: 73 in the sequence listing; FRH$_3$ represents an arbitrary amino acid sequence consisting of 32 amino acids; CDRH$_3$ represents the amino acid sequence represented by SEQ ID NO: 75 in the sequence listing; and FRH$_4$ represents an arbitrary amino acid sequence consisting of 11 amino acids, wherein these amino acids are linked to each other through peptide bonds; and ii) having a light chain polypeptide comprising an amino acid sequence represented by the general formula (II):

-FRL$_1$-CDRL$_1$-FRL$_2$-CDRL$_2$-FRL$_3$-CDRL$_3$-FRL$_4$-    (II)

wherein FRL$_1$ represents an arbitrary amino acid sequence consisting of 23 amino acids; CDRL$_1$ represents the amino acid sequence represented by SEQ ID NO: 77 in the sequence listing; FRL$_2$ represents an arbitrary amino acid sequence consisting of 15 amino acids; CDRL$_2$ represents the amino acid sequence represented by SEQ ID NO: 79 in the sequence listing; FRL$_3$ represents an arbitrary amino acid sequence consisting of 32 amino acids; CDRL$_3$ represents the amino acid sequence represented by SEQ ID NO: 81 in the sequence listing; and FRL$_4$ represents an arbitrary amino acid sequence consisting of 10 amino acids, wherein these amino acids are linked to each other through peptide bonds.

4. Pharmaceutical Agent Comprising Anti-EPHA2 Antibody

The anti-EPHA2 antibody of the present invention is useful as a pharmaceutical agent, particularly, a pharmaceutical composition intended for cancer treatment, or as an antibody for immunological diagnosis of such disease.

Preferable examples of cancer types can include, but not limited to, breast cancer, esophagus cancer, prostate cancer, gastric cancer, non-small cell lung cancer, colon cancer, and glioblastoma multiforme.

The present invention also provides a pharmaceutical composition comprising a therapeutically effective amount of the anti-EPHA2 antibody and a pharmaceutically acceptable diluent, carrier, solubilizing agent, emulsifying agent, preservative, and/or adjuvant.

It is preferred that the substances pharmaceutically used that are acceptable in the pharmaceutical composition of the present invention should be nontoxic, at the dose or administration concentration used, to individuals that receive the pharmaceutical composition.

The pharmaceutical composition of the present invention can contain a pharmaceutical substance for changing, maintaining, or retaining pH, osmotic pressure, viscosity, transparency, color, isotonicity, sterility, stability, the rate of dissolution, the rate of sustained release, absorptivity, or permeability.

Examples of the pharmaceutical substance can include, but not limited to, the following: amino acids such as glycine, alanine, glutamine, asparagine, arginine, and lysine; antimicrobial agents; antioxidants such as ascorbic acid, sodium sulfate, and sodium bisulfite; buffers such as phosphate, citrate, and borate buffers, hydrogen carbonate, and Tris-HCl solutions; fillers such as mannitol and glycine; chelating agents such as ethylenediaminetetraacetic acid (EDTA); complexing agents such as caffeine, polyvinyl pyrrolidine, β-cyclodextrin, and hydroxypropyl-β-cyclodextrin; extenders such as glucose, mannose, and dextrin; monosaccharides, disaccharides, glucose, mannose, and other hydrocarbons such as dextrin; coloring agents; flavoring agents; diluents; emulsifying agents; hydrophilic polymers such as polyvinyl pyrrolidine; low-molecular-weight polypeptides; salt-forming counterions; antiseptics such as benzalkonium chloride, benzoic acid, salicylic acid, thimerosal, phenethyl alcohol, methylparaben, propylparaben, chlorhexidine, sorbic acid, and hydrogen peroxide; solvents such as glycerin, propylene glycol, and polyethylene glycol; sugar alcohols such as mannitol and sorbitol; suspending agents; surfactants such as PEG, sorbitan ester, polysorbates such as polysorbate 20 and polysorbate 80, Triton, tromethamine, lecithin, and cholesterol; stability enhancers such as sucrose and sorbitol; elasticity enhancers such as sodium chloride, potassium chloride, mannitol, and sorbitol; delivery vehicles; diluents; excipients; and/or pharmaceutical adjuvants.

The amounts of these pharmaceutical substances added are preferably 0.01 to 100 times, particularly, 0.1 to 10 times higher than the weight of the anti-EPHA2 antibody.

In this context, the present invention also encompasses a pharmaceutical composition containing an immunoliposome containing the anti-EPHA2 antibody in a liposome or the anti-EPHA2 antibody bound with a liposome (U.S. Pat. No. 6,214,388).

The preferable composition of the pharmaceutical composition in a preparation can be determined appropriately by those skilled in the art according to applicable disease, an applicable administration route, etc.

The excipients or carriers in the pharmaceutical composition may be liquid or solid. The appropriate excipients or carriers may be injectable water, saline, cerebrospinal fluids, or other substances usually used in parenteral administration.

Neutral saline or serum albumin-containing saline can also be used as a carrier. The pharmaceutical composition can also contain a Tris buffer (pH 7.0 to 8.5) or an acetate buffer (pH 4.0 to 5.5) as well as sorbitol or other compounds. The pharmaceutical composition of the present invention is prepared in a freeze-dried or liquid form as an appropriate drug having the selected composition and necessary purity.

The pharmaceutical composition comprising the anti-EPHA2 antibody can also be prepared in a freeze-dried form using an appropriate excipient such as sucrose.

The pharmaceutical composition of the present invention can be prepared for parenteral administration or can also be prepared for gastrointestinal absorption.

The composition and concentration of the preparation can be determined depending on an administration method. When the anti-EPHA2 antibody contained in the pharmaceutical composition of the present invention has higher affinity for EPHA2, i.e., higher affinity (lower Kd value) for EPHA2 with respect to a dissociation constant (Kd value), the drug containing this antibody can be efficacious at a lower dose in humans. Based on this result, the dose of the pharmaceutical composition of the present invention in human can also be determined.

The dose of the anti-EPHA2 antibody in humans may be usually be approximately 0.1 to 100 mg/kg once per 1 to 180 days.

Examples of dosage forms of the pharmaceutical composition of the present invention include injections including drip, suppositories, nasal agents, sublingual agents, and transdermally absorbable agents.

The administration of the pharmaceutical composition of the present invention can inhibit the growth of EPHA2-expressing tumors.

EXAMPLES

Hereinafter, the present invention will be described more specifically with reference to the Examples. However, the present invention is not intended to be limited to them.

In the Examples below, procedures related to genetic engineering were performed according to the methods described in "Molecular Cloning", (Sambrook, J., Fritsch, E. F., and Maniatis, T., published by Cold Spring Harbor Laboratory Press, 1989) or methods described in other experimental manuals used by those skilled in the art or according to instructions included in the commercially available reagents or kits used, unless otherwise specified.

Example 1

Preparation of Plasmid

1)-1 Preparation of Vectors Expressing Human EPHA2
1)-1-1 Preparation of a Vector Expressing Full-Length Human EPHA2 cDNA encoding human EPHA2 was amplified by PCR reaction using cDNA synthesized from SK-OV-3 cell-derived total RNA as the template and a primer set:

```
Primer 1:
        (sequence listing sequence ID No. 3)
5'-ggggacaagtttgtacaaaaaagcaggcttcggggatcg
gaccgagagcgagaag-3';
and Primer 2:
        (sequence listing sequence ID No. 4)
5'-ggggaccactttgtacaagaaagctgggtcctagatggg
gatccccacagtgttcacctggtcctt-3'.
```

The PCR product was incorporated into pDONR221 (manufactured by Invitrogen Corp.) using BP Clonase (manufactured by Invitrogen Corp.) to prepare an entry vector. The stop codon was removed from the EPHA2 gene in the entry vector using GeneTailor Site-Directed Mutagenesis System (manufactured by Invitrogen Corp.) and a primer set:

```
Primer 3:
        (sequence listing sequence ID No. 5)
5'-ctgtggggatccccatcgacccagctttc-3';
and Primer 4:
        (sequence listing sequence ID No. 6)
5'-gatggggatccccacagtgttcacctggtc-3'.
```

Recombination reaction between the obtained entry vector and the pcDNA-DEST40 Gateway Vector (manufactured by Invitrogen Corp.) was performed using LR Clonase (manufactured by Invitrogen Corp.) to prepare pcDNA-DEST40-EPHA2 (the present vector has the nucleotide sequence represented by SEQ ID NO: 7 in the sequence listing, between attB1 and attB2 sequences). Moreover, the sequence of the ORF portion of the EPHA2 gene cloned into the present vector is represented by nucleotide Nos. 33 to 2960 of SEQ ID NO: 7 in the sequence listing. Moreover, the amino acid sequence of EPHA2 is represented by SEQ ID NO: 8 in the sequence listing.

1)-1-2 Preparation of EPHA2 Extracellular Region Expression Vector cDNA encoding a human EPHA2 extracellular region polypeptide (consisting of an amino acid sequence represented by amino acid Nos. 1 to 534 of SEQ ID NO: 8 in the sequence listing; hereinafter, abbreviated to "EPHA2-ECD") was amplified by PCR reaction using a primer set:

```
Primer 5:
        (sequence listing sequence ID No. 9)
5'-aaaaagcttatggagctccaggcagcccgc-3';
and Primer 6:
        (sequence listing sequence ID No. 10)
5'-aaagggccctcagttgccagatccctccgg-3'.
```

The obtained PCR product was cleaved with HindIII and ApaI and cloned into the HindIII/ApaI site of pcDNA3.1 (hereinafter, the resulting vector is abbreviated to "pcDNA3.1-EPHA2-ECD"; and in the description below and the drawings, the recombinant protein expressed by "pcDNA3.1-EPHA2-ECD" is referred to as "rEPHA2-ECD").

1)-1-3 Preparation of Expression Vectors of Truncated EPHA2 Proteins

To construct vectors expressing a region consisting of an amino acid sequence represented by amino acid Nos. 315 to 540 of SEQ ID NO: 8 in the sequence listing of EPHA2 (hereinafter, referred to as "FnIII-NC"), a region consisting of an amino acid sequence represented by amino acid Nos. 315 to 430 thereof (hereinafter, referred to as "FnIII-N"), or a region consisting of an amino acid sequence represented by amino acid Nos. 426 to 540 thereof (hereinafter, referred to as "FnIII-C"), PCR reactions with pcDNA-DEST40-EPHA2 as the templates were performed using each primer set:

Primer Set for FnIII-NC Amplification:

```
Primer 7:
            (sequence listing sequence ID No. 11)
5'-gcaggatcatcgaaggtcgtgggcgggcacctcaggacccag-3';
and Primer 8:
            (sequence listing sequence ID No. 12)
5'-gtacaagaaagctgggtgctagccgccaatcaccgccaag-3';
```

Primer Set for FnIII-N Amplification:

```
Primer 7,
and

Primer 9:
            (sequence listing sequence ID No. 13)
5'-gtacaagaaagctgggtgctaggcagtacggaagctgcgg-3';
```

Primer Set for FnIII-C Amplification:

```
Primer 10:
            (sequence listing sequence ID No. 14)
5'-gcaggcttcatcgaaggtcgtgggagatccgtactgccagtg-3';
and Primer 8.
```

To add attB1 and attB2 sites to both ends of the obtained PCR products, PCR reaction with each PCR product as a template was performed using a primer set:

```
Primer 11:
            (sequence listing sequence ID No. 15)
5'-ggggacaagtttgtacaaaaaagcaggcttcatcgaaggtcgtgg
g-3';
and Primer 12:
            (sequence listing sequence ID No. 16)
5'-ggggaccactttgtacaagaaagctgggt-3'.
```

The PCR products obtained in this procedure were incorporated into pDONR221 using BP Clonase to prepare entry vectors. Recombination reactions between each entry vector and a destination vector prepared by cleaving the NdeI and BamHI sites of pET15b (manufactured by Novagen) with restriction enzymes, blunting the cleaved sites, and then ligating Reading Frame Cassette C.1 of Gateway Vector Conversion System (manufactured by Invitrogen Corp.) into the blunted sites were performed using LR Clonase in order to prepare expression vectors (hereinafter, recombinant proteins expressed by the FnIII-NC-, FnIII-N-, and FnIII-C-incorporated expression vectors are referred to as rFnIII-NC, rFnIII-N, and rFnIII-C, respectively).

1)-2 Preparation of Human EPHB2 Extracellular Region Expression Vector cDNA encoding human EPHB2 was obtained by PCR reaction using cDNA synthesized from HCC70 cell-derived total RNA as the template and a primer set:

```
Primer 13:
            (sequence listing sequence ID No. 17)
5'-ggggacaagtttgtacaaaaaagcaggatcgccccgggaagcgcag cc-3';
and Primer 14:
            (sequence listing sequence ID No. 18)
5'-ggggaccactttgtacaagaaagctgggtcctaaacctccacagac tgaatctggttcatctg-3'.
```

The nucleotide sequence of human EPHB2 cDNA is represented by SEQ ID NO: 19 in the sequence listing. The amino acid sequence thereof is represented by SEQ ID NO: 20 in the sequence listing. PCR reaction was performed using a primer set for amplifying cDNA encoding a human EPHB2 extracellular region (region consisting of an amino acid sequence represented by amino acid Nos. 1 to 542 of SEQ ID NO: 20 in the sequence listing) (hereinafter, abbreviated to "EPHB2-ECD"):

```
Primer 15:
            (sequence listing sequence ID No. 21)
5'-aaaaagcttatggctctgcggaggctgggg-3';
and Primer 16:
            (sequence listing sequence ID No. 22)
5'-aaagatatctcatggcaacttctcctggat-3'.
```

The obtained PCR product was cleaved with HindIII and EcoRV and cloned into the HindIII/EcoRV site of pcDNA3.1 (hereinafter, the resulting vector is abbreviated to "pcDNA3.1-EPHB2-ECD"; and in the description below and the drawings, the recombinant protein expressed by "pcDNA3.1-EPHB2-ECD" is referred to as rEPHB2-ECD).

1)-3 Preparation of human ERBB2 expression vector

PCR reaction with Human clone collection (manufactured by STRATAGENE, #C33830) as the template was performed using a primer set:

```
Primer 17:
            (sequence listing sequence ID No. 23)
5'-caccatggagctggcggccttg-3';
and Primer 18:
            (sequence listing sequence ID No. 24)
5'-tcccactggcacgtccagacc-3'.
```

The obtained PCR product was incorporated into pENTR/D-TOPO (manufactured by Invitrogen Corp.) using pENTR Directional TOPO Cloning kit (manufactured by Invitrogen Corp.) to prepare an entry vector. To repair mutations caused by amino acid substitution, the entry vector was digested with EcoRI, and a fragment containing the pENTR/D-TOPO-derived sequence among the obtained fragments was ligated with the second largest fragment (approximately 1.6 kbp) among fragments obtained by digested Human clone collection (manufactured by STRATAGENE, #C14640) with EcoRI. Recombination reactions between the obtained entry vector and the pcDNA-DEST40 Gateway vector were performed using LR Clonase in order to prepare pcDNA-DEST40-ERBB2 (the vector has the nucleotide sequence represented by SEQ ID NO: 25 in the sequence listing, between attB1 and attB2 sequences).

Example 2

Preparation of Monoclonal Antibody

2)-1 Preparation of Antigen

To express EPHA2-ECD, FreeStyle 293-F cells (manufactured by Invitrogen Corp.) were transfected with pcDNA3.1-EPHA2-ECD using 293fectin (manufactured by Invitrogen Corp.) and cultured at 37° C. in 8% $CO_2$ for 5 days. After the culture, the culture supernatant was collected by centrifugation and used as a source for rEPHA2-ECD purification. The obtained culture supernatant was dialyzed against 20 mM Tris-HCl, pH 7.5, using a dialysis tube having a molecular cutoff of 15000, then filtered through a filter (0.45 µm, PES), and then applied to HiPrep 16/10 Q XL (manufactured by GE Healthcare Bio-Sciences Corp.) equilibrated with 20 mM Tris-HCl, pH 7.5. Elution was performed with a linear concentration gradient of NaCl (20 mM Tris-HCl, pH 7.5, 0-1 M NaCl). An aliquot of the eluted fractions was separated by SDS-polyacrylamide gel electrophoresis (hereinafter, abbreviated to "SDS-PAGE"). Then, the gel was stained with Coomassie Brilliant Blue (hereinafter, abbreviated to "CBB-stained") to confirm rEPHA2-ECD-containing fractions. Next, the rEPHA2-ECD-containing fractions were combined and applied to HiLoad 26/60 Superdex 200 pg (manufactured by GE Healthcare Bio-Sciences Corp.) equilibrated with PBS. After elution with PBS, an aliquot of the eluted fractions was separated by SDS-PAGE. Then, the gel was CBB-stained to confirm rEPHA2-ECD-containing fractions. The rEPHA2-ECD-containing fractions were combined and used as an antigen for immunization and an antigen for epitope determination. The protein concentration was measured using BCA Protein Assay Reagent (manufactured by PIERCE).

2)-2 Immunization 4- to 6-week-old BALB/cAnNCrlCrlj mice (Charles River Laboratories Japan, Inc.) were used. On day 0, a mixture of 50 µg of rEPHA2-ECD and Adjuvant Complete Freund H37 Rv (manufactured by Wako Pure Chemical Industries, Ltd.) (1:1 in terms of volume ratio) was subcutaneously administered to the mouse dorsal region. Likewise, a mixture of 50 µg of rEPHA2-ECD and TiterMax Gold Adjuvant (manufactured by Sigma-Aldrich, Inc.) (1:1 in terms of volume ratio) was subcutaneously administered to the dorsal region of another individual. On days 22 and 36, a mixture of 50 µg of rEPHA2-ECD and Adjuvant Incomplete Freund (manufactured by Wako Pure Chemical Industries, Ltd.) (1:1 in terms of volume ratio) was subcutaneously administered to the dorsal region of each mouse. On day 53, 50 µg of rEPHA2-ECD was intraperitoneally administered to each mouse. On day 56, the mouse spleen was collected and used in hybridoma preparation.

2)-3 Hybridoma Preparation

Cell fusion between the spleen cells and mouse myeloma P3X63Ag8U.1 cells was performed using PEG4000 (manufactured IBL (Immuno-Biological Laboratories, Co., Ltd.)) to prepare hybridomas. A culture supernatant of the obtained hybridomas was used for screening anti-EPHA2 antibody-producing hybridomas.

2)-4 Antibody Screening

2)-4-1 Preparation of Cells Expressing a Gene Encoding an Antigen 293T cells were seeded at $5\times10^4$ cells/cm$^2$ onto a collagen type I-coated flask (manufactured by IWAKI) and cultured overnight at 37° C. in 5% $CO_2$ in DMEM containing 10% FBS. On the next day, the 293T cells were transfected with pcDNA-DEST40-EPHA2 or pcDNA-DEST40-ERBB2 as a control using Lipofectamine 2000 (manufactured by Invitrogen Corp.) and further incubated overnight at 37° C. in 5% $CO_2$. On the next day, the transfected 293T cells were treated with trypsin, then washed with DMEM containing 10% FBS, and then suspended in PBS containing 5% FBS. The obtained cell suspension was used in Cell-ELISA and flow cytometry analysis.

2)-4-2 Cell-ELISA

The cell suspension prepared in the paragraph 2)-4-1 was centrifuged, and the supernatant was removed. Then, the EPHA2-expressing 293T cells and the ERBB2-expressing 293T cells were separately suspended by the addition of the hybridoma culture supernatant and incubated at 4° C. for 1 hour. The cells in the wells were washed twice with PBS containing 5% FBS. Then, the cells were suspended by the addition of Goat anti-Mouse IgG, Peroxidase Conjugated (manufactured by Millipore (Chemicon), #AP181P) diluted 500 times with PBS containing 5% FBS, and incubated at 4° C. for 1 hour. The cells in the wells were washed twice with PBS containing 5% FBS. Then, OPD Color Developing Solution (o-phenylenediamine dihydrochloride (manufactured by Wako Pure Chemical Industries, Ltd.) and $H_2O_2$ were dissolved at concentrations of 0.4 mg/ml and 0.6% (v/v), respectively, in an OPD solution (0.05 M trisodium citrate, 0.1 M disodium hydrogen phosphate dodecahydrate, pH 4.5)) was added at 100 µl/well. Color reaction was performed with stirring and terminated by the addition of 1 M HCl at 100 µl/well. The cells were precipitated by centrifugation, and the supernatant was then transferred to a new 96-well flat-bottom microplate. The absorbance at 490 nm was measured using a plate reader (ARVO, PerkinElmer). To select hybridomas producing antibodies which specifically bind to EPHA2 expressed on the surface of the cell membrane, hybridomas producing a culture supernatant exhibiting higher absorbance in the EPHA2-expressing 293T cells than in the ERBB2-expressing 293T cells (controls) were selected to be positive for production of anti-EPHA2 antibody.

2)-4-3 Flow Cytometric Analysis

To eliminate false positives in Cell-ELISA, antibodies produced by the hybridoma determined to be positive in Cell-ELISA were further examined for their binding specificities for EPHA2 by flow cytometry. The cell suspension prepared in paragraph 2)-4-1 was centrifuged, and the supernatant was removed. Then, the EPHA2-expressing 293T cells and the ERBB2-expressing 293T cells were separately suspended by the addition of the hybridoma culture supernatant and incubated at 4° C. for 1 hour. The cells in the wells were washed twice with PBS containing 5% FBS. Then, the cells were suspended by the addition of "Fluorescein-conjugated goat IgG fraction to mouse IgG" (Whole Molecule) (manufactured by ICN Pharmaceuticals, Inc., #55493) diluted 1000 times with PBS containing 5% FBS, and incubated at 4° C. for 1 hour. The cells were washed twice with PBS containing 5% FBS and then resuspended in PBS containing 5% FBS and further containing 2 µg/ml 7-aminoactinomycin D (manufactured by Invitrogen Corp. (Molecular Probes)), followed by analysis using a flow cytometer (FC500, Beckman Coulter, Inc.). The data was analyzed using Flowjo (Tree Star, Inc.). 7-aminoactinomycin D-positive dead cells were excluded using a gate. Then, the FITC fluorescence intensity histograms of live cells were plotted. Hybridomas producing samples that provided stronger fluorescence intensity in the fluorescence intensity histogram of the EPHA2-expressing 293T cells than in the histogram of the ERBB2-expressing 293T cells as controls were obtained as anti-EPHA2 antibody-producing hybridomas.

2)-5 Separation of Hybridoma into Single Clones

The anti-EPHA2 antibody-producing hybridomas were diluted with ClonaCell-HY Selection Medium D (manufactured by StemCell Technologies, #03804) and cultured, and the formed colonies were collected as single clones. The collected clones were separately cultured and examined for their binding activities for EPHA2 using the culture supernatants in the same way as in paragraph 2)-4-3 to establish hybridomas producing anti-EPHA2 monoclonal antibodies (SH348-1, SH357-1, Ab57-1, Ab65-1, Ab96-1, Ab100-1, Ab105-1, Ab106-13, Ab136-1, Ab148-1, Ab151-4, Ab230-1, Ab373-1, and Ab382-1).

2)-6 Confirmation of Binding Activity of Monoclonal Antibody for Cancer Cell Line Whether or not the monoclonal antibodies obtained in paragraph 2)-5 bound to cancer cells highly expressing EPHA2 was studied by the flow cytometric method in the same way as in paragraph 2)-4-3. A human breast cancer cell line (MDA-MB-231), a human lung cancer cell line (A549), and a human prostate cancer cell line (PC-3) were used instead of the transfected 293T cells. As a result, all the established monoclonal antibodies were confirmed to bind to these cancer cell lines.

2)-7 Isotype Determination of Monoclonal Antibody

The isotypes of the monoclonal antibodies were determined using Mouse monoclonal isotyping kit (manufactured by AbD Serotec). As a result, the isotypes were IgG1 (Ab57-1 and Ab230-1), IgG2a (SH348-1, SH357-1, Ab65-1, Ab96-1, Ab100-1, Ab136-1, Ab148-1, and Ab151-4), and IgG2b (Ab105-1, Ab106-13, Ab373-1, and Ab382-1).

2)-8 Preparation of Monoclonal Antibody

The monoclonal antibodies were purified from ascites of hybridoma-transplanted mice or a hybridoma culture supernatant (hereinafter, referred to as a "source for antibody purification").

The mouse ascites were prepared as follows: first, 7- to 8-week-old BALB/cAJcl-nu/nu mice (CLEA Japan, Inc.) were treated with pristane (manufactured by Sigma-Aldrich, Inc.). Approximately 3 weeks later, the hybridomas washed with saline were intraperitoneally transplanted in an amount of $1 \times 10^7$ cells/mouse. 1 to 2 weeks later, ascites accumulated in the peritoneal cavity was collected, then sterilized through a 0.22-μm filter, and used as a source for antibody purification.

The hybridoma culture supernatant was prepared using CELLine (manufactured by BD Biosciences). The hybridomas were cultured according to the manufacturer's instructions except that ClonaCell-HY Growth Medium E (manufactured by StemCell Technologies, #03805) was used as a medium. The collected culture supernatant was filtered through a 0.45-μm filter and used as a source for antibody purification.

The antibodies were purified using an affinity column comprising Recombinant Protein A rPA50 (manufactured by RepliGen Corp.) immobilized on Formyl-Cellulofine (manufactured by Seikagaku Corp.) (hereinafter, abbreviated to "Formyl-Cellulofine Protein A") or HiTrap MabSelect SuRe (manufactured by GE Healthcare Bio-Sciences Corp.). For the Formyl-Cellulofine Protein A, the source for antibody purification was diluted three times with Binding Buffer (3 M NaCl, 1.5 M glycine, pH 8.9) and applied to the column, which was then washed with Binding Buffer, followed by elution with 0.1 M citric acid, pH 4.0. On the other hand, for the HiTrap MabSelect SuRe, the source for antibody purification was added to the column, which was then washed with PBS, followed by elution with 2 M arginine-HCl, pH 4.0. The antibody eluate was neutralized, and the buffer was then replaced with PBS.

The antibody concentrations were determined by eluting the antibodies bound with POROS G 20 μm Column, PEEK, 4.6 mm×100 mm, 1.7 ml (Applied Biosystems) and measuring the absorbance (O.D. 280 nm) of the eluate. Specifically, the antibody sample diluted with PBS was applied to POROS G 20 μm equilibrated with Equilibrating Buffer (30.6 mM sodium dihydrogen phosphate dodecahydrate, 19.5 mM monopotassium phosphate, 0.15 M NaCl, pH 7.0). The column was washed with Equilibrating Buffer, and the antibody bound to the column was then eluted with an eluent (0.1% (v/v) HCl, 0.15 M NaCl). The peak area of the absorbance (O.D. 280 nm) of the eluate was measured, and the concentration was calculated according to the following equation:

Concentration of antibody sample(mg/ml)=(Peak area of antibody sample)/(Peak area of standard(human IgG1))×Concentration of standard(mg/ml)× Dilution factor.

Moreover, the concentration of endotoxin contained in the obtained antibodies was measured using Endospecy ES-50M Set (Seikagaku Corp., #020150) and Endotoxin Standard CSE-L Set (Seikagaku Corp., #020055) and was confirmed to be 1 EU/mg or lower. The resulting antibodies were used in the subsequent experiments.

Example 3

Properties of SH348-1 and SH357-1

3)-1 Study of Anti-EPHA2 Antibody for its Activity of Inducing Phosphorylation of EPHA2 Tyrosine Residues and its Activity of Inducing Decrease in EPHA2 Protein Level 3)-1-1 Preparation of antibody-stimulated cell lysate MDA-MB-231 cells suspended in RPMI1640 containing 10% FBS, 50 units/ml penicillin, and 50 μg/ml streptomycin (hereinafter, abbreviated to "10% FBS-containing RPMI1640 (with antibiotics)") were seeded at $6 \times 10^5$ cells/well onto a 6-well dish and cultured overnight at 37° C. in 5% $CO_2$. On the next day, the medium was discarded, and RPMI1640 was added thereto. The cells were further cultured overnight at 37° C. in 5% $CO_2$. On the next day, SH348-1, SH357-1, Mouse $IgG_{2A}$ Isotype Control (in the description below and the drawings, abbreviated to "mIgG2a"; manufactured by R&D Systems, Inc., #MAB003) as an isotype control antibody, Recombinant Mouse Ephrin-A1/Fc Chimera (in the description below and the drawings, abbreviated to "Ephrin-A1/Fc"; manufactured by R&D Systems, Inc., #602-A1-200) as a soluble EPHA2 ligand, and Recombinant Human $IgG_1$ Fc (in the description below and the drawings, abbreviated to "$hG_1Fc$"; manufactured by R&D Systems, Inc., #110-HG-100) as a control protein for the soluble ligand were separately diluted at a concentration shown in FIGS. 1A and 1B or FIGS. 2A and 2B (SH348-1, SH357-1, and mIgG2a: 10 μg/ml or 50 μg/ml in FIG. 1A and 50 μg/ml in FIG. 2A, Ephrin-A1/Fc and $hG_1Fc$: 1 μg/ml in FIGS. 1A and 1B and FIGS. 2A and 2B) with RPMI1640. The resulting solution was added to the MDA- MB-231 cells after discarding of the medium and incubated at 37° C. in 5% $CO_2$ for the predetermined time in 5% $CO_2$. Moreover, in the experiments in the presence of a cross-linking antibody, SH348-1, SH357-1, or mIgG2a and Goat anti-mouse IgG, Fcγ fragment specific (min X Hu, Bov, Hrs Sr Prot) (manufactured by Jackson ImmunoResearch Laboratories, Inc., #115-005-071) as a cross-linking antibody were mixed at each concentration of 10 µg/ml or 50 µg/ml (FIG. 1B) and 50 µg/ml (FIG. 2B) in RPMI1640. The resulting solution was added to the MDA-MB-231 cells after discarding of the medium and incubated at 37° C. in 5% $CO_2$ for the predetermined time. At the predetermined time, the supernatant was removed, and the cells were lysed by the addition of 1×Cell Lysis Buffer (manufactured by Cell Signaling Technology, Inc.) containing 1 mM PMSF (manufactured by Sigma-Aldrich, Inc.) and centrifuged at 15000 rpm for 5 minutes. The supernatants of cell lysates were used as samples in immunoprecipitation and Western blotting. The protein concentrations of the samples were measured using BCA Protein Assay Reagent (manufactured by PIERCE).

3)-1-2 Verification of Activity of Inducing Phosphorylation of EPHA2 Tyrosine Residues To immunoprecipitate EPHA2, first, 8 µg of anti-Eck/EphA2, clone D7 (in the description below and the drawings, abbreviated to "anti-EPHA2 antibody (D7)"; manufactured by Millipore (Upstate), #05-480) was added to 25 µl of a suspension of Protein G magnetic beads (manufactured by NEW ENGLAND BioLabs, Inc.) per sample, and the mixture was inverted for mixing at 4° C. for 2 hours.

Then, FBS was added thereto at a final concentration of 10%, and the mixture was further inverted for mixing at 4° C. for 30 minutes. The beads were washed three times with 1×Cell Lysis Buffer containing 1 mM PMSF. Then, 200 µg of the cell lysate supernatants prepared in paragraph 3)-1-1 were added thereto, and the mixtures were inverted for mixing overnight at 4° C. On the next day, the beads were washed three times with 1×Cell Lysis Buffer containing 1 mM PMSF. Then, SDS-Sample Buffer (56.3 mM Tris-HCl, pH 6.8, 1.8% (w/v) SDS, 9% glycerol, 0.72 M 2-mercaptoethanol, 0.045 mg/ml bromophenol blue) was added to the beads, and the mixtures were heated at 98° C. for 5 minutes. The proteins dissociated from the beads were separated by SDS-PAGE.

To perform Western blotting, the proteins were transferred from the gels to polyvinylidene difluoride membranes (hereinafter, abbreviated to a "PVDF membrane"; 0.45 µm in pore size; manufactured by Millipore). After the transfer, the PVDF membranes were blocked by shaking in Blocking Solution (one pouch of Block Ace powder (manufactured by Dainippon Sumitomo Pharma Co., Ltd. (Snow Brand Milk Products Co., Ltd.)) was dissolved in 100 ml of ultrapure water, to which Tween 20 and sodium azide were then added at final concentrations of 0.1% (v/v) and 0.02% (w/v), respectively). First, to detect the immunoprecipitated EPHA2, the PVDF membranes thus blocked were soaked in an anti-EPHA2 antibody (D7) solution diluted to 0.25 µg/ml with Blocking Solution, and shaken at room temperature for 1 hour. The PVDF membranes were washed for 10 minutes three times with TBST (50 mM Tris-HCl, pH 8.0, 138 mM NaCl, 2.7 mM KCl, 0.1% (v/v) Tween 20). Then, the PVDF membranes were soaked in an Anti-Mouse Ig, HRP-Linked Whole Ab Sheep (manufactured by GE Healthcare Bio-Sciences Corp.) solution diluted 3000 times with TBST, and shaken at room temperature for 30 minutes. The PVDF membranes were further washed for 10 minutes three times with TBST. Then, signals were detected on a film for chemiluminescence using ECL Plus (manufactured by GE Healthcare Bio-Sciences Corp.).

Next, to remove the antibodies from these PVDF membranes, the PVDF membranes were soaked in Stripping Solution (50 mM Tris-HCl, pH 6.8, 2% (w/v) SDS, 100 mM 2-mercaptoethanol) and shaken at 55° C. for 30 minutes. Then, the PVDF membranes were soaked in Quenching Solution (TBST containing 1% (v/v) $H_2O_2$ and 0.1% (w/v) $NaN_3$), then shaken at room temperature for 20 minutes, and further washed for 10 minutes three times with TBST. To detect the phosphorylated state of the EPHA2 tyrosine residues, these PVDF membranes were blocked by shaking in sodium azide-free Blocking Solution (one pouch of Block Ace powder was dissolved in 100 ml of ultrapure water, to which Tween 20 was then added at a final concentration of 0.1% (v/v)). Then, the PVDF membranes were soaked in an Anti-Phosphotyrosine, recombinant 4G10 HRP-conjugate (in the figures, abbreviated to "4G10 antibody"; manufactured by Millipore (Upstate), #16-184) solution diluted 10000 times with sodium azide-free Blocking Solution, and shaken at room temperature for 1 hour. The PVDF membranes were washed for 10 minutes three times with TBST and then further washed for 5 minutes three times with $H_2O$. Signals were detected on a film for chemiluminescence using ECL Plus.

As a result, by the addition of the soluble ligand Ephrin-A1/Fc, EPHA2 tyrosine residues were phosphorylated in 10 minutes. By contrast, when the antibodies SH348-1 and SH357-1 were added at a concentration of 10 µg/ml or 50 µg/ml, the effect of inducing the phosphorylation of EPHA2 tyrosine residues as seen by the ligand was not observed at all in the predetermined times (10 minutes, 30 minutes, and 60 minutes) (FIG. 1A). Likewise, even in the presence of the cross-linking antibody, the effect of inducing the phosphorylation of EPHA2 tyrosine residues as seen in the ligand was not observed in the presence of antibodies SH348-1 and SH357-1 (FIG. 1B).

3)-1-3 Verification of Activity of Inducing Decrease in EPHA2 Protein Level

10 µg of the cell lysate supernatants prepared in paragraph 3)-1-1 were separated by SDS-PAGE. Then, the proteins in the gel were transferred to PVDF membranes and subjected to Western blotting using an anti-EPHA2 antibody (D7) and Monoclonal Anti-β-Actin clone AC-15 (in the description below and the figures, abbreviated to "anti-β-actin antibody"; manufactured by Sigma-Aldrich, Inc., #A-5441) as a control for the sample protein level. Specifically, after the transfer, the PVDF membranes were blocked by shaking in Blocking Solution and then cut with a razor into two pieces centered around a molecular weight of 70 kDa. The PVDF membranes containing 70 kDa or larger proteins were soaked in an anti-EPHA2 antibody (D7) solution diluted to 0.25 µg/ml with Blocking Solution, while the PVDF membranes containing 70 kDa or smaller proteins were soaked in an anti-β-actin antibody solution diluted 1000 times with Blocking Solution. Each PVDF membrane was shaken at room temperature for 1 hour. Each PVDF membrane was washed for 10 minutes three times with TBST. Then, each PVDF membrane was soaked in an Anti-Mouse Ig, HRP-Linked Whole Ab Sheep solution diluted 3000 times with TBST, and shaken at room temperature for 30 minutes. Each PVDF membrane was washed for 10 minutes three times with TBST. Then, signals were detected using ECL Plus and NightOWL LB983 (Berthold Technologies GmBH & Co. KG). The signal intensity of the bands was quantified using Gel-Pro Analyzer Version 4.5 for Windows (registered trademark; Media Cybernetics, Inc.).

As a result, by the addition of the soluble ligand Ephrin-A1/Fc, a significant decrease in EPHA2 protein level was observed (FIGS. 2A and 2B). By the addition of the antibody SH348-1, a decrease in EPHA2 protein level, albeit weaker than the activity of the ligand, was observed both in the presence and absence of the cross-linking antibody (FIGS. 2A and 2B). On the other hand, in the antibody SH357-1, almost no change in EPHA2 protein level was observed regardless of the presence or absence of the cross-linking antibody (FIGS. 2A and 2B).

To analyze the EPHA2 protein level after 24 hours of the SH348-1 addition, an average of {the signal intensity of the EPHA2 band/the signal intensity of the β-actin band} was calculated from three experimental results corrected with a ligand/antibody-nonsupplemented sample. As a result, the value after 24 hours of the SH348-1 addition was 70% in the absence of the cross-linking antibody and 69% in the presence of the cross-linking antibody, when the value after 24 hours of the mIgG2a addition is defined as 100%.

3)-2 ADCC Activity

3)-2-1 Preparation of Effector Cells

The spleen was aseptically collected from CAnN.Cg-Foxn1$^{nu}$/CrlCrlj nude mice (Charles River Laboratories Japan, Inc.). The collected spleen was homogenized with two slide glasses and hemolyzed using BD Pharm Lyse (manufactured by BD Biosciences, #555899). The obtained spleen cells were suspended in phenol red-free RPMI1640 (manufactured by Invitrogen Corp.) containing 10% Fetal Bovine Serum, Ultra-low IgG (manufactured by Invitrogen Corp.) (hereinafter, abbreviated to a "medium for ADCC") and passed through a cell strainer (40 μm in pore size; manufactured by BD Biosciences). Then, the number of live cells was counted by a trypan blue exclusion test. The spleen cell suspension was centrifuged, and the medium was then removed. The cells were resuspended at a live cell density of $1.5 \times 10^7$ cells/ml in a medium for ADCC and used as effector cells.

3)-2-2 Preparation of Target Cells

MDA-MB-231, A549, or PC-3 cells were treated with trypsin. The cells were washed with RPMI1640 containing 10% FBS and then resuspended in RPMI1640 containing 10% FBS. Each cell ($4 \times 10^6$ cells) was mixed with Chromium-51 (5550 kBq) sterilized through a 0.22-μm filter, and labeled therewith at 37° C. in 5% $CO_2$ for 1 hour. The labeled cells were washed three times with a medium for ADCC and resuspended at a concentration of $2 \times 10^5$ cells/ml in a medium for ADCC to prepare target cells.

3)-2-3 $^{51}$Cr Release Assay

The target cells ($2 \times 10^5$ cells/ml) were dispensed at 50 μl/well to a 96-well U-bottom microplate. 50 μl of SH348-1, SH357-1, or an isotype control antibody (mIgG2a) diluted to 2.5 μg/ml (in terms of a final concentration after addition of the effector cells) with a medium for ADCC was added thereto and incubated at 4° C. for 1 hour. 100 μl of the effector cells ($1.5 \times 10^7$ cells/ml) was added thereto and incubated overnight at 37° C. in 5% $CO_2$. On the next day, the supernatant was collected into LumaPlate (manufactured by PerkinElmer). The dose of released gamma rays was measured using a gamma counter. The cell lysis rate attributed to the ADCC activity was calculated according to the following equation:

Cell lysis rate(%)=$(A-B)/(C-B) \times 100$

A: counts in sample wells

B: an average (n=3) of counts in spontaneous release (antibody/effector cell-nonsupplemented wells). Instead of the antibody and the effector cells, 50 μl and 100 μl, respectively, of a medium for ADCC were added. The other procedures were performed in the same way as in the sample wells.

C: an average (n=3) of counts in the maximum release (wells containing the target cells dissolved in a detergent). 50 μl of a medium for ADCC was added instead of the antibody, and 100 μl of a medium for ADCC containing 2% (v/v) Triton-X100 was added instead of the effector cells. The other procedures were performed in the same way as in the sample wells.

FIGS. 3A and 3B show an average of three experiments, wherein the error bar represents a standard deviation, and the P value was calculated by Student's t-test. As a result, the antibody SH348-1 exhibited cell lysis activities of 8.2%, 9.1%, and 4.7% against the MDA-MB-231 cells (FIG. 3A), the A549 cells (FIG. 3B), and the PC-3 cells (FIG. 3C), respectively. The antibody SH357-1 exhibited cell lysis activities of 8.8%, 13.0%, and 9.0% against the MDA-MB-231 cells (FIG. 3A), the A549 cells (FIG. 3B), and the PC-3 cells (FIG. 3C), respectively. These results demonstrated that both the antibodies have an ADCC activity against MDA-MB-231 cells, A549 cells, and PC-3 cells.

3)-3 CDC Activity

MDA-MB-231, A549, or PC-3 cells suspended in 10% FBS-containing RPMI1640 (with antibiotics) were seeded at 5000 cells/well onto a 96-well microplate and cultured overnight at 37° C. in 5% $CO_2$. On the next day, SH348-1, SH357-1, or an isotype control antibody (mIgG2a) diluted to 25 μg/ml (in terms of a final concentration after addition of complements) with 10% FBS-containing RPMI1640 (with antibiotics) was added thereto and incubated at 4° C. for 1 hour. Rabbit complements (manufactured by CEDARLANE, #CL3051) diluted to 30% with RPMI1640 were added thereto at a final concentration of 5%, then incubated at 37° C. in 5% $CO_2$ for 1 hour, and further left standing at room temperature for 30 minutes. To measure the cell viability, CellTiter-Glo Luminescent Cell Viability Assay (manufactured by Promega Corp.) was added in an amount equal to that of the culture solution, and the mixture was stirred at room temperature for 10 minutes. Then, the amount of light emitted was measured using a plate reader. The cell viability was calculated according to the following equation:

Cell viability(%)=$(a-b)/(c-b) \times 100$ a: the amount of light emitted from sample wells b: an average (n=8) of the amount of light emitted as a background (cell/antibody-nonsupplemented wells). 10% FBS-containing RPMI1640 (with antibiotics) was added, instead of the seeded cells, in an amount equal to that of the cell suspension, and 10% FBS-containing RPMI1640 (with antibiotics) was added, instead of the antibody, in an amount equal to that of the antibody dilution. The other procedures were performed in the same way as in the sample wells.

c: an average (n=3) of the amount of light emitted from antibody-nonsupplemented wells. 10% FBS-containing RPMI1640 (with antibiotics) was added, instead of the antibody, in an amount equal to that of the antibody dilution. The other procedures were performed in the same way as in the sample wells.

FIGS. 4A through 4F show an average of three experiments, wherein the error bar represents a standard deviation, and the P value was calculated by Student's t-test. As a result, the antibody SH348-1 induced 44%, 31%, and 41% decreases in the cell viability of the MDA-MB-231 cells (FIG. 4A), the A549 cells (FIG. 4B), and the PC-3 cells (FIG. 4C), respectively, in the presence of the complements. The antibody SH357-1 also induced 65%, 60%, and 65% decreases in the cell survival rates of the MDA-MB-231 cells (FIG. 4D), the A549 cells (FIG. 4E), and the PC-3 cells (FIG. 4F), respectively, in the presence of the complements. These results demonstrated that both the antibodies have a CDC activity against MDA-MB-231 cells, A549 cells, and PC-3 cells.

3)-4 Epitope Determination

3)-4-1 Preparation of Truncated EPHA2 Polypeptides (rFnIII-NC, rFnIII-N, and rFnIII-C)

*Escherichia coli* BL21 and *Escherichia coli* Origami (DE3) (manufactured by Novagen) were separately transformed with the expression plasmid prepared in paragraph 1)-1-3, and cultured in an LB medium supplemented with 50 μg/ml ampicillin (manufactured by Sigma-Aldrich, Inc.). Expression of truncated EPHA2 polypeptides was induced using Autoinduction System (manufactured by Novagen) for BL21 and the addition of 0.5 mM IPTG for Origami (DE3). The bacterial cells were collected by centrifugation at 6000 rpm for 20 minutes, then suspended in a homogenizing buffer (50 mM Tris HCl, pH 7.5, 150 mM NaCl, 0.1% (v/v) Triton-X100, 10% (v/v) glycerol), and then sonicated on ice. The supernatant was collected by centrifugation at 14000 rpm for 15 minutes and applied to 0.5 ml of Ni-NTA (manufactured by Invitrogen Corp.). The Ni-NTA was washed with a washing buffer (50 mM Tris-HCl, pH 7.5, 150 mM NaCl, 50 mM imidazole, 10% (v/v) glycerol), followed by elution with an eluting buffer (50 mM Tris-HCl, pH 7.5, 150 mM NaCl, 400 mM imidazole, 10% (v/v) glycerol). The eluted samples were further purified by gel filtration column chromatography (Superdex 75 10/300; manufactured by GE Healthcare Bio-Sciences Corp.) using PBS as a solvent. The protein concentrations of the obtained recombinant proteins were measured using Protein Assay (manufactured by Bio-Rad Laboratories, Inc).

3)-4-2 Preparation of EPHB2 Extracellular Region Polypeptide (rEPHB2-ECD)

To express EPHB2-ECD, FreeStyle 293-F cells were transfected with pcDNA3.1-EphA2-ECD using 293fectin and cultured at 37° C. in 8% $CO_2$ for 72 hours. After the culture, the culture solution was collected by centrifugation and used as a source for rEPHB2-ECD purification. The obtained culture supernatant was dialyzed against 20 mM Tris-HCl, pH 7.5, using a dialysis tube having a molecular cutoff of 15000, then filtered through a filter (0.45 μm, PES), and then applied to HiPrep 16/10 Q XL equilibrated with 20 mM Tris-HCl, pH 7.5. Elution was performed with a linear concentration gradient of NaCl (20 mM Tris-HCl, pH 7.5, 0-1 M NaCl). An aliquot of the eluted fractions was separated by SDS-PAGE. Then, the gel was CBB-stained to confirm that there were rEPHB2-ECD-containing fractions. Next, the rEPHB2-ECD-containing fractions were combined and applied to HiLoad 26/60 Superdex 200 pg equilibrated with PBS. After elution with PBS, an aliquot of the elution fractions was separated by SDS-PAGE. Then, the gel was CBB-stained to confirm that there were rEPHB2-ECD-containing fractions. The rEPHB2-ECD-containing fractions were combined and used as an antigen for epitope determination. The protein concentration was measured using BCA Protein Assay Reagent.

3)-4-3 Determination of Binding Sites in Antigens by ELISA rEPHA2-ECD, rFnIII-NC, rFnIII-N, rFnIII-C, or a control protein rEPHB2-ECD was diluted to 1 μg/ml with PBS, then dispensed at 100 μl/well onto an immunoplate (manufactured by Nunc, #442404), and incubated overnight at 4° C. to thereby adsorb the protein to the plate. On the next day, the solution in the wells was removed, and a Block Ace solution (one pouch of Block Ace powder was dissolved in 100 ml of ultrapure water) diluted 4 times with PBS was dispensed at 200 μl/well and incubated at room temperature for 1 hour. The solution in the wells was removed, and SH348-1, SH357-1, or an isotype control antibody (mIgG2a) diluted to 5 μg/ml with Diluting Buffer (PBS, 0.05% (v/v) Tween 20) was then added at 50 μl/well. The plate was incubated at room temperature for 1 hour. Then, the solution in the wells was removed, and the wells were washed twice with a diluting buffer. Goat anti-Mouse IgG, Peroxidase Conjugated, diluted 3000 times with Diluting Buffer was added at 50 μl/well and incubated at room temperature for 1 hour. The solution in the wells was removed, and the wells were washed twice with Diluting Buffer. Then, a color reaction was performed with stirring by the addition of OPD Color Developing Solution at 100 μl/well. After color development, the color reaction was terminated by the addition of 1 M HCl at 100 μl/well. The absorbance at 490 nm was measured using a plate reader.

FIG. 5A shows the EPHA2 domain structure prediction (NCBI CDD version 2.11, CBS TMHMM Server v.2.0) and the positions of EPHA2-ECD, FnIII-NC, FnIII-N, and FnIII-C in EPHA2. Ligand-BD represents a ligand-binding domain, FN3 represents a fibronectin type 3 domain, TM represents a transmembrane region, Trk kinase represents a tyrosine kinase domain, and SAM represents a SAM domain.

Recombinant proteins of the EPHA2 extracellular region (EPHA2-ECD), the region containing two fibronectin type 3 domains (FnIII-NC), the region containing the N-terminal fibronectin type 3 domain (FnIII-N), and the region containing the C-terminal fibronectin type 3 domain (FnIII-C) were prepared and studied for their binding activities with respect to SH348-1 and SH357-1. As a result, the antibodies SH348-1 and SH357-1 exhibited binding activities with respect to rEPHA2-ECD, rFnIII-NC, and rFnIII-C (FIG. 5B). Thus, the antibodies SH348-1 and SH357-1 were shown to bind to a region from amino acids 426 to 534 containing the C-terminal fibronectin type 3 domain (amino acid sequence represented by amino acid Nos. 426 to 534 of SEQ ID NO: 8 in the sequence listing).

Example 4

In Vivo Antitumor Effect

MDA-MB-231 cells were dissociated from a culture flask by trypsin treatment and then suspended in 10% FBS-containing RPMI1640 (with antibiotics). After centrifugation, the supernatant was removed. The cells were washed twice with the same medium as above, then suspended in BD Matrigel Basement Membrane Matrix (manufactured by BD Biosciences), and subcutaneously transplanted at a concentration of $5 \times 10^6$ cells/mouse into the dorsal region of 6-week-old BALB/cAJc1-nu/nu ((CLEA Japan, Inc.). When the day of transplantation is defined as day 0, SH348-1 or SH357-1 was intraperitoneally administered at a dose of 500 μg/mouse on days 9, 16, 23, and 30. PBS having the same volume (500 μl) as that of the antibody was intraperitoneally administered as a control. The tumor volume was measured on days 9, 13, 16, 20, 23, 28, 30, 34, and 37 to study the antitumor effect attributed to the antibody administration. As a result, tumor growth was significantly inhibited in the SH348-1- and SH357-1-administered groups compared to in the PBS-administered group (in the tumor volume comparison with the PBS-administered group on day 37, P values for SH348-1 and SH357-1 were both P<0.001; the P values were calculated by Student's t-test). Moreover, the tumor growth inhibitory rate (=100−(average of tumor volumes of the antibody-administered group)/(average of tumor volumes of the PBS-administered group)×100) on day 37 was 89.5% for SH348-1 and 84.1% for SH357-1. Their very strong antitumor effects were observed in vivo (FIGS. 6A and 6B).

Of 14 anti-EPHA2 monoclonal antibodies studied for their antitumor effects on the MDA-MB-231 cell-transplanted mice, only the antibodies SH348-1 and SH357-1 binding to FnIII-C were shown to be effective (Table 1).

TABLE 1

| Antibody | Binding activity to antigen | | | | Inhibitory effect on tumor growth (in vivo) |
|---|---|---|---|---|---|
| | rEPHA2-ECD | rFnIII-NC | rFnIII-N | rFnIII-C | |
| SH 348-1 | + | + | − | + | + |
| SH 357-1 | + | + | − | + | + |
| Ab 57-1 | + | + | + | − | − |
| Ab 65-1 | + | − | − | − | − |
| Ab 96-1 | + | − | − | − | − |
| Ab 100-1 | + | − | − | − | − |
| Ab 105-1 | + | − | − | − | − |
| Ab 106-13 | + | − | − | − | − |
| Ab 136-1 | + | − | − | − | − |
| Ab 148-1 | + | − | − | − | − |
| Ab 151-4 | + | − | − | − | − |
| Ab 230-1 | + | + | + | − | − |
| Ab 373-1 | + | − | − | − | − |
| Ab 382-1 | + | − | − | − | − |

These results demonstrated that SH348-1 and SH357-1 are antibodies which recognize the previously unreported epitope (amino acid sequence represented by amino acid Nos. 426 to 534 of SEQ ID NO: 8 in the sequence listing) and exhibit an antitumor effect. Moreover, the region to which SH348-1 or SH357-1 binds was shown to serve as a promising target of anti-tumor monoclonal antibodies targeted for EPHA2.

Example 5

Identification of SH348-1 and SH357-1 Antibody Genes

To determine the heavy and light chain N-terminal amino acid sequences of the mouse anti-human EPHA2 antibodies SH348-1 and SH357-1, an aliquot of a solution containing the SH348-1 or SH357-1 purified in paragraph 2)-8 was separated by SDS-PAGE. The proteins in the gel thus separated were transferred from the gel to a PVDF membrane (0.45 µm in pore size; manufactured by Invitrogen Corp.). The PVDF membrane was washed with a washing buffer (25 mM NaCl, 10 mM sodium borate buffer, pH 8.0), then stained by soaking in a staining solution (50% methanol, 20% acetic acid, 0.05% Coomassie Brilliant Blue) for 5 minutes, and then destained with 90% methanol. Band portions corresponding to the heavy and light chains (heavy chain: the band with smaller mobility, light chain: the band with larger mobility) visualized on the PVDF membrane were excised, and an attempt was made to identify their respective N-terminal amino acid sequences by an automatic Edman method (see Edman, P., et al. (1967) Eur. J. Biochem. 1, 80) using Procise (registered trademark) cLC Protein Sequencer Model 492cLC (Applied Biosystems). For the SH348-1 heavy chain, the amino acid sequence could not be identified by the method. Therefore, the N-terminal pyroglutamic acid was removed using Pfu Pyroglutamate Aminopeptidase (manufactured by TAKARA BIO INC.), and the same procedure as above was then performed to identify an amino acid sequence starting at the second amino acid from the N-terminus.

As a result, the amino acid sequence (starting at the second amino acid from the N-terminus) of the band corresponding to the SH348-1 heavy chain was (SEQ ID NO: 26 in the sequence listing)
I-Q-L-V-Q-S-G-P.

The N-terminal amino acid sequence of the band corresponding to the SH348-1 light chain was (SEQ ID NO: 27 in the sequence listing)
D-V-L-M-T-Q-S-P-L-S-L.

The N-terminal amino acid sequence of the band corresponding to the SH357-1 heavy chain was (SEQ ID NO: 28 in the sequence listing)
Q-I-Q-L-V-Q-S-G-P.

The N-terminal amino acid sequence of the band corresponding to the SH357-1 light chain was (SEQ ID NO: 29 in the sequence listing)
D-V-L-M-T-Q-T-P-L-S-L-P-V-S-L-G-D-Q-A.

These amino acid sequences were compared with antibody amino acid sequence database prepared by Kabat et al. (see Kabat, E. A. et al., (1991) in Sequences of Proteins of Immunological Interest Vol. I and II, U.S. Department of Health and Human Services). As a result, the subtype of the SH348-1 heavy chain (γ2a chain) was miscellaneous, and the subtype of the light chain was kappa light II. Moreover, the subtype of the SH357-1 heavy chain (γ2a chain) was determined to be miscellaneous, and the subtype of the light chain was determined to be kappa light II.

Thus, the following oligonucleotide primers were synthesized, which respectively hybridized to the 5'-terminal region of an antibody gene coding region belonging to these mouse subtypes and the 3'-terminal region thereof containing a stop codon (see Kabat et al., ibid; Matti Kartinen et al. (1988) 25, 859-865; and Heinrich, G. et al. (1984) J. Exp. Med. 159, p. 417-435):

(DB3F1: sequence listing sequence ID No. 30)
5'-cagatccagttggtgcagtctggacct-3'

(MIG2AEVR1: sequence listing sequence ID No. 31)
5'-aagatatctcatttacccggagtccgggagaa-3'

(MK19EIF1: sequence listing sequence ID No. 32)
5'-aagaattcatgaagttgcctgttagg-3'

(KEVR1: sequence listing sequence ID No. 33)
5'-aagatatcttaacactcattcctgttgaagct-3'

To clone cDNAs encoding the SH348-1 and SH357-1 heavy and light chains, mRNA was prepared from the SH348-1- or SH357-1-producing hybridomas using Quick Prep mRNA Purification Kit (manufactured by GE Healthcare Bio-Sciences Corp., #27-9254-01). From each mRNA thus obtained, cDNA encoding each antibody heavy or light chain was amplified using TaKaRa One Step RNA PCR Kit (AMV) (manufactured by TAKARA BIO INC., #RR024A) and the primer set for the heavy chain (combination of DB3F1 and MIG2AEVR1) or the primer set for the light chain (combination of MK19EIF1 and KEVR1). These cDNAs amplified by PCR were cloned using Zero Blunt TOPO PCR Cloning Kit (manufactured by Invitrogen Corp.). Each of the cloned heavy and light chain nucleotide sequences was determined using a gene sequence analyzer ("ABI PRISM 3700 DNA Analyzer; Applied Biosystems" or "Applied Biosystems 3730×1 Analyzer; Applied Biosystems"). In the sequencing reaction, GeneAmp 9700 (Applied Biosystems) was used.

The determined nucleotide sequence of the cDNA encoding the SH348-1 heavy chain is represented by SEQ ID NO: 34 in the sequence listing, and the amino acid sequence thereof is represented by SEQ ID NO: 35. The nucleotide sequence of the cDNA encoding the SH348-1 light chain is represented by SEQ ID NO: 36 in the sequence listing, and the amino acid sequence thereof is represented by SEQ ID NO: 37 in the sequence listing. The nucleotide sequence of the cDNA encoding the SH357-1 heavy chain is represented by SEQ ID NO: 38 in the sequence listing, and the amino acid sequence thereof is represented by SEQ ID NO: 39. The nucleotide sequence of the cDNA encoding the SH357-1 light chain is represented by SEQ ID NO: 40 in the sequence listing, and the amino acid sequence thereof is represented by SEQ ID NO: 41. Sequences represented by nucleotide Nos. 1 to 27 and 1327 to 1350 of SEQ ID NO: 34, a sequence represented by nucleotide Nos. 637 to 660 of SEQ ID NO: 36, sequences represented by nucleotide Nos. 1 to 27 and 1327 to 1350 of SEQ ID NO: 38, and a sequence represented by nucleotide Nos. 637 to 660 of SEQ ID NO: 40 are sequences derived from the primers.

Moreover, the amino acid sequences of these heavy and light chains were analyzed by comparison with antibody amino acid sequence database prepared by Kabat et al. (see Kabat, E. A., et al. (1991) in "Sequence of Proteins of Immunological Interest Vol. I and II"; U.S. Department of Health and Human Services). As a result, the SH348-1 heavy chain was shown to have an amino acid sequence represented by amino acid Nos. 1 to 119 of SEQ ID NO: 35 in the sequence listing as a variable region and have an amino acid sequence represented by amino acid Nos. 120 to 449 thereof as a constant region. Moreover, the SH348-1 light chain was shown to have an amino acid sequence represented by amino acid Nos. 1 to 112 of SEQ ID NO: 37 in the sequence listing as a variable region and have an amino acid sequence represented by amino acid Nos. 113 to 219 thereof as a constant region.

The SH357-1 heavy chain was shown to have an amino acid sequence represented by amino acid Nos. 1 to 119 of SEQ ID NO: 39 in the sequence listing as a variable region and have an amino acid sequence represented by amino acid Nos. 120 to 449 thereof as a constant region. Moreover, the SH357-1 light chain was shown to have an amino acid sequence represented by amino acid Nos. 1 to 112 of SEQ ID NO: 41 in the sequence listing as a variable region and have an amino acid sequence represented by amino acid Nos. 113 to 219 thereof as a constant region.

The nucleotide sequence encoding the SH348-1 heavy chain variable region is represented by SEQ ID NO: 42 in the sequence listing, and the amino acid sequence thereof is represented by SEQ ID NO: 43. The nucleotide sequence encoding the SH348-1 heavy chain constant region is represented by SEQ ID NO: 44, and the amino acid sequence thereof is represented by SEQ ID NO: 45. The nucleotide sequence encoding the SH348-1 light chain variable region is represented by SEQ ID NO: 46 in the sequence listing, and the amino acid sequence thereof is represented by SEQ ID NO: 47. The nucleotide sequence encoding the SH348-1 light chain constant region is represented by SEQ ID NO: 48, and the amino acid sequence thereof is represented by SEQ ID NO: 49. Sequences represented by nucleotide Nos. 1 to 27 of SEQ ID NO: 42, a sequence represented by nucleotide Nos. 970 to 993 of SEQ ID NO: 44, and sequences represented by nucleotide Nos. 301 to 324 of SEQ ID NO: 48, are sequences derived from the primers.

Moreover, the nucleotide sequence encoding the SH357-1 heavy chain variable region is represented by SEQ ID NO: 50 in the sequence listing, and the amino acid sequence thereof is represented by SEQ ID NO: 51. The nucleotide sequence encoding the SH357-1 heavy chain constant region is represented by SEQ ID NO: 52, and the amino acid sequence thereof is represented by SEQ ID NO: 53. The nucleotide sequence encoding the SH357-1 light chain variable region is represented by SEQ ID NO: 54 in the sequence listing, and the amino acid sequence thereof is represented by SEQ ID NO: 55. The nucleotide sequence encoding the SH357-1 light chain constant region is represented by SEQ ID NO: 56, and the amino acid sequence thereof is represented by SEQ ID NO: 57. Sequences represented by nucleotide Nos. 1 to 27 of SEQ ID NO: 50, a sequence represented by nucleotide Nos. 970 to 993 of SEQ ID NO: 52, and sequences represented by nucleotide Nos. 301 to 324 of SEQ ID NO: 56 are sequences derived from the primers.

Furthermore, the positions and sequences of CDRs in each of the amino acid sequences of the heavy and light chain variable regions were analyzed and determined by homology comparison with an antibody amino acid sequence database prepared by Kabat et al. (see Kabat, E. A., et al. (1991) ibid). According to the document, even different antibodies have framework regions which have an amino acid length almost equal to each other and are observed to have amino acid sequence commonality in the variable regions, if they are in the same subtype. On the other hand, CDRs are specific sequences flanked by these framework regions. Thus, the amino acid sequences of the heavy and light chains were analyzed by comparison with those of the same subtype thereas. As a result, CDRs in the SH348-1 heavy chain were determined to have amino acid sequences represented by amino acid Nos. 26 to 35 of SEQ ID NO: 35 in the sequence listing ($CDRH_1$), amino acid Nos. 50 to 66 thereof ($CDRH_2$), and amino acid Nos. 99 to 108 thereof ($CDRH_3$). CDRs in the SH348-1 light chain were determined to have amino acid sequences represented by amino acid Nos. 24 to 39 of SEQ ID NO: 37 in the sequence listing ($CDRL_1$), amino acid Nos. 55 to 61 thereof ($CDRL_2$), and amino acid Nos. 94 to 102 thereof ($CDRL_3$). CDRs in the SH357-1 heavy chain were determined to have amino acid sequences represented by amino acid Nos. 26 to 35 of SEQ ID NO: 39 in the sequence listing ($CDRH_1$), amino acid Nos. 50 to 66 thereof ($CDRH_2$), and amino acid Nos. 99 to 108 thereof ($CDRH_3$). CDRs in the SH357-1 light chain were determined to have amino acid sequences represented by amino acid Nos. 24 to 39 of SEQ ID NO: 41 in the sequence listing ($CDRL_1$), amino acid Nos. 55 to 61 thereof ($CDRL_2$), and amino acid Nos. 94 to 102 thereof ($CDRL_3$).

The nucleotide sequence encoding the SH348-1 $CDRH_1$ is represented by SEQ ID NO: 58 in the sequence listing, and the amino acid sequence thereof is represented by SEQ ID NO: 59. The nucleotide sequence encoding the SH348-1 $CDRH_2$ is represented by SEQ ID NO: 60, and the amino acid sequence thereof is represented by SEQ ID NO: 61. The nucleotide sequence encoding the SH348-1 $CDRH_3$ is represented by SEQ ID NO: 62, and the amino acid sequence thereof is represented by SEQ ID NO: 63. The nucleotide sequence encoding the SH348-1 $CDRL_1$ is represented by SEQ ID NO: 64, and the amino acid sequence thereof is represented by SEQ ID NO: 65. The nucleotide sequence encoding the SH348-1 $CDRL_2$ is represented by SEQ ID NO:

66, and the amino acid sequence thereof is represented by SEQ ID NO: 67. The nucleotide sequence encoding the SH348-1 CDRL$_3$ is represented by SEQ ID NO: 68, and the amino acid sequence thereof is represented by SEQ ID NO: 69. Moreover, the nucleotide sequence encoding the SH357-1 CDRH$_1$ is represented by SEQ ID NO: 70, and the amino acid sequence thereof is represented by SEQ ID NO: 71. The nucleotide sequence encoding the SH357-1 CDRH$_2$ is represented by SEQ ID NO: 72, and the amino acid sequence thereof is represented by SEQ ID NO: 73. The nucleotide sequence encoding the SH357-1 CDRH$_3$ is represented by SEQ ID NO: 74, and the amino acid sequence thereof is represented by SEQ ID NO: 75. The nucleotide sequence encoding the SH357-1 CDRL$_1$ is represented by SEQ ID NO: 76, and the amino acid sequence thereof is represented by SEQ ID NO: 77. The nucleotide sequence encoding the SH357-1 CDRL$_2$ is represented by SEQ ID NO: 78, and the amino acid sequence thereof is represented by SEQ ID NO: 79. The nucleotide sequence encoding the SH357-1 CDRL$_3$ is represented by SEQ ID NO: 80, and the amino acid sequence thereof is represented by SEQ ID NO: 81.

Example 6

Binding Activity of Anti-EPHA2 Antibody to EPHA2 Extracellular Region

A solution of an EPHA2 extracellular region polypeptide (manufactured by R&D Systems, Inc., #3035-A2-100) or bovine serum albumin (in the description below and the figures, abbreviated to "BSA") as a control diluted to 1 μg/ml with PBS was dispensed at 100 μl/well onto an immunoplate (manufactured by Nunc, #442404) and incubated overnight at 4° C. to thereby adsorb the protein to the plate.

On the next day, the solution in the wells was removed, and a Block Ace solution (one pouch of Block Ace powder (manufactured by Dainippon Sumitomo Pharma Co., Ltd. (Show Brand Milk Products Co., Ltd.)) was dissolved in 100 ml of ultrapure water) diluted 4 times with PBS was dispensed at 200 μl/well and incubated at room temperature for 1 hour. The wells were washed twice with Diluting Buffer (PBS, 0.05% (v/v) Tween 20). Then, SH348-1, SH357-1, and Ab96-1 were separately diluted with PBS to a concentration of $1.25 \times 10^{-4}$ μg/ml, $1.25 \times 10^{-3}$ μg/ml, $1.25 \times 10^{-2}$ μg/ml, $1.25 \times 10^{-1}$ μg/ml, 1.25 μg/ml, 12.5 μg/ml, or 125 μg/ml, and the resulting solution (containing 0.05% (v/v) (final concentration) Tween 20) was added at 100 μl/well.

The plate was incubated at room temperature for 1 hour. Then, the solution in the wells was removed, and the wells were washed twice with Diluting Buffer. Goat anti-Mouse IgG, Peroxidase Conjugated (manufactured by Millipore (Chemicon), #AP181P) diluted 1000 times with Diluting Buffer was added at 100 μl/well and incubated at room temperature for 1 hour. The solution in the wells was removed, and the wells were washed twice with Diluting Buffer. Then, a color reaction was performed with stirring by the addition of OPD Color Developing Solution at 100 μl/well. After color development, the color reaction was terminated by the addition of 1 M HCl at 100 μl/well. The absorbance at 490 nm was measured using a plate reader (FIG. 7).

FIG. 7A) shows the results of SH348-1, FIG. 7B) shows the results of SH357-1, and FIG. 7C) shows the results of Ab96-1. In each graph, the absorbance is indicated in mean±standard deviation (n=3). Stronger absorbance represents stronger binding activity. As shown in the graphs, all the antibodies SH348-1, SH357-1, and Ab96-1 exhibited no affinity for BSA, demonstrating that they specifically bind to the EPHA2 extracellular region.

Example 7

Influence of Anti-EPHA2 Antibody on Ligand Binding

An EPHA2 extracellular region polypeptide (manufactured by R&D Systems, Inc., #3035-A2-100)-immobilized immunoplate was prepared according to the method described in Example 6. The immunoplate wells were washed twice with Diluting Buffer. Then, SH348-1, SH357-1, Ab96-1, or Mouse IgG$_{2A}$ Isotype Control (in the description below and the figures, abbreviated to "mIgG2a"; manufactured by R&D Systems, Inc., #MAB003) as an isotype control antibody diluted to 10 μg/ml or 50 μg/ml with Diluting Buffer was added at 100 μl/well. The plate was incubated at room temperature for 1 hour. Then, Recombinant Mouse Ephrin-A1/Fc Chimera (in the description below and the figures, abbreviated to "Ephrin-A1/Fc"; manufactured by R&D Systems, Inc., #602-A1-200) as a soluble ligand or Recombinant Human IgG$_1$ Fc (in the description below and the figures, abbreviated to "hG$_1$Fc"; manufactured by R&D Systems, Inc., #110-HG-100) as a negative control protein for the soluble ligand was added at a final concentration of 1 μg/ml and incubated at room temperature for 1 hour.

Next, according to the method described in Example 6, the solution in the wells was removed, and the wells were washed with Diluting Buffer. Peroxidase AffiniPure Goat Anti-Human IgG Fcγ Fragment Specific (Jackson ImmunoResearch Laboratories, Inc., #109-035-098) was added thereto. A color reaction was performed using OPD Color Developing Solution. The absorbance at 490 nm was measured using a plate reader (FIG. 8).

In FIG. 8, the absorbance is indicated in mean±standard deviation (n=3). The antibody Ab96-1 even at a concentration of 10 μg/ml strongly inhibited the binding of the EPHA2 ligand ephrin-A1 to EPHA2. By contrast, the antibodies SH348-1 and SH357-1, even when added at a concentration of 50 μg/ml (five times the concentration of Ab96-1), did not inhibit the binding of Ephrin-A1/Fc to EPHA2. These results demonstrated that the antibodies SH348-1 and SH357-1 do not inhibit the binding of Ephrin-A1/Fc to EPHA2.

Example 8

Verification of Inhibitory Activity of Anti-EPHA2 Antibody Against Ephrin-A1-Dependent Phosphorylation of EPHA2 Tyrosine Residues 8)-1 Preparation of Cell Lysates
MDA-MB-231 cells suspended in RPMI1640 containing 10% FBS, 50 units/ml penicillin, and 50 μg/ml streptomycin (hereinafter, abbreviated to "10% FBS-containing RPMI1640 (with antibiotics)") were seeded at $2.5 \times 10^5$ cells/well onto a 12-well dish and cultured overnight at 37° C. in 5% CO$_2$. Next, the medium in the wells was discarded, and RPMI1640 was newly added thereto. The cells were further cultured overnight at 37° C. in 5% CO$_2$. Next, the medium in the wells was removed, and only RPMI1640 or RPMI1640 containing the antibody (mIgG2a, SH348-1, or SH357-1) at a concentration of 10 μg/ml or 50 μg/ml was added to each well and preincubated at 37° C. in 5% CO$_2$ for 1 hour.

To the thus-preincubated wells supplemented with only RPMI1640, a 1/50 volume of Ephrin-A1/Fc or hG$_1$Fc (final concentration of 1 μg/ml) or RPMI1640 with the same volume thereas (in FIG. 9, represented by (−)) were added. Moreover, to the wells supplemented with mIgG2a, SH348-1, or SH357-1, a 1/50 volume of Ephrin-A1/Fc (final concentration of 1 μg/ml) was added.

The dishes were further incubated at 37° C. in 5% $CO_2$ for 15 minutes. After discarding of the supernatants, 1×Cell Lysis Buffer (manufactured by Cell Signaling Technology, Inc.) containing 1 mM PMSF (manufactured by Sigma-Aldrich, Inc.) and Protease Inhibitor Cocktail (manufactured by Sigma-Aldrich, Inc., #P8340) (hereinafter, abbreviated to PPCLB) was added thereto to lyse the cells. The lysates were centrifuged at 15000 rpm for 5 minutes, and the obtained supernatants were used as immunoprecipitation samples. The protein concentrations of the samples were measured using BCA Protein Assay Reagent (manufactured by PIERCE).

8)-2 Detection of Phosphorylated State of EPHA2 by Immunoprecipitation

25 μl of a suspension of Protein G magnetic beads (manufactured by NEW ENGLAND BioLabs, Inc.) and 4 μg of anti-EphA2 Antibody (manufactured by Santa Cruz Biotechnology, Inc., #sc-924) were added per sample, and the mixture was inverted for mixing at 4° C. for 2 hours. Next, FBS was added thereto at a final concentration of 10%, and the mixture was further inverted for mixing at 4° C. for 30 minutes. Next, the beads were washed with PPCLB. Next, 200 μg of the cell lysate supernatants prepared in paragraph 8)-1 were added thereto, and the mixtures were inverted for mixing overnight at 4° C.

On the next day, the beads were washed three times with PPCLB. Then, SDS-Sample Buffer (56.3 mM Tris-HCl, pH 6.8, 1.8% (w/v) SDS, 9% glycerol, 0.72 M 2-mercaptoethanol, 0.045 mg/ml bromophenol blue) was added to the beads, and the mixtures were heated at 98° C. for 5 minutes. The proteins dissociated from the beads were separated by SDS-PAGE.

The proteins were transferred from the gel to a PVDF membrane (0.45 μm in pore size; manufactured by Millipore). The PVDF membrane was blocked by shaking in sodium azide-free Blocking Solution (one pouch of Block Ace powder was dissolved in 100 ml of ultrapure water, to which Tween 20 was then added at a final concentration of 0.1% (v/v)).

To detect the phosphorylated state of the EPHA2 tyrosine residues, the PVDF membrane was soaked in a solution of Anti-Phosphotyrosine, recombinant 4G10 HRP-conjugate (manufactured by Upstate, #16-184) diluted 10000 times with sodium azide-free Blocking Solution, and reacted at room temperature for 1 hour. The PVDF membrane was washed for 10 minutes three times with TBST (50 mM Tris-HCl, pH 8.0, 138 mM NaCl, 2.7 mM KCl, 0.1% (v/v) Tween 20) and then further washed for 5 minutes three times with $H_2O$. Signals were detected on a film for chemiluminescence using ECL Plus (manufactured by GE Healthcare Bio-Sciences Corp.).

Next, to detect the immunoprecipitated EPHA2 present on this PVDF membrane, the PVDF membrane after the detection of the phosphorylated state of the EPHA2 tyrosine residues was soaked in Stripping Solution (50 mM Tris-HCl, pH 6.8, 2% (w/v) SDS, 100 mM 2-mercaptoethanol) and shaken at 55° C. for 30 minutes. Then, the PVDF membrane was soaked in Quenching Solution (TBST containing 1% (v/v) $H_2O_2$ and 0.1% (w/v) $NaN_3$) and shaken at room temperature for 20 minutes to remove the antibody on the PVDF membrane. The PVDF membrane was washed for 10 minutes three times with TBST and blocked in Blocking Solution (one pouch of Block Ace powder was dissolved in 100 ml of ultrapure water, to which Tween 20 and sodium azide were then added at final concentrations of 0.1% (v/v) and 0.02% (w/v), respectively). Then, the PVDF membrane was soaked in a solution of an anti-EphA2 Antibody (manufactured by Santa Cruz Biotechnology, Inc., #sc-924) diluted 4000 times with Blocking Solution, and reacted at room temperature for 1 hour. The PVDF membrane was washed for 10 minutes three times with TBST. Then, the PVDF membrane was soaked in a solution of Anti-rabbit IgG, HRP-linked Antibody (manufactured by Cell Signaling Technology, Inc., #7074) diluted 10000 times with TBST, and reacted at room temperature for 30 minutes. Then, this PVDF membrane was washed for 10 minutes three times with TBST. Then, signals were detected on a film for chemiluminescence using ECL Plus.

The soluble ligand Ephrin-A1/Fc-induced phosphorylation of EPHA2 tyrosine residues was not inhibited by the isotype control antibody mIgG2a but was inhibited in a dose-dependent manner by the addition of the antibodies SH348-1 and SH357-1 (FIG. 9).

These results demonstrated that the antibodies SH348-1 and SH357-1 do not inhibit the binding of the ligand ephrin-A1 to EPHA2 but inhibit the ligand-induced phosphorylation of EPHA2 tyrosine residues.

Example 9

Epitope Identification for Anti-EPHA2 Antibody

Deletion mutants of EPHA2 consisting of a region shown in FIG. 10 were prepared, and a region binding to SH348-1 or SH357-1 was determined.

9)-1 Preparation of Deletion Mutants of EPHA2

To express deletion mutants of EPHA2 as proteins having GST-Tag and His-Tag added to the N-terminus and S-Tag added to the C-terminus, the following primers were synthesized, and gene fragments amplified by a method shown below were cloned into pET-49b (+) (manufactured by Novagen):

```
                        (primer N1: sequence ID No. 82)
5'-attaggatccgagcttccgtactgccagtgtc-3'

(primer N2: sequence ID No. 83)
5'-attaggatccgcccccaaggtgaggct-3'

(primer N3: sequence ID No. 84)
5'-attaggatccggtcacttaccgcaagaagggaga-3'

(primer N4: sequence ID No. 85)
5'-attaggatccggtccaggtgcaggcactgacg-3'

(primer C1: sequence ID No. 86)
5'-aattaagcttgccgccaatcaccgccaagtt-3'

(primer C2: sequence ID No. 87)
5'-aattaagcttgttgccagatccctccggggac-3'

(primer C3: sequence ID No. 88)
5'-aattaagcttcaggtaggtggtgtctggg-3'

(primer C4: sequence ID No. 89)
5'-aattaagcttctcgtacttccacactcggc-3'
```

Each region was amplified by PCR reaction using pcDNA-DEST40-EPHA2 as the template and a primer set: the primers N1 and C1 for a region consisting of an amino acid sequence represented by amino acid Nos. 426 to 540 of SEQ ID NO: 8 in the sequence listing (hereinafter, referred to as "m1"); the primers N1 and C2 for a region consisting of an amino acid sequence represented by amino acid Nos. 426 to 534 thereof (hereinafter, referred to as "m2"); the primers N1 and C3 for a region consisting of an amino acid sequence represented by amino acid Nos. 426 to 504 thereof (hereinafter, referred to as "m3"); the primers N1 and C4 for a region consisting of an amino acid sequence represented by amino acid Nos. 426 to 470 thereof (hereinafter, referred to as "m4"); the primers N2 and C2 for a region consisting of an amino acid sequence represented by amino acid Nos. 439 to 534 thereof (hereinafter, referred to as "m5"); the primers N3 and C2 for a region consisting of an amino acid sequence represented by amino acid Nos. 471 to 534 thereof (hereinafter, referred to as "m6"); the primers N4 and C2 for a region consisting of an amino acid sequence represented by amino acid Nos. 505 to 534 thereof (hereinafter, referred to as "m7"); the primers N2 and C3 for a region consisting of an amino acid sequence represented by amino acid Nos. 439 to 504 thereof (hereinafter, referred to as "m8"); and the primers N2 and C4 for a region consisting of an amino acid sequence represented by amino acid Nos. 439 to 470 thereof (hereinafter, referred to as "m9"). The obtained PCR products were cleaved with BamHI and HindIII and subcloned into the BamHI/HindIII site of pET-49b (+).

9)-2 Expression of Deletion Mutants of EPHA2

*Escherichia coli* BL21 (DE3) was transformed with the plasmid DNA constructed in paragraph 9)-1 or pET-49b (+) as a negative control. The obtained transformants were cultured in an LB medium supplemented with 30 μg/ml kanamycin (manufactured by Invitrogen Corp.). Expression of the deletion mutants of EPHA2 was induced using Autoinduction System (manufactured by Novagen). The bacterial cells were collected by centrifugation and washed with PBS. Then, the bacterial cells were lysed with a 2% SDS solution containing 1 mM PMSF and Protease Inhibitor Cocktail (manufactured by Sigma-Aldrich, Inc., #P8340). The supernatant was collected by centrifugation and used in epitope identification.

The expression level of proteins (consisting of pET-49b (+)-derived GST-Tag, His-Tag, and S-Tag and linker portions for connecting them; in the description below and the figures, referred to as "Vec") expressed in the bacterial cell lysate of *Escherichia coli* transformed with pET-49b (+) was estimated by a method described below. Dilution series of the Vec-expressing bacterial cell lysate and dilution series of 6×His Protein Ladder (manufactured by QIAGEN) were separately dissolved in SDS-Sample Buffer and heated at 98° C. for 5 minutes. Then, the proteins were separated by SDS-PAGE, and the proteins in the gel were transferred to a PVDF membrane. The PVDF membrane was blocked in TBST containing 5% BSA. Then, the PVDF membrane was soaked in a solution of Penta-His HRP Conjugate (manufactured by QIAGEN) diluted 1000 times with TBST containing 5% BSA, and reacted at room temperature for 1 hour. This PVDF membrane was washed for 10 minutes three times with TBST. Then, signals were detected using ECL Plus. Signal intensity was compared between the dilution series of the Vec-expressing bacterial cell lysate and the dilution series of 6×His Protein Ladder, and the concentration of the Vec protein contained in the Vec-expressing bacterial cell lysate was estimated from the protein level per band contained in 6×His Protein Ladder. Deletion mutants of EPHA2 with an amount that exhibited reactivity equivalent to that of 20 ng of Vec in Western blotting using S-Tag Monoclonal Antibody (Novagen) were used in the subsequent epitope identification experiment.

9)-3) Epitope Identification

The cell lysates containing the deletion mutants of EPHA2 prepared in paragraph 9)-2 were dissolved in SDS-Sample Buffer and heated at 98° C. for 5 minutes. The resulting samples were separated by SDS-PAGE, and the proteins in the gels were transferred to PVDF membranes. After the transfer, the PVDF membranes were blocked by shaking in Blocking Solution (one pouch of Block Ace powder was dissolved in 100 ml of ultrapure water, to which Tween 20 and sodium azide were then added at final concentrations of 0.1% (v/v) and 0.02% (w/v), respectively). Then, these PVDF membranes were reacted overnight at 4° C. in Blocking Solution containing 2 μg/ml SH348-1 or SH357-1. These PVDF membranes were washed for 10 minutes three times with TBST and further reacted at room temperature for 30 minutes in a solution of Anti-Mouse Ig, HRP-Linked Whole Ab Sheep diluted 5000 times with TBST. Subsequently, the PVDF membranes were washed for 10 minutes three times with TBST. Then, signals were detected on a film for chemiluminescence using ECL Plus.

Next, the PVDF membranes were soaked in Stripping Solution (50 mM Tris-HCl, pH 6.8, 2% (w/v) SDS, 100 mM 2-mercaptoethanol), then shaken at 55° C. for 30 minutes, and then washed for 10 minutes three times with TBST. These PVDF membranes were blocked in Blocking Solution and then washed for 10 minutes three times with TBST. The PVDF membranes were soaked in a solution of S-Tag Monoclonal Antibody diluted 10000 times with TBST, and reacted at room temperature for 30 minutes. The PVDF membranes were washed for 10 minutes three times with TBST. Then, the PVDF membranes were soaked in a solution of Anti-Mouse Ig, HRP-Linked Whole Ab Sheep diluted 5000 times with TBST, and reacted at room temperature for 30 minutes. Next, the PVDF membranes were washed for 10 minutes three times with TBST. Then, signals were detected on a film for chemiluminescence using ECL Plus.

As a result, both the antibodies SH348-1 (FIG. 11A) and SH357-1 (FIG. 11C) exhibited binding activities only to m1, m2, and m5. Moreover, in this procedure, the deletion mutants of EPHA2 were present in an almost constant amount on each of the PVDF membranes (SH348-1: FIG. 11B, SH357-1: FIG. 11D). These results demonstrated that the antibodies SH348-1 and SH357-1 bind to a region consisting of an amino acid sequence represented by amino acid Nos. 439 to 534 of SEQ ID NO: 8 in the sequence listing in the EPHA2 amino acid sequence.

Example 10

Design of Humanized Antibody

10)-1 Design of Humanized Antibody of SH348-1

10)-1-1 Molecular Modeling of SH348-1 Variable Regions

The molecular modeling of SH348-1 variable regions was conducted according to homology modeling (Methods in Enzymology, 203, 121-153, (1991)). The primary sequences (three-dimensional structures derived from X-ray crystal structures are available) of human immunoglobulin variable regions registered in Protein Data Bank (Nuc. Acid Res. 35, D301-D303 (2007)) were compared with the SH348-1 variable regions determined in Example 5. As a result, 2JEL and 1A4J were respectively selected as sequences having the highest sequence homology to the SH348-1 light or heavy chain variable regions. The three-dimensional structures of framework regions were prepared based on a "framework model" obtained by combining the coordinates of 2JEL and 1A4J corresponding to the SH348-1 light and heavy chains. For SH348-1 CDRs, $CDRL_1$, $CDRL_2$, $CDRL_3$, $CDRH_1$, and $CDRH_2$ were assigned to clusters 16A, 7A, 9A, 10A, and 10A, respectively, according to the classification of Thornton et al. (J. Mol. Biol., 263, 800-815, (1996)). $CDRH_3$ was classified in e (9) D according to the H3-rules (FEBS letters 399, 1-8 (1996)). Subsequently, the typical conformation of each CDR was incorporated in the framework model.

Finally, to obtain possible molecular models of the SH348-1 variable regions in terms of energy, an energy calculation was conducted for excluding disadvantageous interatomic contact. These procedures were performed using a commercially available three-dimensional protein structure prediction program Prime and coordinate search program MacroModel (Schrödinger, LLC).

10)-1-2 Design of Amino Acid Sequence of Humanized SH348-1

Humanized SH348-1 antibodies were constructed according to CDR grafting (Proc. Natl. Acad. Sci. USA 86, 10029-10033 (1989)). Acceptor antibodies were selected based on amino acid homology within the framework regions. The sequences of the SH348-1 framework regions were compared with those of all human frameworks registered in the Kabat Database (Nuc. Acid Res. 29, 205-206 (2001)) involving antibody amino acid sequences. A GSD2B5B10'CL antibody was selected as an acceptor due to their having, at 72%, the highest sequence homology between their framework regions. The amino acid residues of the framework regions in GSD2B5B10'CL were aligned with the corresponding amino acid residues in SH348-1 to identify positions where different amino acids therebetween were used. The positions of these residues were analyzed using the three-dimensional model of SH348-1 thus constructed. Then, donor residues to be grafted on the acceptor were selected according to the criteria provided by Queen et al. (Proc. Natl. Acad. Sci. USA 86, 10029-10033 (1989)). Humanized SH348-1 sequences were determined by transferring some selected donor residues to the acceptor antibody GSD2B5B10'CL. As a result, the humanized sequences of two types of light chains and two types of heavy chains were obtained as shown below. Hereinafter, variable and constant regions and CDRs were classified based on the antibody amino acid sequence database prepared by Kabat et al.

10-1-3) Humanization of SH348-1 Light Chain 10-1-3-1) hSH348-T1L-Type Light Chain:

A humanized SH348-1 light chain was designed by substituting amino acid Nos. 2 (valine), 3 (leucine), 14 (serine), 15 (leucine), 17 (aspartic acid), 18 (glutamine), 50 (lysine), 79 (arginine), 88 (leucine), 105 (glycine), 109 (leucine), and 114 (alanine) of SH348-1 light chain variable region shown in SEQ ID NO: 37 of the sequence listing with isoleucine, valine, threonine, proline, glutamic acid, proline, glutamine, lysine, valine, glutamine, valine, and threonine, respectively, and was designated as a "hSH348-T1L-type light chain".

The nucleotide sequence encoding the hSH348-1-T1L-type light chain is represented by SEQ ID NO: 90 in the sequence listing, and the amino acid sequence thereof is represented by SEQ ID NO: 91. The nucleotide sequence represented by nucleotide Nos. 1 to 60 of SEQ ID NO: 90 is a secretion signal sequence. The nucleotide sequence represented by nucleotide Nos. 61 to 402 thereof is a variable region. The nucleotide sequence represented by nucleotide Nos. 403 to 717 thereof is a constant region. The nucleotide sequence represented by nucleotide Nos. 130 to 177 thereof is CDRL$_1$. The nucleotide sequence represented by nucleotide Nos. 223 to 243 thereof is CDRL$_2$. The nucleotide sequence represented by nucleotide Nos. 340 to 363 thereof is CDRL$_3$.

The amino acid sequence represented by amino acid Nos. 1 to 20 of SEQ ID NO: 91 of the sequence listing is a secretion signal sequence. The amino acid sequence represented by amino acid Nos. 21 to 134 thereof is a variable region. The amino acid sequence represented by amino acid Nos. 135 to 239 thereof is a constant region. The amino acid sequence represented by amino acid Nos. 44 to 59 thereof is CDRL$_1$. The amino acid sequence represented by amino acid Nos. 75 to 81 thereof is CDRL$_2$. The amino acid sequence represented by amino acid Nos. 114 to 121 thereof is CDRL$_3$.

Moreover, the nucleotide sequence encoding the hSH348-1-T1L-type light chain CDRL$_1$ is represented by SEQ ID NO: 92 in the sequence listing, the amino acid sequence thereof is represented by SEQ ID NO: 93, the nucleotide sequence of CDRL$_2$ is represented by SEQ ID NO: 94 in the sequence listing, the amino acid sequence thereof is represented by SEQ ID NO: 95, the nucleotide sequence of CDRL$_3$ is represented by SEQ ID NO: 96 in the sequence listing, and the amino acid sequence thereof is represented by SEQ ID NO: 97.

10-1-3-2) hSH348-T3L-Type Light Chain:

A humanized SH348-1 light chain was designed by substituting amino acid Nos. 14 (serine), 15 (leucine), 17 (aspartic acid), 18 (glutamine), 50 (lysine), 79 (arginine), 88 (leucine), 105 (glycine), 109 (leucine), and 114 (alanine) of SH348-1 light chain variable region shown in SEQ ID NO: 37 of the sequence listing with threonine, proline, glutamic acid, proline, glutamine, lysine, valine, glutamine, valine, and threonine, respectively, and was designated as a "hSH348-1-T3L-type light chain".

The nucleotide sequence encoding the hSH348-1-T3L-type light chain is represented by SEQ ID NO: 98 in the sequence listing, and the amino acid sequence thereof is represented by SEQ ID NO: 99. The nucleotide sequence represented by nucleotide Nos. 1 to 60 of SEQ ID NO: 98 is a secretion signal sequence. The nucleotide sequence represented by nucleotide Nos. 61 to 402 thereof is a variable region. The nucleotide sequence represented by nucleotide Nos. 403 to 717 thereof is a constant region. The nucleotide sequence represented by nucleotide Nos. 130 to 177 thereof is CDRL$_1$. The nucleotide sequence represented by nucleotide Nos. 223 to 243 thereof is CDRL$_2$. The nucleotide sequence represented by nucleotide Nos. 340 to 363 thereof is CDRL$_3$.

The amino acid sequence represented by amino acid Nos. 1 to 20 of SEQ ID NO: 99 of the sequence listing is a secretion signal sequence. The amino acid sequence represented by amino acid Nos. 21 to 134 thereof is a variable region. The amino acid sequence represented by amino acid Nos. 135 to 239 thereof is a constant region. The amino acid sequence represented by amino acid Nos. 44 to 59 thereof is CDRL$_1$. The amino acid sequence represented by amino acid Nos. 75 to 81 thereof is CDRL$_2$. The amino acid sequence represented by amino acid Nos. 114 to 121 thereof is CDRL$_3$.

Moreover, the nucleotide sequence encoding the hSH348-1-T3L-type light chain CDRL$_1$ is represented by SEQ ID NO: 100 in the sequence listing, and the amino acid sequence thereof is represented by SEQ ID NO: 101, the nucleotide sequence of CDRL$_2$ is represented by SEQ ID NO: 102 in the sequence listing, the amino acid sequence thereof is represented by SEQ ID NO: 103, the nucleotide sequence of CDRL$_3$ is represented by SEQ ID NO: 104 in the sequence listing, and the amino acid sequence thereof is represented by SEQ ID NO: 105.

10-1-4) Humanization of SH348-1 Heavy Chain 10-1-4-1) hSH348-1-T1H-Type Heavy Chain:

A humanized SH348-1 heavy chain was designed by substituting amino acid Nos. 2 (isoleucine), 9 (proline), 11 (leucine), 16 (glutamic acid), 17 (threonine), 20 (isoleucine), 38 (lysine), 43 (lysine), 46 (lysine), 68 (phenylalanine), 69 (alanine), 70 (phenylalanine), 71 (serine), 72 (leucine), 73 (glutamic acid), 76 (alanine), 80 (phenylalanine), 82 (glutamine), 83 (isoleucine), 84 (asparagine), 85 (asparagine), 87 (lysine), 88 (asparagine), 93 (threonine), 95 (phenylalanine), 114 (threonine), and 115 (leucine) of SH348-1 heavy chain variable region shown in SEQ ID NO: 43 of the sequence listing with valine, alanine, valine, serine, serine, valine, arginine, glutamine, glutamic acid, valine, threonine, isoleucine, threonine, alanine, aspartic acid, threonine, tyrosine, glutamic acid, leucine, serine, serine, arginine, serine, valine, tyrosine, leucine and valine, respectively, and was designated as a "hSH348-1-T1H-type heavy chain".

The nucleotide sequence encoding the hSH348-1-T1H-type heavy chain is represented by SEQ ID NO: 106 in the sequence listing, and the amino acid sequence thereof is represented by SEQ ID NO: 107. The nucleotide sequence represented by nucleotide Nos. 1 to 57 of SEQ ID NO: 106 is a secretion signal sequence. The nucleotide sequence represented by nucleotide Nos. 58 to 414 thereof is a variable region. The nucleotide sequence represented by nucleotide Nos. 415 to 1404 thereof is a constant region. The nucleotide sequence represented by nucleotide Nos. 148 to 162 thereof is $CDRH_1$. The nucleotide sequence represented by nucleotide Nos. 205 to 255 thereof is $CDRH_2$. The nucleotide sequence represented by nucleotide Nos. 352 to 381 thereof is $CDRL_3$.

The amino acid sequence represented by amino acid Nos. 1 to 19 of SEQ ID NO: 107 of the sequence listing is a secretion signal sequence. The amino acid sequence represented by amino acid Nos. 20 to 138 thereof is a variable region. The amino acid sequence represented by amino acid Nos. 139 to 468 thereof is a constant region. The amino acid sequence represented by amino acid Nos. 50 to 54 thereof is $CDRH_1$. The amino acid sequence represented by amino acid Nos. 69 to 85 thereof is $CDRH_2$. The amino acid sequence represented by amino acid Nos. 118 to 127 thereof is $CDRH_3$.

Moreover, the nucleotide sequence encoding the hSH348-1-T1H-type heavy chain $CDRH_1$ is represented by SEQ ID NO: 108 in the sequence listing, the amino acid sequence thereof is represented by SEQ ID NO: 109, the nucleotide sequence of $CDRH_2$ is represented by SEQ ID NO: 110 in the sequence listing, the amino acid sequence thereof is represented by SEQ ID NO: 111, the nucleotide sequence of $CDRH_3$ is represented by SEQ ID NO: 112 in the sequence listing, and the amino acid sequence thereof is represented by SEQ ID NO: 113.

10-1-4-2) hSH348-1-T3H-Type Heavy Chain:

A humanized SH348-1 heavy chain was designed by substituting amino acid Nos. 9 (proline), 11 (leucine), 16 (glutamic acid), 17 (threonine), 20 (isoleucine), 38 (lysine), 43 (lysine), 73 (glutamic acid), 76 (alanine), 80 (phenylalanine), 82 (glutamine), 83 (isoleucine), 84 (asparagine), 85 (asparagine), 87 (lysine), 88 (asparagine), 93 (threonine), 95 (phenylalanine), 114 (threonine), and 115 (leucine) of SH348-1 heavy chain variable domains shown in SEQ ID NO: 43 of the sequence listing with alanine, valine, serine, serine, valine, arginine, glutamine, aspartic acid, threonine, tyrosine, glutamic acid, leucine, serine, serine, arginine, serine, valine, tyrosine, leucine and valine, respectively, and was designated as a "hSH348-1-T3H-type heavy chain".

The nucleotide sequence encoding the hSH348-1-T3H-type heavy chain is represented by SEQ ID NO: 114 in the sequence listing, and the amino acid sequence thereof is represented by SEQ ID NO: 115. The nucleotide sequence represented by nucleotide Nos. 1 to 57 of SEQ ID NO: 114 is a secretion signal sequence. The nucleotide sequence represented by nucleotide Nos. 58 to 414 thereof is a variable region. The nucleotide sequence represented by nucleotide Nos. 415 to 1404 thereof is a constant region. The nucleotide sequence represented by nucleotide Nos. 148 to 162 thereof is $CDRH_1$. The nucleotide sequence represented by nucleotide Nos. 205 to 255 thereof is $CDRH_2$. The nucleotide sequence represented by nucleotide Nos. 352 to 381 thereof is $CDRL_3$.

The amino acid sequence represented by amino acid Nos. 1 to 19 of SEQ ID NO: 115 of the sequence listing is a secretion signal sequence. The amino acid sequence represented by amino acid Nos. 20 to 138 thereof is a variable region. The amino acid sequence represented by amino acid Nos. 139 to 468 thereof is a constant region. The amino acid sequence represented by amino acid Nos. 50 to 54 thereof is $CDRH_1$. The amino acid sequence represented by amino acid Nos. 69 to 85 thereof is $CDRH_2$. The amino acid sequence represented by amino acid Nos. 118 to 127 thereof is $CDRH_3$.

Moreover, the nucleotide sequence encoding the hSH348-1-T3H-type heavy chain $CDRH_1$ is represented by SEQ ID NO: 116 in the sequence listing, the amino acid sequence thereof is represented by SEQ ID NO: 117, the nucleotide sequence of $CDRH_2$ is represented by SEQ ID NO: 118 in the sequence listing, the amino acid sequence thereof is represented by SEQ ID NO: 119, the nucleotide sequence of $CDRH_3$ is represented by SEQ ID NO: 120 in the sequence listing, and the amino acid sequence thereof is represented by SEQ ID NO: 121.

10)-2 Design of Humanized Antibody of SH357-1

10)-2-1 Molecular Modeling of SH357-1 Variable Region

2JEL and 1A4J were selected as sequences having the highest sequence homology to the SH357-1 light and heavy chain variable regions, respectively, in the same way as in paragraph 10)-1-1. $CDRL_1$, $CDRL_2$, $CDRL_3$, $CDRH_1$, and $CDRH_2$ were assigned to clusters 16A, 7A, 9A, 10A, and 10A, respectively. $CDRH_3$ was classified in e(9)D.

10)-2-2 Design of Amino Acid Sequence for Humanized SH357-1

A GSD2B5B10'CL antibody was selected as an acceptor in the same way as in paragraph 10)-1-2, and the sequence of humanized SH357-1 was determined. As a result, the humanized sequences of two types of light chains and two types of heavy chains were obtained as shown below.

10-2-3) Humanization of SH357-1 Light Chain 10-2-3-1) hSH357-1-T1L-Type Light Chain:

A humanized SH357-1 light chain designed by substituting amino acid Nos. 2 (valine), 3 (leucine), 7 (threonine), 14 (serine), 15 (leucine), 17 (aspartic acid), 18 (glutamine), 50 (lysine), 88 (leucine), 105 (glycine), 109 (leucine), and 114 (alanine) of SH357-1 light chain shown in SEQ ID NO: 41 of the sequence listing with isoleucine, valine, serine, threonine, proline, glutamic acid, proline, glutamine, valine, glutamine, valine, and threonine, respectively, was designated as a "hSH357-1-T1L-type light chain".

The nucleotide sequence encoding the hSH357-1-T1L-type light chain is represented by SEQ ID NO: 122 in the sequence listing, and the amino acid sequence thereof is represented by SEQ ID NO: 123. The nucleotide sequence represented by nucleotide Nos. 1 to 60 of SEQ ID NO: 122 is a secretion signal sequence. The nucleotide sequence represented by nucleotide Nos. 61 to 402 thereof is a variable region. The nucleotide sequence represented by nucleotide Nos. 403 to 717 thereof is a constant region. The nucleotide sequence represented by nucleotide Nos. 130 to 177 thereof is $CDRL_1$. The nucleotide sequence represented by nucleotide Nos. 223 to 243 thereof is $CDRL_2$. The nucleotide sequence represented by nucleotide Nos. 340 to 363 thereof is $CDRL_3$.

The amino acid sequence represented by amino acid Nos. 1 to 20 of SEQ ID NO: 123 of the sequence listing is a secretion signal sequence. The amino acid sequence represented by amino acid Nos. 21 to 134 thereof is a variable region. The amino acid sequence represented by amino acid Nos. 135 to 239 thereof is a constant region. The amino acid sequence represented by amino acid Nos. 44 to 59 thereof is CDRL$_1$. The amino acid sequence represented by amino acid Nos. 75 to 81 thereof is CDRL$_2$. The amino acid sequence represented by amino acid Nos. 114 to 121 thereof is CDRL$_3$.

Moreover, the nucleotide sequence encoding the hSH357-1-T1L-type light chain CDRL$_1$ is represented by SEQ ID NO: 124 in the sequence listing, the amino acid sequence thereof is represented by SEQ ID NO: 125, the nucleotide sequence of CDRL$_2$ is represented by SEQ ID NO: 126 in the sequence listing, the amino acid sequence thereof is represented by SEQ ID NO: 127, the nucleotide sequence of CDRL$_3$ is represented by SEQ ID NO: 128 in the sequence listing, and the amino acid sequence thereof is represented by SEQ ID NO: 129.

10-2-3-2) hSH357-1-T3L-Type Light Chain:

A humanized SH357-1 light chain designed by substituting amino acid Nos. 7 (threonine), 14 (serine), 15 (leucine), 17 (aspartic acid), 18 (glutamine), 50 (lysine), 88 (leucine), 105 (glycine), 109 (leucine), and 114 (alanine) of SH357-1 light chain shown in SEQ ID NO: 41 with serine, threonine, proline, glutamic acid, proline, glutamine, valine, glutamine, valine, and threonine, respectively, was designated as a "hSH357-1-T3L-type light chain".

The nucleotide sequence encoding the hSH357-1-T3L-type light chain is represented by SEQ ID NO: 130 in the sequence listing, and the amino acid sequence thereof is represented by SEQ ID NO: 131. A nucleotide sequence represented by nucleotide Nos. 1 to 60 of SEQ ID NO: 130 is a secretion signal sequence. A nucleotide sequence represented by nucleotide Nos. 61 to 402 thereof is a variable region. A nucleotide sequence represented by nucleotide Nos. 403 to 717 thereof is a constant region. A nucleotide sequence represented by nucleotide Nos. 130 to 177 thereof is CDRL$_1$. A nucleotide sequence represented by nucleotide Nos. 223 to 243 thereof is CDRL$_2$. A nucleotide sequence represented by nucleotide Nos. 340 to 363 thereof is CDRL$_3$.

The amino acid sequence represented by amino acid Nos. 1 to 20 of SEQ ID NO: 131 of the sequence listing is a secretion signal sequence. The amino acid sequence represented by amino acid Nos. 21 to 134 thereof is a variable region. The amino acid sequence represented by amino acid Nos. 135 to 239 thereof is a constant region. The amino acid sequence represented by amino acid Nos. 44 to 59 thereof is CDRL$_1$. The amino acid sequence represented by amino acid Nos. 75 to 81 thereof is CDRL$_2$. The amino acid sequence represented by amino acid Nos. 114 to 121 thereof is CDRL$_3$.

Moreover, the nucleotide sequence encoding the hSH357-1-T3L-type light chain CDRL$_1$ is represented by SEQ ID NO: 132 in the sequence listing, the amino acid sequence thereof is represented by SEQ ID NO: 133, the nucleotide sequence of CDRL$_2$ is represented by SEQ ID NO: 134 in the sequence listing, the amino acid sequence thereof is represented by SEQ ID NO: 135, the nucleotide sequence of CDRL$_3$ is represented by SEQ ID NO: 136 in the sequence listing, and the amino acid sequence thereof is represented by SEQ ID NO: 137.

10-2-4) Humanization of SH357-1 Heavy Chain 10-2-4-1) hSH357-1-T1H-Type Heavy Chain:

A humanized SH357-1 heavy chain was designed by substituting amino acid Nos. 2 (isoleucine), 9 (proline), 11 (leucine), 16 (glutamic acid), 17 (threonine), 20 (isoleucine), 38 (lysine), 43 (lysine), 46 (lysine), 68 (phenylalanine), 69 (alanine), 70 (phenylalanine), 71 (serine), 72 (leucine), 73 (glutamic acid), 76 (alanine), 82 (glutamine), 83 (isoleucine), 85 (asparagine), 87 (lysine), 88 (asparagine), 93 (serine), 95 (phenylalanine), 114 (threonine), and 115 (leucine) of SH357-1 heavy chain variable region shown in SEQ ID NO: 51 of the sequence listing with valine, alanine, valine, alanine, serine, valine, arginine, glutamine, glutamic acid, valine, threonine, isoleucine, threonine, alanine, aspartic acid, threonine, glutamic acid, leucine, serine, arginine, serine, valine, tyrosine, leucine and valine, respectively, and was designated as a "hSH357-1-T1H-type heavy chain".

The nucleotide sequence encoding the hSH357-1-T1H-type heavy chain is represented by SEQ ID NO: 138 in the sequence listing, and the amino acid sequence thereof is represented by SEQ ID NO: 139. The nucleotide sequence represented by nucleotide Nos. 1 to 57 of SEQ ID NO: 138 is a secretion signal sequence. The nucleotide sequence represented by nucleotide Nos. 58 to 414 thereof is a variable region. The nucleotide sequence represented by nucleotide Nos. 415 to 1404 thereof is a constant region. The nucleotide sequence represented by nucleotide Nos. 145 to 162 thereof is CDRH$_1$. The nucleotide sequence represented by nucleotide Nos. 205 to 255 thereof is CDRH$_2$. The nucleotide sequence represented by nucleotide Nos. 352 to 381 thereof is CDRL$_3$.

The amino acid sequence represented by amino acid Nos. 1 to 19 of SEQ ID NO: 139 of the sequence listing is a secretion signal sequence. The amino acid sequence represented by amino acid Nos. 20 to 138 thereof is a variable region. The amino acid sequence represented by amino acid Nos. 139 to 468 thereof is a constant region. The amino acid sequence represented by amino acid Nos. 49 to 54 thereof is CDRH$_1$. The amino acid sequence represented by amino acid Nos. 69 to 85 thereof is CDRH$_2$. The amino acid sequence represented by amino acid Nos. 118 to 127 thereof is CDRH$_3$.

Moreover, the nucleotide sequence encoding the hSH357-1-T1H-type heavy chain CDRH$_1$ is represented by SEQ ID NO: 140 in the sequence listing, the amino acid sequence thereof is represented by SEQ ID NO: 141, the nucleotide sequence of CDRH$_2$ is represented by SEQ ID NO: 142 in the sequence listing, the amino acid sequence thereof is represented by SEQ ID NO: 143, the nucleotide sequence of CDRH$_3$ is represented by SEQ ID NO: 144 in the sequence listing, and the amino acid sequence thereof is represented by SEQ ID NO: 145.

10-2-4-2) hSH357-1-T3H-Type Heavy Chain:

A humanized SH357-1 heavy chain was designed by substituting amino acid Nos. 9 (proline), 11 (leucine), 16 (glutamic acid), 17 (threonine), 20 (isoleucine), 38 (lysine), 43 (lysine), 73 (glutamic acid), 76 (alanine), 82 (glutamine), 83 (isoleucine), 85 (asparagine), 87 (lysine), 88 (asparagine), 93 (serine), 95 (phenylalanine), 114 (threonine), and 115 (leucine) of SH357-1 heavy chain variable region shown in SEQ ID NO: 51 with alanine, valine, alanine, serine, valine, arginine, glutamine, aspartic acid, threonine, glutamic acid, leucine, serine, arginine, serine, valine, tyrosine, leucine and valine, respectively, and was designated as a "hSH357-1-T3H-type heavy chain".

The nucleotide sequence encoding the hSH357-1-T3H-type heavy chain is represented by SEQ ID NO: 146 in the sequence listing, and the amino acid sequence thereof is represented by SEQ ID NO: 147. The nucleotide sequence represented by nucleotide Nos. 1 to 57 of SEQ ID NO: 146 is a secretion signal sequence. The nucleotide sequence represented by nucleotide Nos. 58 to 414 thereof is a variable region. The nucleotide sequence represented by nucleotide Nos. 415 to 1404 thereof is a constant region. The nucleotide sequence represented by nucleotide Nos. 145 to 162 thereof is CDRH$_1$. The nucleotide sequence represented by nucleotide Nos. 205 to 255 thereof is CDRH$_2$. The nucleotide sequence represented by nucleotide Nos. 352 to 381 thereof is CDRL$_3$.

The amino acid sequence represented by amino acid Nos. 1 to 19 of SEQ ID NO: 147 of the sequence listing is a secretion signal sequence. The amino acid sequence represented by amino acid Nos. 20 to 138 thereof is a variable region. The amino acid sequence represented by amino acid Nos. 139 to 468 thereof is a constant region. The amino acid sequence represented by amino acid Nos. 49 to 54 thereof is CDRH$_1$. The amino acid sequence represented by amino acid Nos. 69 to 85 thereof is CDRH$_2$. The amino acid sequence represented by amino acid Nos. 118 to 127 thereof is CDRH$_3$.

Moreover, the nucleotide sequence encoding the hSH357-1-T3H-type heavy chain CDRH$_1$ is represented by SEQ ID NO: 148 in the sequence listing, the amino acid sequence thereof is represented by SEQ ID NO: 149, the nucleotide sequence of CDRH$_2$ is represented by SEQ ID NO: 150 in the sequence listing, the amino acid sequence thereof is represented by SEQ ID NO: 151, the nucleotide sequence of CDRH$_3$ is represented by SEQ ID NO: 152 in the sequence listing, and the amino acid sequence thereof is represented by SEQ ID NO: 153.

Example 11

Preparation of Humanized Anti-EPHA2 Antibodies

To measure the activities of the humanized SH348-1 and the humanized SH357-1, plasmids having the heavy and light chains of the humanized anti-EPHA2 antibodies obtained in Example 10 were constructed as shown below.

11)-1 Construction of Humanized Anti-EPHA2 Antibody Expression Vectors

11)-1-1 Preparation of Versatile Humanized Antibody Light Chain Expression Vector (pEF6/KCL)

A gene encoding a human antibody light chain signal sequence and a human Ig light chain (κ chain) constant region, described in SEQ ID NO: 154 in the sequence listing, was synthesized (Invitrogen Corp.; artificial gene synthesis service) and cleaved with restriction enzymes NheI and PmeI. The cleaved DNA fragment was inserted into the NheI/PmeI site of a vector pEF6/V5-HisB (Invitrogen Corp.) to construct a versatile humanized antibody light chain expression vector (pEF6/KCL).

11)-1-2 Preparation of Versatile Humanized Antibody Heavy Chain Expression Vector (pEF1/FCCU-1)

A gene encoding a human antibody heavy chain signal sequence and a human IgG1 constant region, described in SEQ ID NO: 155 in the sequence listing, was synthesized (Invitrogen Corp.; artificial gene synthesis service) and cleaved with restriction enzymes NheI and PmeI. The cleaved DNA fragment was inserted into the NheI/PmeI site of a vector pEF1/myc-HisB (Invitrogen Corp.) to construct a versatile humanized antibody H chain expression vector (pEF1/FCCU-1).

11)-1-3 hSH348-1-T1L and hSH348-1-T3L-Type Light Chain Expression Vectors

Each DNA containing a gene encoding a hSH348-1-T1L or hSH348-1-T3L-type light chain variable region represented by SEQ ID NO: 156 and 157 of the sequence listing, fused with a secretion signal was synthesized (Invitrogen Corp., Artificial Gene Synthesis Service) and digested with restriction enzymes NdeI and BsiWI. The resulting DNA fragments were separately inserted into sites of the versatile vector for humanized antibody light chain expression (pEF6/KCL) digested in advance with restriction enzymes NdeI and BsiWI to thereby construct hSH348-1-T1L and hSH348-1-T3L-type light chain expression vectors. The obtained expression vectors were designated as "pEF6/KCL/hSH348-1-T1L" and "pEF6/KCL/hSH348-1-T3L", respectively.

11)-1-4 Construction of hSH348-1-T1H and hSH348-1-T3H-Type Heavy Chain Expression Vectors Each DNA containing a gene encoding a hSH348-1-T1H or hSH348-1-T3H-type heavy chain variable region represented by SEQ ID NO: 158 and 159, respectively, of the sequence listing was synthesized (Invitrogen Corp., Artificial Gene Synthesis Service) and digested with a restriction enzyme BlpI. The resulting DNA fragments were separately inserted into sites of the versatile vector for humanized antibody H chain expression (pEF1/FCCU-1) digested in advance with a restriction enzyme BlpI to thereby construct hSH348-1-T1H and hSH348-1-T3H-type heavy chain expression vectors. The obtained expression vectors were designated as "pEF1/FCCU/hSH348-1-T1H" and "pEF1/FCCU/hSH348-1-T3H", respectively.

11)-1-5 Construction of hSH357-1-T1L and hSH357-1-T3L-Type Light Chain Expression Vectors Each DNA containing a gene encoding a hSH357-1-T1L or hSH357-1-T3L-type light chain variable region represented by SEQ ID NO: 160 or 161, respectively, of the sequence listing, fused with a secretion signal was synthesized (Invitrogen Corp., Artificial Gene Synthesis Service) and digested with restriction enzymes NdeI and BsiWI. The resulting DNA fragments were separately inserted into sites of the versatile vector for humanized antibody L chain expression (pEF6/KCL) digested in advance with restriction enzymes NdeI and BsiWI to thereby construct hSH357-1-T1L and hSH357-1-T3L-type light chain expression vectors. The obtained expression vectors were designated as "pEF6/KCL/hSH357-1-T1L" and "pEF6/KCL/hSH357-1-T3L", respectively.

11)-1-6 Construction of hSH357-1-T1H and hSH357-1-T3H-Type Heavy Chain Expression Vectors Each DNA containing a gene encoding a hSH357-1-T1H or hSH357-1-T3H-type heavy chain variable region represented by SEQ ID NO: 162 or 163, respectively, of the sequence listing was synthesized (Invitrogen Corp., Artificial Gene Synthesis Service) and digested with a restriction enzyme BlpI. The resulting DNA fragments were separately inserted into sites of the versatile vector for humanized antibody H chain expression (pEF1/FCCU-1) digested in advance with a restriction enzyme BlpI to thereby construct hSH357-1-T1H and hSH357-1-T3H-type heavy chain expression vectors. The obtained expression vectors were designated as "pEF1/FCCU/hSH357-1-T1H" and "pEF1/FCCU/hSH357-1-T3H", respectively.

11)-2 Production of Humanized Antibody $1.2 \times 10^9$ cells of 293 FreeStyle cells at the log growth phase were seeded onto 1.2 L of fresh FreeStyle 293 Expression Medium (Invitrogen Corp.) and shake-cultured (125 rpm) in an incubator at 37° C. in 8% $CO_2$. 12 mg of Polyethyleneimine (Polyscience #24765) was dissolved in 40 mL of an Opti-Pro SFM medium (manufactured by Invitrogen Corp.) and left at room temperature for 5 minutes. An H chain expression plasmid (0.6 mg) and an L chain expression plasmid (1.8 mg) prepared using a PureLink HiPure Plasmid kit (Invitrogen Corp.) were suspended in 40 mL of an Opti-Pro SFM medium (Invitrogen Corp.). 40 mL of the expression plasmid/OptiPro SFM mixed solution was added to 40 mL of the Polyethyleneimine/OptiPro SFM mixed solution thus left at room temperature for 5 minutes and further left at room temperature for 5 minutes. Next, 80 mL of the Polyethyleneimine/expression plasmid/OptiPro SFM mixed solution was added to the 293 FreeStyle cell suspension, and shake-culture was continued. After 7-day culture at 37° C. in 8% CO2, the culture supernatant was collected.

11)-3 Purification of Humanized Antibody

The culture supernatant obtained in paragraph 11)-2 was filtered through a Disposable Capsule Filter (Advantec MFS Inc., #CCS-045-E1H) and then purified by Protein A affinity column chromatography. The culture supernatant was applied to MabSelect SuRe HiTrap 1 mL (manufactured by GE Healthcare Bio-sciences Corp.) equilibrated with PBS, and washed with PBS. Next, a 2 M arginine solution (pH 4.0) was applied thereto to collect antibody-containing fractions. The pH was adjusted to 7, and the antibody-containing fractions were applied to a HiPrep Desalting Column (26/10, 50 mL) (GE Healthcare Bio-sciences Corp.) equilibrated with PBS in advance. After replacement with PBS, the antibody-containing fractions were passed through a 0.2-µm filter to prepare a purified sample.

The antibody concentration was determined by eluting the antibodies bound to a POROS G 20 µm Column, PEEK, 4.6 mm×100 mm, 1.7 ml (manufactured by Applied Biosystems) and measuring the absorbance (O.D. 280 nm) of the eluate, followed by peak area comparison with a standard (human IgG1).

A humanized antibody SH348-1 obtained by the combination between pEF6/KCL/hSH348-1-T1L and pEF1/FCCU/hSH348-1-T1H was designated as "hSH348-1-T1"; and a humanized antibody SH348-1 obtained by the combination between pEF6/KCL/hSH348-1-T3L and pEF1/FCCU/hSH348-1-T3H was designated as "hSH348-1-T3".

Moreover, a humanized antibody SH357-1 obtained by the combination between pEF6/KCL/hSH357-1-T1L and pEF1/FCCU/hSH357-1-T1H was designated as "hSH357-1-T1"; and a humanized antibody SH357-1 obtained by the combination between pEF6/KCL/hSH357-1-T3L and pEF1/FCCU/hSH357-1-T3H was designated as "hSH357-1-T3".

Example 12

Confirmation of Binding Activity of Humanized Anti-EPHA2 Antibody to Antigen

The abilities of the antibodies hSH348-1-T1, hSH348-1-T3, hSH357-1-T1, and hSH357-1-T3 to bind to the antigen were confirmed according to the method described in Example 6 except that Peroxidase AffiniPure Goat Anti-Human IgG Fcγ Fragment Specific (manufactured by Jackson ImmunoResearch Laboratories, Inc., #109-035-098) was used as a secondary antibody.

In the graphs of FIGS. 12A) to 12D), the absorbance is indicated in mean±standard deviation (n=3). As a result, all the humanized anti-EPHA2 antibodies hSH348-1-T1, hSH348-1-T3, hSH357-1-T1, and hSH357-1-T3 were confirmed to have binding activity to the EPHA2 extracellular region.

Example 13

Measurement of Competitive Inhibitory Activity Against Binding of SH348-1 or SH357-1 to EPHA2

The competitive inhibitory activities of hSH348-1-T1 and hSH348-1-T3 against the binding of SH348-1 to EPHA2 as well as the competitive inhibitory activities of hSH357-1-T1 and hSH357-1-T3 against the binding of SH357-1 to EPHA2 were measured by a method described below.

The mouse monoclonal antibodies SH348-1 and SH357-1 were separately biotinylated using EZ-Link Sulfo-NHS-LC Biotinylation Kit (manufactured by Thermo Fisher Scientific K.K., #21435) according to the protocol included therein (hereinafter, the biotinylated SH348-1 and SH357-1 were referred to as "bSH348-1" and "bSH357-1", respectively). The concentrations of bSH348-1, bSH357-1, and unlabeled antibodies (SH348-1, SH357-1, hSH348-1-T1, hSH348-1-T3, hSH357-1-T1, hSH357-1-T3, and Ab96-1) used in the competitive inhibition experiment were measured using BCA Protein Assay Reagent (manufactured by PIERCE).

An EPHA2 extracellular region polypeptide (manufactured by R&D Systems, Inc., #3035-A2-100) was diluted to 0.5 µg/ml with PBS, then dispensed at 100 µl/well onto an immunoplate (manufactured by Nunc, #442404), and incubated overnight at 4° C. to thereby adsorb the protein onto the plate. On the next day, the wells were washed once with Diluting Buffer (PBS, 0.05% (v/v) Tween 20). Then, a Block Ace solution (one pouch of Block Ace powder was dissolved in 100 ml of ultrapure water) diluted 4 times with PBS was dispensed at 200 µl/well and incubated at room temperature for 4 hours. The solution in the wells was removed. Then, mixed solutions of the biotinylated antibodies (5 µg/ml) and various concentrations (0 µg/ml, 1 µg/ml, 5 µg/ml, 25 µg/ml, 50 µg/ml, and 125 µg/ml) of the unlabeled antibodies (solvent: PBS containing 0.05% (v/v) (final concentration) Tween 20) were separately dispensed at 100 µl/well and incubated at room temperature for 1 hour. The wells were washed twice with Diluting Buffer (PBS, 0.05% (v/v) Tween 20). Then, Streptavidin-horseradish Peroxidase Conjugate (manufactured by GE Healthcare Bio-Sciences Corp., #RPN1231V) diluted 500 times with Diluting Buffer was added at 100 µl/well and incubated at room temperature for 1 hour. The solution in the wells was removed, and the wells were washed twice with Diluting Buffer. Then, a color reaction was performed with stirring by the addition of OPD Color Developing Solution at 100 µl/well. After color development, the color reaction was terminated by the addition of 1 M HCl at 100 µl/well. The absorbance at 490 nm was measured using a plate reader.

As a result, the absorbance of the wells supplemented with only bSH348-1 or bSH357-1 was 0.780±0.016 and 0.978±0.007 (mean±standard deviation (n=3)), respectively.

In the graphs of FIGS. 13A) and 13B), the absorbance is indicated in mean±standard deviation (n=3). The binding of SH348-1 or SH357-1 to EPHA2 was not inhibited by Ab96-1 differing in epitope therefrom. On the other hand, the binding of SH348-1 to EPHA2 was shown to be inhibited by the antibody SH348-1 itself or its humanized antibodies hSH348-1-T1 and hSH348-1-T3 (FIG. 13A). Likewise the binding of SH357-1 to EPHA2 was shown to be inhibited by the antibody SH357-1 itself or its humanized antibodies hSH357-1-T1 and hSH357-1-T3 (FIG. 13B).

Example 14

Inhibitory Effect of Humanized Anti-EPHA2 Antibody on Ephrin-A1-Dependent Phosphorylation of EPHA2 Tyrosine Residues The ability of the humanized anti-EPHA2 antibody to inhibit ephrin-A1-dependent phosphorylation of EPHA2 tyrosine residues was examined according to the method described in Example 8. As a result, all the antibodies hSH348-1-T1, hSH348-1-T3, hSH357-1-T1, and hSH357-1-T3 were shown to maintain an activity of inhibiting Ephrin-A1/Fc-induced phosphorylation of EPHA2 tyrosine residues (FIG. 14).

INDUSTRIAL APPLICABILITY

An anti-EPHA2 antibody of the present invention has an antitumor activity. A pharmaceutical composition comprising the anti-EPHA2 antibody can be used as an anticancer agent.

While illustrative embodiments have been illustrated and described, it will be appreciated that various changes can be made therein without departing from the spirit and scope of the invention.

The embodiments of the invention in which an exclusive property or privilege is claimed are defined as follows:

1. An antibody produced by the hybridoma SH348-1 (FERM BP-10836).

2. An isolated antibody which binds specifically to EPHA2 consisting of a heavy chain polypeptide comprising an amino acid sequence represented by amino acid Nos. 1 to 119 of SEQ ID NO: 35 in the sequence listing and a light chain polypeptide comprising an amino acid sequence represented by amino acid Nos. 1 to 112 of SEQ ID NO: 37 in the sequence listing.

3. An isolated antibody which specifically binds to EPHA2 consisting of a heavy chain polypeptide comprising the amino acid sequence represented by SEQ ID NO: 35 in the sequence listing and a light chain polypeptide comprising the amino acid sequence represented by SEQ ID NO: 37 in the sequence listing.

4. An antibody obtained by humanizing an antibody according to any one of claims 1, 2, and 3.

5. An isolated antibody which binds specifically to EPHA2 consisting of the following 1) and 2):

1) a heavy chain polypeptide comprising an amino acid sequence represented by amino acid Nos. 20 to 468 of SEQ ID NO: 107 in the sequence listing or a heavy chain polypeptide comprising an amino acid sequence represented by amino acid Nos. 20 to 468 of SEQ ID NO: 115 in the sequence listing; and 2) a light chain polypeptide comprising an amino acid sequence represented by amino acid Nos. 21 to 239 of SEQ ID NO: 91 in the sequence listing or a light chain polypeptide comprising an amino acid sequence represented by amino acid Nos. 21 to 239 of SEQ ID NO: 99 in the sequence listing.

6. An isolated antibody which binds specifically to EPHA2 consisting of a heavy chain polypeptide comprising an amino acid sequence represented by amino acid Nos. 20 to 468 of SEQ ID NO: 107 in the sequence listing and a light chain polypeptide comprising an amino acid sequence represented by amino acid Nos. 21 to 239 of SEQ ID NO: 91 in the sequence listing.

7. A Fab, F(ab')$_2$, Fv, scFv, a diabody, a linear antibody, or a multispecific antibody derived from any antibodies according to any of claims 1, 2, 3, 5, and 6.

8. The mouse hybridoma SH348-1 (FERM BP-10836).

9. An isolated antibody which specifically binds to EPHA2 consisting of a heavy chain polypeptide comprising an amino acid sequence represented by amino acid Nos. 20 to 468 of SEQ ID NO: 115 in the sequence listing and a light chain polypeptide comprising an amino acid sequence represented by amino acid Nos. 21 to 239 of SEQ ID NO: 99 in the sequence listing.

10. An isolated antibody which specifically binds to a polypeptide consisting of the amino acid sequence represented by SEQ ID NO: 8 in the sequence listing, wherein the antibody has the amino acid sequence represented by SEQ ID NO: 109 as CDRH1, SEQ ID NO: 111 as CDRH2, and SEQ ID NO: 113 as CDRH3, and has the amino acid sequence represented by SEQ ID NO: 93 as CDRL1, SEQ ID NO: 95 as CDRL2, and SEQ ID NO: 97 as CDRL3 in the sequence listing.

11. An isolated antibody which specifically binds to EPHA2 consisting of the following 1) and 2):

1) a heavy chain polypeptide comprising an amino acid sequence represented by amino acid Nos. 20 to 138 of SEQ ID NO: 107 in the sequence listing or a heavy chain polypeptide comprising an amino acid sequence represented by amino acid Nos. 20 to 138 of SEQ ID NO: 115 in the sequence listing; and 2) a light chain polypeptide comprising an amino acid sequence represented by amino acid Nos. 21 to 134 of SEQ ID NO: 91 in the sequence listing or a light chain polypeptide comprising an amino acid sequence represented by amino acid Nos. 21 to 134 of SEQ ID NO: 99 in the sequence listing.

12. An isolated antibody which specifically binds to EPHA2 consisting of a heavy chain polypeptide comprising an amino acid sequence represented by amino acid Nos. 20 to 138 of SEQ ID NO: 107 in the sequence listing; and a light chain polypeptide comprising an amino acid sequence represented by amino acid Nos. 21 to 134 of SEQ ID NO: 91 in the sequence listing.

13. An isolated antibody which specifically binds to EPHA2 consisting of a heavy chain polypeptide comprising an amino acid sequence represented by amino acid Nos. 20 to 138 of SEQ ID NO: 115 in the sequence listing; and a light chain polypeptide comprising an amino acid sequence represented by amino acid Nos. 21 to 134 of SEQ ID NO: 99 in the sequence listing.

14. A pharmaceutical composition comprising at least one antibody selected from the antibodies according to any one of claim 1, 2, 3, 5, 6, or 9-13.

15. A method for inhibiting tumor growth in a mammal, wherein the tumor expresses EPHA2, comprising administering any antibody selected from the group consisting of antibodies according to any one of claim 1, 2, 3, 5, 6, or 9-13.

* * * * *